(12) United States Patent
Kudo et al.

(10) Patent No.: US 7,226,911 B2
(45) Date of Patent: Jun. 5, 2007

(54) HAIR KERATIN-ASSOCIATED PROTEINS

(75) Inventors: Jun Kudo, Tokyo (JP); Kazunori Shibuya, Tokyo (JP); Nobuyoshi Shimizu, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 10/846,374

(22) Filed: May 13, 2004

(65) Prior Publication Data

US 2005/0170366 A1    Aug. 4, 2005

Related U.S. Application Data

(63) Continuation-in-part of application No. PCT/JP02/11851, filed on Nov. 13, 2002.

(30) Foreign Application Priority Data

Nov. 13, 2001 (JP) ............................... 2001-348050

(51) Int. Cl.
- A61K 38/08 (2006.01)
- A61K 38/17 (2006.01)
- A61K 8/64 (2006.01)
- A61K 8/65 (2006.01)
- C07K 7/06 (2006.01)

(52) U.S. Cl. .................. 514/15; 530/328; 530/357; 424/70.1

(58) Field of Classification Search ................ 514/15; 530/328, 357; 424/70.1
See application file for complete search history.

(56) References Cited

OTHER PUBLICATIONS

Zhumabaeva et al., "Cloning and structural characteristics of human hair keratin genes rich in sulfur," Mol Biol 26:813-820, 1992.*

Zhumabaeva et al., GenBank Record No. CAA44938, corresponds to Mol Biol 26:813-820, 1992.*

Rogers et al., "Characterization of a cluster of human high/ultrahigh sulfur keratin-associated protein genes embedded in the type I keratin gene domain on chromosome 17q12-21," J Biol Chem 276(22):19440-19541, 2001.*

Rogers et al., GenBank Record No. NP_114163, keratin associated protein 1.5 [*Homo sapiens*], corresponds to J Biol Chem 276(22):19440-19451, 2001.*

Aoki et al., GenBank Record No. BAB61026, direct submission, Jun. 21, 2001.*

(Continued)

*Primary Examiner*—Jon Weber
*Assistant Examiner*—Rosanne Kosson
(74) *Attorney, Agent, or Firm*—Frommer Lawrence & Haug LLP; Thomas J. Kowalski; Deborah L. Lu

(57) ABSTRACT

The present invention relates to provide a protein group binding to keratin which is the major component of body hair, or genes encoding the same, particularly to keratin-associated proteins (KAP) which bind specifically and strongly to hair keratin or genes encoding the same. The base sequence of eurochromtic region of approximately 33.5 Mb of human chromosome 21 was determined, a dot-matrix analysis of the base sequence of the long arm region of chromosome 21 (21q22.3) was carried out, homology search was made to low frequency repetitive sequences and 16 KAP genes being expressed only in hair root cells were found. Moreover, the high frequency repetitive sequences present in the sequence spanning for approximately 1 Mb between CLDN8 gene and TIAM1 gene in the long arm region of chromosome 21(21q22.11) were masked, the presence or absence of short low frequency repetitive sequence was searched, and 22 KAP genes were found. Moreover, a group of functional peptide was designed from the above mentioned KAPs.

4 Claims, 34 Drawing Sheets

OTHER PUBLICATIONS

Adachi et al., submission to EMBL/GenBank/DDBJ databases in Jul. 2000, released as Uniprot database record No. Q9D3H7 on Jun. 1, 2001.*

Michael A. Rogers et al., "Characterization of a Cluster of Human High/Ultrahigh Sulfur Keratin-associated Protein Gense Embedded in the Type 1 Keratin Gene Domain on Chromosome 17q12-21*", The Journal of Biological Chemistry, vol. 276, No. 22, Issue of Jun. 1, pp. 19440-19451, 2001.

M. Hattori et al., "The DNA sequence of human chromosome 21", Nature, vol. 405, pp. 311-319, May 18, 2000.

* cited by examiner

Figure 3

| | KAP17 | KAP15 | KAP14 | KAP13 | KAP12 | KAP11 | KAP10 | KAP09 | KAP08 | KAP07 | KAP06 | KAP05 | KAP04 | KAP03 | KAP02 | KAP01 |
|---|---|---|---|---|---|---|---|---|---|---|---|---|---|---|---|---|
| KAP17 | | 15% | 19% | 14% | 16% | 64% | 67% | 67% | 72% | 58% | 59% | 66% | 54% | 68% | 63% | 67% |
| KAP15 | | | 60% | 76% | 44% | 13% | 15% | 13% | 15% | 11% | 11% | 14% | 9% | 16% | 13% | 14% |
| KAP14 | | | | 47% | 34% | 16% | 17% | 16% | 18% | 14% | 13% | 17% | 12% | 19% | 17% | 16% |
| KAP13 | | | | | 39% | 13% | 13% | 11% | 15% | 10% | 10% | 14% | 8% | 15% | 12% | 13% |
| KAP12 | | | | | | 13% | 16% | 13% | 15% | 11% | 11% | 14% | 9% | 14% | 14% | 14% |
| KAP11 | | | | | | | 68% | 81% | 61% | 65% | 65% | 74% | 57% | 64% | 70% | 79% |
| KAP10 | | | | | | | | 69% | 62% | 52% | 56% | 69% | 44% | 68% | 71% | 70% |
| KAP09 | | | | | | | | | 63% | 65% | 63% | 78% | 56% | 64% | 77% | 83% |
| KAP08 | | | | | | | | | | 52% | 50% | 62% | 46% | 62% | 59% | 66% |
| KAP07 | | | | | | | | | | | 86% | 58% | 83% | 50% | 54% | 64% |
| KAP06 | | | | | | | | | | | | 58% | 75% | 49% | 54% | 61% |
| KAP05 | | | | | | | | | | | | | 52% | 62% | 73% | 87% |
| KAP04 | | | | | | | | | | | | | | 42% | 46% | 55% |
| KAP03 | | | | | | | | | | | | | | | 61% | 64% |
| KAP02 | | | | | | | | | | | | | | | | 74% |
| KAP01 | | | | | | | | | | | | | | | | |

Figure 6

```
KAP09    1 ATGGCCGCGTCCACCATGTCCATCCGCTCCAGCGCTTACTCCGACTCCTGGCAGGTGGAC    60
KAP09    1 MetAlaAlaSerThrMetSerIleArgSerSerAlaTyrSerAspSerTrpGlnValAsp   20
           :::::::: ::::::::::::::: :::::::::  :  :: :::::::::::::::::
KAP02    1 ATGGCCGCCTCCACCATGTCCATCTGCTCCAGCGCCTGCACCAACTCCTGGCAGGTGGAC   60
KAP02    1 MetAlaAlaSerThrMetSerIleCysSerSerAlaCysThrAsnSerTrpGlnValAsp   20

KAP09   61 GACTGCCCAGAGAGCTGCTGTGAGCCCCCTGCTGCGCCACCAGCTGCTGCGCCCCGGCC   120
KAP09   21 AspCysProGluSerCysCysGluProProCysCysAlaThrSerCysCysAlaProAla  40
           :::::::::::::::::::
KAP02   61 GACTGCCCAGAGAGCTGCT------------------------------------------  79
KAP02   21 AspCysProGluSerCysT------------------------------------------  27

KAP09  121 CCCTGCCTGACCCTGGTCTGCACCCCAGTGAGCCGTGTATCCAGCCCTGCTGCCAGGGC   180
KAP09   41 ProCysLeuThrLeuValCysThrProValSerArgValSerSerProCysCysGlnGly  60
                                                                     :::
KAP02   80 ------------------------------------------------------------GGC  82
KAP02   27 ------------------------------------------------------------rpP  28

KAP09  181 CAGCCGGGCTCAGGCCCCACCTCCCTGCCAGTCCTTGGACCTCCCAGCCCACCCAGCCTC  240
KAP09   61 GlnProGlySerGlyProThrSerLeuProValLeuGlyProProSerProProSerLeu  80
           ::::::::::::::::::::::::::::::::::::::::::::::::::::::::::::
KAP02   83 CAGCCGGGCTCAGGCCCCACCTCCCTGCCAGTCCTTGGACCTCCCAGCCCACCCAGCCTC 142
KAP02   28 roAlaGlyLeuArgProHisLeuProAlaSerProTrpThrSerGlnProThrGlnProG  48

KAP09  241 AGCACAGCTCAACACAGAAGGAGCAGCCCCAGCCACAGCCGCCCAGCCCCGGGGTCTCAG  300
KAP09   81 SerThrAlaGlnHisArgArgSerSerProSerHisSerArgProAlaProGlySerGln 100
           :::::::::: :::::::::::::::::::::::::::::::::::::::::::::::::
KAP02  143 AGCACAGCTCAGCACAGAAGGAGCAGCCCCAGCCACAGCCGCCCAGCCCCGGGGTCTCAG  202
KAP02   48 lnHisSerSerAlaGlnLysGluGlnProGlnProGlnProProSerProGlyValSerA  68

KAP09  301 ATGCTCACTGGCTCCTCCCTGACCTCCCCCCGGGCAGGCGAGCCCTGGCTTCTCCTCAC   360
KAP09  101 MetLeuThrGlySerSerLeuThrSerProProGlyArgArgAlaLeuAlaSerProHis 120
           ::::::::::::::::: ::::::::: :: :::: ::::::::::::::::::::::::
KAP02  203 ATGCTCACTGGCTCCTCTCTGACCTCCCGCC-GGGCGGGCGAGCCCTGGCTTCTCCTCAC  261
KAP02   68 spAlaHisTrpLeuLeuSerAspLeuProPr oGlyGlyArgAlaLeuAlaSerProHis  87

KAP09  361 GGTGCTTCCTGGCTGCAGACCACAACCCTCCGCTGGTCGCTGGTCGCTGGTTGGGGA    417
KAP09  121 GlyAlaSerTrpLeuGlnThrThrThrLeuArgTrpSerLeuValAlaGlyTrpGly   139
           ::::::::::::::::::::::::::::::::::::::::::::::::::::::::
KAP02  262 GGTGCTTCCTGGCTGCAGACCACAACCCTCCGCTGGTCGCTGGTCGCTGGTTGGGGA   318
KAP02   88 GlyAlaSerTrpLeuGlnThrThrThrLeuArgTrpSerLeuValAlaGlyTrpGly   106
```

Figure 7
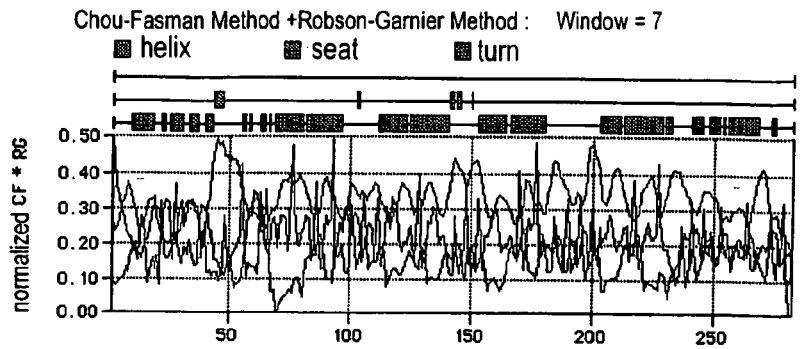
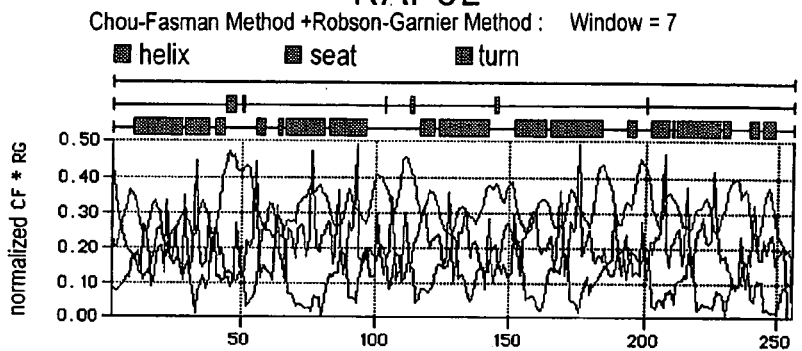
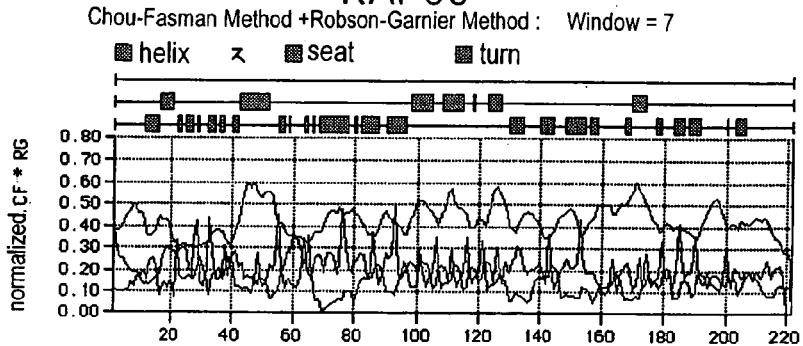
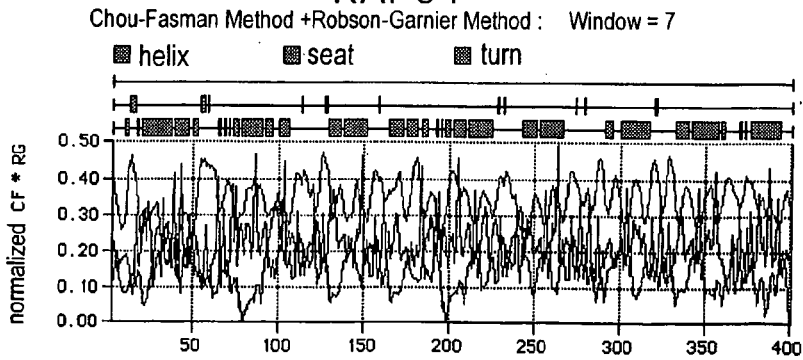
(continuation on the next page)

Figure 7(continued)
KAP05
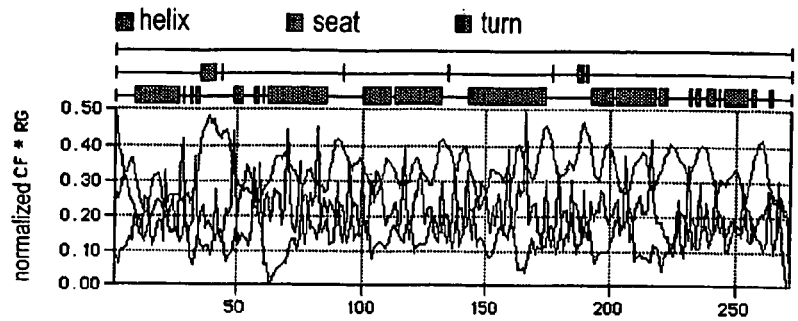
KAP06
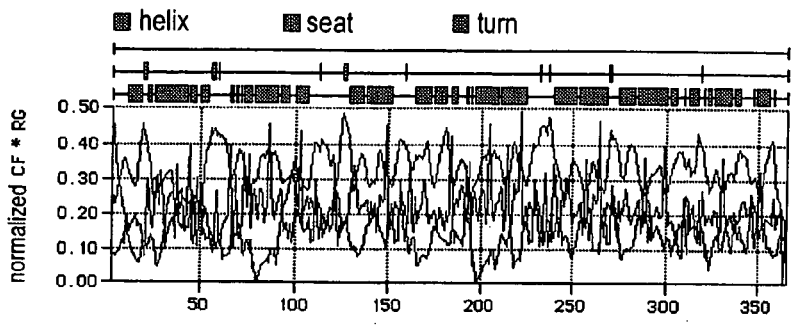
KAP07
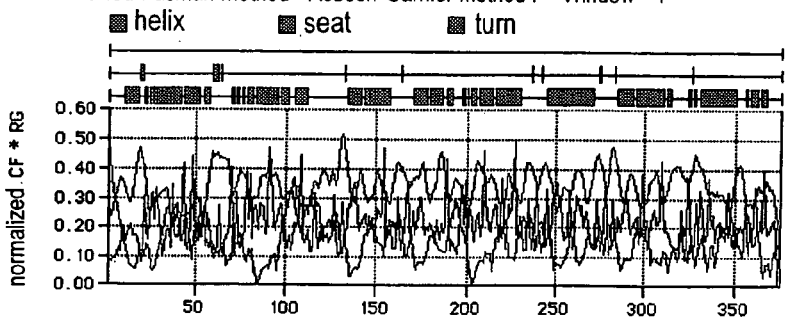
KAP08
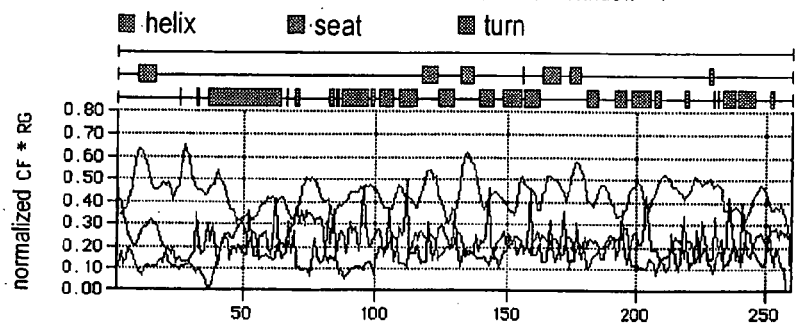
(continuation on the next page)

Figure 7(continued)
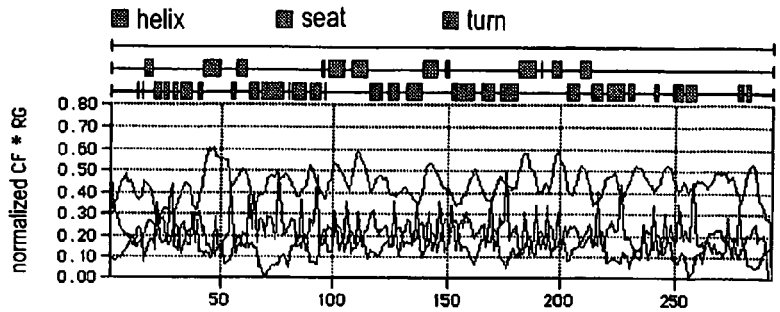
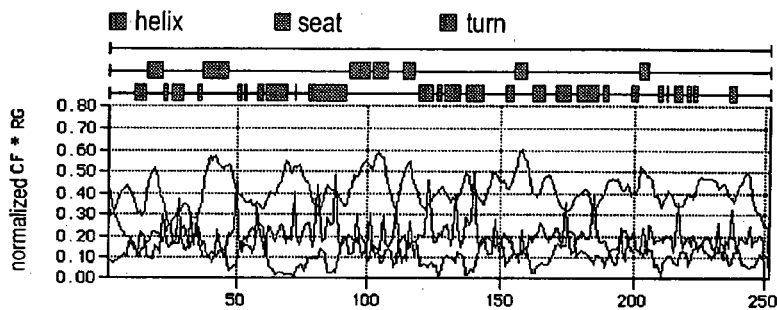
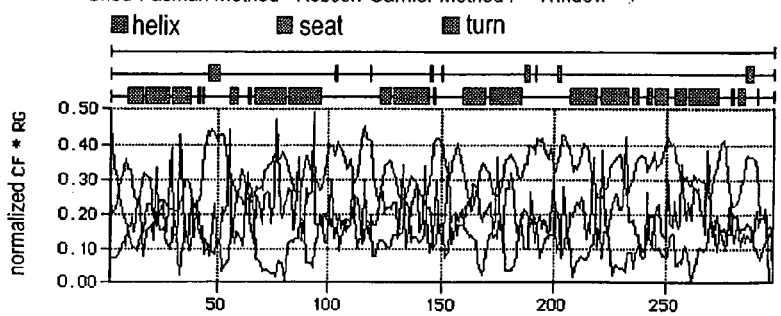
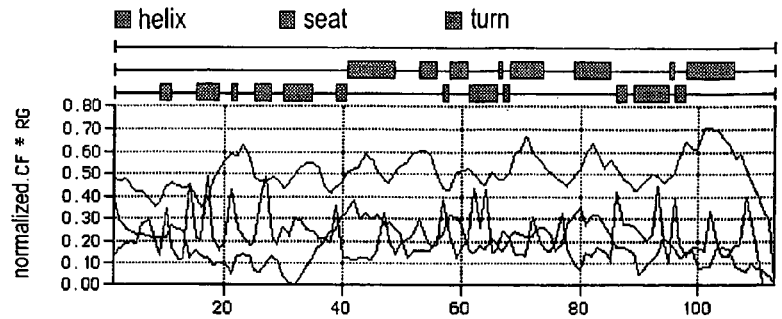
(continuation on the next page)

Figure 7(continued)
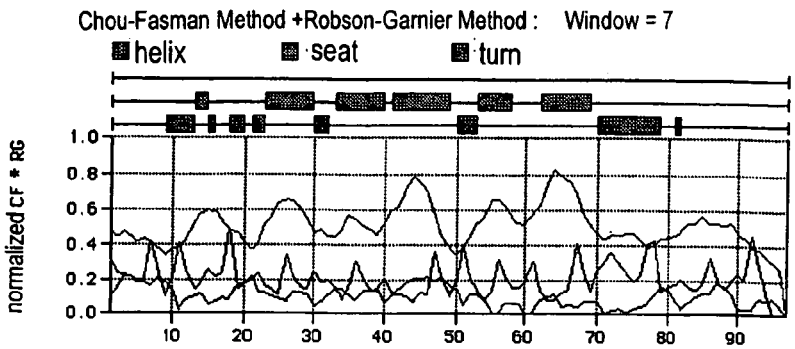
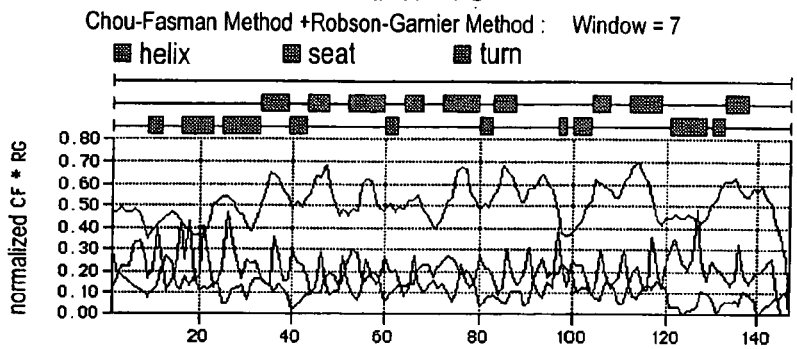
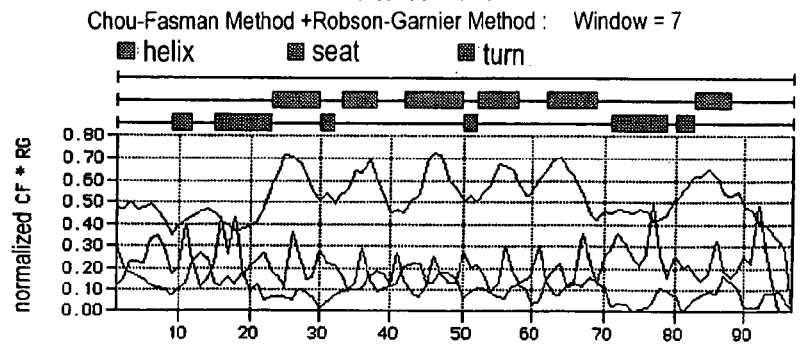
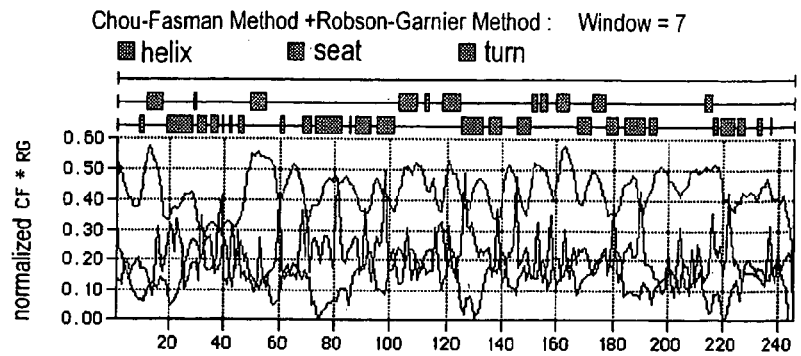

+ : RT+  — : RT—  G: human genomic DNA

Figure 11
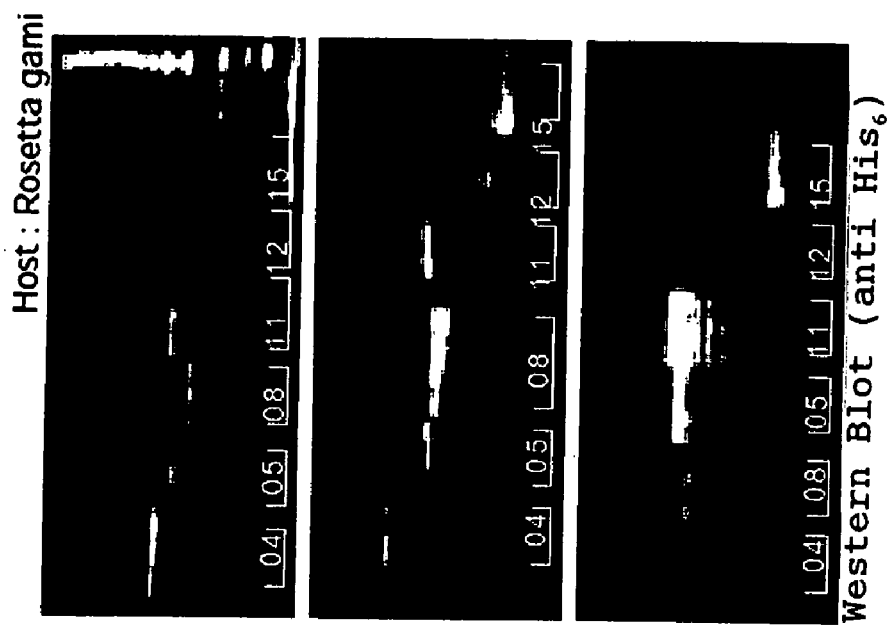
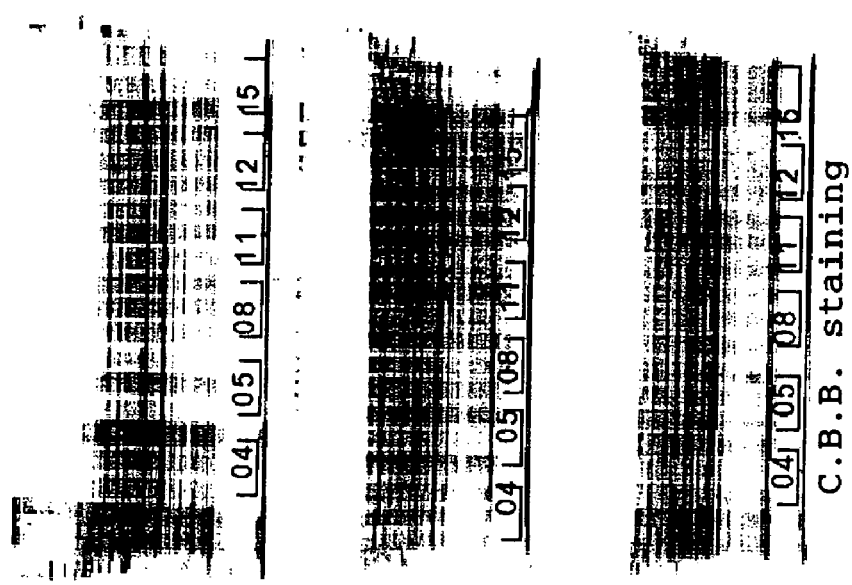

Figure 16

```
                      .    .    10   .    .    20   .    .    30   .    .    40   .    .    50   .    .    60   .    .    70   .    .    80
MMUKrtap14.aa    1:MSCNSCSGTfSQ.SFGGQDQYP1sBCGSiSYPN.NVFYSTDEQTPItH....QlGSSLHSGCQETFCEPTNCQTAYVVSRP: 74
MMUKrtap15.aa    1:MSYTCNSGNySSQSFGGFERQPVStNSFYPTSNVVYS....PKNF....QlGSSFYNGQQRTFSEPLEGHLFCVGSAS: 71
MMUHac1-1.aa     1:MSfNCStRNCSSRPVGGRYTAPVGPVTtASARDADCISG.LYLPSsF...QTGSWLLDHCQEsyCEPTVCQPTCYQRTS: 75
consensus        1:*!!**-****!-*-**!!-*--**--!---*----!**-------*!--!*---*-!!***!!*-**-*--*: 80*

.    .    90   .    .    100  .    .    110  .    .    120  .    .    130  .    .    140  .    .    150  .    .    160
MMUKrtap14.aa   75:CQR......LSTVRpEGPAGCQsTESGSI........GFGSRGFQSFGCGYPSQ.GFG..SHGFQSVG.....CGT:129
MMUKrtap15.aa   72:FHts......CFRPKQYFSSP..CQGGFtGSF........GYGNTGFGAFG......FG..SsGIRSQG......CG.:118
MMUHac1-1.aa    76:CIstPAQVTCNRQTTCVSNP..CStPCSRPL........FVStGCQPLGGISSSCQPVGGIStTCQPVGGISTTCQP:143
consensus       81:*-**!---*!-----*----*--*!*------*---!*!--*-----*!*!-*---*!----*!------:160-

.    .    170  .    .    180  .    .    190  .    .    200  .    .    210
MMUKrtap14.aa  130:P....TFSSlNCGSsFYRPTCFStKSCQSVSYQPT....CGtGFP...:166
MMUKrtap15.aa  118:........SNFYRPGYFSSKSIQSsYYQPG..YSSGICGSNF....:150
MMUHac1-1.aa   144:VGGISTTCQQvGGISTVCQPVGGISTVCQPtCGVSR..THQQ!CVSSCRRTC:193
consensus      161:------**-*-**!-**---*--*-------*!**-*--*:212
```

Figure 17

```
MMUKrtap16.8_78aa    1:MCG.YYGN......YGGR.GYGC......CGCG.GLGVdYG.GLGCGYGSYYGCGY.RGLGCGYG..YGCGYGs.....: 56
MMUKrtap6.1_aa       1:MCG.YYGN......YGGR.GYGC......CGYG.GLGYGYG.GLGCGYGSYYGCGY.RGLGCGYG..YGCGYGt.....: 56
MMUKrtap16.7_128aa   1:MCCNYYGNSCGGCCGYGSRYGCGYGSYGCGYGSYGCGYGSGYGCGYGSGYGCGYGS--*!!!!--*!!!!:  80
consensus            1:!!*-!!!!-----*!!!!-----*!!!!-----*!!!!-*!!!!--*!!!!--*!!!!--*!!!!:  80

MMUKrtap16.8_78aa   56:.RSlYGCGYG......CG...SGYGSGfGyYY...........................: 78
MMUKrtap6.1_aa      56:.RSLYGCGYG......CG...SGYGSGFGYYY...........................: 78
MMUKrtap16.7_128aa  81:YGSGYGCGYGSGYGCGYGtGYGCGySRYGCGYGSRYGCGSGCCSYRKCYSSC:128
consensus           81:-*!!!!----!!!!----!!!!--*!*!*!*!--------------------:128
```

Figure 18

```
                        .    .   10   .    .   20   .    .   30   .    .   40   .    .   50   .    .   60   .    .   70   .    .  80
MMUKrtap16.2_77aa    1:..........LGYGYGSSFGGLGCGCNSIRRI.GCGSG.YGGFGYGS.YGGYG...YGSDAGGYGYDSSYG..........:56
MMUKrtap16.9_87aa    1:MSYYSGYSGGLGYCYGSSRGGPGCGCNSIRRI.GCGSG.YGGFGYGS.YGGYG...YGSDYGGYGYGSSYG..........:66
MMUKrtap16.1_141aa   1:MSYYSGYSGGLGYGYGSSRGGLGCGCNSIRRI.GCGSG.YGGFGYGS(YGGFGGFGYGSGYGGYGYGSGYGGPGYGs:78
MMUKrtap16.5_87aa    1:MSHYSSYYGGLGYGY.GSFGGPGCGCNSIRRIVGFGSG.YGGFGYGSGIGGfG...YGSGYGGYGYGYGSGER.......:66
MMUKrtap16.6_59aa    1:..........................RRLVGFGSG.YCGFGYGSGIGGfG...YGSGYGGYGYGYGSGER.......:38
MMUKrtap16.3_80aa    1:MEAwATAMa......AAllaWaCGCNSIRRI.GCGSG.YGSYGYGSGHGGfG...YGSGFGGYGYGSGHGGfG......:59
MMUKrtap16.4_84aa    1:MSYYNSYYGGLGYGS.GGYGGLGYGY.........GCGCGSFRRLGYGCGFGGYGYGSGYGGfSSGSGYG.........:63
MMUKrtap8-2.aa       1:MSYYGSYYGGLGSGI.RGFGNLGYGY................GCGCG........................FGGYG...........SGYG..........:41
consensus            1:.*.*.*.*****..*-.***.****.....GCGSG.*.*.*.****....*.****......*.****....****:80

.    .  90   .    .  100   .    . 110   .    . 120   .    . 130   .    . 140
MMUKrtap16.2_77aa   56:...............................................GYGCGCRRPSCQGRYGFSNFY.:77
MMUKrtap16.9_87aa   66:...............................................GYGCGCRRPSCQGRYGFSNFY.:87
MMUKrtap16.1_141aa  79:GYGGFGYGSGYGGFGGPGYGSGYGGYGYGSGYGGYGYGSFGGGYGYGS(GYGCGCRRSSCCGGYGFSsFY:141
MMUKrtap16.5_87aa   66:..............................................GYGCGCRRPSCCGGYGFSsFY.:87
MMUKrtap16.6_59aa   38:..............................................GYGCGCRRPSCCGGYGFSsFY.:59
MMUKrtap16.3_80aa   59:..............................................GYGYCGRPSCCGGYGFSsFY..:80
MMUKrtap16.4_84aa   63:..............................................GfGYGYRRPLSYGGYGFStFY.:84
MMUKrtap8-2.aa      41:.....................................YGYGYPRPLYYGGYGFSRFY..:62
consensus           81:-----------------------------------**.*.***.****..:143
```

```
                       .    .    10    .    .    20    .    .    30    .    .    40    .    .    50    .    .    60    .    .    70    .    .    80
mKAP3_1       1 :MACCATSFCGFPTCSTGSSCCQFTCTQSSCCQPSCCIASCCQPSCCETGf..GGGIGCGQBGiSGGVSCRVkWCRPDCf.   : 78
mKAP3_2       1 :MACCATSFCGFPTCSTG......TCG.SSCCQPSCCITSCFQPSCCGTGyGLGGGIGCGQBGiFGGVSCRVrWCRPDCf.   : 73
consensus     1 ::::::::::::::::::-----:::::::::::--:::::!!*-:::::::!!!!!-!!::::::::!*!!:          : 80!!

.    .    90    .    .    100   .    .    110   .    .    120   .    .    130
mKAP3_1      79 :VEGTCLPPCCVVSTPPTCCQLHHAQASCCRPSYCGQSCCRPADCYQPSCFEPS(                              :136
mKAP3_2      74 :VEGTCLPPCCVVSIPSTCCQLHHAQASCCRPSYCGQSCCRPACCCY.......                              :122
consensus    81 ::::::::::::::-:-:::::::::::::::::::::::::--:-------                               :138
```

```
             .    .   10   .    .   20   .    .   30   .    .   40   .    .   50   .    .   60   .    .   70   .    .   80
mKAP5_4    1:............................................................MSCCGCSGGCGSSCGGCGSNCCKPVCCSCSSCGDCKG..........................:  64
mKAP5_5    1:............................................................MSCCGCEGGCGSSC..........CKPVCCVPVCSCSSCGGCKGGCSSCGGCGSCG........:  57
mKAP5_1    1:.................................................................MGCC..PGDCLNCC.......SQEQCCEECCCQQGCCG............CCGSCCGCGG..SSCG:  47
mKAP5_2    1:TRANSLATIMGCCG.CGGCGGCG..................................................CGG..CGCGGCGG.CGG.............CG.CGGCG...CGGCGG:  50
mKAP5_3    1:.........MGCCG.CGGCG.........................................................CGG..CGCGGCG.CGG................CG.CGGCC...CGGCG:  36
consensus  1:-----------------------------------------------*------------*----!-!*!*- *-!!--!-!*!*!*!*-- !!*!!--*-:  80

.    .   90   .    .  100   .    .  110   .    .  120   .    .  130   .    .  140   .    .  150   .    .  160
mKAP5_4   65:GCKGGCGGCGSCGGCKG..GCGSCGGCGSC(.GCKGGCSSCGG......................................CGSCGGCkGGCGSCGGCGSCGGCGSCG:  122
mKAP5_5   57:...GCGSCGGCKG...GCGSCGGCGSC(..GCKGGGCGS:CGG......................................CGSCGGCkGGCGSCGGCGSCGGCGSCG:  111
mKAP5_1   47:......GGC..CGS.GCGGGGCGSS...CCGGSGCG..GG...........................................CGSCGGC...GGC..CGGSGCCG:  89
mKAP5_2   50:......CCGGCG.CGGCGGCGGCG.CGGGGGCGG.  .CCGGCCGCG...............................CCGCCRrSCCRSCG .CGSCGG:  105
mKAP5_3   36:......CGGCG.CGGCGCGRaLWRLRWLWRJCLWLWWLWLWWLWLWLWLWLLWLLWLLWRPQGILLRRrSCCRSCG .CGSCG:  109
consensus 81:--------*------!--!*----!!********---****!-!!*!-!!*!**-----:  160

.    .  170   .    .  180   .    .  190   .    .  200   .    .  210   .    .  220   .    .  230   .    .  240
mKAP5_4  122:GCGSCGCCQSSCCCKPCCCQSSCCKPCCCQSSCC.............................K..PCCCQS..CKPCCCQSSCCAP:  182
mKAP5_5  111:GCKG.GCSSCGGGCGS.GCSSCGGCGSCGAAASPSCVSPAAASPAVQALLLPVQLLQALLLPAQLLPVQLLLSLLCGSSCCPMSCSLP:  189
mKAP5_1   89:..GGG.......G...........................................................CGPVCCGP...TP:  104
mKAP5_2  106:.CGCG........CG.............................................................CCQQKCCCQ:  122
mKAP5_3  110:.CGCG........CG...............................................................CGKGCCGQKCCCQ:  128
consensus 161:-!**---!-!**--------------------------------------------------**-!!-!!**!!-:  240

.    .  250
mKAP5_4  183:VCCQQKI...:189
mKAP5_5  190:IYCQREI...:196
mKAP5_1  105:v.CETK....:109
mKAP5_2  123:QKCGCKKCCC:132
mKAP5_3  129:QKCGCKKCCC:138
consensus 241:*-!-**----:250
```

Figure 24

```
                      .    .    .  10    .    .    .  20    .    .    .  30    .    .    .  40    .    .    .  50    .    .    .  60    .    .    .  70    .    .    .  80
mKAP6_2         1:..........................CCVaRCCSVPtGPatt....................................................................................:  48
mKAP6_4         1:..........................CCVaRCCSVPtGPatt....................................ICSSDKSQRCGVCLPSTCP.HEISLLQ........PTCCDF........:  48
mKAP6_3         1:...MTHTCQP.CCCKTASCRTSsSSEssSESSCPVIICAPSWCSTPCCCKSICC.ICSSDKSCRCGVCLPSTCP.HTIWQLE.......PTCCEN........:  50
mKAP6_5         1:..MTHTCQP.CCCKTASCRTSsSSEssSESSCPVII.........HSTKTvNSCSQLCCIPTCCDIASCDSNC.................:  79
mKAP6_1         1:...MTGICCgSFSSQSCGGgCCQPCCCRDP.CCRPVSCQTTVCRPVTCVPHCTRPICEP...CRIPICCDPCSLQQGC.............:  72
consensus       1:-------------------------***-**-*--*--***-******--*-*---*--*-**------------***-------*****----------:  80

.    .    .  90   .    .    . 100   .    .    . 110   .    .    . 120   .    .    . 130   .    .    . 140   .    .    . 150   .    .    . 160
mKAP6_2        48:.....CPPPCCQPEVYVPTCwLLN....SCHPTPGLsGlNLTTYVCP......GCEsPCEP.CC.............................:  96
mKAP6_4         1:..............................N....SCHPTPGLsGlNLTTYVCP......GCEsPCEP.CC.............................:  30
mKAP6_3        50:.....CPPPCHIPQPCVPTCfLLN....SCHPTPDELTvNLTTYVCP......GCEEPCVPRCC.........................:  99
mKAP6_5        80:CKPTCVTICSTPCCQPSCCVHTCQPTCCEtsCCKTTSFKPSCVIIGCSCPCCQPCCVCESAADNQLPK.:159
mKAP6_1        73:CRP......ICCPTSCIAVVCRP.CCwAST....CQPISVQAPCCRPPCCQAPCRTICRtSPCNTCC...........................:131
consensus      81:-----*-**-***-*--*-*******-*--*-*-*-*******-----*|--**--**--*****|--------*!*--!*---**-*****-------:160

.    .    . 170
mKAP6_2            :..........................:
mKAP6_4            :..........................:
mKAP6_3            :..........................:
mKAP6_5       160:QSHAPARAGMPCVHEAT:177
mKAP6_1            :..........................:178
consensus     161:----------------:178
```

Figure 25

Figure 26 mKAP1_1 : NM_015809 (Krtap5_4)
mKAP1_2 : NM_015808 (Krtap5_1)
mKAP1_3 : XM_109186 (Krtap9_1)
mKAP1_4 : AK003994
mKAP1_5 : NM_015471 (Krtap9_1)

mKAP2_1 : AK009665
mKAP2_2 : AK004258
mKAP2_3 : XM_109669
mKAP2_4 : AK009035
mKAP2_5 : AK004055 mKAP3_1 : AK009730
mKAP3_2 : AK009782 mKAP4_1 : AK016850
mKAP4_2 : AK003712
mKAP4_3 : AK013452
mKAP4_4 : BC027204 mKAP5_1 : AK020698
mKAP5_2 : AK020694
mKAP5_3 : AK017438
mKAP5_4 : AK014785
mKAP5_5 : AK020699 mKAP6_1 : AK017442
mKAP6_2 : BAA19685
mKAP6_3 :
mKAP6_4 : BAB26084
mKAP6_5 : AK014635 mKAP7_1 : D86424
mKAP7_2 : AK020700
mKAP7_3 : AF081797

SEQUENCE LISTING

<160> NUMBER OF SEQ ID NOS: 204

<210> SEQ ID NO 1
<211> LENGTH: 3154
<212> TYPE: DNA
<213> ORGANISM: Homo sapiens
<220> FEATURE:
<221> NAME/KEY: CDS
<222> LOCATION: (2001)..(2849)

<400> SEQUENCE: 1
tttccagaat ttttgtttga ttccatttaa taaatccagt ttgacactga aattctccat      60
ttgttctcta ttttcttgag caagttaatc agcattaaat tccagtttca caattctaat     120

-continued

```
atctagatct cctgcacgtc tgtttctctt gtttgttttt ttcctcttgg tcttttggtc      180
agttggtctt gtcttctaat atccctagta attttttgac tgcatgaagg actttatgaa      240
aatttataag atgatttgag cctctgttga tgctgctgtc tccagaagag atcacttttg      300
tttctgggag gcagttaggc tacaggcaga tcatatgagt tcagtgcgag tttatttaaa      360
gataggtttc attctttctg gttttccctt cctcctaggg agtagcccctt cacttacatt      420 cagcatttcc aactgaaagc ctaggtgtt tttgctagaa tccctccacc ttgtcaggtc       480
ctgaactctg tggttttttt cttctaattc catgagacta ctaaaagctc tgctcagctg      540
atcaggctct cggcctcttg gctgtggtct gtaaattggt aaatgcctca gtaagaaaat      600
ccacaaggaa tattggactc acttctgtgc agtttctctc taatgcggat tcactcactc      660
aagtctcagc tgtcttgata cctcccggcc ccttcgaaca gagattttgt ttgtaaacca      720
gatttcctaa tatttctcag ctagatggcc agtctgatgt aagccagttc cccacacacg      780
aaaggagaac ttgacagagc attttataca gcataagaaa aaggtggcac aatggaatcg      840
cgttcagagc tcaaaattac tcttcaataa tttctccaaa aaagtttatt atttcagccc      900 attttttataa aggcttttcc ttgggccagg catgatttta ggcctttgaa gactgagtgg     960
tgaacaagac aaacacactc cctgctcaca tgcagcttac gtttgaagaa aggaagctga     1020
ggacagcaag gacaatgaac aggaacaggg aagacacgtg gtgcagaaat actgatgatg     1080
gccaggcacc gggctcacgc ctgcaatccc agtactttgg ccaaggcagg agggatcact     1140
tgagacgcca tctgtacaaa aaaaaaaaaa aataaattta agaatattga taacgggact     1200
tgagttatct atggttgaag cacatcataa agctatggcc tttaagagca gaaccaaatc     1260
catgggccag ttcaaaactt ttcttttcctg tccgaaaccc agtcctatcc ccagcgttcc     1320
cacaccaacg tctgagtgga cctcggggaa ggccgtgggg aggggcatgg cctctccttc     1380
cttgctcccc ttctccctgt ttggggctct aatttcttca gtgatgggga tgggggaagg     1440
aatgtgcagg gccaccactg tggggttcgc tggccactgc tgcaccttct ctccggctgc     1500
tccagtgatc ctgtgcttct accagctgct tctgcctctt cagtgaggac ccgctttagg     1560
gaggagacgc ccccacgatc gtgagtggga cagctctcac cctggcatgc cacactttgc     1620
ataaggctga agggccaccc ctgcctccgc agcccccttc ttacaacccg gactgcactg     1680
gtggcgtgct gggaccaggt ccacctccac tcttgccccc agggatccac atgggacagg     1740
ctacagccca gacaggacag gagatttat cctgggcca catcacaggc aaacaaacat     1800
ccctagtcat gacacacgcc acctctcagc aaccaggaag gggacgctgt gggccctgga     1860
acaacaaggc cagaagggt ataaaagcag agccccacga agctcacaca ctcactcaca     1920
cactcagtca ctcacacaca cactgactcc cacactcact cactcacacc tcccgcagct     1980
```

| | | | | | | | | | | | |
|---|---|---|---|---|---|---|---|---|---|---|---|
| cacctcctcc ccaccccagc | atg | gcc | gcg | tcc | acc | atg | tcc | gtc | tgc | tcc | agc | 2033 |
| | Met | Ala | Ala | Ser | Thr | Met | Ser | Val | Cys | Ser | Ser | |
| | 1 | | | 5 | | | | | 10 | | | |

| | | | | | | | | | | | |
|---|---|---|---|---|---|---|---|---|---|---|---|
| gct | tgc | tcc | gac | tcc | tgg | cag | gtg | gat | gcc | tgc | cca gag agc tgc tgt | 2081 |
| Ala | Cys | Ser | Asp | Ser | Trp | Gln | Val | Asp | Ala | Cys | Pro Glu Ser Cys Cys | |
| | 15 | | | | 20 | | | | 25 | | | |

| | | | | | | | | | | | |
|---|---|---|---|---|---|---|---|---|---|---|---|
| gag | ccc | cac | tgc | tgc | gcc | ctc | agc | tgc | tgc | gcc | ccg gcc ccc tgc ctg | 2129 |
| Glu | Pro | His | Cys | Cys | Ala | Leu | Ser | Cys | Cys | Ala | Pro Ala Pro Cys Leu | |
| | 30 | | | | 35 | | | | 40 | | | |

| | | | | | | | | | | | |
|---|---|---|---|---|---|---|---|---|---|---|---|
| acc | ctg | gtc | tgc | acc | cca | gtg | agc | cgt | gtg | tcc | agc ccc tgc tgc cag | 2177 |
| Thr | Leu | Val | Cys | Thr | Pro | Val | Ser | Arg | Val | Ser | Ser Pro Cys Cys Gln | |
| | 45 | | | 50 | | | | 55 | | | | |

| | | | | | | | | | | | |
|---|---|---|---|---|---|---|---|---|---|---|---|
| gca | gcc | tgt | gag | ccc | agc | ccc | tgc | caa | tca | ggc | tgc acc agc tcc tgc | 2225 |

-continued

```
Ala Ala Cys Glu Pro Ser Pro Cys Gln Ser Gly Cys Thr Ser Ser Cys
 60                  65                  70                  75 acg ccc tcg tgc tgc cag cag tct agc tgc cag ccg gct tgc tgc acc     2273
Thr Pro Ser Cys Cys Gln Gln Ser Ser Cys Gln Pro Ala Cys Cys Thr
                 80                  85                  90 tcc tcc ccc tgc cag cag gcc tgc tgc gtg ccc gtc tgc tgc aag cct     2321
Ser Ser Pro Cys Gln Gln Ala Cys Cys Val Pro Val Cys Cys Lys Pro
             95                 100                 105 gtg tgc tgc ctg ccc acc tgc tct aag gat tcc tct tca tgc tgc cag     2369
Val Cys Cys Leu Pro Thr Cys Ser Lys Asp Ser Ser Ser Cys Cys Gln
         110                 115                 120 cag tct agc tgc cag cca act tgc tgt gcc tct tcc tcc agc cag cag     2417
Gln Ser Ser Cys Gln Pro Thr Cys Cys Ala Ser Ser Ser Gln Gln
     125                 130                 135 tcc tgc tgt gtg cct gtt tgc tgc aag cct gtg tgc tat gtg ccc acc     2465
Ser Cys Cys Val Pro Val Cys Cys Lys Pro Val Cys Tyr Val Pro Thr
 140                 145                 150                 155 tgc tct gag gat tcc tct tca tgc tgc cag cag tct agc tgc cat cca     2513
Cys Ser Glu Asp Ser Ser Ser Cys Cys Gln Gln Ser Ser Cys His Pro
                 160                 165                 170 gct tgc tgc acc tcc tcc ccc tgc cag cag gcc tgc tgc gtg ccc gtc     2561
Ala Cys Cys Thr Ser Ser Pro Cys Gln Gln Ala Cys Cys Val Pro Val
             175                 180                 185 cgt tgc aag cct gtc tgc tgc aag ccc atc tgc tgt gtg ccc gtc tgc     2609
Arg Cys Lys Pro Val Cys Cys Lys Pro Ile Cys Cys Val Pro Val Cys
         190                 195                 200 tct ggg gct tcc act tca tgc tgc cag cag tct agc tgc cag ccg gct     2657
Ser Gly Ala Ser Thr Ser Cys Cys Gln Gln Ser Ser Cys Gln Pro Ala
     205                 210                 215 tgc tgc acc acc tcc tgc tgc aga ccc tcc tcc tcc gtg tcc ctc ctc     2705
Cys Cys Thr Thr Ser Cys Cys Arg Pro Ser Ser Ser Val Ser Leu Leu
 220                 225                 230                 235 tgc cgc cct gta tgc cgg ccc gcc tgc tgt atg cct gtc tcc tcc tgc     2753
Cys Arg Pro Val Cys Arg Pro Ala Cys Cys Met Pro Val Ser Ser Cys
                 240                 245                 250 tgt gcc cct gcc tcc tcc tgc cag gcc agc tgc tgc cgc ccg gcc tcc     2801
Cys Ala Pro Ala Ser Ser Cys Gln Ala Ser Cys Cys Arg Pro Ala Ser
             255                 260                 265 tgc gtg tcc ctc ctc tgc cgc ccc gcg tgc tcc cgc ccg gcc tgc tga     2849
Cys Val Ser Leu Leu Cys Arg Pro Ala Cys Ser Arg Pro Ala Cys
         270                 275                 280 ggcctctgct caggccagga gtccagctgc tgatgggcac ccgccctggg ccagctgggc     2909
tcagttcctg acctgggtta ggtggcttcc cccacctagg acgggtcccc gtgtctcccc     2969
tgtgctgagg tgacccccc tccttgctcc caggagcctc catccttgca gctccccagc      3029
tcttgccttc cagcaggtgc ccacctgcct gctaggtccc ctgtcctccc tcccagcttc     3089
tctgctctgg gtcacttggc ctcgacttga acctctcagc acctcctcct gctccccaat     3149
aaact                                                                 3154
```

<210> SEQ ID NO 2
<211> LENGTH: 282
<212> TYPE: PRT
<213> ORGANISM: Homo sapiens

<400> SEQUENCE: 2

```
Met Ala Ala Ser Thr Met Ser Val Cys Ser Ser Ala Cys Ser Asp Ser
 1               5                  10                  15

Trp Gln Val Asp Ala Cys Pro Glu Ser Cys Cys Glu Pro His Cys Cys
```

```
                    20                  25                  30
Ala Leu Ser Cys Cys Ala Pro Ala Pro Cys Leu Thr Leu Val Cys Thr
                35                  40                  45

Pro Val Ser Arg Val Ser Ser Pro Cys Cys Gln Ala Ala Cys Glu Pro
        50                  55                  60

Ser Pro Cys Gln Ser Gly Cys Thr Ser Ser Cys Thr Pro Ser Cys Cys
65                  70                  75                  80

Gln Gln Ser Ser Cys Gln Pro Ala Cys Cys Thr Ser Ser Pro Cys Gln
                85                  90                  95

Gln Ala Cys Cys Val Pro Val Cys Cys Lys Pro Val Cys Cys Leu Pro
            100                 105                 110

Thr Cys Ser Lys Asp Ser Ser Ser Cys Cys Gln Gln Ser Ser Cys Gln
        115                 120                 125

Pro Thr Cys Cys Ala Ser Ser Ser Gln Gln Ser Cys Cys Val Pro
    130                 135                 140

Val Cys Cys Lys Pro Val Cys Tyr Val Pro Thr Cys Ser Glu Asp Ser
145                 150                 155                 160

Ser Ser Cys Cys Gln Gln Ser Ser Cys His Pro Ala Cys Cys Thr Ser
                165                 170                 175

Ser Pro Cys Gln Gln Ala Cys Cys Val Pro Val Arg Cys Lys Pro Val
            180                 185                 190

Cys Cys Lys Pro Ile Cys Cys Val Pro Val Cys Ser Gly Ala Ser Thr
        195                 200                 205

Ser Cys Cys Gln Gln Ser Ser Cys Gln Pro Ala Cys Cys Thr Thr Ser
    210                 215                 220

Cys Cys Arg Pro Ser Ser Ser Val Ser Leu Leu Cys Arg Pro Val Cys
225                 230                 235                 240

Arg Pro Ala Cys Cys Met Pro Val Ser Ser Cys Cys Ala Pro Ala Ser
                245                 250                 255

Ser Cys Gln Ala Ser Cys Cys Arg Pro Ala Ser Cys Val Ser Leu Leu
            260                 265                 270

Cys Arg Pro Ala Cys Ser Arg Pro Ala Cys
        275                 280

<210> SEQ ID NO 3
<211> LENGTH: 3091
<212> TYPE: DNA
<213> ORGANISM: Homo sapiens
<220> FEATURE:
<221> NAME/KEY: CDS
<222> LOCATION: (2001)..(2768)

<400> SEQUENCE: 3
ctctgtggta ttagttttgc tcttctgctt ctgatgtgaa ttttaatcc agctgtttgg      60 tattaaattt ggtattgaag acttgctgtc tttcatcttc aacatttttt attttagaa    120 tcggagactc actggttgag aatgtagatc ctatgtacag accggctggc ttctagtcct   180
ggttctgtca ctgtttttctg tgtggctttg agcagattgc tcaacctctc tgctgaagct   240
tccgcgtctg tccatagtaa cttcgacaag aagttaatgc cgaaattcag tgaattaata    300
gatgccaagt gcttggaatg ctccctggcg cagccacatg ctccgacctc accagcttca    360
tcatcagtgc tactaggggg tcattttcta agatcaccga agctgtcact acagtcacat    420
gctataattt gcagctccag gtctgtggga ccctcccct catactccat tagggaacgc     480
cgctgcctcg gcttcccttc ggctctcacc ctggctccca gtgctgactg ccctgcgtct    540
```

-continued

```
tcagatgaga ggctcttgtc gggagctgag tcttcacaga catcacccct gagaggtcgg    600 agggcttgt ttgacaacag ccatggaggg cggagtgact ggcacgtgct ggaggcccca     660
ggttcagatg gaatttccat cacaatggcg aggcaggtgt gcaggagggg ctgttggggg    720
gctgtgagtt tatcccacgt ccagccgtg cacatggcca gtgacagtca caatggcagt    780
gactcagatc tttaggtgga caattgtgtc acctgcgaat aacagaggtt cacgtctcat    840
ttctatttct cggcttgctg ctttgactgg ccctgtagga caacagagaa aggttctggt    900 gaccagggc ctgctcacct cctgctacgc tatgacagga gagcttccag tgagcctccc    960
tagcgctata ggctttctgg gccaccatga aagcccgtcc caggctgccg tagcctcatc   1020
cccagctgaa agaggctgga aggacactgg gagatgttgc tggttcctgg tgagaaccag   1080
cttcaggcca tgctgggctc aggccccaag acagaggagc tcacctgtga cggtccctgc   1140
cccggggtca gggcctgtcc tgcctgatga cctcccaagc acaggctggc tttgcccacc   1200
ccaagtgtcc ttcactctcc agtgaccctc attccacatc cacctcctca aggcagaggc   1260
ccctccccac ccccaggcct ggatctgcac ccaccactct caggacacct gaccagggct   1320
ccaggggaca acagtccaga cccaaaggcc agtccccaaa ccttgtcctc ctaatgagct   1380
gactgtccag aggccttgcc agaacattcc atctccttct cagaggaggg gaggtcctcc   1440
ctgtcctcct gctcttggca gacatcagga tctcagaaga tcccagagcc cgccaggaag   1500
cgctgtcctc aagcgtcttt tcccaacaca ggcacctcca tcctggctct cccaatcaca   1560
gccacgccag cccaccctgt gaggtccctg cagacagagg ctgggcctcc ccgggccca    1620 gagctcacgc tgggcacagt cacgggacct gccaggtgga agtcaccagg tcagccccag   1680
agaggccaca ccttccctcc tggtgttccc gggggacagg ctcagccagg ggcgccggtc   1740
ctgcccagga ccagccgagt gttaggagca gagtgaggac aagtcatggc aaaggaagca   1800
gaaataatga gggtcctccc ggctccaaac accaacacgg aagtggaggg cgttgctgag   1860
tctcctgctg gaaaacaca ggccctgggc atataaaagc cccagcagcc aacaggctca   1920
cacacacact cactcacaca ctcacacaca cactcactca ctcacacacc tcccccagct   1980
cacctcctcc ccactccagc atg gcc gcc tcc acc atg tcc atc tgc tcc agc   2033
                        Met Ala Ala Ser Thr Met Ser Ile Cys Ser Ser
                         1               5                  10 gcc tgc acc aac tcc tgg cag gtg gac gac tgc cca gag agc tgc tgt     2081
Ala Cys Thr Asn Ser Trp Gln Val Asp Asp Cys Pro Glu Ser Cys Cys
           15                   20                  25 gag ctc ccc tgc ggc acc ccc agc tgc tgt gcc cca gcc ccc tgc ctg     2129
Glu Leu Pro Cys Gly Thr Pro Ser Cys Cys Ala Pro Ala Pro Cys Leu
       30                  35                  40 acc ctg gtc tgc acc cca gtg agc tgt gtg tcc agc ccc tgc tgc cag     2177
Thr Leu Val Cys Thr Pro Val Ser Cys Val Ser Ser Pro Cys Cys Gln
   45                  50                  55 gcg gcc tgt gag ccc agc gcc tgc caa tca ggc tgc acc agc tcc tgc     2225
Ala Ala Cys Glu Pro Ser Ala Cys Gln Ser Gly Cys Thr Ser Ser Cys
60                  65                  70                  75 acg ccc tcg tgc tgc cag cag tct agc tgc cag ccg gct tgc tgc acc     2273
Thr Pro Ser Cys Cys Gln Gln Ser Ser Cys Gln Pro Ala Cys Cys Thr
               80                  85                  90 tcc tcc ccc tgc cag cag gcc tgc tgc gtg ccc gtc tgc tgc aag cct     2321
Ser Ser Pro Cys Gln Gln Ala Cys Cys Val Pro Val Cys Cys Lys Pro
           95                  100                 105 gtg tgc tgt gtg ccc gtc tgc tgt ggg gct tct tca tgc tgc cag cag    2369
Val Cys Cys Val Pro Val Cys Cys Gly Ala Ser Ser Cys Cys Gln Gln
       110                 115                 120
```

-continued

```
tct agc tgc cag cca gct tgc tgt gcc tct tcc tcc tgc cag cag tcc    2417
Ser Ser Cys Gln Pro Ala Cys Cys Ala Ser Ser Ser Cys Gln Gln Ser
    125                 130                 135 tgc cgt gtg cct gtc tgc tgc aaa gct gtg tgc tgc gtg ccc acc tgc    2465
Cys Arg Val Pro Val Cys Cys Lys Ala Val Cys Cys Val Pro Thr Cys
140                 145                 150                 155 tct gag tca tcc tct tca tgc tgc cag cag tct agc tgc cag ccg gct    2513
Ser Glu Ser Ser Ser Ser Cys Cys Gln Gln Ser Ser Cys Gln Pro Ala
                160                 165                 170 tgc tgc acc tcc tcc ccg tgt cag cag tcc tgc tgt gtg tcc gtc tgc    2561
Cys Cys Thr Ser Ser Pro Cys Gln Gln Ser Cys Cys Val Ser Val Cys
                175                 180                 185 tgc aag cct gtc tgc tgc aag tcc atc tgc tgt gta cct gtt tgc tct    2609
Cys Lys Pro Val Cys Cys Lys Ser Ile Cys Cys Val Pro Val Cys Ser
                190                 195                 200 ggg gct tcc tct ccg tgc tgc cag cag tct agc tgc cag cca gct tgc    2657
Gly Ala Ser Ser Pro Cys Cys Gln Gln Ser Ser Cys Gln Pro Ala Cys
    205                 210                 215 tgc acc tcc tcc tgc tgc aga ccc tcc tcc tct gtg tcc ctc ctc tgc    2705
Cys Thr Ser Ser Cys Cys Arg Pro Ser Ser Ser Val Ser Leu Leu Cys
220                 225                 230                 235 cgc ccc gtg tgc tcc cgc cca gcc tcc tgc agc ttt tcc tca ggc caa    2753
Arg Pro Val Cys Ser Arg Pro Ala Ser Cys Ser Phe Ser Ser Gly Gln
                240                 245                 250 aag tct agc tgc tga tggccatgtc cccagggcc agccgggctc aggccccacc    2808
Lys Ser Ser Cys
    255 tccctgccag tccttggacc tcccagccca cccagcctca gcacagctca gcacagaagg    2868 agcagcccca gccacagccg cccagccccg gggtctcaga tgctcactgg ctcctctctg    2928 acctcccgcc gggcgggcga gccctggctt ctcctcacgg tgcttcctgg ctgcagacca    2988 caaccctccg ctggtcgctg gtcgctggtt ggggatgggc cctcctgacc tgggtctcac    3048 ccccaggagc gtcaccctct gcctctgagc accaataaag cgt    3091
```

```
<210> SEQ ID NO 4
<211> LENGTH: 255
<212> TYPE: PRT
<213> ORGANISM: Homo sapiens

<400> SEQUENCE: 4

Met Ala Ala Ser Thr Met Ser Ile Cys Ser Ser Ala Cys Thr Asn Ser
 1               5                  10                  15

Trp Gln Val Asp Asp Cys Pro Glu Ser Cys Cys Glu Leu Pro Cys Gly
            20                  25                  30

Thr Pro Ser Cys Cys Ala Pro Ala Pro Cys Leu Thr Leu Val Cys Thr
        35                  40                  45

Pro Val Ser Cys Val Ser Pro Cys Cys Gln Ala Ala Cys Glu Pro
    50                  55                  60

Ser Ala Cys Gln Ser Gly Cys Thr Ser Ser Cys Thr Pro Ser Cys Cys
65                  70                  75                  80

Gln Gln Ser Ser Cys Gln Pro Ala Cys Cys Thr Ser Ser Pro Cys Gln
                85                  90                  95

Gln Ala Cys Cys Val Pro Val Cys Cys Lys Pro Val Cys Cys Val Pro
            100                 105                 110

Val Cys Cys Gly Ala Ser Ser Cys Cys Gln Gln Ser Ser Cys Gln Pro
        115                 120                 125
```

| | | | | | | | | | | | |
|---|---|---|---|---|---|---|---|---|---|---|---|
|Ala|Cys|Cys|Ala|Ser|Ser|Cys|Gln|Gln|Ser|Cys|Arg|Val|Pro|Val|
| |130| | | |135| | | |140| | |

Ala Cys Cys Ala Ser Ser Cys Gln Gln Ser Cys Arg Val Pro Val
      130                 135                 140

Cys Cys Lys Ala Val Cys Val Pro Thr Cys Ser Glu Ser Ser Ser
145             150                 155                 160

Ser Cys Cys Gln Gln Ser Ser Cys Gln Pro Ala Cys Cys Thr Ser Ser
            165                 170                 175

Pro Cys Gln Gln Ser Cys Cys Val Ser Val Cys Cys Lys Pro Val Cys
        180                 185                 190

Cys Lys Ser Ile Cys Cys Val Pro Val Cys Ser Gly Ala Ser Ser Pro
            195                 200                 205

Cys Cys Gln Gln Ser Ser Cys Gln Pro Ala Cys Cys Thr Ser Ser Cys
    210                 215                 220

Cys Arg Pro Ser Ser Ser Val Ser Leu Leu Cys Arg Pro Val Cys Ser
225                 230                 235                 240

Arg Pro Ala Ser Cys Ser Phe Ser Ser Gly Gln Lys Ser Ser Cys
                245                 250                 255

<210> SEQ ID NO 5
<211> LENGTH: 2914
<212> TYPE: DNA
<213> ORGANISM: Homo sapiens
<220> FEATURE:
<221> NAME/KEY: CDS
<222> LOCATION: (2001)..(2666)

<400> SEQUENCE: 5

```
gttgttcaat ttccatgtag ttgtgtggtt ttgagtgagt ttcttaatct tgagatctaa      60
tttgattgca ctgtggtccg gtagactttg ttatgatttc agttcttttg catttgctga     120
ggagtgtttt actttcaatt ataaagtcaa ttttagaata agtgccatgt gacactgaga     180
agaatgtatc ttctgttgat ttggggtgga gagttctgca gatgtctatt aggtccattt     240
gatccagagc tgagttcaag ttctgaatat ccttgttaat tttctgtcac attgatctgt     300
ctaatattga cagcagggtg ttaaagtttc ccactattat tgtgtgggag tctaagtctc     360
tttgtaggtc tctaagagct tgttttatga aactgggtgc ttttatattt ggtgcatata     420
tatttaggat aattagctct tctcattgaa ttgatccctt tatcattatg taatgccctt     480
cttttgtcttt tttgatcttt gttggcttaa agtctgtttt atcagagact aggattgcaa     540
cccctgctta cgttgctttc catttgcttg gtacattttc ctccattcct ttattttgag     600
cctatgtgtg tctttgcaag tgagatgggt ctcctgaata cagcacactg acgggtcatg     660
actcttcatc caatttgcca gtctgtgtcc agctattatt tctatgaaat aatattttc     720
cactgtagtc tgactttgcc aggtagtcct ccaacagagc ccttagccat actcatcaaa     780
ggtcagaggc ttcaaaccct gcagcctatg gccccccacc aagcactcag tggaccctg     840
gcctaatttt ggaaagccct gcagcctaga gcatcatcag agcctctgcc tttgccatt     900
caaagattta gtagaaaata gcgatcatag agtgaggaga tgaggatcc atgatcagaa     960
ctttgggggc ttactagcgc acaggtatgg tcccgggcac aggcatgggc tgatacacac    1020
aggtgtatag gtatttgtga gacaaggctc tgcaatcaga cccttttatt tgtacattta    1080
ctatgacaat gtccaggagc caacagtaga actaatacat tctgatgact ttctggccca    1140
taagggaaga gaccttggag ctcccaagga caccattgca ggtgatgttg cccgagatgt    1200
gagaggagaa ggtgtgaaca ctattgtgca caccacgggg ggaaggcccc ataacagttc    1260
aacgtgaaat gaaacaaagg tgcttgcccc tcatctccat ccctactgtg ctgggcctgc    1320
```

```
agctgcctcc ctgctcccct ctgcgagcca atctctgccc aggaagacac tattccctca    1380
cacctgcccc agggctcacc cccagcagaa atatgcccca tggttcccac tgacaaccag    1440
cagtgtcaac ccacagggtg gatctcgccg tgtggccagg ccaactgagc atcttcaaac    1500
ttgtccacag cagaacacat ctctcccttt cctcaaggcc cagaaactga ggttctccta    1560
acctcatccc tccttaggtg tagaagtctt tttttaagtg caaactcctc ctgggatgga    1620
gcagagggct gtcaattcca gaatatctcc taactgccac tgtccctgct tctgcagtgt    1680
gctttgatgc aatcaatata tttctactag tttatctctg tggacaagcc cacattaggg    1740
aagccctaac tccagtcagg agcctcacaa accagaacat ccacaaacaa tgaaccaaca    1800
ctactaacac aacagtgcct acaacaacaa caaggaagag gaaggcttct cgaagccagg    1860
caggggcagc acaatcaaca cagagggta taaaggttcc gaccactcag aggcctggca    1920
cgatcactca ctcactccct cactcactcc cacactcact cactcacgtc tcccccagct    1980
cacctcctcc ccaccccagc atg gcc acg tct acc atg tcc gtc tgc tcc agc    2033
                         Met Ala Thr Ser Thr Met Ser Val Cys Ser Ser
                          1               5                  10 gct tac tct gac tcc tgg cag gtg gac gcc tgc cca gag agc tgc tgt        2081
Ala Tyr Ser Asp Ser Trp Gln Val Asp Ala Cys Pro Glu Ser Cys Cys
         15                  20                  25 gag ccc ccc tgc tgc gcc acc agc tgc tgc gcc ccg gcc ccc tgc ctg        2129
Glu Pro Pro Cys Cys Ala Thr Ser Cys Cys Ala Pro Ala Pro Cys Leu
             30                  35                  40 acc ctg gtc tgc acc cca gtg agc tgt gtg tcc agc ccc tgc tgc cag        2177
Thr Leu Val Cys Thr Pro Val Ser Cys Val Ser Ser Pro Cys Cys Gln
 45                  50                  55 gcg gcc tgt gag ccc agc ccc tgc cag tca ggc tgc acc agc tcc tgc        2225
Ala Ala Cys Glu Pro Ser Pro Cys Gln Ser Gly Cys Thr Ser Ser Cys
 60                  65                  70                  75 acg ccc tcg tgc tgc cag cag tct agc tgc cag cca gct tgc tgc aca        2273
Thr Pro Ser Cys Cys Gln Gln Ser Ser Cys Gln Pro Ala Cys Cys Thr
             80                  85                  90 tcc tcc ccc tgc cag cag gcc tgc tgc gtg cct gtc tgc tgc aag cca        2321
Ser Ser Pro Cys Gln Gln Ala Cys Cys Val Pro Val Cys Cys Lys Pro
             95                 100                 105 gtc tgc tgt gtg ccc gtc tgc tgc aag cct gtc tgc tgc aag ccc atc        2369
Val Cys Cys Val Pro Val Cys Cys Lys Pro Val Cys Cys Lys Pro Ile
            110                 115                 120 tgc tgt gtg ccc gtc tgc tct ggg gct tcc tct tca tgc tgc cag cag        2417
Cys Cys Val Pro Val Cys Ser Gly Ala Ser Ser Ser Cys Cys Gln Gln
            125                 130                 135 tct agc cgc cag ccg gct tgc tgc acc acc tcc tgc tgc aga ccc tcc        2465
Ser Ser Arg Gln Pro Ala Cys Cys Thr Thr Ser Cys Cys Arg Pro Ser
140                 145                 150                 155 tcc tcc gtg tcc ctc ctc tgc cgc ccc gtg tgc agg tcc acc tgc tgt        2513
Ser Ser Val Ser Leu Leu Cys Arg Pro Val Cys Arg Ser Thr Cys Cys
            160                 165                 170 gtg ccc atc ccc tcc tgc tgt gcc cct gcc tcc acc tgc cag ccc agc        2561
Val Pro Ile Pro Ser Cys Cys Ala Pro Ala Ser Thr Cys Gln Pro Ser
            175                 180                 185 tgc tgc cgc ccg gcc tcc tgc gtg tcc ctc ctc tgc cgc ccc acg tgc        2609
Cys Cys Arg Pro Ala Ser Cys Val Ser Leu Leu Cys Arg Pro Thr Cys
            190                 195                 200 tcc cgc ctc tct tcc gcg tgc tgc ggc ctc tcc tca ggc cag aag tcc        2657
Ser Arg Leu Ser Ser Ala Cys Cys Gly Leu Ser Ser Gly Gln Lys Ser
            205                 210                 215 agc tgc tga cgggcaggtc ccgtttctcc agagttgttc cagggccatc               2706
Ser Cys
```

```
Ser Cys
220 tctgacttcc gaaatccttt gcagccctga gccctgtctg agtctcctct gcccatagcc      2766 actgcacctc cagccagcaa tgctgagctt tcatgccgat tccctccagg catgcatctc      2826 tcccacaccc tcatctccat gctggccagc cggtggtcac tgtgtcctgc cccatgtgag      2886 tgatcagtct gtcaacaaat aaagtcac                                         2914

<210> SEQ ID NO 6
<211> LENGTH: 221
<212> TYPE: PRT
<213> ORGANISM: Homo sapiens

<400> SEQUENCE: 6

Met Ala Thr Ser Thr Met Ser Val Cys Ser Ser Ala Tyr Ser Asp Ser
 1               5                  10                  15

Trp Gln Val Asp Ala Cys Pro Glu Ser Cys Cys Glu Pro Pro Cys Cys
                20                  25                  30

Ala Thr Ser Cys Cys Ala Pro Ala Pro Cys Leu Thr Leu Val Cys Thr
            35                  40                  45

Pro Val Ser Cys Val Ser Ser Pro Cys Cys Gln Ala Ala Cys Glu Pro
        50                  55                  60

Ser Pro Cys Gln Ser Gly Cys Thr Ser Ser Cys Thr Pro Ser Cys Cys
    65                  70                  75                  80

Gln Gln Ser Ser Cys Gln Pro Ala Cys Thr Ser Ser Pro Cys Gln
                85                  90                  95

Gln Ala Cys Cys Val Pro Val Cys Cys Lys Pro Val Cys Cys Val Pro
            100                 105                 110

Val Cys Cys Lys Pro Val Cys Cys Lys Pro Ile Cys Cys Val Pro Val
        115                 120                 125

Cys Ser Gly Ala Ser Ser Cys Cys Gln Gln Ser Ser Arg Gln Pro
    130                 135                 140

Ala Cys Cys Thr Thr Ser Cys Cys Arg Pro Ser Ser Ser Val Ser Leu
145                 150                 155                 160

Leu Cys Arg Pro Val Cys Arg Ser Thr Cys Cys Val Pro Ile Pro Ser
                165                 170                 175

Cys Cys Ala Pro Ala Ser Thr Cys Gln Pro Ser Cys Cys Arg Pro Ala
            180                 185                 190

Ser Cys Val Ser Leu Leu Cys Arg Pro Thr Cys Ser Arg Leu Ser Ser
        195                 200                 205

Ala Cys Cys Gly Leu Ser Ser Gly Gln Lys Ser Ser Cys
    210                 215                 220

<210> SEQ ID NO 7
<211> LENGTH: 3593
<212> TYPE: DNA
<213> ORGANISM: Homo sapiens
<220> FEATURE:
<221> NAME/KEY: CDS
<222> LOCATION: (2001)..(3206)

<400> SEQUENCE: 7
gattatagct caagtaatag ataaacattc tttagtccac acatagataa ataaataagg       60
aagcaaatag acacacagaa gagcgggaca gctcctcctc ccgggagaat tcaattagt       120 aagtgtggaa ggaacaaggc agggaggaga atcctcaaca gagccccaca ggaccgtgc      180 gggcgaggcc cccggagggg caccagcact gccgggcaaa cgcctgggca gacgcaggac      240
```

```
agctgccaag tctcagacat gaccaattac agagggaaac ggcggcaccg cgagggatgg      300
gccgcggccg tgtcacctcc atgccccacg cacactgctc ctgtgggatt cctcccccaa      360
cgcgatgccc actctgacca cgaggaaacc tcaagcaagt ccacgtggag gggcattcta      420
caaaacaccc aaccggtcaa ggtcgctgag gccaaggaga gattgggcaa ccgtcacaaa      480
ccagagaagt cgaggagacc tttcagccaa cgccatgtgg ggtcctgagc aggacccacc      540
ggaagttggt gcagctgcct aaagaccgtc ctggctgaga gaaacagag cagcgctgct       600 ttctcagagc tgggaaccaa cctgcggtgg tgtcgggaag ctggcaaagg gcgatgtgaa      660
ccccgctttt cagccactat tccctaaaac cattccacga ggtcaagcca cacctcacaa      720
gcaaaggctg ctgagtgccc agtgctgggc acctgctgtc ctgtgctacc ctcgccaccc      780
cccatgctcc acctgcccca ggcccaagtc acaagaaaac acttctgccg tgcttgcctt      840
cccatcccgg gttctgctcc cgtgcccacg tcctcatccc aggttctgcc attgtgtctg      900
cttgctgtgg attgaattgt gtccctcaaa aggtgccgaa gtcctgaccg ctggtacatg      960
tgaatgtgac cctatatgga aatagggtct ttgtaggtga tcaagttaag aggaggctgt     1020
taggataggc cctactgcaa taatgctttg tatccttata aaaggggag atttggacac       1080 acacacacac acacacacac acacacacac acacacacac acacacacgg agaagctgtg     1140
tgaagataaa ggcagagctc aggtgaggcc actgtaagcc aaggacccca aagatagcag     1200
cagcccacag gagtgagggg agcggggtga gacagtgccc ctcgcagcct cagaaggaac     1260
ccatgctgtc cactgtccac acctcgatct cagacttctg gcttccaaaa ccatgagaca     1320
cggaatttct gttgtgtgac cagccagttt gtggtactgt ttgtcatggc agcccaagga     1380
aaagaataca ttacagcata caaaccatga ctcacattat ctttacttag aacccaaaca     1440
aacctctctc cctaagcttt caatcacaga ggcacatgat cttgttcagc agcctagaaa     1500
accaaggccc agcggagcca cccgtaggca cccactcccc atagcctggc acacacacac     1560
ggcagagcca cccacaggca cccactcctc atagtccagc acacacacgg cagagccacc     1620
cgcaggcacc cactccccat agcccggcac acacgtggac catgccaccc tccacgtgcg     1680
cctggggagc aaagcagcac agcctgaact gcccctcagc tcttcctcct gagtctaaaa     1740
cacgcacatg cgccccaggc caattccaag ttttgtaaac tgagcaacag ctcttgggaa     1800
acaaaaacac agctactgtt tattctcctg gagctggctg tacacccaa caaggaaggg      1860 agggcttgct gagcctcctg tctggacaac atgcaccaag gaggagtata aaagccccac     1920
aaacccgagc acctcactca ctcgctcacc cactccctcc catctccccc agctcaaccc     1980
ccagcacagc agcatccacc atg tcc gtc tgc tcc agc gac ctg agc tac agc     2033
                       Met Ser Val Cys Ser Ser Asp Leu Ser Tyr Ser
                        1               5                   10 agc cgc gtc tgc ctt cct ggt tcc tgt gac tct tgc tcc gac tcc tgg        2081
Ser Arg Val Cys Leu Pro Gly Ser Cys Asp Ser Cys Ser Asp Ser Trp
             15                  20                  25 cag gtg gac gac tgc cca gag agc tgc tgc gag ccc ccc tgc tgc gcc        2129
Gln Val Asp Asp Cys Pro Glu Ser Cys Cys Glu Pro Pro Cys Cys Ala
         30                  35                  40 ccc agc tgc tgc gcc ccg gcc ccc tgc ctg agc ctg gtc tgc acc cca        2177
Pro Ser Cys Cys Ala Pro Ala Pro Cys Leu Ser Leu Val Cys Thr Pro
     45                  50                  55 gtg agc cgt gtg tcc agc ccc tgc tgc cca gtg acc tgt gag ccc agc        2225
Val Ser Arg Val Ser Ser Pro Cys Cys Pro Val Thr Cys Glu Pro Ser
 60                  65                  70                  75
```

-continued

| | | | | | | | | | | | | | | | | |
|---|---|---|---|---|---|---|---|---|---|---|---|---|---|---|---|---|
| ccc | tgc | caa | tca | ggc | tgc | acc | agc | tcc | tgc | acg | ccc | tcg | tgc | tgc | cag | 2273 |
| Pro | Cys | Gln | Ser | Gly | Cys | Thr | Ser | Ser | Cys | Thr | Pro | Ser | Cys | Cys | Gln | |
| | | | 80 | | | | 85 | | | | 90 | | | | | |
| cag | tct | agc | tgc | cag | ctg | gct | tgc | tgt | gcc | tcc | tcc | ccc | tgc | cag | cag | 2321 |
| Gln | Ser | Ser | Cys | Gln | Leu | Ala | Cys | Cys | Ala | Ser | Ser | Pro | Cys | Gln | Gln | |
| | | | 95 | | | | 100 | | | | 105 | | | | | |
| gcc | tgc | tgc | gtg | ccc | gtc | tgc | tgc | aag | act | gtc | tgc | tgc | aag | cct | gtg | 2369 |
| Ala | Cys | Cys | Val | Pro | Val | Cys | Cys | Lys | Thr | Val | Cys | Cys | Lys | Pro | Val | |
| | | 110 | | | | | 115 | | | | | 120 | | | | |
| tgc | tgt | gtg | ccc | gtc | tgc | tgt | ggg | gat | tct | tca | tgc | tgc | cag | cag | tct | 2417 |
| Cys | Cys | Val | Pro | Val | Cys | Cys | Gly | Asp | Ser | Ser | Cys | Cys | Gln | Gln | Ser | |
| | 125 | | | | | 130 | | | | | 135 | | | | | |
| agc | tgc | cag | tca | gct | tgc | tgc | acc | tcc | tcc | ccc | tgc | cag | cag | gcc | tgc | 2465 |
| Ser | Cys | Gln | Ser | Ala | Cys | Cys | Thr | Ser | Ser | Pro | Cys | Gln | Gln | Ala | Cys | |
| 140 | | | | 145 | | | | | 150 | | | | | | 155 | |
| tgt | gtg | ccc | atc | tgc | tgc | aag | cct | gtc | tgc | tct | ggg | att | tcc | tct | tcg | 2513 |
| Cys | Val | Pro | Ile | Cys | Cys | Lys | Pro | Val | Cys | Ser | Gly | Ile | Ser | Ser | Ser | |
| | | | 160 | | | | 165 | | | | 170 | | | | | |
| tgc | tgc | cag | cag | tct | agc | tgt | gtg | agc | tgt | gtg | tcc | agc | ccc | tgc | tgc | 2561 |
| Cys | Cys | Gln | Gln | Ser | Ser | Cys | Val | Ser | Cys | Val | Ser | Ser | Pro | Cys | Cys | |
| | | | 175 | | | | 180 | | | | 185 | | | | | |
| cag | gcg | gtc | tgt | gag | ccc | agc | ccc | tgc | caa | tca | ggc | tgc | atc | agc | tcc | 2609 |
| Gln | Ala | Val | Cys | Glu | Pro | Ser | Pro | Cys | Gln | Ser | Gly | Cys | Ile | Ser | Ser | |
| | | 190 | | | | | 195 | | | | | 200 | | | | |
| tgc | acg | ccc | tcg | tgc | tgc | cag | cag | tct | agc | tgc | cag | ccg | gct | tgc | tgc | 2657 |
| Cys | Thr | Pro | Ser | Cys | Cys | Gln | Gln | Ser | Ser | Cys | Gln | Pro | Ala | Cys | Cys | |
| | 205 | | | | | 210 | | | | | 215 | | | | | |
| acc | tcc | tcc | tcc | tgc | cag | cag | gcc | tgc | tgc | gtg | ccc | gtc | tgc | tgc | aag | 2705 |
| Thr | Ser | Ser | Ser | Cys | Gln | Gln | Ala | Cys | Cys | Val | Pro | Val | Cys | Cys | Lys | |
| 220 | | | | | 225 | | | | | 230 | | | | | 235 | |
| act | gtc | tgc | tgc | aag | cct | gtg | tgc | tct | gag | gat | tcc | tct | tca | tgc | tgc | 2753 |
| Thr | Val | Cys | Cys | Lys | Pro | Val | Cys | Ser | Glu | Asp | Ser | Ser | Ser | Cys | Cys | |
| | | | 240 | | | | 245 | | | | 250 | | | | | |
| cag | cag | tct | agc | tgc | cag | ccg | gct | tgc | tgc | acc | tcc | tct | ccc | tgc | cag | 2801 |
| Gln | Gln | Ser | Ser | Cys | Gln | Pro | Ala | Cys | Cys | Thr | Ser | Ser | Pro | Cys | Gln | |
| | | | 255 | | | | 260 | | | | 265 | | | | | |
| cag | gct | tgc | tgt | gtg | cct | gtc | tgc | tgc | aag | cct | gtg | tgc | tgc | aag | cct | 2849 |
| Gln | Ala | Cys | Cys | Val | Pro | Val | Cys | Cys | Lys | Pro | Val | Cys | Cys | Lys | Pro | |
| | | 270 | | | | | 275 | | | | | 280 | | | | |
| gtc | tgc | tct | gtg | ccc | atc | tgc | tct | ggg | gct | tcc | tct | ctg | tgc | tgc | cag | 2897 |
| Val | Cys | Ser | Val | Pro | Ile | Cys | Ser | Gly | Ala | Ser | Ser | Leu | Cys | Cys | Gln | |
| 285 | | | | | 290 | | | | | 295 | | | | | | |
| cag | tct | agc | tgc | cag | cca | gct | tgc | tgc | acc | tcc | tcc | caa | agc | cag | cag | 2945 |
| Gln | Ser | Ser | Cys | Gln | Pro | Ala | Cys | Cys | Thr | Ser | Ser | Gln | Ser | Gln | Gln | |
| 300 | | | | | 305 | | | | | 310 | | | | | 315 | |
| ggc | tgc | tgc | gtg | ccc | gtc | tgc | tgc | aag | cct | gtg | agc | tgt | gtg | cct | gtt | 2993 |
| Gly | Cys | Cys | Val | Pro | Val | Cys | Cys | Lys | Pro | Val | Ser | Cys | Val | Pro | Val | |
| | | | 320 | | | | 325 | | | | 330 | | | | | |
| tgc | tct | ggg | gct | tcc | tct | tca | tgc | tgc | cag | caa | tct | agc | tgc | cag | cca | 3041 |
| Cys | Ser | Gly | Ala | Ser | Ser | Ser | Cys | Cys | Gln | Gln | Ser | Ser | Cys | Gln | Pro | |
| | | 335 | | | | | 340 | | | | | 345 | | | | |
| gct | tgc | tgc | acc | acc | tcc | tgc | tgc | aga | ccc | tcc | tcc | tcc | gtg | tcc | ctc | 3089 |
| Ala | Cys | Cys | Thr | Thr | Ser | Cys | Cys | Arg | Pro | Ser | Ser | Ser | Val | Ser | Leu | |
| | 350 | | | | | 355 | | | | | 360 | | | | | |
| ctc | tgc | cgc | ccc | gtg | tgc | agg | ccc | gcc | tgc | tgt | gtg | ccc | gtc | cct | tcc | 3137 |
| Leu | Cys | Arg | Pro | Val | Cys | Arg | Pro | Ala | Cys | Cys | Val | Pro | Val | Pro | Ser | |
| | 365 | | | | | 370 | | | | | 375 | | | | | |
| tgc | tgt | gct | ccc | acc | tcc | tcc | tgc | caa | ccc | agc | tgc | tgc | cgc | cca | gcc | 3185 |
| Cys | Cys | Ala | Pro | Thr | Ser | Ser | Cys | Gln | Pro | Ser | Cys | Cys | Arg | Pro | Ala | |
| 380 | | | | | 385 | | | | | 390 | | | | | 395 | |

```
tcc tgc gtg tcc ctc ctc tga cgccccgtgt gctcccgccc agcctgctga       3236
Ser Cys Val Ser Leu Leu
                400 ggcctccgct caggtcagaa gcccagctgc tgatggacac gccccccagt gccagccagg   3296 ctcaggtccc acctgaaagc tgatagtcgc gtcctgaatt gctcctgcac tttgaccatt   3356 tcctggtgtc tgctgttgag ctggacaatg gaagaactga agtctatac tcaatgctgc    3416 agccctcttg cggggggagg ggggcgcttc tagaaagttc ccatggcagt ggcctcccct   3476 ccatatctcc cacctctcat gagggtcagt tcagccttga cccgtgaggt ctctgtcctc   3536 ctggctcaga gccgcagagc cttctttgga cgccctcaag ctgaccaata aaggccc      3593
```

<210> SEQ ID NO 8
<211> LENGTH: 401
<212> TYPE: PRT
<213> ORGANISM: Homo sapiens

<400> SEQUENCE: 8

```
Met Ser Val Cys Ser Ser Asp Leu Ser Tyr Ser Ser Arg Val Cys Leu
  1               5                  10                  15

Pro Gly Ser Cys Asp Ser Cys Ser Asp Ser Trp Gln Val Asp Asp Cys
             20                  25                  30

Pro Glu Ser Cys Cys Glu Pro Pro Cys Cys Ala Pro Ser Cys Cys Ala
         35                  40                  45

Pro Ala Pro Cys Leu Ser Leu Val Cys Thr Pro Val Ser Arg Val Ser
     50                  55                  60

Ser Pro Cys Cys Pro Val Thr Cys Glu Pro Ser Pro Cys Gln Ser Gly
 65                  70                  75                  80

Cys Thr Ser Ser Cys Thr Pro Ser Cys Cys Gln Gln Ser Ser Cys Gln
                 85                  90                  95

Leu Ala Cys Cys Ala Ser Ser Pro Cys Gln Gln Ala Cys Cys Val Pro
            100                 105                 110

Val Cys Cys Lys Thr Val Cys Cys Lys Pro Val Cys Cys Val Pro Val
        115                 120                 125

Cys Cys Gly Asp Ser Ser Cys Cys Gln Gln Ser Ser Cys Gln Ser Ala
    130                 135                 140

Cys Cys Thr Ser Ser Pro Cys Gln Gln Ala Cys Cys Val Pro Ile Cys
145                 150                 155                 160

Cys Lys Pro Val Cys Ser Gly Ile Ser Ser Cys Cys Gln Gln Ser
                165                 170                 175

Ser Cys Val Ser Cys Val Ser Ser Pro Cys Cys Gln Ala Val Cys Glu
            180                 185                 190

Pro Ser Pro Cys Gln Ser Gly Cys Ile Ser Ser Cys Thr Pro Ser Cys
        195                 200                 205

Cys Gln Gln Ser Cys Gln Pro Ala Cys Cys Thr Ser Ser Ser Cys
    210                 215                 220

Gln Gln Ala Cys Cys Val Pro Val Cys Cys Lys Thr Val Cys Cys Lys
225                 230                 235                 240

Pro Val Cys Ser Glu Asp Ser Ser Cys Cys Gln Gln Ser Ser Cys
                245                 250                 255

Gln Pro Ala Cys Cys Thr Ser Ser Pro Cys Gln Gln Ala Cys Cys Val
            260                 265                 270

Pro Val Cys Cys Lys Pro Val Cys Cys Lys Pro Val Cys Ser Val Pro
        275                 280                 285
```

-continued

```
Ile Cys Ser Gly Ala Ser Ser Leu Cys Cys Gln Gln Ser Ser Cys Gln
    290                 295                 300
Pro Ala Cys Cys Thr Ser Ser Gln Ser Gln Gln Gly Cys Cys Val Pro
305                 310                 315                 320
Val Cys Cys Lys Pro Val Ser Cys Val Pro Val Cys Ser Gly Ala Ser
                325                 330                 335
Ser Ser Cys Cys Gln Gln Ser Ser Cys Gln Pro Ala Cys Cys Thr Thr
            340                 345                 350
Ser Cys Cys Arg Pro Ser Ser Ser Val Ser Leu Leu Cys Arg Pro Val
        355                 360                 365
Cys Arg Pro Ala Cys Cys Val Pro Val Pro Ser Cys Cys Ala Pro Thr
    370                 375                 380
Ser Ser Cys Gln Pro Ser Cys Cys Arg Pro Ala Ser Cys Val Ser Leu
385                 390                 395                 400
Leu
```

<210> SEQ ID NO 9
<211> LENGTH: 3111
<212> TYPE: DNA
<213> ORGANISM: Homo sapiens
<220> FEATURE:
<221> NAME/KEY: CDS
<222> LOCATION: (2001)..(2816)

<400> SEQUENCE: 9

```
cagagggcgt ggatcacaaa taggaataaa gagacaagga atcaccacac ccattcgatt      60
aaggaggctg ccagagatag cgatgggaaa actaaagcaa attatcatac aggccccagg     120
gcttgtccca gaagccatgt cagccttacc acatcccgct ggctcaggac cacctgcctc     180
cctgcctgcc actcaggaag cacgcactct tctgggagct gtgtgacaga acggagccat     240
gtatggccgt gagggaaagg agtgagagct cgcggttgtc aggttcactg ccggccagct     300
gtcctctttc aaggttactt atcttctctc atcatttctg caactgtcaa atgggctgc     360
agagtcaccc ctcacgcggt ggctgatgtg gagaccgcac ctgcgccgtg catgtctgta     420
gcacacccgc tgatatgacg tcatcctagc cttcctggct ttcctgtcat ttcctgaaag     480
gagcatcgag tccttcagtc ccagaaagtg ggttaagcac acagttctcg cacaacctct     540
actaataatc actgaaagga tattcaaaga gttataaaaa ataaaatcaa aattgtctaa     600
caaaaaggga ggctctttaa aatcctttat atatttgtag aaaagagaaa cagatggaaa     660
caaattagaa tgtaaactgg atcaggaccc caatgccctg gaataaaata gtctttact      720
cagaaaatca aatgaactgc caccaatgag cagagcttaa ctgatgtcca gtgaaacgag     780
gggaaaaacg tttaaatgct caacataaca tcattacagt gagccaaaaa tgtatttcat     840
tcatcgtgag acaaaattaa agtcacaaaa ggaaagacct tgagagatga gttattttta     900
agagcgcaaa acacttcctg agtctccaca ttgaaaggct caatgaattc taaccacaga     960
aagtaaaata atgcacacgc atagaaacaa aagaagaata aaagaaaac caaatgttcc    1020
cagagagtta aacggagaga gagagacaaa ctataaaaaa tgacaaatga ccaacctcag    1080
tctctcatca gcaacgctgg acactacaga aaaatggtga cacaggttca tcattttgag    1140
aaaacagatt ttttgttatt atttataata ataattctga cttaaaacca gaattatata    1200
cccagctaaa ctatcatata agtgtgaggg taaagttgag tacatttta ggcaagaaag    1260
aaatcttaaa atgtatgtcc taaaatcacc atatgtgaaa aagtacttga tctgtcacca    1320
tgaggaaata aaaatggaga aaacccagag cgcagcttca aataaaacag agagagggct    1380
```

-continued

```
ctgagggtgg catggaagag ctgaagagac aaggataaag cacagatcca ccagatacca    1440
aatctctgag cattcccctt acgaggcaca aggggttgaa gagagggcca cttagcttca    1500
tcgtaccctc tgtgccagct gcattttata agaaatgcat attttctac ctatttatat     1560 tttaatatgc taaaagtaat aaaatatatc caatcagtcc aaacacagga taggtgaaac    1620
tagaattcct cccttagag aagtcttcat ctctaaaacc tctactcaac aaaagtttgc     1680
ttgaaatatt ttccaccaca tttctggggc taaaataaga accgatgaag aaacacggcc    1740
ctgcaacata cacacaagtt taatgaggga aaaacaaaca gataaaccag catgaatgac    1800
gcatctccag ccaccagctc taaacaccaa caaggaagag aagcttgtgg agcctcctgt    1860
cgggacaaca cacgccaggg agggatttaa aagccccaca gccctgagca cctcactcac    1920
tcactccctc cttcactcac tcacacactc actcactcac acctccccca gctcccagct    1980
cacgtcttcc ccaccccagc atg gcc gcg tgc acc atg tcc gtc tgc tcc agc    2033
                      Met Ala Ala Cys Thr Met Ser Val Cys Ser Ser
                       1               5                      10 gct tgc tct gac tcc tgg cga gtg gac gac tgc cca gag agc tgc tgt      2081
Ala Cys Ser Asp Ser Trp Arg Val Asp Asp Cys Pro Glu Ser Cys Cys
            15                  20                  25 gag ccc ccc tgc ggc acc gcc ccc tgc ctg acc ctg gtc tgc acc cca      2129
Glu Pro Pro Cys Gly Thr Ala Pro Cys Leu Thr Leu Val Cys Thr Pro
        30                  35                  40 gtg agc tgt gtg tcc agc ccc tgc tgc cag gcg gcc tgt gag ccc agc      2177
Val Ser Cys Val Ser Ser Pro Cys Cys Gln Ala Ala Cys Glu Pro Ser
    45                  50                  55 ccc tgc caa tca ggc tgc acc agc tcc tgc acg ccc tcg tgc tgc cag      2225
Pro Cys Gln Ser Gly Cys Thr Ser Ser Cys Thr Pro Ser Cys Cys Gln
60                  65                  70                  75 ccg gct tgc tgc gcc tcc tcc ccc tgc cag cag gcc tgc tgt gtg ccc      2273
Pro Ala Cys Cys Ala Ser Ser Pro Cys Gln Gln Ala Cys Cys Val Pro
                80                  85                  90 gtc tgc tgc aag cct gtg tgc tgc ctg ccc acc tgc tct aag gat tcc      2321
Val Cys Cys Lys Pro Val Cys Cys Leu Pro Thr Cys Ser Lys Asp Ser
            95                 100                 105 tct tca tgc tgc cag cag tct agc tgc cag cca act tgc tgt gcc tct      2369
Ser Ser Cys Cys Gln Gln Ser Ser Cys Gln Pro Thr Cys Cys Ala Ser
        110                 115                 120 tcc tcc tgc cag cag tcc tgc tgt gtg cct gtc tgc tgc aag ccc gtg      2417
Ser Ser Cys Gln Gln Ser Cys Cys Val Pro Val Cys Cys Lys Pro Val
    125                 130                 135 tgc tgt gtg ccc acc tgt tct gag gat tcc tct tca tgc tgc cag cat      2465
Cys Cys Val Pro Thr Cys Ser Glu Asp Ser Ser Ser Cys Cys Gln His
140                 145                 150                 155 tct agc tgc cag ccg act tgc tgc acc tcc tcc ccc tgc cag cag tcc      2513
Ser Ser Cys Gln Pro Thr Cys Cys Thr Ser Ser Pro Cys Gln Gln Ser
                160                 165                 170 tgc tac gtg cct gtc tgt tgc aag cct gtc tgc tgc aaa ccc atc tgc      2561
Cys Tyr Val Pro Val Cys Cys Lys Pro Val Cys Cys Lys Pro Ile Cys
            175                 180                 185 tgt gtg ccc gtc tgc tct ggg gct tcc act tca tgc tgc cag cag tct      2609
Cys Val Pro Val Cys Ser Gly Ala Ser Thr Ser Cys Cys Gln Gln Ser
        190                 195                 200 agc tgt cag ccg gct tgc tgc acc acc tcc tgc tgc aga ccc tcc tcc      2657
Ser Cys Gln Pro Ala Cys Cys Thr Thr Ser Cys Cys Arg Pro Ser Ser
    205                 210                 215 tcc gtg tcc ctc ctc tgc cgc ccc ata tgc agg ccc gcc tgc tgc ctg      2705
Ser Val Ser Leu Leu Cys Arg Pro Ile Cys Arg Pro Ala Cys Cys Leu
```

-continued

```
                220                 225                 230                 235
ccc atc tcc tcc tgc tgt gcc cct gcc tcc tcc tac cag gcc agc tgc         2753
Pro Ile Ser Ser Cys Cys Ala Pro Ala Ser Ser Tyr Gln Ala Ser Cys
                240                 245                 250 tgc cgc ccg gcc tcc tgc gtg tcc ctc ctc tgc cgc ccc gcg tgc tcc         2801
Cys Arg Pro Ala Ser Cys Val Ser Leu Leu Cys Arg Pro Ala Cys Ser
                255                 260                 265 ccc ctg gcc tgc tga ggcctctgct caggccagga gtccagttgc tgatgtgcac         2856
Pro Leu Ala Cys
            270 atccccagg gccaactggt cctgactcgg gttaggaggt tgccccccgct tgggacgggg       2916 cccccatgtg ctgaggtgac ccccccctcc atactcccag gaatctccat cctcgaagct       2976
ccccagctcc tgcctcccag caggggccca cctgcctgtt gggtcccctg tcctccctcc       3036
cagcttctct gccccatgtc acttggcctc gacttgaacc tgtcagcacc tcctcctgct       3096
ccccaataaa ctccc                                                        3111

<210> SEQ ID NO 10
<211> LENGTH: 271
<212> TYPE: PRT
<213> ORGANISM: Homo sapiens

<400> SEQUENCE: 10

Met Ala Ala Cys Thr Met Ser Val Cys Ser Ser Ala Cys Ser Asp Ser
 1               5                  10                  15

Trp Arg Val Asp Asp Cys Pro Glu Ser Cys Glu Pro Pro Cys Gly
            20                  25                  30

Thr Ala Pro Cys Leu Thr Leu Val Cys Thr Pro Val Ser Cys Val Ser
            35                  40                  45

Ser Pro Cys Cys Gln Ala Ala Cys Glu Pro Ser Pro Cys Gln Ser Gly
        50                  55                  60

Cys Thr Ser Ser Cys Thr Pro Ser Cys Cys Gln Pro Ala Cys Cys Ala
 65                  70                  75                  80

Ser Ser Pro Cys Gln Gln Ala Cys Cys Val Pro Val Cys Cys Lys Pro
                85                  90                  95

Val Cys Cys Leu Pro Thr Cys Ser Lys Asp Ser Ser Cys Cys Gln
            100                 105                 110

Gln Ser Ser Cys Gln Pro Thr Cys Cys Ala Ser Ser Cys Gln Gln
        115                 120                 125

Ser Cys Cys Val Pro Val Cys Cys Lys Pro Val Cys Cys Val Pro Thr
130                 135                 140

Cys Ser Glu Asp Ser Ser Ser Cys Cys Gln His Ser Ser Cys Gln Pro
145                 150                 155                 160

Thr Cys Cys Thr Ser Ser Pro Cys Gln Gln Ser Cys Tyr Val Pro Val
                165                 170                 175

Cys Cys Lys Pro Val Cys Cys Lys Pro Ile Cys Cys Val Pro Val Cys
            180                 185                 190

Ser Gly Ala Ser Thr Ser Cys Cys Gln Gln Ser Cys Gln Pro Ala
        195                 200                 205

Cys Cys Thr Thr Ser Cys Cys Arg Pro Ser Ser Val Ser Leu Leu
    210                 215                 220

Cys Arg Pro Ile Cys Arg Pro Ala Cys Cys Leu Pro Ile Ser Ser Cys
225                 230                 235                 240

Cys Ala Pro Ala Ser Ser Tyr Gln Ala Ser Cys Cys Arg Pro Ala Ser
                245                 250                 255
```

Cys Val Ser Leu Leu Cys Arg Pro Ala Cys Ser Pro Leu Ala Cys
          260                 265                 270

<210> SEQ ID NO 11
<211> LENGTH: 3364
<212> TYPE: DNA
<213> ORGANISM: Homo sapiens
<220> FEATURE:
<221> NAME/KEY: CDS
<222> LOCATION: (2001)..(3098)

<400> SEQUENCE: 11

```
aatgtcggtc ttgcaagatc tggtgtctga tgggcgggca cacccagcac actttcaaca      60
agcaatttat ccctagtgt gcaggtccct cgcccagttc ctcgcagcct gagtactatg     120
gggtcacagg cttcctggac gtcacctaag tttcattatc cccttataag gttacatctt    180
gtccccttcc ccactttaca tttgatttct caatggcaaa agtttctttc cttttatgtg    240
ttagccatcc gtcactttt cttcctcccc tctgacttct gtgagtctta tcactcttcc    300
cagatgtctg tactgtgtgg cttgtcacat ctgcaaggga gctgcctgga cttgccaggg    360
cctgttttct gaatacggac cacttgaaat gtacttctta cagggtggag tcttatcatg    420
tcaatgggtc gcaatgaggc cctaaacctc agaagtcttc tcaggacaca aaggcactcc    480
agtgcacagc ctctgtaaac cggctggagc cagtccatgg ttgggggtcc cttatcagga    540
ggaggttcct gaagtcagtc tcctgcccag tcagagctgt ggtcatggct gtggaacgtg    600
gtcagttggc atctgctggt ggatgagctg cagtcgtttg aaccttgctc atcctcatcg    660
cggggccagt gcgtgtttag ccactgtaga aaaacagcag ctgtggcgtg agagcagagt    720
ccgtcctctc agtgtagggc acgcggcttg tcccttgcct ggcgcggcct gaggtcctgt    780
ttgtaatttg atatcttatt gccagagtct gctctgtggg tcttacggtc tctattttaa    840
ctttagtgct gggtagtggt tgtgtcgaaa ccctaaaggg aggggtgta acgaggcgtg    900
tctgacctcc cttcctgtca tggccaggaa cgcagttttt cggggtcccc cgtgggcaag    960
atgggatcca tttagtcagt tgagggggctt aggattttat gtttcgttta cactggcaat   1020
gggtttgcag tgagatcaac ttctcatgga cccattttgt gtcttctgtg cgggttcttt   1080
ggacagatgt cccttaattt taaggtggtg acactaagag gcctggcaca gggcttggaa   1140
gacagggctg ggaaatgggc ccagcaggag gctgggtggg ggctgacggg cagcctcgga   1200
gaagcagagc acacagagga gccacccag gcggggacga gggctgctga ccgcccgctg   1260
ctcagcacgg ttactctgca ggttcagaac ccaaaaccac agcccagaag gctgtcatgc   1320
tgtccaagca gggaggggcc aagcccaccg tccttgccct ggaacacaca ggtcctgctg   1380
cctccaaaac acaaagacga ggtggacacg aaacagggcc ggaggtgaag aggctgtggg   1440
gatgagaagt cgtccagagc tcaaagccaa gaggtctggg cacagttaca gctgcccccc   1500
accccccacca tgccatggcc cagggcaggt caatgaaggc tcatgggccc caggttgtcc   1560
ctcagaagat ggccacagtc ctgtgtccgg tgatggggga aggaccacgc tggatgaggg   1620
gttttcacca caaggacact tcctgaggcc ggcttcctgc agagggactc tgtgtcccgg   1680
ggctgctggg gccaggggtg gacgatgccg cgacctgtgg ctctcccagc tccccgaacc   1740
cagctgggac caggccccgc ccaattcctg ccgccaggga tccacatggg atgggacaca   1800
gcccagatgt gatgggagat ttatgagctg gcccacatca cgggcgaaca aacaccccta   1860
atcccggcag actccagctc tcggcaacac ggaagggaa gctgtggggcc cggggacaac   1920
```

-continued

```
aaggccaggt ggaataaaag cccgagagcc tcagcacctc acaggctcac tccctcaccc    1980
tccaccagtt caacccagc atg gcc gcg tcc acc atg tcc gtc tgc tcc agc     2033
                     Met Ala Ala Ser Thr Met Ser Val Cys Ser Ser
                      1               5                      10 gac ctg agc tac ggc agc cgc gtc tgc ctt cct ggt tcc tgt gac tct      2081
Asp Leu Ser Tyr Gly Ser Arg Val Cys Leu Pro Gly Ser Cys Asp Ser
            15                  20                  25 tgc tcc gac tcc tgg cag gtg gac gac tgc cca gag agc tgc tgt gag      2129
Cys Ser Asp Ser Trp Gln Val Asp Asp Cys Pro Glu Ser Cys Cys Glu
        30                  35                  40 ccc ccc tgc tgc gcc ccg gcc ccc tgc ctg agc ctg gtc tgc acc cca      2177
Pro Pro Cys Cys Ala Pro Ala Pro Cys Leu Ser Leu Val Cys Thr Pro
    45                  50                  55 gtg agc cgt gtg tcc agc ccc tgc tgc cca gtg acc tgt gag ccc agc      2225
Val Ser Arg Val Ser Ser Pro Cys Cys Pro Val Thr Cys Glu Pro Ser
60                  65                  70                  75 ccc tgc caa tca ggc tgc acc agc tcc tgc acg ccc tcg tgc tgc cag      2273
Pro Cys Gln Ser Gly Cys Thr Ser Ser Cys Thr Pro Ser Cys Cys Gln
            80                  85                  90 cag tct agc tgc cag ctg gct tgc tgt gcc tcc tcc ccc tgc cag cag      2321
Gln Ser Ser Cys Gln Leu Ala Cys Cys Ala Ser Ser Pro Cys Gln Gln
        95                  100                 105 gcc tgc tgc gtg ccc gtc tgc tgc aag act gtc tgc tgc aag cct gtg      2369
Ala Cys Cys Val Pro Val Cys Cys Lys Thr Val Cys Cys Lys Pro Val
    110                 115                 120 tgt tgt gtg tcc gtc tgc tgt ggg gat tct tca tgc tgc cag cag tct      2417
Cys Cys Val Ser Val Cys Cys Gly Asp Ser Ser Cys Cys Gln Gln Ser
125                 130                 135 agc tgc cag tca gct tgc tgc acc tcc tcc ccc tgc cag cag gcc tgc      2465
Ser Cys Gln Ser Ala Cys Cys Thr Ser Ser Pro Cys Gln Gln Ala Cys
140                 145                 150                 155 tgt gtg ccc gtc tgc tgc aag cct gtc tgc tct ggg att tcc tct tcg      2513
Cys Val Pro Val Cys Cys Lys Pro Val Cys Ser Gly Ile Ser Ser Ser
        160                 165                 170 tgc tgc cag cag tct agc tgt gtg agc tgt gtg tcc agc ccc tgc tgc      2561
Cys Cys Gln Gln Ser Ser Cys Val Ser Cys Val Ser Ser Pro Cys Cys
    175                 180                 185 cag gcg gtc tgt gag ccc agc ccc tgc caa tca ggc tgc acc agc tcc      2609
Gln Ala Val Cys Glu Pro Ser Pro Cys Gln Ser Gly Cys Thr Ser Ser
190                 195                 200 tgc aca ccc tca tgc tgc cag cag tct agc tgc cag cca act tgc tgc      2657
Cys Thr Pro Ser Cys Cys Gln Gln Ser Ser Cys Gln Pro Thr Cys Cys
205                 210                 215 acc tcc tcc ccc tgc cag cag gcc tgc tgc gtg ccc gtc tgc tgc gtg      2705
Thr Ser Ser Pro Cys Gln Gln Ala Cys Cys Val Pro Val Cys Cys Val
220                 225                 230                 235 cct gtg tgc tgt gtg ccc acc tgc tct gag gat tcc tct tca tgc tgc      2753
Pro Val Cys Cys Val Pro Thr Cys Ser Glu Asp Ser Ser Ser Cys Cys
            240                 245                 250 cag cag tct agc tgc cag cca gct tgc tgc acc tcc tcc ccc tgc cag      2801
Gln Gln Ser Ser Cys Gln Pro Ala Cys Cys Thr Ser Ser Pro Cys Gln
        255                 260                 265 cac gcc tgc tgt gtg ccc gtc tgc tct ggg gct tcc aca tca tgc tgc      2849
His Ala Cys Cys Val Pro Val Cys Ser Gly Ala Ser Thr Ser Cys Cys
    270                 275                 280 cag cag tct agc tgc cag ccg gct tgc tgc acc gcc tcc tgc tgc aga      2897
Gln Gln Ser Ser Cys Gln Pro Ala Cys Cys Thr Ala Ser Cys Cys Arg
285                 290                 295 tcc tcc tcc tcc gtg tcc ctc ctc tgc cac cct gtg tgc aag tcc acc      2945
```

-continued

| | | | | | | | | | | | | |
|---|---|---|---|---|---|---|---|---|---|---|---|---|
| Ser | Ser | Ser | Ser | Val | Ser | Leu | Leu | Cys | His | Pro | Val | Cys | Lys | Ser | Thr |
| | 300 | | | | 305 | | | | 310 | | | | 315 | | |

```
tgc tgc gtg ccc gtc ccc tcc tgt ggt gcc tct gcc tcc tcc tgc cag       2993
Cys Cys Val Pro Val Pro Ser Cys Gly Ala Ser Ala Ser Ser Cys Gln
            320                 325                 330 ccc agc tgc tgc cgc acg gcc tcc tgt gtt tcc ctc ctc tgc cgc ccc       3041
Pro Ser Cys Cys Arg Thr Ala Ser Cys Val Ser Leu Leu Cys Arg Pro
        335                 340                 345 atg tgc tcc cgc cct gcc tgc tac agc ctc tgc tct ggc cag aag tcc       3089
Met Cys Ser Arg Pro Ala Cys Tyr Ser Leu Cys Ser Gly Gln Lys Ser
            350                 355                 360 agc tgc tga cagccctgga tgtgatccgg agtcccttcc caccagggc              3138
Ser Cys
    365 tgacctccca gctgcccag caagctctgc cctctctggc tttgacaccc tcagaagatg    3198 gggcaggctc tttgtcttag ggaccaggat gctcccctg tccttcccag atgctggctg    3258 catgagagac cccagctact cccccagacc caagttctgc agaactaacc cccagcaggc   3318 ctggttccac cctgggcagc accccctcta gttctaataa agccgc                  3364

<210> SEQ ID NO 12
<211> LENGTH: 365
<212> TYPE: PRT
<213> ORGANISM: Homo sapiens

<400> SEQUENCE: 12

Met Ala Ala Ser Thr Met Ser Val Cys Ser Ser Asp Leu Ser Tyr Gly
 1               5                  10                  15

Ser Arg Val Cys Leu Pro Gly Ser Cys Asp Ser Cys Ser Asp Ser Trp
                20                  25                  30

Gln Val Asp Asp Cys Pro Glu Ser Cys Cys Glu Pro Pro Cys Cys Ala
            35                  40                  45

Pro Ala Pro Cys Leu Ser Leu Val Cys Thr Pro Val Ser Arg Val Ser
        50                  55                  60

Ser Pro Cys Cys Pro Val Thr Cys Glu Pro Ser Pro Cys Gln Ser Gly
 65                  70                  75                  80

Cys Thr Ser Ser Cys Thr Pro Ser Cys Gln Gln Ser Ser Cys Gln
                85                  90                  95

Leu Ala Cys Cys Ala Ser Ser Pro Cys Gln Gln Ala Cys Cys Val Pro
            100                 105                 110

Val Cys Cys Lys Thr Val Cys Cys Lys Pro Val Cys Cys Val Ser Val
        115                 120                 125

Cys Cys Gly Asp Ser Ser Cys Cys Gln Gln Ser Ser Cys Gln Ser Ala
    130                 135                 140

Cys Cys Thr Ser Ser Pro Cys Gln Gln Ala Cys Cys Val Pro Val Cys
145                 150                 155                 160

Cys Lys Pro Val Cys Ser Gly Ile Ser Ser Cys Cys Gln Gln Ser
                165                 170                 175

Ser Cys Val Ser Cys Val Ser Ser Pro Cys Cys Gln Ala Val Cys Glu
            180                 185                 190

Pro Ser Pro Cys Gln Ser Gly Cys Thr Ser Ser Cys Thr Pro Ser Cys
        195                 200                 205

Cys Gln Gln Ser Ser Cys Gln Pro Thr Cys Cys Thr Ser Ser Pro Cys
    210                 215                 220

Gln Gln Ala Cys Cys Val Pro Val Cys Cys Val Pro Val Cys Cys Val
225                 230                 235                 240
```

```
Pro Thr Cys Ser Glu Asp Ser Ser Cys Cys Gln Ser Ser Cys
             245                 250                 255

Gln Pro Ala Cys Cys Thr Ser Pro Cys Gln His Ala Cys Cys Val
         260                 265                 270

Pro Val Cys Ser Gly Ala Ser Thr Ser Cys Cys Gln Ser Ser Cys
     275                 280                 285

Gln Pro Ala Cys Cys Thr Ala Ser Cys Cys Arg Ser Ser Ser Val
 290                 295                 300

Ser Leu Leu Cys His Pro Val Cys Lys Ser Thr Cys Cys Val Pro Val
305                 310                 315                 320

Pro Ser Cys Gly Ala Ser Ala Ser Ser Cys Gln Pro Ser Cys Cys Arg
             325                 330                 335

Thr Ala Ser Cys Val Ser Leu Leu Cys Arg Pro Met Cys Ser Arg Pro
             340                 345                 350

Ala Cys Tyr Ser Leu Cys Ser Gly Gln Lys Ser Ser Cys
             355                 360                 365

<210> SEQ ID NO 13
<211> LENGTH: 3540
<212> TYPE: DNA
<213> ORGANISM: Homo sapiens
<220> FEATURE:
<221> NAME/KEY: CDS
<222> LOCATION: (2001)..(3113)

<400> SEQUENCE: 13
cgcttccaaa acaatgctga aaccttagaa aactttcact ccatttatcc ttctcacctt      60
ttattgttaa tgtcatcatg cattactttt ctacttctag tttagacccc acaagagatt     120
ataaatataa taatattacc ctttcagatc ctcctggttc cttcctgcat ttttatcctt     180
ccgtcatcct gcctaaaaaa atccccttc atagttactg tagagtaggt ctgctcgtgt      240
tcagtttgct cagttgttat ccagaattgt tttgtttcat atttcacctt tgaacaatgt     300
tcttcctggt ctagaattct aggttttgcag tgattttctt tcagctcttt aaagatgtca     360
ttctattacc tttagtttct tcaacagctc ttttaggaga gctttaaagg aatcattttt      420
aaaacatttt gttcagcttt tcaagttgtt ctcagcagga gtatatgtct gacatagcta     480
ctttgtccca tatggaagca gaggccccca ttttctctct ctctctctct ctctctctct     540
ctctctctct ccttccatcc cataggacca gatcctgtac ctctggaggg accaggccat     600
gctcaaattt atattatttt tatagttcaa aatatacaga aagacaattc atcccaccgt     660
gtaactgaat ttctagccct ctgaggcctt ttgtactttt cctaaatccc ctaggagtta     720
agaggcctgg actgggaaac acagatagag acacaggaca ccctgagcct ctgagacttg     780
cctgggcatc aaacccccacc agaagggccc ctggagccct ctccctggg taggggccac     840 ttctcagggc cgcatgcatg ctgggctatg gctggtcatc actgacatca ccaggcacca     900
agcagcccac ctccctcct ggtggggtcc acagtcaggg ttactacccc ttcactttca     960
cattctcagc acctggtgca atttccagca tgtgggagga ctcactgcat catgaataaa    1020
tgaatgcttg agaagtaaaa gtatcggata caattggaaa catttagcag aaacaaccaa    1080
aaagatgtgg tggccaattg gatattattt gcagaagaaa tggagactta gatcagatgt    1140
ctagctgggg tgaccaagga cttagctggc aatcaagaaa acacactgca agcgaaagca    1200
gtgcttgctg cttttcacac ggcagtgctg ttgagagtgg ctgtgctttt tgcggaggag    1260
gtgttctggg ttagacttac aggtttgcag tgcttgggat aaaaccaaat ggaaatgggg    1320
```

-continued

```
gccccaaaca gggatctggg gcctccctaa gtgcccagat ggaagagggg gtgcacggcc      1380
ccccaggaac tactgtgaac ctgacgggaa atggctcaca ccactgtcca cccttcccg       1440 tttgccactt gctctaaagc ccttgggggg actttatgca ccagagagag tgtggggagt      1500
cacttctagg aatgttccac cctcatgcca tcattgacag gggcttctct agcctggcat      1560
tccagaagcc acagccaccc agacaagcag agtcccctgg cgatggccca caggcgctgg     1620
gattaggatg gatggatctc tcctgcagcc agcacaggcc cctgggacac tctatttgca      1680
gacattacac cctgtctact tcaatattat gctctggagc caaggtaggt gagggtgcg       1740 tcaacggaac caaatataga ctcaggactt tacaaactga acggcatctc ataggactaa      1800
acatgaaact cgcactaata agcgttctct aggttttaaa cacaaacaag gaaggggcag     1860
gagttgttga cactccagct gggacaacag accaggagaa catataaaag ccaacatccc     1920
tgagcaccta acacacggac tcactcactc attcactcac tcaccactc actcccatct      1980 cctccagttc aatcccagc atg gct gcg tcc act atg tct gtc tgc tcc agc      2033
                      Met Ala Ala Ser Thr Met Ser Val Cys Ser Ser
                        1               5                  10 gac ctg agc tac ggc agc cgc gtc tgc ctt cct ggt tcc tgt gac tct        2081
Asp Leu Ser Tyr Gly Ser Arg Val Cys Leu Pro Gly Ser Cys Asp Ser
         15                  20                  25 tgc tcc gac tcc tgg cag gtg gac gac tgc cca gag agc tgc tgc gag        2129
Cys Ser Asp Ser Trp Gln Val Asp Asp Cys Pro Glu Ser Cys Cys Glu
        30                  35                  40 ccc ccc tgc tgc gcc ccg gcc ccc tgc ctg agc ctg gtc tgc acc cca        2177
Pro Pro Cys Cys Ala Pro Ala Pro Cys Leu Ser Leu Val Cys Thr Pro
    45                  50                  55 gtg agc tat gtg tcc agc ccc tgc tgc cga gtg acc tgt gag ccc agc        2225
Val Ser Tyr Val Ser Ser Pro Cys Cys Arg Val Thr Cys Glu Pro Ser
60                  65                  70                  75 ccc tgc caa tca ggc tgc acc agc tcc tgc acg ccc tcg tgc tgc cag        2273
Pro Cys Gln Ser Gly Cys Thr Ser Ser Cys Thr Pro Ser Cys Cys Gln
                80                  85                  90 cag tct agc tgc cag ctg gct tgc tgt gcc tcc tcc ccc tgc cag cag        2321
Gln Ser Ser Cys Gln Leu Ala Cys Cys Ala Ser Ser Pro Cys Gln Gln
                    95                 100                 105 gcc tgc tgc gtg ccc gtc tgc tgc aag act gtc tgc tgc aag cct gtg        2369
Ala Cys Cys Val Pro Val Cys Cys Lys Thr Val Cys Cys Lys Pro Val
            110                 115                 120 tac tgt gtg cct gtc tgc agt ggg gat tct tca tgc tgc cag cag tct        2417
Tyr Cys Val Pro Val Cys Ser Gly Asp Ser Ser Cys Cys Gln Gln Ser
125                 130                 135 agc tgc cag tca gct tgc tgc acc tcc tcc ccc tgc cag cag gcc tgc        2465
Ser Cys Gln Ser Ala Cys Cys Thr Ser Ser Pro Cys Gln Gln Ala Cys
140                 145                 150                 155 tgt gtg ccc atc tgc tgc aag cct gtc tgc tct ggg att tcc tct tcg        2513
Cys Val Pro Ile Cys Cys Lys Pro Val Cys Ser Gly Ile Ser Ser Ser
                160                 165                 170 tgc tgc cag cag tct agc tgt gtg agc tgt gtg tcc agt ccc tgc tgc        2561
Cys Cys Gln Gln Ser Ser Cys Val Ser Cys Val Ser Ser Pro Cys Cys
                    175                 180                 185 cag gcg gtc tgt gag ccc agc ccc tgc caa tca ggc tgc atc agc tcc        2609
Gln Ala Val Cys Glu Pro Ser Pro Cys Gln Ser Gly Cys Ile Ser Ser
            190                 195                 200 tgc acg ccc tcg tgc tgc cag cag tct agc tgc aag ccg gct tgc tgc        2657
Cys Thr Pro Ser Cys Cys Gln Gln Ser Ser Cys Lys Pro Ala Cys Cys
205                 210                 215
```

| | | | | | | | | | | | | | | | | |
|---|---|---|---|---|---|---|---|---|---|---|---|---|---|---|---|---|
| acc | tcc | tcc | cct | tgc | cag | cag | gcc | tgc | tgt | gtg | cct | gtc | tgc | tgc | aag | 2705 |
| Thr | Ser | Ser | Pro | Cys | Gln | Gln | Ala | Cys | Cys | Val | Pro | Val | Cys | Cys | Lys | |
| 220 | | | | 225 | | | | 230 | | | | 235 | | | | |
| ccc | gtc | tgc | tgt | gtg | ccc | acc | tgc | tct | gat | gat | tcc | ggt | tca | tgc | tgc | 2753 |
| Pro | Val | Cys | Cys | Val | Pro | Thr | Cys | Ser | Asp | Asp | Ser | Gly | Ser | Cys | Cys | |
| | | 240 | | | | | 245 | | | | | 250 | | | | |
| cag | cca | gct | tgc | tgc | acc | tcc | tcc | caa | agc | cag | cag | ggc | tgc | tgc | gtg | 2801 |
| Gln | Pro | Ala | Cys | Cys | Thr | Ser | Ser | Gln | Ser | Gln | Gln | Gly | Cys | Cys | Val | |
| | | 255 | | | | | 260 | | | | | 265 | | | | |
| ccc | gtc | tgc | tgt | aag | cct | gtg | tgc | tgt | gtg | ccc | gtc | tgc | tct | ggg | gct | 2849 |
| Pro | Val | Cys | Cys | Lys | Pro | Val | Cys | Cys | Val | Pro | Val | Cys | Ser | Gly | Ala | |
| | | 270 | | | | | 275 | | | | | 280 | | | | |
| tcc | act | tca | tgc | tgc | cag | cag | tct | agc | tgc | cag | ccg | gct | tgc | tgc | acc | 2897 |
| Ser | Thr | Ser | Cys | Cys | Gln | Gln | Ser | Ser | Cys | Gln | Pro | Ala | Cys | Cys | Thr | |
| 285 | | | | | 290 | | | | | 295 | | | | | | |
| acc | tcc | tgc | tgc | aga | ccc | tcc | tcc | gtg | tcc | ctc | ctc | tgc | cgc | ccc | | 2945 |
| Thr | Ser | Cys | Cys | Arg | Pro | Ser | Ser | Ser | Val | Ser | Leu | Leu | Cys | Arg | Pro | |
| 300 | | | | 305 | | | | 310 | | | | 315 | | | | |
| gtg | tgc | agg | ccc | gcc | tgc | tgt | gtg | ccc | gtc | ccc | tcc | tgc | tgc | gcc | ccc | 2993 |
| Val | Cys | Arg | Pro | Ala | Cys | Cys | Val | Pro | Val | Pro | Ser | Cys | Cys | Ala | Pro | |
| | | 320 | | | | | 325 | | | | | 330 | | | | |
| acc | tcc | tcc | tgc | cag | gcc | agc | tgc | tgc | cgc | cca | gcc | tcc | tgt | gtg | tct | 3041 |
| Thr | Ser | Ser | Cys | Gln | Ala | Ser | Cys | Cys | Arg | Pro | Ala | Ser | Cys | Val | Ser | |
| | | 335 | | | | | 340 | | | | | 345 | | | | |
| ctc | ctt | tgc | cgc | ccc | gca | tgc | tcc | cgc | ccg | gcc | tgc | tgt | ggc | ccc | acc | 3089 |
| Leu | Leu | Cys | Arg | Pro | Ala | Cys | Ser | Arg | Pro | Ala | Cys | Cys | Gly | Pro | Thr | |
| | | 350 | | | | | 355 | | | | | 360 | | | | |
| tca | acc | cag | aag | tcc | agc | tgc | tga | gtgatctcct | | | taagatcatc | | | caaagcctga | | 3143 |
| Ser | Thr | Gln | Lys | Ser | Ser | Cys | | | | | | | | | | |
| | 365 | | | | 370 | | | | | | | | | | | |

| | |
|---|---|
| gtgctcactg ccacctgcac ccctggattc tttacccttg acggctctcc acatcccgct | 3203 |
| cctaagccct gcagtggacg tcagtggtca gctggccatc cagtgtgcgc ttctcctcct | 3263 |
| agaagcagct cagctgtttc tccaagtctt gactttcccc caattaccca gccctgcttc | 3323 |
| cccagcaaca ggtgggcagt gaccccagca aggccagcgg gtgctcccag gccatagccc | 3383 |
| ggtgtgggga gaaatgaggg tagacaggta ccaactgggt ttctcgtcac tgtcccagct | 3443 |
| cagtggcgag ccctgctcct cccctgctgt gggcctgggc ctctttctct gtcttccctg | 3503 |
| accacgggag caggtcagac ccttctaata aactcct | 3540 |

<210> SEQ ID NO 14
<211> LENGTH: 370
<212> TYPE: PRT
<213> ORGANISM: Homo sapiens

<400> SEQUENCE: 14

Met Ala Ala Ser Thr Met Ser Val Cys Ser Ser Asp Leu Ser Tyr Gly
1               5                   10                  15

Ser Arg Val Cys Leu Pro Gly Ser Cys Asp Ser Cys Ser Asp Ser Trp
            20                  25                  30

Gln Val Asp Asp Cys Pro Glu Ser Cys Cys Glu Pro Pro Cys Cys Ala
        35                  40                  45

Pro Ala Pro Cys Leu Ser Leu Val Cys Thr Pro Val Ser Tyr Val Ser
    50                  55                  60

Ser Pro Cys Cys Arg Val Thr Cys Glu Pro Ser Pro Cys Gln Ser Gly
65                  70                  75                  80

Cys Thr Ser Ser Cys Thr Pro Ser Cys Cys Gln Gln Ser Ser Cys Gln
                85                  90                  95

```
Leu Ala Cys Cys Ala Ser Ser Pro Cys Gln Gln Ala Cys Cys Val Pro
                100                 105                 110
Val Cys Cys Lys Thr Val Cys Cys Lys Pro Val Tyr Cys Val Pro Val
            115                 120                 125
Cys Ser Gly Asp Ser Ser Cys Cys Gln Gln Ser Ser Cys Gln Ser Ala
        130                 135                 140
Cys Cys Thr Ser Ser Pro Cys Gln Gln Ala Cys Cys Val Pro Ile Cys
145                 150                 155                 160
Cys Lys Pro Val Cys Ser Gly Ile Ser Ser Cys Cys Gln Gln Ser
                165                 170                 175
Ser Cys Val Ser Cys Val Ser Ser Pro Cys Cys Gln Ala Val Cys Glu
        180                 185                 190
Pro Ser Pro Cys Gln Ser Gly Cys Ile Ser Ser Cys Thr Pro Ser Cys
                195                 200                 205
Cys Gln Gln Ser Ser Cys Lys Pro Ala Cys Cys Thr Ser Ser Pro Cys
        210                 215                 220
Gln Gln Ala Cys Cys Val Pro Val Cys Cys Lys Pro Val Cys Cys Val
225                 230                 235                 240
Pro Thr Cys Ser Asp Asp Ser Gly Ser Cys Cys Gln Pro Ala Cys Cys
                245                 250                 255
Thr Ser Ser Gln Ser Gln Gln Gly Cys Cys Val Pro Val Cys Cys Lys
                260                 265                 270
Pro Val Cys Cys Val Pro Val Cys Ser Gly Ala Ser Thr Ser Cys Cys
            275                 280                 285
Gln Gln Ser Ser Cys Gln Pro Ala Cys Cys Thr Thr Ser Cys Cys Arg
        290                 295                 300
Pro Ser Ser Ser Val Ser Leu Leu Cys Arg Pro Val Cys Arg Pro Ala
305                 310                 315                 320
Cys Cys Val Pro Val Pro Ser Cys Cys Ala Pro Thr Ser Ser Cys Gln
                325                 330                 335
Ala Ser Cys Cys Arg Pro Ala Ser Cys Val Ser Leu Leu Cys Arg Pro
            340                 345                 350
Ala Cys Ser Arg Pro Ala Cys Cys Gly Pro Thr Ser Thr Gln Lys Ser
        355                 360                 365
Ser Cys
    370

<210> SEQ ID NO 15
<211> LENGTH: 3090
<212> TYPE: DNA
<213> ORGANISM: Homo sapiens
<220> FEATURE:
<221> NAME/KEY: CDS
<222> LOCATION: (2001)..(2780)

<400> SEQUENCE: 15
agcagagcat aaaagtttga aaaatttgta gcctgactat gcaatagaaa agaaaaaccc      60
attttctagg gagaaattca agccggatgc agaaatttgc ataagtagca aggagcctat     120
tgttaatccc caagaccatg gggaaaatat ctccaggcca tgtcagagac cttcatggca     180
gcccctccca tcagaggcct ggaggcctgg gaggaaaaag tggtttcgtg ggtccagggt     240
ccccatgctg tatgcagcct gggtgaaagg agccaatgta cagctcagac tgtggcttca     300
gagggtggaa gccccaagcc ttggcagctt ccatgttgcg ttgagcctgc aggtgcacag     360
aagtcaagaa ttgaagtttg ggaaccctcc gcctagattt cagaagatata tggaaacgca     420
```

-continued

```
tggatgccca ggcagaagtt tgctgcaggg gtggggccct catggagaac ctctgctacg      480
gcagtgcaga agggaaatgt agggccaggg cccccacaca gagtccctac tggggcactg      540
cctagtggag ctgtgataag agggccacca tcctccagac cccagaatgg tagatctatt      600
gacaccttgc accatgtgcc tggaaaagct gctgacactc aacaccagcc catgaaagca      660
gccaggaggg aggctgtacc ctgcaaagcc acagggtgg agctgtccga gaccatggga       720
acccacctct tgcatcatta tgacctggat gtgagacctg gagtcaaacg agatcatttt      780
ggagctttaa aatttgactc ccctgctgga ttttggactt gcatgggccc tgtaaaatcc      840 cttttgttttg ccaatttct gccatttgga atggctgtat ttacccaata cctgtacccc      900
tattttatct aggaagaaac tagcttgttt ttgattttac aggctcatag gtggaagaga      960
cttgtcttgt ctcagatgaa actttggact gtggactttt gggttaatgc tgaaatgagt     1020
taagactttg ggggactgtt gggaaggcat gactggtttt gaaatgtgaa gacataagat     1080
ttggaagggc cagggacaga atgatatggt ttggctgtgt ccttacccaa atctcgactt     1140
gaatttcatc tcccagcatt cctacatgtt gtgggaggaa cccaggggga gataattgaa     1200 tcatggggc cggtcttttc ctgtgctatt ctagtggtag tgaataagtc tcacaagatc      1260
tgatgggttt atcagggggct tctgcttttg cttcttcctc attttctctt gctgccacca    1320
tgtaagaagt gcctgtcagc tcccaccaag attctgcggc ctccccagcc atgtggaact    1380
gtaagtccaa ttaaagccct ttttcttctc agtcttgggt atgtctctat cagcagtgtg     1440
aaaatggact aatacagggg catcgccacca tagtttgcag atggaacagg tagggtggc    1500 agggtgggga ccaggggc attcctagcc gagacaccca ttgttcaatg gagcagaact      1560
ctgggacagg tggagaacat ctgctggtaa aaaacaccc caccctggt accaaatacc       1620 ccaatagcaa agacatacag gcaaagacag gaggaaagtg gggctgggtt ttccagactt    1680
gccaactcac gatctgttca actcccagct ccaccagcag acacgcagca tcactgtgtg     1740
tggttgcagg gcacagacac ctgcaagtgg tcagcatcac ccaaccacat gcagcagtcc    1800
tgggaccaca gtaacatccc acagcaagta aactaattag ggttgcctgg aggcaaagtc     1860
tcagccacaa caaggaaagg gaaggcttgt gagactcctg tgaggaaaat acccagggag    1920
ggtataaaac ctcagcagcc agggcacaca aacccacaca cctcacacca gcactcacac    1980
cacccagtcc agcacccacc atg gct gac gcc tgc tgc acc agg acg tat gtg     2033
                     Met Ala Asp Ala Cys Cys Thr Arg Thr Tyr Val
                      1               5                   10 att gct gca tcc acc atg tct gtc tgc tcc agt gac gtg ggc cgt gtc       2081
Ile Ala Ala Ser Thr Met Ser Val Cys Ser Ser Asp Val Gly Arg Val
            15                  20                  25 agc cga gtc tcc tcc ccc agc acc tgc act ggc tcc tcc tgg cag gtg       2129
Ser Arg Val Ser Ser Pro Ser Thr Cys Thr Gly Ser Ser Trp Gln Val
        30                  35                  40 gac aat tgc cag gaa agc tgc tgc gag ccc cgc tcc tgt gcc tcc agc       2177
Asp Asn Cys Gln Glu Ser Cys Cys Glu Pro Arg Ser Cys Ala Ser Ser
    45                  50                  55 tgc tgt acc cct agc tgc tgt gcc cca gcc ccc tgc ctg gcc ctg gtc       2225
Cys Cys Thr Pro Ser Cys Cys Ala Pro Ala Pro Cys Leu Ala Leu Val
60                  65                  70                  75 tgt gcc cca gtg agc tgt gag ccc agc ccc tgc caa tca ggc tgc acc       2273
Cys Ala Pro Val Ser Cys Glu Pro Ser Pro Cys Gln Ser Gly Cys Thr
                80                  85                  90 gac tcc tgc aca cct tca tgc tgc cag cag tct agc tgc cag ccg gct       2321
Asp Ser Cys Thr Pro Ser Cys Cys Gln Gln Ser Ser Cys Gln Pro Ala
```

```
                    95                  100                 105
tgc tgc acc tcc tcc ccc tgc caa cag gcc tgc tgt gtg cct gtg tgc        2369
Cys Cys Thr Ser Ser Pro Cys Gln Gln Ala Cys Cys Val Pro Val Cys
            110                 115                 120 tgc aag tcc aac tgc tgc aag ccc gtg tgc tgt gtg tcc atc tgc tct        2417
Cys Lys Ser Asn Cys Cys Lys Pro Val Cys Cys Val Ser Ile Cys Ser
    125                 130                 135 gga gct tcc tcc cca tgc tgc cag cag tct agc tgc cag tca gct tgc        2465
Gly Ala Ser Ser Pro Cys Cys Gln Gln Ser Ser Cys Gln Ser Ala Cys
140                 145                 150                 155 tgc acc ttc tcc cca tgc aa cag gcc tgc tgt gtg ccc atc tgc tgc         2513
Cys Thr Phe Ser Pro Cys Gln Gln Ala Cys Cys Val Pro Ile Cys Cys
                160                 165                 170 aag ccc atc tgc tgt gtg cct gtc tgc tct ggg gct tcc tct ctg tgc        2561
Lys Pro Ile Cys Cys Val Pro Val Cys Ser Gly Ala Ser Ser Leu Cys
            175                 180                 185 tgc cag aag tct agc tgc cag ccg gct tgc tgc acc acc tcc tgc tgc        2609
Cys Gln Lys Ser Ser Cys Gln Pro Ala Cys Cys Thr Thr Ser Cys Cys
    190                 195                 200 aga ccc tcc tcc tcc gtg tcc ctc ctc tgc cgc cct gtg tgc cgg cct        2657
Arg Pro Ser Ser Ser Val Ser Leu Leu Cys Arg Pro Val Cys Arg Pro
205                 210                 215 gcc tgc tgt gtg cct gtc ccc tcc tgt tgt gtc cct gcc tcc tcc tgc        2705
Ala Cys Cys Val Pro Val Pro Ser Cys Cys Val Pro Ala Ser Ser Cys
220                 225                 230                 235 cag ccc agc tgc tgc cac ccg gcc tcc tgc ctg tcc ttc ctc tgc cgc        2753
Gln Pro Ser Cys Cys His Pro Ala Ser Cys Leu Ser Phe Leu Cys Arg
                240                 245                 250 ccc gcg tgc tcc cgc ctg gcc tgc tga ggcctctgct caggccagga              2800
Pro Ala Cys Ser Arg Leu Ala Cys
            255                 260 gtccagctgc tgatgggcac gtcccccagg gccagccggc tccggtcctg tcctgggtta    2860
agtggctgcc cctacctggg atggggtctc catgtctccc ctgtgctgag gtgacctctc    2920
cctccttact cccaggagcc tccatcctca ctgctcccca gctcttgcct tccagcaggt    2980
gcccacctgc ctgctgggtc ccctgtcctc cctcccagct tctctgctct gggtcacttg    3040
gcctcgactt gaacctctca gcacctcctc ctactcccca ataaactctc                3090
```

<210> SEQ ID NO 16
<211> LENGTH: 259
<212> TYPE: PRT
<213> ORGANISM: Homo sapiens

<400> SEQUENCE: 16

Met Ala Asp Ala Cys Cys Thr Arg Thr Tyr Val Ile Ala Ala Ser Thr
1               5                   10                  15

Met Ser Val Cys Ser Ser Asp Val Gly Arg Val Ser Arg Val Ser Ser
                20                  25                  30

Pro Ser Thr Cys Thr Gly Ser Ser Trp Gln Val Asp Asn Cys Gln Glu
            35                  40                  45

Ser Cys Cys Glu Pro Arg Ser Cys Ala Ser Ser Cys Cys Thr Pro Ser
        50                  55                  60

Cys Cys Ala Pro Ala Pro Cys Leu Ala Leu Val Cys Ala Pro Val Ser
65                  70                  75                  80

Cys Glu Pro Ser Pro Cys Gln Ser Gly Cys Thr Asp Ser Cys Thr Pro
                85                  90                  95

Ser Cys Cys Gln Gln Ser Ser Cys Gln Pro Ala Cys Cys Thr Ser Ser

```
                100              105                110
Pro Cys Gln Gln Ala Cys Cys Val Pro Val Cys Lys Ser Asn Cys
            115                120                125
Cys Lys Pro Val Cys Val Ser Ile Cys Ser Gly Ala Ser Ser Pro
        130                135                140
Cys Cys Gln Gln Ser Ser Cys Gln Ser Ala Cys Cys Thr Phe Ser Pro
145                150                155                160
Cys Gln Gln Ala Cys Cys Val Pro Ile Cys Cys Lys Pro Ile Cys Cys
                165                170                175
Val Pro Val Cys Ser Gly Ala Ser Ser Leu Cys Cys Gln Lys Ser Ser
            180                185                190
Cys Gln Pro Ala Cys Cys Thr Thr Ser Cys Cys Arg Pro Ser Ser Ser
            195                200                205
Val Ser Leu Leu Cys Arg Pro Val Cys Arg Pro Ala Cys Cys Val Pro
        210                215                220
Val Pro Ser Cys Cys Val Pro Ala Ser Ser Cys Gln Pro Ser Cys Cys
225                230                235                240
His Pro Ala Ser Cys Leu Ser Phe Leu Cys Arg Pro Ala Cys Ser Arg
                245                250                255
Leu Ala Cys

<210> SEQ ID NO 17
<211> LENGTH: 3197
<212> TYPE: DNA
<213> ORGANISM: Homo sapiens
<220> FEATURE:
<221> NAME/KEY: CDS
<222> LOCATION: (2001)..(2879)

<400> SEQUENCE: 17
gccctcagag actgagtggt gaacaagaca accacacttc ctgcccacat gaagcttacc      60
tttgaagaat gggagctgag cacagcaaag aaaatgagca tgaaaagtta ggagacttgg     120
cacagaaata ctgatgatgg ccacgcacg  gtggcttacg cctgtagtcc cagcaatttg     180
ggaggccaag gcaggaggat cacttgagcc caggagttca agaccagctg gcaacatag     240
caagactctg tctctacaa  aaaaaatttt tttttacaaa aagaaatatt gataatggga     300
cttgaattat ctatgattga agcgtatcat aaagctatgg cctgaaagag cagaaccaaa     360
tccatagccc aaaatggacc agttcaaaac ttttctatcc tgtctgaaac ccagtccctat    420
ccccagcgtt cccacatgca agtctgagtg gacctcgggg aaggccgcgg ggagcggcat     480
ggcctctctt ccttgctcc  ccttctccct gttttgggct ctaatttctt cagtgatggg     540
gacgggggaa ggaatgtgca gggccaccac tgtggggctc actggccact gctgcacctt     600
ctctccggct gctccagtga tcctgtgctt ctaccagctg cttctgcctc ttcagtgagg     660
acccacttta gagacacccc cagggacagt agctggagga ctctctccct gggacaccac     720
actttgcgta agactgaagg gccacccctg cctccacagc ctccttctta caacctgggc     780
agcactggtg gggtgtggca gctggccata gctggtcaac ttctgtctta ttttagaaac     840
cctgtgggga caggtctgac ccagaatgtt agcattattt ttagaatgag aggccgtttc     900
cagctttgcc agattcacag caacaaagac gttctactca acatcgtgta atacgtctta     960
ctttataatg aaatatgcgt atgtgtactt gaattttta  ataaaaatgt gaaatcacaa    1020
tcaatattat aattagctgc tgggtagcaa tgttcctgga aagtgatcag ggccatttta    1080
taaggcaaga agctcgggac ttcatcatgc cctgtggtga taacaattca tcatcaaaga    1140
```

-continued

```
tcatgcagcc gtgagagttg cctgtggctg acctgggggt gtgtgatggg gcctgtgggc    1200
agggctggtg agaaaaagat gcttgcagtg cagggcacac ggaggagatg gctccagcag    1260
tggcgagggc tggcggctgc ctgctgccta gcacagctac ttcacgggtt cagaacccga    1320
aaccacagcc cacgatgctg ccattgtgcc tcagcaagga gtgggctgag cccacgatcc    1380
ctgccctgga acagagtcct gctgcctccc agcaaagga cagggtgggc aatgaacaga     1440
gggcaggagg cacagaggcc atggggatta gaaattggcg agtcctgtgt cctacagcag    1500
gggaaggacc atactagagg aggagtttgc accacaggaa ataattccta agggccggct    1560
tcctgcagag gaagcccgtg tcctgaggct gctggggcca gtggctggac gatgcccag     1620 caaccaaaga tggccccagg cacatcccac ccacatccca cccaccagac gcccacagcc    1680
gtccttgcct ccagaaccca gctgggatca ggcccacccc aactcctgcc cctgaggttc    1740
cacatgcaac agactatagc ccaggtgtga caggagattt gtgagctggg caatgtcacc    1800
agcaaacaaa catccctaat catggcagac gccgcctctc agcaacaagg aaggggaagc    1860
tgtgggccct ggaacaacaa ggccaggagg ggtataaaag cctgagagcc caagaaccct    1920
cacacactca caaactcact cactgacaca ctcacacact cacttacacc tcccccagct    1980
cacctcctcc ccacccagc atg gcc gcg tcc acc atg tcc atc cgc tcc agc    2033
                      Met Ala Ala Ser Thr Met Ser Ile Arg Ser Ser
                       1               5                  10 gct tac tcc gac tcc tgg cag gtg gac gac tgc cca gag agc tgc tgt    2081
Ala Tyr Ser Asp Ser Trp Gln Val Asp Asp Cys Pro Glu Ser Cys Cys
         15                  20                  25 gag ccc ccc tgc tgc gcc acc agc tgc tgc gcc ccg gcc ccc tgc ctg    2129
Glu Pro Pro Cys Cys Ala Thr Ser Cys Cys Ala Pro Ala Pro Cys Leu
        30                  35                  40 acc ctg gtc tgc acc cca gtg agc cgt gta tcc agc ccc tgc tgc cag    2177
Thr Leu Val Cys Thr Pro Val Ser Arg Val Ser Ser Pro Cys Cys Gln
        45                  50                  55 gtg acc tgt gag ccc agc ccc tgc caa tca ggc tgc acc agc tcc tgc    2225
Val Thr Cys Glu Pro Ser Pro Cys Gln Ser Gly Cys Thr Ser Ser Cys
 60                  65                  70                  75 acg ccc tcg tgc tgc cag cag tct agc tgc cag ccg gct tac tgc acc    2273
Thr Pro Ser Cys Cys Gln Gln Ser Ser Cys Gln Pro Ala Tyr Cys Thr
            80                  85                  90 tcc tcc ccc tgc cag cag gcc tgc tgc gtg ccc gtc tgc tgc aag cct    2321
Ser Ser Pro Cys Gln Gln Ala Cys Cys Val Pro Val Cys Cys Lys Pro
            95                 100                 105 gtg tgc tgc gtg ccc gtc tgc tgt ggg gct tct tcg tgc tgc caa cag    2369
Val Cys Cys Val Pro Val Cys Cys Gly Ala Ser Ser Cys Cys Gln Gln
       110                 115                 120 tct agc tac cag cca gct tgc tgt gcc tct tcc tcc tgc cag ccg gcc    2417
Ser Ser Tyr Gln Pro Ala Cys Cys Ala Ser Ser Cys Gln Pro Ala
       125                 130                 135 tgc tgt gtg ccc gtc tgc tgc aaa cct gtg tgc tgt gcg ccc acc tgc    2465
Cys Cys Val Pro Val Cys Cys Lys Pro Val Cys Cys Ala Pro Thr Cys
140                 145                 150                 155 tct gag gat tcc tat tca tgc tgc caa cag tct agc tgc cag cca gct    2513
Ser Glu Asp Ser Tyr Ser Cys Cys Gln Gln Ser Ser Cys Gln Pro Ala
                160                 165                 170 tgc tgc act tcc tcc ccc tgc cag cag tcc tac tgt gtg cct gtc tgc    2561
Cys Cys Thr Ser Ser Pro Cys Gln Gln Ser Tyr Cys Val Pro Val Cys
            175                 180                 185 tgt aag cct gtc tgc tgc aaa ccc atc tgc tgt gtg cct gtc tgc tct    2609
Cys Lys Pro Val Cys Cys Lys Pro Ile Cys Cys Val Pro Val Cys Ser
```

-continued

```
                   190                 195                 200
ggg gct tcc tct ttg tgc tgc cag cag tct ggc tgc cag ccg gct tgc      2657
Gly Ala Ser Ser Leu Cys Cys Gln Gln Ser Gly Cys Gln Pro Ala Cys
    205                 210                 215 tgc acc acc tcc tgc tgc aga ccc tcc tcc tct gtg tcc ctc ctc tgc      2705
Cys Thr Thr Ser Cys Cys Arg Pro Ser Ser Ser Val Ser Leu Leu Cys
220                 225                 230                 235 cgc cct gtg tgc agg ccc gcc tgc tgc gtg ccc gtc tcc tcc tgc tgt      2753
Arg Pro Val Cys Arg Pro Ala Cys Cys Val Pro Val Ser Ser Cys Cys
                240                 245                 250 gcc ccc acc tcc tcc cgc cag ccc agc tat tgc cgc cag gcc tcc tgt      2801
Ala Pro Thr Ser Ser Arg Gln Pro Ser Tyr Cys Arg Gln Ala Ser Cys
            255                 260                 265 gtg tcc ctt ctc tgc cgc cct gtg tgc tcc cgc ccg gcc tgc tac agc      2849
Val Ser Leu Leu Cys Arg Pro Val Cys Ser Arg Pro Ala Cys Tyr Ser
        270                 275                 280 ttc tcc tca ggc cag aag tcc agc tgc tga cggtcatgtc ccccagggcc        2899
Phe Ser Ser Gly Gln Lys Ser Ser Cys
    285                 290 agccgggctc aggccccacc tccctgccag tccttggacc tcccagccca cccagcctca    2959
gcacagctca acacagaagg agcagcccca gccacagccg cccagccccg ggtctcaga    3019 tgctcactgg ctcctccctg acctccccccc cgggcaggcg agccctggct tctcctcacg   3079
gtgcttcctg gctgcagacc acaaccctcc gctggtcgct ggttggggac gggccctcct   3139
gacccgggtc tcaccccag cagcgtcacc ctctgcccct gagcaccaat aaagcgtc     3197
```

<210> SEQ ID NO 18
<211> LENGTH: 292
<212> TYPE: PRT
<213> ORGANISM: Homo sapiens

<400> SEQUENCE: 18

```
Met Ala Ala Ser Thr Met Ser Ile Arg Ser Ser Ala Tyr Ser Asp Ser
1               5                   10                  15

Trp Gln Val Asp Asp Cys Pro Glu Ser Cys Cys Glu Pro Pro Cys Cys
            20                  25                  30

Ala Thr Ser Cys Cys Ala Pro Ala Pro Cys Leu Thr Leu Val Cys Thr
        35                  40                  45

Pro Val Ser Arg Val Ser Ser Pro Cys Cys Gln Val Thr Cys Glu Pro
    50                  55                  60

Ser Pro Cys Gln Ser Gly Cys Thr Ser Ser Cys Thr Pro Ser Cys Cys
65                  70                  75                  80

Gln Gln Ser Ser Cys Gln Pro Ala Tyr Cys Thr Ser Ser Pro Cys Gln
                85                  90                  95

Gln Ala Cys Cys Val Pro Val Cys Lys Pro Val Cys Cys Val Pro
            100                 105                 110

Val Cys Cys Gly Ala Ser Ser Cys Gln Gln Ser Ser Tyr Gln Pro
        115                 120                 125

Ala Cys Cys Ala Ser Ser Cys Gln Pro Ala Cys Cys Val Pro Val
    130                 135                 140

Cys Cys Lys Pro Val Cys Cys Ala Pro Thr Cys Ser Glu Asp Ser Tyr
145                 150                 155                 160

Ser Cys Cys Gln Gln Ser Ser Cys Gln Pro Ala Cys Cys Thr Ser Ser
                165                 170                 175

Pro Cys Gln Gln Ser Tyr Cys Val Pro Val Cys Cys Lys Pro Val Cys
            180                 185                 190
```

```
Cys Lys Pro Ile Cys Cys Val Pro Val Cys Ser Gly Ala Ser Ser Leu
            195                 200                 205

Cys Cys Gln Gln Ser Gly Cys Gln Pro Ala Cys Cys Thr Thr Ser Cys
    210                 215                 220

Cys Arg Pro Ser Ser Ser Val Ser Leu Leu Cys Arg Pro Val Cys Arg
225                 230                 235                 240

Pro Ala Cys Cys Val Pro Val Ser Ser Cys Cys Ala Pro Thr Ser Ser
                245                 250                 255

Arg Gln Pro Ser Tyr Cys Arg Gln Ala Ser Cys Val Ser Leu Leu Cys
            260                 265                 270

Arg Pro Val Cys Ser Arg Pro Ala Cys Tyr Ser Phe Ser Ser Gly Gln
        275                 280                 285

Lys Ser Ser Cys
        290

<210> SEQ ID NO 19
<211> LENGTH: 3022
<212> TYPE: DNA
<213> ORGANISM: Homo sapiens
<220> FEATURE:
<221> NAME/KEY: CDS
<222> LOCATION: (2001)..(2756)

<400> SEQUENCE: 19
aaagtgcatt agcagatgaa tggataaatg aaatgtggcg tgtcccttg atggaatatg        60 attcagccaa gaaaaggaat ggcgttctga acataccca acacaggtg taccttgaaa       120 acatgctgag tgaacaaagc tagacacaaa gaccacatat tccatgactg cgtctatatg      180
aaatgtgcag aacaggcaaa tccatagaga caagcagaat agtattggtt gccaggggct      240
gggcatggct gcttaatagt accggggttc cttcgggagc gatgatagta ttctggaact      300
aggtagtggg gatggttgca caacattatg actgtactgt cactgaattg cacactttaa      360
aatgggtaaa atggtacatt ttattttatg gttgatcaca atttaaataa aattacacct      420
gccaagggtt tctaagaatg aagcccctcg ctctgcaatg ctggatatta tcagcatttt      480
aaatcttgtt tgctcttaca ggtgggagac gtgtgtttaa acctgagaaa ctttagttat      540
taatgagatc aactagctgt tcatctcatt catgcttatt ggaaatttaa aattttagt      600 cttctattca tttctttgt atcttatcct gttttagtgg taaggacttc aaattttca       660 cattaatctt ccacctgtca tggagattac aagtactttc tggcagttca tatcttcatt      720
tgtgtaccca atgattcctt cagggctgtg atgggaacgt cgtggatgct gagctgagct      780
gaggcatgtg gaccggtctc cagcacccaa ccctgccggg tttccagggg acatacgttg      840
tatgtgttct ggtcaaggtt tatgcttcg ttcacatctg accctctgac attccactgg       900
gcattttata cttgggtctg ctggctgacg gcttcctttt cccattgtat ttccacactg      960
tcatggcagg ggtacaggta ggggtgctg ggtgcagtga ctttgtctct catccagccc      1020
ttcagtgagc gtggcctggg acagtcactc tgatcctagg tggacaatga tgtcacctac     1080
agatactaga aattcacatc acatttcaac ttcttggcat gtggcttcag ccaaagtgca     1140
aacatagagt aagaccaggc gtccgggcag tgggctgac tgtggcccca tctgacactt      1200
ttctcatcca gaccccaagt atcctccact ctccacgcaa ccctcactcc acacctgcct     1260
ctccaaggta gaggccctc cccaccctca gaccctgacc tgcacccgcc cctctcagga      1320
cacctgacca gggctccagg ggatggcagt ccagacccaa aggccagtcc ccaaaccttg     1380
```

-continued

```
tcctcctaat gagctgactg tccagaggcc ttgccagaac attccatctc ctcagaggag    1440
gggaggtcct ccctgtcctc ctgcccttgg cagacatcag gatctcagaa gatcccagag    1500
cccgccagga agcgctgtct tcaagcatct tttcccaaca caggcacctc cgtcctggct    1560
ctcccaatct cagccacgcc agcccacccc gtgaggtccc tgcagacaga ggctgggcct    1620
cccccaggct gagggcccac gctgggcaca gtcacgggac ctgccaggtg aagtcacca    1680 ggtcagcccc agagaggtca caccttccct cctggtgttc ccgggagaca ggctcagcca    1740
ggggcgccgg tcctgcccag gaccagccaa gtgttaggag cagagtgagg acaagtcatg    1800
gcaaaggaag cagaaataat gagggtcctc ccggctccaa acaccaacac ggaaggggag    1860
ggcattgctg agtctcctgc tgggaaaaca caggccctgg gcatataaaa gccccagcag    1920
ctgacaggct cacacacaca ctcactcaca cactcactca ctcacacacc tcccccagct    1980
caccgcctcc ccactccagc atg gcc gcc tcc acc atg tcc atc tgc tcc agc    2033
                      Met Ala Ala Ser Thr Met Ser Ile Cys Ser Ser
                       1               5                      10 gcc tgc act gac tct tgg cgg gta gtc gac tgc cca gag agc tgc tgc      2081
Ala Cys Thr Asp Ser Trp Arg Val Val Asp Cys Pro Glu Ser Cys Cys
            15                  20                  25 gag ccc tgc tgc tgt gcc cca gcc ccc agc ttg acc ctg gtc tgc acc      2129
Glu Pro Cys Cys Cys Ala Pro Ala Pro Ser Leu Thr Leu Val Cys Thr
        30                  35                  40 cca gtg agc tgt gtg tcc agc ccc tgc tgc cag acg gcc tgt gag ccc      2177
Pro Val Ser Cys Val Ser Ser Pro Cys Cys Gln Thr Ala Cys Glu Pro
    45                  50                  55 agc gcc tgc caa tca ggc tac acc agc tcc tgc aca acc cca tgc tac      2225
Ser Ala Cys Gln Ser Gly Tyr Thr Ser Ser Cys Thr Thr Pro Cys Tyr
60                  65                  70                  75 cag cag tct agc tgc cag ccg gat tgc tgc acc tcc tcc ccc tgc cag      2273
Gln Gln Ser Ser Cys Gln Pro Asp Cys Cys Thr Ser Ser Pro Cys Gln
                80                  85                  90 cag gcc tgc tgt gtg cct gtc tgc tgt gtg ccc gtc tgc tgc gtg ccc      2321
Gln Ala Cys Cys Val Pro Val Cys Cys Val Pro Val Cys Cys Val Pro
                95                 100                 105 gtc tgt aac aag cct gtg tgc ttc gtg cct acc tgc tcc gag tct tcc      2369
Val Cys Asn Lys Pro Val Cys Phe Val Pro Thr Cys Ser Glu Ser Ser
            110                 115                 120 cct tca tgc tgc cag cag tct agc tgc cag cca act tgc tgc acc tcc      2417
Pro Ser Cys Cys Gln Gln Ser Ser Cys Gln Pro Thr Cys Cys Thr Ser
        125                 130                 135 tcc cca tgc cag cag gcc tgc tgt gtg cct gtc tgc tct aag tcc gtc      2465
Ser Pro Cys Gln Gln Ala Cys Cys Val Pro Val Cys Ser Lys Ser Val
140                 145                 150                 155 tgc tat gtg cct gtg tgc tct ggg gct tcc act tca tgc tgc cag cag      2513
Cys Tyr Val Pro Val Cys Ser Gly Ala Ser Thr Ser Cys Cys Gln Gln
                160                 165                 170 tct agc tgc cag cct gct tgc tgc acc gcc tcc tgc tgc aga ccc tcc      2561
Ser Ser Cys Gln Pro Ala Cys Cys Thr Ala Ser Cys Cys Arg Pro Ser
                175                 180                 185 tcc tcc gtg tcc ctc ctc tgc cac cct gtg tgc aag tcc acc tgc tgc      2609
Ser Ser Val Ser Leu Leu Cys His Pro Val Cys Lys Ser Thr Cys Cys
            190                 195                 200 gtg ccc gtc ccc tcc tgc ggt gcc tct gcc tcc tgc cag ccc agc          2657
Val Pro Val Pro Ser Cys Gly Ala Ser Ala Ser Cys Gln Pro Ser
        205                 210                 215 tgc tgc cgc acg gcc tcc tgt gtt tcc ctc ctc tgc cgc ccc gtg tgc      2705
Cys Cys Arg Thr Ala Ser Cys Val Ser Leu Leu Cys Arg Pro Val Cys
220                 225                 230                 235
```

| | | | | | | | | | | | | |
|---|---|---|---|---|---|---|---|---|---|---|---|---|
| tcc | cgc | cct | gcc | tgc | tac | agc | ctc | tgc | tct | ggc | cag | aag tcc agc tgc | 2753 |
| Ser | Arg | Pro | Ala | Cys | Tyr | Ser | Leu | Cys | Ser | Gly | Gln | Lys Ser Ser Cys |
| | 240 | | | | | 245 | | | | | 250 | |

| | | | |
|---|---|---|---|
| tga cagccctgga tgtgatccgg agtcccttcc caccaggggc tgacctccca | 2806 |
| gctgccccag caagctctgc cctctctggc tttgacaccc tcagaaggtg gggcaggctc | 2866 |
| tttgtcttgg ggaccaggat gctcccccag tccttcccag atgatggctg cctgtgggac | 2926 |
| cccagctact cccccagacc caagttctgc agaactaacc cccagcaggc ctggttccac | 2986 |
| cctgggcagc accccctcta gttctaataa agccgc | 3022 |

<210> SEQ ID NO 20
<211> LENGTH: 251
<212> TYPE: PRT
<213> ORGANISM: Homo sapiens

<400> SEQUENCE: 20

| | | | | | | | | | | | |
|---|---|---|---|---|---|---|---|---|---|---|---|
| Met | Ala | Ser | Thr | Met | Ser | Ile | Cys | Ser | Ser | Ala | Cys Thr Asp Ser |
| 1 | | | | 5 | | | | 10 | | | 15 |
| Trp | Arg | Val | Val | Asp | Cys | Pro | Glu | Ser | Cys | Cys | Glu Pro Cys Cys |
| | | | 20 | | | | 25 | | | | 30 |
| Ala | Pro | Ala | Pro | Ser | Leu | Thr | Leu | Val | Cys | Thr | Pro Val Ser Cys Val |
| | | 35 | | | | 40 | | | | 45 | |
| Ser | Ser | Pro | Cys | Cys | Gln | Thr | Ala | Cys | Glu | Pro | Ser Ala Cys Gln Ser |
| | 50 | | | | 55 | | | | 60 | | |
| Gly | Tyr | Thr | Ser | Ser | Cys | Thr | Thr | Pro | Cys | Tyr | Gln Gln Ser Ser Cys |
| 65 | | | | 70 | | | | 75 | | | 80 |
| Gln | Pro | Asp | Cys | Cys | Thr | Ser | Ser | Pro | Cys | Gln | Gln Ala Cys Cys Val |
| | | | 85 | | | | 90 | | | | 95 |
| Pro | Val | Cys | Cys | Val | Pro | Val | Cys | Cys | Val | Pro | Val Cys Asn Lys Pro |
| | | | 100 | | | | 105 | | | | 110 |
| Val | Cys | Phe | Val | Pro | Thr | Cys | Ser | Glu | Ser | Ser | Pro Ser Cys Cys Gln |
| | | 115 | | | | 120 | | | | 125 | |
| Gln | Ser | Ser | Cys | Gln | Pro | Thr | Cys | Cys | Thr | Ser | Ser Pro Cys Gln Gln |
| | 130 | | | | 135 | | | | 140 | | |
| Ala | Cys | Cys | Val | Pro | Val | Cys | Ser | Lys | Ser | Val | Cys Tyr Val Pro Val |
| 145 | | | | 150 | | | | 155 | | | 160 |
| Cys | Ser | Gly | Ala | Ser | Thr | Ser | Cys | Cys | Gln | Gln | Ser Cys Gln Pro |
| | | | 165 | | | | 170 | | | | 175 |
| Ala | Cys | Cys | Thr | Ala | Ser | Cys | Cys | Arg | Pro | Ser | Ser Ser Val Ser Leu |
| | | 180 | | | | 185 | | | | 190 | |
| Leu | Cys | His | Pro | Val | Cys | Lys | Ser | Thr | Cys | Cys | Val Pro Val Pro Ser |
| | | 195 | | | | 200 | | | | 205 | |
| Cys | Gly | Ala | Ser | Ala | Ser | Ser | Cys | Gln | Pro | Ser | Cys Cys Arg Thr Ala |
| | 210 | | | | 215 | | | | 220 | | |
| Ser | Cys | Val | Ser | Leu | Leu | Cys | Arg | Pro | Val | Cys | Ser Arg Pro Ala Cys |
| 225 | | | | 230 | | | | 235 | | | 240 |
| Tyr | Ser | Leu | Cys | Ser | Gly | Gln | Lys | Ser | Ser | Cys | |
| | | | | 245 | | | | 250 | | | |

<210> SEQ ID NO 21
<211> LENGTH: 3181
<212> TYPE: DNA
<213> ORGANISM: Homo sapiens
<220> FEATURE:
<221> NAME/KEY: CDS
<222> LOCATION: (2001)..(2897)

<400> SEQUENCE: 21

```
tataaaaaat gaaatcaaaa ttatctaaca aaaacgggag gctcagcagg gtccttcata        60
tgtttgtaga aaagagaagc agacagaaac aggttaggga gtaaattgga gcaggaccct       120
aatgcactgg aataaaatag tcttttattc agaaaactga atgaactgcc accaatgagc       180
agactatctg atgtccaagg aaacaagaaa aaaacattta aaaactcaaa gtaacatcat       240
cagagtgaat ggataacata tttcattcat cacaagatga aataaaaagt cataaaaaga       300
gagaccagga aagatgaaat tattattaaa atggaaaaa cacttcggag ataagtcttt        360
atattgaaag gctcaataag ttctaaccac tgaaagtaaa ataatgcatt agcctagaaa       420
caaaagcgtg acactttaga acaataaaaa gaaacccaaa tgctcccaga gagttaagga      480
aagagagaaa ctaaaaaatg acaaatgacc agtatcagac tgtcatcggc aacactggac       540
atcacaaaaa aatggtgaca tgtgttcatc attttgagga aaagtaattt aaaaccagaa       600
ttttataccc agctaaacta tcattataaa tgtgaggata aagttgacat attttcagac       660
aagcaaggaa tcttaaaatg tatgtcctaa aatcaccata tatgaaaaag tacttgatct       720
ttcaccaagg caaaatgaaa attgaaataa tccagagtgc agcttcaaat aaaacaaaga      780
gcctctgagg gtggcatgga agagctgaag agacaaaaat aaagcttgga tccaccagct      840
actgaatctc tgagcattct ccttacaagg tgtgagggat cgaagggagg gccacttagc      900
tttttttttt ttttttgaga cagagtcttg ctctgtcacc taggctgggg tgcaatggtg      960
caatctcagc tcactgcaac ctccacctcc tgggttcaag aattctcctg cctcagccta     1020
agtagctggg actacaggca catgccacca tgcctggcta attttttgta tttttagtag     1080
agaccgggtt tcaccatgct ggccaggctg gtctcaaact cctgacctcg tgatccaccc     1140
acctcagccc cccaaagtac tgggattaga ggcatgagtc accacgctca gccagcttcc     1200
tcttatctta tcgtctgtgc cgttttattt tcatatgaag tgtacatttt tctccatgtt     1260
tatgttttaa gatgctaaaa gtaataaaat atatctaatc agtccagaaa caggataggt     1320
ggaaacagaa ttgcttcctt tggagaaacg ttcatctcta aaacctcaac tcaacaaaag     1380
cttgcttgaa atattttccg gccggacgcg gtggctcacg cctgtaatcc cagcactttg     1440
ggaggctgag gcgggtagat catgaggtca ggagttcaag accagcctgg ccaagatggt     1500
gaaacccgt ctctactaaa aatacaaaaa ttacagcgtg cctgtaatcc cagctactcg      1560
ggaggctgag gtgggagaat cgcttgaacc caggggggcgg aggttgcagt gagctgagat    1620
cgcgccactg cactccagcc tgggtgacag agcaagactc cctctcaaaa aaaaaaaaa     1680
aaaaaaaaa aaaaaggaa atattttcca ccacatttct gtggccaaaa taaaactga      1740
tgaagaaaca gagccctgcg acatacatac cagtttaata agggaaaaac aaagagataa     1800
accagcatga atgatgcatc tccagccacc agctgtaaac accaacaagg aagaaaagct     1860
tgtggagcct cctgttggga caacacatgc cagggaggga tttaaaagcc ccacagccct     1920
gagcacctca ctcactcact cacacacaca ctcacacact cacttacacc tcccccagct     1980
cacctcctcc ccaccccagc atg gcc gcg tcc acc atg tct gtc tgc tcc agc    2033
                       Met Ala Ala Ser Thr Met Ser Val Cys Ser Ser
                         1               5                  10 gct tac tcc gac tcc tgg cag gtg gac gac tgc cca gag agc tgc tgt      2081
Ala Tyr Ser Asp Ser Trp Gln Val Asp Asp Cys Pro Glu Ser Cys Cys
            15                  20                  25 gag ccc ccc tgc agc gcc ccc agc tgc tgc gcc ccg gcc ccc tcc ctg      2129
Glu Pro Pro Cys Ser Ala Pro Ser Cys Cys Ala Pro Ala Pro Ser Leu
```

```
                    30                  35                  40
agc ctg gtc tgc acc cca gtg agc tgt gtg tcc agc ccc tgc tgc cag       2177
Ser Leu Val Cys Thr Pro Val Ser Cys Val Ser Ser Pro Cys Cys Gln
     45                  50                  55 gcg gcc tgt gag ccc agc gcc tgc caa tca ggc tgc acc agc tcc tgc       2225
Ala Ala Cys Glu Pro Ser Ala Cys Gln Ser Gly Cys Thr Ser Ser Cys
 60                  65                  70                  75 acg ccg tca tgc tgc cag cag tct agc tgc cag ccg gct tgc tgc acc       2273
Thr Pro Ser Cys Cys Gln Gln Ser Ser Cys Gln Pro Ala Cys Cys Thr
                 80                  85                  90 tcc tcc ccc tgc cag cag gcc tgc tgt gtg cct gtc tgc tgc aag act       2321
Ser Ser Pro Cys Gln Gln Ala Cys Cys Val Pro Val Cys Cys Lys Thr
             95                  100                 105 gtc tgc tgc aag cct gtg tgc tgt gtg cct gtc tgc tgt ggg gct gct       2369
Val Cys Cys Lys Pro Val Cys Cys Val Pro Val Cys Cys Gly Ala Ala
         110                 115                 120 tct tcg tgc tgc cgg cag tct agc tgc cag cca gct tgc tgt gcc tct       2417
Ser Ser Cys Cys Arg Gln Ser Ser Cys Gln Pro Ala Cys Cys Ala Ser
     125                 130                 135 tcc tcc tgc cag ccg gcc tgc tgt gtg ccc gtc tgc tgc aag cct gtg       2465
Ser Ser Cys Gln Pro Ala Cys Cys Val Pro Val Cys Cys Lys Pro Val
140                 145                 150                 155 tgc tgt gtg tcc acc tgc tct gag gat tcc tct tca tgc tgc cag cag       2513
Cys Cys Val Ser Thr Cys Ser Glu Asp Ser Ser Ser Cys Cys Gln Gln
                160                 165                 170 tct agc tgc cag cca gct tgc tgc acc tcc tcc tcc tac cag cag gcc       2561
Ser Ser Cys Gln Pro Ala Cys Cys Thr Ser Ser Ser Tyr Gln Gln Ala
            175                 180                 185 tgc tgc gtg cct gtc tgc tgc aag act gtc tac tgc aag ccc atc tgc       2609
Cys Cys Val Pro Val Cys Cys Lys Thr Val Tyr Cys Lys Pro Ile Cys
        190                 195                 200 tgt gtg cct gtc tgc tct agg gct tcc tct tca cgc tgc cag cag cct       2657
Cys Val Pro Val Cys Ser Arg Ala Ser Ser Ser Arg Cys Gln Gln Pro
    205                 210                 215 agc tgc cag cca gct tgc tgc acc acc tcc tgc tgc aga ccc tcc tcc       2705
Ser Cys Gln Pro Ala Cys Cys Thr Thr Ser Cys Cys Arg Pro Ser Ser
220                 225                 230                 235 tct gtg tcc ctc ctc tgc cac ccc gtg tgc agg tcc acc tgc tgt gtg       2753
Ser Val Ser Leu Leu Cys His Pro Val Cys Arg Ser Thr Cys Cys Val
                240                 245                 250 ccc gtc tcc tcc tgc tgt gcc ccc acc tcc tcc tgc cag tcc agc tgc       2801
Pro Val Ser Ser Cys Cys Ala Pro Thr Ser Ser Cys Gln Ser Ser Cys
            255                 260                 265 tgc tgc ccg gcc tcc tgc gtg tcc ctc ctc tgc cgc ccc gca agc tcc       2849
Cys Cys Pro Ala Ser Cys Val Ser Leu Leu Cys Arg Pro Ala Ser Ser
        270                 275                 280 cgc ctg gcc tgc tac agc ctc tgc tca ggc aag aag tcc agc tgc tga       2897
Arg Leu Ala Cys Tyr Ser Leu Cys Ser Gly Lys Lys Ser Ser Cys
    285                 290                 295 gtgctcaatc cttgtctcct gctgactgtg tctttgctgc aagcaggat tctccagtct      2957 caggagcccc tggagtcctc agaatccacc agctccatca gtagccacag agctgctgcc     3017
tgaaggggat tttgagcgcg tcacactttc ctccccactg tctgggaaga caacccac      3077 aaatccctca gcaggtggac tgtggctttc tggagccccc ttctccaaat gtgttgctta    3137
tacccaatgt gacaaagaag aactgctcta atcaataaat tctt                     3181

<210> SEQ ID NO 22
<211> LENGTH: 298
```

```
<212> TYPE: PRT
<213> ORGANISM: Homo sapiens

<400> SEQUENCE: 22

Met Ala Ala Ser Thr Met Ser Val Cys Ser Ser Ala Tyr Ser Asp Ser
  1               5                  10                  15

Trp Gln Val Asp Asp Cys Pro Glu Ser Cys Cys Glu Pro Pro Cys Ser
             20                  25                  30

Ala Pro Ser Cys Cys Ala Pro Ala Pro Ser Leu Ser Leu Val Cys Thr
         35                  40                  45

Pro Val Ser Cys Val Ser Ser Pro Cys Cys Gln Ala Ala Cys Glu Pro
     50                  55                  60

Ser Ala Cys Gln Ser Gly Cys Thr Ser Cys Thr Pro Ser Cys Cys
 65                  70                  75                  80

Gln Gln Ser Ser Cys Gln Pro Ala Cys Cys Thr Ser Ser Pro Cys Gln
                 85                  90                  95

Gln Ala Cys Cys Val Pro Val Cys Cys Lys Thr Val Cys Cys Lys Pro
            100                 105                 110

Val Cys Cys Val Pro Val Cys Cys Gly Ala Ala Ser Ser Cys Cys Arg
        115                 120                 125

Gln Ser Ser Cys Gln Pro Ala Cys Cys Ala Ser Ser Cys Gln Pro
    130                 135                 140

Ala Cys Cys Val Pro Val Cys Cys Lys Pro Val Cys Cys Val Ser Thr
145                 150                 155                 160

Cys Ser Glu Asp Ser Ser Ser Cys Gln Gln Ser Ser Cys Gln Pro
                165                 170                 175

Ala Cys Cys Thr Ser Ser Ser Tyr Gln Gln Ala Cys Cys Val Pro Val
            180                 185                 190

Cys Cys Lys Thr Val Tyr Cys Lys Pro Ile Cys Cys Val Pro Val Cys
        195                 200                 205

Ser Arg Ala Ser Ser Ser Arg Cys Gln Gln Pro Ser Cys Gln Pro Ala
    210                 215                 220

Cys Cys Thr Thr Ser Cys Cys Arg Pro Ser Ser Ser Val Ser Leu Leu
225                 230                 235                 240

Cys His Pro Val Cys Arg Ser Thr Cys Val Pro Val Ser Ser Cys
                245                 250                 255

Cys Ala Pro Thr Ser Ser Cys Gln Ser Ser Cys Cys Cys Pro Ala Ser
            260                 265                 270

Cys Val Ser Leu Leu Cys Arg Pro Ala Ser Ser Arg Leu Ala Cys Tyr
        275                 280                 285

Ser Leu Cys Ser Gly Lys Lys Ser Ser Cys
    290                 295

<210> SEQ ID NO 23
<211> LENGTH: 3078
<212> TYPE: DNA
<213> ORGANISM: Homo sapiens
<220> FEATURE:
<221> NAME/KEY: CDS
<222> LOCATION: (2001)..(2339)

<400> SEQUENCE: 23
aatcaaaaaa ttattgaaga cagtggaaaa aaaagacact tctcatacaa ggtataaggt      60
tcttgcaagg atgagaaaat ccctcacttc tcagcaaaaa cagtggaggc cagaagacaa     120
tggaacaact tctttaaaat gctcaaaaaa aatttgccaa cccagaattc tatacctatg     180
```

-continued

```
aaaaaaatcc ttcaaaacat gttgaggtaa aaacctgttc agaagagcaa aagctgggag    240
aaatcctccc ctgcagatgt gcactgcagg tgacgtgcac ggatgtcctt taggttgact    300
aggacgaggc caggtgggcc ctgacctgca ggaaggagta ggaggaacag ggaaggtaa     360
aggagcagat aaatatcaaa gacgcatcct tgttcttctg taatcgactc gtaagacaac    420
caacttttaa aatggattac ttggtgacta gctcacaatc actgtggctg ccccaattct    480
cttggttttt aagtgtgatt ctgaactata gcagtgaaag gagttgcctg tgaacttgtg    540
gcctcgcccg gcttgtccct aggccttaag gtgactccca catggccaca gatcggctct    600
gggtccatag acttctaagt tctgtccaca gctctgagac cccacttggt cttcagcctt    660
ggagggatt tcattaatgt ggtgtctgac ttgtctgaag gcttcttggc aggaatcacc      720
catatccacc accagcaggc acaggaggac ccacacagga gcagagggtg ccctgggag     780
ctgcctggga tggacagagt agctctgccc tgagagatgg ctcatccccc accgtgtgac    840
accaccgtag aataaagcgc tgtggccaat ccatcaagag aacagagctg gagtgtgagg    900
aggagcgtgt catccacact cctgcccgct gcttcccaag ttcagggca tcctggaatt     960
tcacaccagc tcctcacttt cccccaagct gcctctgcag gggtgagact gatcagaccc   1020
acagcgaggg agaggaacca gatatgaata gctcatgccc gactccgtga tgggtcctcc   1080
tgggctccgt ctgcagagga ggtgtcctgt ggccattagt gctactcgtg ggaagtgggc   1140
acttctgagg tgtggtgtca ggaagcccac tgtggtcaca cgcctgagcc atgctctgca   1200
gacgccaacg tggctgatgt tttcgtccat cttctctgtc cgagctggtt caggacttca   1260
ggatgagtca cttattgaac cttcaagccc tagtataatt tggcacagtg gtaacgacca   1320
tggatcccag agtgaaacta agcagtccag atccctgcac ctctgcagtg gtgcagacac   1380
gcacccattg tgcaaaccct ctatgactta caaattgcac atctgtaaaa tggggtatcg   1440
gccaccccga atgctggcaa agatgaatga gataatcaca gcctggcaca gtgctagacc   1500
tctgtgcatt actgttacct caataatcat cattattatt ccacaatata gagcccagta   1560
gtttggctct cgttacttgg gaagaccctg atgatgactg agcttctcag tcaaaacggg   1620
gccccctggtg tagtgagtgt gactgtgctt gtgtgagctc cagatggcat ttacaacggg  1680
gggaccttga acatccatga ggtgggcccc tggcctcact gacagccctt caccagctac   1740
ccctgctctg tttccaggaa acacacggtc tgctgaatga tagggcaccc ctagctgaaa   1800
gagtttcctg aactgagtaa cctcaacaga aaaacacaga aagatcaacc agacagggca   1860
gaggaggaaa aaccacccac gaggaagatg ccaggggggct tgttgccagg atgccggtag   1920
cctgggtata aaggccacct aaggaagcag gctccagacc agccctgtcc tctgcgcccc   1980
ccacctgtcc acactccatc atg tgc cac acc agc cac tct tcg ggc tgc cca   2033
                         Met Cys His Thr Ser His Ser Ser Gly Cys Pro
                          1               5                  10
atg gcc tgc cct ggc tcc ccg tgc tgt gtc ccc agc acc tgc tac cca      2081
Met Ala Cys Pro Gly Ser Pro Cys Cys Val Pro Ser Thr Cys Tyr Pro
            15                  20                  25
ccc gag ggc tat ggg acc tcc tgc tgc tgc tca gcc ccc tgt gtg gct      2129
Pro Glu Gly Tyr Gly Thr Ser Cys Cys Cys Ser Ala Pro Cys Val Ala
        30                  35                  40
ctg ctg tgc cgg ccc ctg tgt ggg gta tcc acc tgc tgc cag cca gcc      2177
Leu Leu Cys Arg Pro Leu Cys Gly Val Ser Thr Cys Cys Gln Pro Ala
    45                  50                  55
tgc tgt gtg ccc agc ccc tgc cag gtg gcc tgc tgt gtg cct gtg agc      2225
Cys Cys Val Pro Ser Pro Cys Gln Val Ala Cys Cys Val Pro Val Ser
60                  65                  70                  75
```

```
tgc aag cct gtt ttg tgt gtg gct tcc ttc tgc cca acc tct ggg tgc    2273
Cys Lys Pro Val Leu Cys Val Ala Ser Phe Cys Pro Thr Ser Gly Cys
            80                  85                  90 tgc cag ccc ttc tgc ccc acc ctg gtc tat aga cct gtc acc tgg agc    2321
Cys Gln Pro Phe Cys Pro Thr Leu Val Tyr Arg Pro Val Thr Trp Ser
            95                 100                 105 acc ccc act ggc tgc tga gcaggtggcc tcctatgacc ctcgtaggtg           2369
Thr Pro Thr Gly Cys
            110 cgaggtcaga agccagcagg ctctctgaac tcctgccagg cagtccccac atcctcccac  2429 agcaaactgt cgtcacctga ctagaccgcc tgcctccttt gcggcaccgt cactagatcc  2489 cagccggtga ggccatgcgc ctttctacac agtttctcct gggttcacag cctgggccat  2549 ccacagggcc ctccgcactg tctgatgtta ggtctcttgc aaatatcata ataccagat   2609 gctgagtgct cacctgagtc tgtgtgatgc cttctcctca gtgtctttcc cacactcctt  2669 cctcaggagg taccttcccc aggattctgg aaagctcctt ccctgcagag aagggcagg   2729 taccagatga atgttaggcc tggtgagcgg cctctcaaca gcaccctctc gggctagtgg  2789 gccgtgctcc tgagcttggc ctgatgggaa cccccaaccc cagtcacatc aggcttcctt  2849 cgtcccactt tgttccttaa atgtatgagg tcagttctta ctctcttctg ggtgagattg  2909 aggacaaatc actaattttg tagtttgatc cattttaggt aaaacgggcc atctgcttat  2969 tagctggtat gtgcaaccca ctcttgtcaa gaaattaaaa ccttaaacta aatttaaatc  3029 tatagctact ccttcatcca actggatggg aaagaggttt gtggtgttg              3078
```

<210> SEQ ID NO 24
<211> LENGTH: 112
<212> TYPE: PRT
<213> ORGANISM: Homo sapiens

<400> SEQUENCE: 24

```
Met Cys His Thr Ser His Ser Ser Gly Cys Pro Met Ala Cys Pro Gly
 1               5                  10                  15

Ser Pro Cys Cys Val Pro Ser Thr Cys Tyr Pro Glu Gly Tyr Gly
            20                  25                  30

Thr Ser Cys Cys Ser Ala Pro Cys Val Ala Leu Leu Cys Arg Pro
        35                  40                  45

Leu Cys Gly Val Ser Thr Cys Cys Gln Pro Ala Cys Cys Val Pro Ser
50                  55                  60

Pro Cys Gln Val Ala Cys Val Pro Val Ser Cys Lys Pro Val Leu
65                  70                  75                  80

Cys Val Ala Ser Phe Cys Pro Thr Ser Gly Cys Cys Gln Pro Phe Cys
                85                  90                  95

Pro Thr Leu Val Tyr Arg Pro Val Thr Trp Ser Thr Pro Thr Gly Cys
            100                 105                 110
```

<210> SEQ ID NO 25
<211> LENGTH: 2730
<212> TYPE: DNA
<213> ORGANISM: Homo sapiens
<220> FEATURE:
<221> NAME/KEY: CDS
<222> LOCATION: (2187)..(2477)

<400> SEQUENCE: 25

```
gccatctctc agggcagagc tactctgtcc atcccaggca gctcccaggg gcaccctctg   60
```

```
ctcctgtgtg ggtcctcctg tgcctgctgg tggtggatat gggtgattcc tgccaagaag      120
ccttcagaca agtcagacac cacattaatg aaatcccctc caaggctgaa gaccaagtgg      180
ggtctcagag ctgtggacag aacttagaag tctatggacc cagagccgat ctgtggccat      240
gtgggagtca ccttaaggcc tagggacaag ccgggcgagg ccacaagttc acaggcaact      300
cctttcactg ctatagttca gaatcacact taaaaaccaa gagaattggg gcagccacag      360
tgattgtgag ctagtcacca agtaatccat tttaaaagtt ggttgtctta cgagtcgatt      420
acagaagaac aaggatgcgt ctttgatatt tatctgctcc tttaccttcc cctgttcctc      480
ctactccttc ctgcaggtca gggcccacct ggcctcgtcc tagtcaacct aaaggacatc      540
cgtgcacgtc acctgcagtg cacatctgca ggggaggatt ctcccagct tttgctcttc       600 tgaacaggtt tttacctcaa catgttttga aggattttt tcataggtat agaattctgg       660
gttggcaaat ttttttgag cattttaaag aagttgttcc attgtcttct ggcctccact       720 gttttgctg agaagtgagg gattttctca tccttgcaag aaccttatac cttgtatgag       780
aagtgtcttt ttttccact gtcttcaata atttttgat tttcattact cttactattt        840
gatgcttgga tatggttttc tttgtgttga tcctcctaaa ggttctgaga ttcttgggtc      900
tgtaagttgt tattttttaa atcatatttg gtgccttggg ccattatttt tttgaaactt     960
atttatggtt cagtatcgct ctcttctctt tccaaggttc aaactactag tatgttagac     1020
agttcagtac tgtctcatat gtcttttcat ttttctagat tctttctcct cttcttgaga     1080
caagataatt tctactggtg tgtcttcagg ttcactgatt ctttttccat ctgactccta     1140
accccaaatc ccagaccccc ccagcatggg attctgatgc ttggttcttg ggtcctcatg     1200
atctgaccag ttcacctgca cccatggccc aacacccaga gtacaggatt cctgcctccc     1260
ctggacatac cagtttctga agcagcatcc tcactctctc catggccaca ttgtctcctc     1320
acagacgccc cccagaccac ccaccagcac ccccattact atctcctgaa cccatttttcc    1380 ccagcactca gccctgtatg gaattatttc atgcattcat ttcttccttt actcatttat    1440
tcattgccca ctgctagaat gctcttgagg ccaagacctc gttgctgctg gtacacaata    1500
tatatttgtt gcattaacaa ataacttctt gtatagatta ctctatggca gggttggcta    1560
actttctgta aagggcagac agcaaatatt ttagcctttg catgttacag tctcttccat    1620
aactattcag ttgtgccact atagtgcaaa agaagccaca gacaacacat aaactaatga    1680
catgctgtga tccaataaga gttcatttga aaaacaggca gtgggccaaa tgtggctcac    1740
agacgatagt ttgccaacct atgctttaaa gttttactct acaaaattaa agctcaaaat    1800
acattattgc ctcaacatct tccttgatag catgaaacaa aagtgaaaca acgggattcg    1860
gtactttgag tcgagccagt ggtgctatgt gcacggtagt agcctgaaaa aaattgacaa    1920
aaaacctgca taacgtcaaa ccagaacatc ctgtttacag aagaaactaa cctcaaggcc    1980 gaagctatt atggtggagc atgacgcggg aaagtacacg cggaaaata agatgttggg      2040 aaacacagtg gaaacaacca caaggaagac aacagttgtg tttttgtgtt acccagatga    2100
caggacccag gtataaagac caccagagaa gcagcttcca gacatcacca tcctcctccc    2160
cagtaccagc ccagccacac gccacc atg tgc cac acc agc tgc tcc cca gcc     2213
                              Met Cys His Thr Ser Cys Ser Pro Ala
                               1               5 tgc cag cca acc tgc tgc ata cac agc ccc tgc cag gca tcc tgc tat      2261
Cys Gln Pro Thr Cys Cys Ile His Ser Pro Cys Gln Ala Ser Cys Tyr
     10                  15                  20                  25 gtg ccc gtg agc tgc cag tcc tcc gtg tgc atg ccc gtg agc tgc acg      2309
```

| | | | | | | | | | | | | |
|---|---|---|---|---|---|---|---|---|---|---|---|---|
| Val | Pro | Val | Ser | Cys | Gln | Ser | Ser | Val | Cys | Met | Pro | Val Ser Cys Thr |
| | | | 30 | | | | 35 | | | | 40 | |

```
cgc att gtg tgc gtg gct ccc tcc tgc cag ccc tcc gtg tgc gtg ccc       2357
Arg Ile Val Cys Val Ala Pro Ser Cys Gln Pro Ser Val Cys Val Pro
             45                  50                  55 gtg agc tgc agg ccc atc ata tat gtg act ccc tct tgc caa tct tcg       2405
Val Ser Cys Arg Pro Ile Ile Tyr Val Thr Pro Ser Cys Gln Ser Ser
         60                  65                  70 ggg tgc tgc cag ccc ccc tgc acc act gcc ctc tgc aga ccc atc tcc       2453
Gly Cys Cys Gln Pro Pro Cys Thr Thr Ala Leu Cys Arg Pro Ile Ser
     75                  80                  85 tgc agc acc cct tcc tgc tgc tga ccagctgctc ctggtacacg ggggtacaca      2507
Cys Ser Thr Pro Ser Cys Cys
 90                  95 cctgtatccc tccgtgaata agcatctggt ggaccccccag attgcacaca tagggcagat    2567
gaaaagcatg cccaaggaaa cctctgaact ctggggtgag aacgtggaaa aatgattcag     2627
accttccatg accctgggaa ccccctcaag gaagtcttgg ctgccagagt ccttctctca     2687
ctccagcagg aaactaaaac ccatgtgagc caaataaatc ggc                       2730
```

<210> SEQ ID NO 26
<211> LENGTH: 96
<212> TYPE: PRT
<213> ORGANISM: Homo sapiens

<400> SEQUENCE: 26

```
Met Cys His Thr Ser Cys Ser Pro Ala Cys Gln Pro Thr Cys Cys Ile
 1               5                  10                  15

His Ser Pro Cys Gln Ala Ser Cys Tyr Val Pro Val Ser Cys Gln Ser
             20                  25                  30

Ser Val Cys Met Pro Val Ser Cys Thr Arg Ile Val Cys Val Ala Pro
         35                  40                  45

Ser Cys Gln Pro Ser Val Cys Val Pro Val Ser Cys Arg Pro Ile Ile
     50                  55                  60

Tyr Val Thr Pro Ser Cys Gln Ser Ser Gly Cys Cys Gln Pro Pro Cys
 65                  70                  75                  80

Thr Thr Ala Leu Cys Arg Pro Ile Ser Cys Ser Thr Pro Ser Cys Cys
                 85                  90                  95
```

<210> SEQ ID NO 27
<211> LENGTH: 2776
<212> TYPE: DNA
<213> ORGANISM: Homo sapiens
<220> FEATURE:
<221> NAME/KEY: CDS
<222> LOCATION: (2091)..(2531)

<400> SEQUENCE: 27

```
aaatatcagc tattgtacat tttagttcta gcattcccat ttaaaaaata gtttcaattt      60
ccctactgag attctctatc tttgatcttg agttaatttt gtatatggtg tgaggtaagg     120
gttaaaaata atcttttgtg tgtggatatc ctgttttccc actgccattt gttaaaaagt     180
ctgttcttcc ctcactgaaa ggtcttgaca gccttgccga aaattatttg actgtagttg     240
tgagagttta tttctgggct ctctatgcta ttccattagt ctatatattg gtctttatgc     300
cagtaccaca gttttgatta gtgtagcttt gtagtaagtt ttgaaatcag aaagtgtgac     360
tcctccagct ctattctttt cttaagattg atttggctat ttagggtccc ttgagactcc     420
acataaactt taggatgggt ttttctattt ctgcaagaaa tgtccttggg attttgacag     480
```

-continued

```
ggattgcatt gaatctgtag attgctttgg ttagtatgga catattaaca atattaattt      540
ccaattcatg aacatgggat gtgtttccat ttatttctgt tgcctttaat ttctttcaac      600
gttttgtagt ttttgttaca caattatttt aattctttgg ttaactcctg agtattttgt      660 tcttttaat gtattgtaaa tggaattgtt attgtacttt cctttgaga ttatgcttgt        720 tagtttatgg aaatagaact gattttgtg ttttgctttt gtatcctgct actttgctga      780
attcatttat tctaaaattt ttgtgtgtgg aatatttaga gttttctaca tataaaaatc      840
atgtcatctg tgaacacagc taactttact tcttgctttt caatttggat gcttttgtt      900 tctttctttc ttccttttaa aaacaattgc ctagttgctc ttagtaaaac ttctagtact      960
atgctggctt tgttcccaat attagagaaa aagccttcag tttttcacca gtgggtatga    1020
ggcttgctgt gggtctttca tgtatggctt gtattgtgtt gaggtagttt cttctattc     1080 ttagtttgtt gattgttgtc atcatgaaag aatcttgaat tttgtgaaat gccttttcta    1140
tatcaattga gatgatcacg tggttttttc cttcattctg ttatcatgat gccaagttcc    1200
aagtgatctg tgttgacat ctgtaggctc agagattcta ctgtccctgc agtacaggg     1260 gcacatggct ttctgctgaa catacccaga agtcattctg gcccttggaa ccttctatat    1320
tcagctcaca catatcctgc tgtggctgtc catgggaccc ttcactgcc tcacatgctt     1380 ccctgggaac atgcttggac cagcttgatt tccttagagc tgtgtctcca tgcatgaggg    1440
ccagtggtgt tgtctcatct tggttcttaa ctaggaggat ttctcaagac aaagatccat    1500
ggtcaccact cacaagaagt tctctgtgac ccacacctt tgtccccact catcctatgg    1560
acaagtgatt tccatgttct tcctccatct gctagctctc atccagctct aagctctcag    1620
gacacccaca gatcagctag acacgtcctg ttctacctca cattgactgt ggagccttcc    1680
tgagccatga gaggagtgta aacttctgtg gtttaaggaa catcatcaca cagagaggaa    1740
aaaaatctgg agatctgagt ttttggaatc tcacaaaagt aactcaggta aaatttaaa     1800 gaacaaggaa gaatcttgat gaagccagta aaacactctg gcaggtttcc aagcatacca    1860
agagttcgaa gaaggtgcaa ttagtcatga agctaagggc caaacaaaac ccagagacac    1920
ctacaacaga aaattaagct ccaggagaca gcactgagga agaaaaacaa ggaagacagg    1980
tgtgcttctg tgctgtgggg atgcctgggc ccaggtataa aggctgccca gggaggccgt    2040
ccccagacat cactgccctc tgcctcgacc ttatccagcc acacgccacc atg tgt       2096
                                                              Met Cys
                                                                1 cat acc agc tgc tcc tcg ggc tgc cag cca gcc tgc tgc gcg ccc agc      2144
His Thr Ser Cys Ser Ser Gly Cys Gln Pro Ala Cys Cys Ala Pro Ser
        5                  10                  15 ccc tgc cag cca gcc tgt tgt gtg ccc agc tcc tgc cag gca tcc tgc      2192
Pro Cys Gln Pro Ala Cys Cys Val Pro Ser Ser Cys Gln Ala Ser Cys
    20                  25                  30 tgt gtg cct gtg ggc tgc cag tcc tcc gtg tgt gtg ccc gtg agc ttc      2240
Cys Val Pro Val Gly Cys Gln Ser Ser Val Cys Val Pro Val Ser Phe
35                  40                  45                  50 aag cca gcc gtg tgc ctg ccc gtg agc tgc cag tct tct gtg tgt gtg      2288
Lys Pro Ala Val Cys Leu Pro Val Ser Cys Gln Ser Ser Val Cys Val
                55                  60                  65 ccc atg agc ttc aag tca gct gtg tgc gtg ccc gtg agc tgc cag tct      2336
Pro Met Ser Phe Lys Ser Ala Val Cys Val Pro Val Ser Cys Gln Ser
            70                  75                  80 tct gtg tgt gtg cct gtg agc tgc agg ccc att gtg tgt gca gcc ccc      2384
Ser Val Cys Val Pro Val Ser Cys Arg Pro Ile Val Cys Ala Ala Pro
```

```
                 85                  90                  95
tcc tgc cag tcc tcc ctg tgc gtg cct gtg agc tgc agg cct gtc gtg       2432
Ser Cys Gln Ser Ser Leu Cys Val Pro Val Ser Cys Arg Pro Val Val
    100                 105                 110 tat gcg gct ccg tcc tgc cag tcc tct ggg tgc tgc cag ccc tcc tgc       2480
Tyr Ala Ala Pro Ser Cys Gln Ser Ser Gly Cys Cys Gln Pro Ser Cys
115                 120                 125                 130 acc agc gtc ctc tgc aga ccc atc tcc tac agt atc tct tcc tgc tgc       2528
Thr Ser Val Leu Cys Arg Pro Ile Ser Tyr Ser Ile Ser Ser Cys Cys
                135                 140                 145 tga gcatgaatct ccagacccgc tgctcccagt gcagatgagg ccacacctgt            2581
acactccctg gatgagtcct cagttggtct tctgcacatg gtgcaggtga aaagcatgct    2641
cagttgaacc ctctgaattc tggattgaga atgtgacaga atgatctgga gcccttgctg    2701
accttgccca tcccccagg gaagtctggg gtcccagagt cattctctga ccccatgaga     2761
gccaaataaa ccagc                                                      2776
```

<210> SEQ ID NO 28
<211> LENGTH: 146
<212> TYPE: PRT
<213> ORGANISM: Homo sapiens

<400> SEQUENCE: 28

```
Met Cys His Thr Ser Cys Ser Ser Gly Cys Gln Pro Ala Cys Cys Ala
 1               5                  10                  15

Pro Ser Pro Cys Gln Pro Ala Cys Cys Val Pro Ser Ser Cys Gln Ala
            20                  25                  30

Ser Cys Cys Val Pro Val Gly Cys Gln Ser Ser Val Cys Val Pro Val
        35                  40                  45

Ser Phe Lys Pro Ala Val Cys Leu Pro Val Ser Cys Gln Ser Ser Val
    50                  55                  60

Cys Val Pro Met Ser Phe Lys Ser Ala Val Cys Val Pro Val Ser Cys
 65                  70                  75                  80

Gln Ser Ser Val Cys Val Pro Val Ser Cys Arg Pro Ile Val Cys Ala
                85                  90                  95

Ala Pro Ser Cys Gln Ser Ser Leu Cys Val Pro Val Ser Cys Arg Pro
            100                 105                 110

Val Val Tyr Ala Ala Pro Ser Cys Gln Ser Ser Gly Cys Cys Gln Pro
        115                 120                 125

Ser Cys Thr Ser Val Leu Cys Arg Pro Ile Ser Tyr Ser Ile Ser Ser
    130                 135                 140

Cys Cys
145
```

<210> SEQ ID NO 29
<211> LENGTH: 2625
<212> TYPE: DNA
<213> ORGANISM: Homo sapiens
<220> FEATURE:
<221> NAME/KEY: CDS
<222> LOCATION: (2091)..(2381)

<400> SEQUENCE: 29

```
tagacttccg gattgccagt tattgttgct cagcatttta aagatgtgtc tccactgttt     60
ctcatgagaa gccagggcgt ttttcttatc cttgttcctt tgtatgtaaa gtgtcttcct    120
gtcactgctt ttgagatttt gtcttcattt ttggttttca tcacttcatg atgtgcctgg    180
```

-continued

```
atgtggtttt cttcctattt atcctactgg gggctttctg agattcctgg atttggacgt    240
tgttgatttt tgaagtcaaa tttggtgtat ttaaaatttc taactactgt acttttcagt    300
tctaggattc ccatttttaaa aaatagcttc aattactcta ctgagattcc ctatttatcc   360
attcatgaag acaatgtttt cctttaatta tttgaacagt tttcttggat tttttggaag    420
atgtctataa tagctgctta cagtcatcat ttgccatgtc caatatctag accatatcag    480
gtttattttt tttaacagtg aattaaattt acctatatct tttaatatct gatgatttgt    540
tttttgagac gggtcttgc tctgttgccc tggctggaat gcagtggtgt gatcataact     600
catggcatcc tcaacctccc aggctcaata gaccctcctg cctcaaccta ccgtgtagct    660
gggaccacaa gcatgcacca ccatgtctgg ctaattttta accattttttt tgtagagaca   720 gagtctcact atgttgccca ggctggtctg aaactcctag cctcaagcaa tcttcccatc    780
ttggtctccc aaagtgctgg gattacaggc ataaacaacc gtgcctggtc aatatctgat    840
gattttgatt gtgtatgagg tatcataata atgcatttac agactctgag ctgtatcatg    900
tttctgattt tgttctagc cgtcagttac tggagaatga ccttaatctt gtgcagtttt     960
tgttcaacac tttgctaggg tggatctctg gaagcatct acaacttgga acactctgta     1020
tcttggtggg actcacattc caaactgtct tccctaaaaa tcctattctg aattggttta    1080
ggctttgttc gggctggcct aggcgggtct cactgtagtc tgtggtcctt actcatttgg    1140
tgccgggctg tagggggtct cggctggatg tcgacgtggg gactggaggg gggcttcact    1200
ctcaatcctc tagcagcttc tctctggtga gcctgtggtt gccttgccct gggaatgcac    1260
agccctgccc cgttccacag attcacagtc agcttccaca gtgtggggcc tgctctccac    1320
acggatcctt ctttccgctt ctctgctcct cggactccag ggcttcagct gcttgagcgc    1380
tggccccttc ctcctcggca gagttgggtc actgtattct gctctgactc cggctggtga   1440
cactgcattt tggaaggtga cactgcattt tggaagcctg ccccagcaga gagctgggaa    1500
atgggagttt atctcctaag tttcttctct ctcaggaagc acagtctgca ctgctggttg    1560
acggctgcct gaaaacgagc atctcctaaa tctcaactgt atagttgata gagtagccag    1620 cttttgcatca ctcactccag caggttcccc agtatgattt cattgtctat attcagttct   1680
ggtctcttcc ccaaagtttc tggttgatgc aacagaagtt gcggttcgag gagctctttt    1740
gggtaccact catgtctgct tcagcgtaga actaacgaag ggaggcagat atcaggcagg    1800
tggagctaaa actgcctgtg catcactgat aaatttgggc aggtttccaa atgtaacaag    1860
agcttgaaga gggtgcaatt agtcacgaaa caaagggcca gataaaaaac atcatctacg    1920
acagaaaact gagttccagg aaacagcctt gaggaagaaa acaaggaag acaacaggtg     1980 tgtgcttctg tgctgtgggg atgcctgggt ccaggtataa aggctaccca gggaggccat    2040
ccccagacat cactgccctc tgcctcgacc ttatccagcc acacgccacc atg tgc       2096
                                                         Met Cys
                                                           1 cac acc agc tgc tcc tcg ggc tgc cag cca gcc tgc tgc gcg ccc agc      2144
His Thr Ser Cys Ser Ser Gly Cys Gln Pro Ala Cys Cys Ala Pro Ser
         5                  10                  15 ccc tgc cag gca tcc tgt tac atc ccc gtg ggc tgc cag tcc tcc gtg      2192
Pro Cys Gln Ala Ser Cys Tyr Ile Pro Val Gly Cys Gln Ser Ser Val
         20                  25                  30 tgc gtg ccc gtg agc ttc aag cca gcc gtg tgt gtg ccc gtg aga tgc      2240
Cys Val Pro Val Ser Phe Lys Pro Ala Val Cys Val Pro Val Arg Cys
 35                  40                  45                  50 cag tcc tct gtg tgc gtg ccc gtg agc tgc agg ccc gtc gtg tat gcg      2288
```

```
Gln Ser Ser Val Cys Val Pro Val Ser Cys Arg Pro Val Val Tyr Ala
            55                  60                  65 gct ccc tcc tgc cag tcc tct ggg tgc tgc cag cct tcc tgc acc agc    2336
Ala Pro Ser Cys Gln Ser Ser Gly Cys Cys Gln Pro Ser Cys Thr Ser
            70                  75                  80 gtc ctc tgc aga ccc atc tcc tgc agc acc cct tcc tgc tgc tga        2381
Val Leu Cys Arg Pro Ile Ser Cys Ser Thr Pro Ser Cys Cys
            85                  90                  95 gcatgaatct ccagacccgc tgctcccagt gcagatgagg ccacacctgt acactccctg  2441
gatgagtcct cagttggtct tctgcacatg gtgcaggtga aaagcatgct cagtgaaccc  2501
tctgaattct ggatcgagaa tataatagaa tgatctggag ccctggctga acttgcctat  2561
ccccccaggg aagtctgggg tcccagagtc attctctgac cccatgagag tcaaataaac  2621
cagc                                                              2625

<210> SEQ ID NO 30
<211> LENGTH: 96
<212> TYPE: PRT
<213> ORGANISM: Homo sapiens

<400> SEQUENCE: 30

Met Cys His Thr Ser Cys Ser Ser Gly Cys Gln Pro Ala Cys Cys Ala
 1               5                  10                  15

Pro Ser Pro Cys Gln Ala Ser Cys Tyr Ile Pro Val Gly Cys Gln Ser
            20                  25                  30

Ser Val Cys Val Pro Val Ser Phe Lys Pro Ala Val Cys Val Pro Val
            35                  40                  45

Arg Cys Gln Ser Ser Val Cys Val Pro Val Ser Cys Arg Pro Val Val
    50                  55                  60

Tyr Ala Ala Pro Ser Cys Gln Ser Ser Gly Cys Cys Gln Pro Ser Cys
65                  70                  75                  80

Thr Ser Val Leu Cys Arg Pro Ile Ser Cys Ser Thr Pro Ser Cys Cys
                85                  90                  95

<210> SEQ ID NO 31
<211> LENGTH: 3060
<212> TYPE: DNA
<213> ORGANISM: Homo sapiens
<220> FEATURE:
<221> NAME/KEY: CDS
<222> LOCATION: (2001)..(2738)

<400> SEQUENCE: 31
ctgtggcttt ggggcattca cactctcctg gtcctgtcct ggcacctttg ctcccactgg   60
actggacgct gtgctgtctc tcaggtacgc aagtgcacca cagactctga tatgtacaga  120
acaggcccct gggtctcggt ccccaaagca cctcttctca gaccttctac tgagaggtcg  180
ggggtcgggt catgacacac agcaggaaat gaatgcacga ctcaggccag aggcatcagc  240
tggtcctccc tcccttgggc ctctccctgg ccatgcccca acctggctca cactccctca  300
gggttgcaat gacctccgat cccaagaccc ttttcccaag tccaatttt  cctccaagtt  360 cctggtccct tgtggtgggc cagtttattc agcttaggag aaatgattgt taaatattca  420
gaatcttctc aagcaggttg ttaaactgct catagcttga aatcagccag gatatgaata  480
tttacaccac ggatgacagc taacactcca cgccagggtt ctcatctcac cgcagcggga  540
caggggtaca cgcccacaca cagggtttca tctcatcaca gggtaatgtt tacaacgcag  600
agaccagcag acaccacaca ccagggcttt tcacttcaag gggcccatcc accacacacc  660
```

-continued

```
tcgagccctc acctgctggt cactgcctgt gggcctgaag ccctccaact ttccaggcag      720
agccaagcag ctctccctta atctcaggat cctccaggct agatgagccc tggggctcta      780
gagtcctcaa ccacaaaggc tgccgaatgt cttcttctca aaattaaaaa caattcactt      840
cccataaaga aatctttcaa cctcctagaa caacccctct gaactctgaa ctggaccttc      900
ccttcacaat aatgtttttt cacattccca ctcataaata aacccaaatc ctctctcttt      960
agatggaagg agctcctttt ttatagctag acccaaccgt ctgggcaccc atcagatatt     1020
ttcacatcaa tcccacaccg ccatgtctaa accatgctcc gccccgctct tctcacacaa     1080
tctgggtttc tcattctgat ttcccatgtc ccttgctctc tgaggcagca gaggttaatg     1140
gctaagaaca tagaatacgg gcctgccagg cctccagtgt atgctcctct gcctgctggt     1200
gcagcctttt gcacaagttc ttcattgtga ctcagtttct ccatctgtag agtggggata     1260
ataacagccc ctactttaca aggttgatgt atgggttagt gaggtcatat ttacaaactt     1320
gctcagaata cttcctgaca cacagcaaga cctatcacat gactgtttgc cgaaaaaaat     1380
aaaaataaat ccagctccca agccattcat tggtctacgg attcaagata aagagaatat     1440
aaaacaagaa gaaaaacatc cttgactcaa ctgagtgtga agaaattagg gggaaataat     1500
agtaagcaat accaaatgac aatcacagag gggcggccaa gggctgctga ccttctgtgg     1560
tccacgcaga ggctgggctc cagcccattg ccggctccc tccacggccc cacggtcccg      1620
ctcagttctg acacctgggg agcttcagga gctaagctac gctacacggt tcatggtgag     1680
catcctcaag aaaccacccc aaacaccaac aaggaaagaa gcctgggcc ttgtgctggg      1740 acaacacaca caccct tgag agatatataa gctcctagca cccagacact cactcactcc     1800
ctccttccca tccagcaccc agacgctcac tcactccctc cctcctgccc atccagcacc     1860
cagacgctca ctcactccct ccctcctgcc catccagcac cagacactc actcactccc      1920 tccttcccat ccagcaccca gacactcact gtctccctct cagctccccc agctcaaccc     1980
ccagcacggc tgcatccacc atg tcc gtc tgc tcc agc gac ctg agc tat ggc     2033
                      Met Ser Val Cys Ser Ser Asp Leu Ser Tyr Gly
                       1               5                  10 agc cgc gtc tgc ctt cct ggt tcc tgt gac tct tgc tcc gac tcc tgg        2081
Ser Arg Val Cys Leu Pro Gly Ser Cys Asp Ser Cys Ser Asp Ser Trp
         15                  20                  25 cag gtg gac gac tgc cca gag agc tgc tgt gag ccc ccc tgc tgc gcc        2129
Gln Val Asp Asp Cys Pro Glu Ser Cys Cys Glu Pro Pro Cys Cys Ala
     30                  35                  40 ccg gcc ccc tgc ctg agc ctg gtc tgc acc cca gtg agc cgt gta tcc        2177
Pro Ala Pro Cys Leu Ser Leu Val Cys Thr Pro Val Ser Arg Val Ser
 45                  50                  55 agc ccc tgc tgc cga gtg acc tgt gag ccc agc ccc tgc caa tca ggc        2225
Ser Pro Cys Cys Arg Val Thr Cys Glu Pro Ser Pro Cys Gln Ser Gly
 60                  65                  70                  75 tgc acc agc tcc tgc acg ccc tcg tgc tgc cag cag tct agc tgc cag        2273
Cys Thr Ser Ser Cys Thr Pro Ser Cys Cys Gln Gln Ser Ser Cys Gln
             80                  85                  90 ccg gct tgc tgc acc tcc tcc ccc tgc cag cag gcc tgc tgc gtg ccc        2321
Pro Ala Cys Cys Thr Ser Ser Pro Cys Gln Gln Ala Cys Cys Val Pro
         95                 100                 105 gtc tgc tgc aag act gtc tgc tgc aag cct gtg tgc tgt atg ccc gtc        2369
Val Cys Cys Lys Thr Val Cys Cys Lys Pro Val Cys Cys Met Pro Val
     110                 115                 120 tgc tgt ggg cct tct tct tca tgc tgc cag cag tct agc tgc cag cca        2417
Cys Cys Gly Pro Ser Ser Ser Cys Cys Gln Gln Ser Ser Cys Gln Pro
```

| | | |
|---|---|---|
| gct tgc tgc atc tcc tcc ccg tgt caa cag tcc tgc tgt gtg ccc gtc<br>Ala Cys Cys Ile Ser Ser Pro Cys Gln Gln Ser Cys Cys Val Pro Val<br>140                         145                     150                     155 | 2465 |
| tgc tgc aag ccc atc tgc tgt gtg cct gtc tgc tct ggg gcc tcc tct<br>Cys Cys Lys Pro Ile Cys Cys Val Pro Val Cys Ser Gly Ala Ser Ser<br>                160                     165                     170 | 2513 |
| ctg tgc tgc cag cag tct agc tgc cag cca gct tgc tgc acc acc tcc<br>Leu Cys Cys Gln Gln Ser Ser Cys Gln Pro Ala Cys Cys Thr Thr Ser<br>                175                     180                     185 | 2561 |
| tgc tgc aga ccc tcc tcc tcc gtg tcc ctc ctc tgc cgc cct gtg tgc<br>Cys Cys Arg Pro Ser Ser Ser Val Ser Leu Leu Cys Arg Pro Val Cys<br>           190                     195                     200 | 2609 |
| aga ccc gcc cgc cgc gtg ccc gtc ccc tcc tgc tgt gtc ccc acc tcc<br>Arg Pro Ala Arg Arg Val Pro Val Pro Ser Cys Cys Val Pro Thr Ser<br>205                         210                     215 | 2657 |
| tcc tgc cag cca agc tgc ggc cgc ctg gcc tcc tgc ggg tcc ctc ctc<br>Ser Cys Gln Pro Ser Cys Gly Arg Leu Ala Ser Cys Gly Ser Leu Leu<br>220                       225                     230                     235 | 2705 |
| tgc cgc ccc aca tgt tcc cgc ctg gcc tgc tga ggcctctgct caggccagaa<br>Cys Arg Pro Thr Cys Ser Arg Leu Ala Cys<br>           240                     245 | 2758 |
| gtccagctgc tgccaggcat gtcccccagg gccactgggc actatgagtc ccccacctct | 2818 |
| cccactactg gcccctcggc tgctctggtg tctgtctctt ccttggagat gcgtgcacag | 2878 |
| cctctcttcc cctaagccct gggggctcct gctaagctcc agatgaccct gcctccaccc | 2938 |
| actcccccgg ctcttccaga ccacttccca cattccaggc ccctgtggtc tcgcctcctt | 2998 |
| ggaagctgct gtgcctcctc tggccattgt aggaccatgc ttggaagtcc taataaacac | 3058 |
| cc | 3060 |

<210> SEQ ID NO 32
<211> LENGTH: 245
<212> TYPE: PRT
<213> ORGANISM: Homo sapiens

<400> SEQUENCE: 32

Met Ser Val Cys Ser Ser Asp Leu Ser Tyr Gly Ser Arg Val Cys Leu
 1               5                  10                  15

Pro Gly Ser Cys Asp Ser Cys Ser Asp Ser Trp Gln Val Asp Asp Cys
             20                  25                  30

Pro Glu Ser Cys Cys Glu Pro Pro Cys Cys Ala Pro Ala Pro Cys Leu
         35                  40                  45

Ser Leu Val Cys Thr Pro Val Ser Arg Val Ser Pro Cys Cys Arg
     50                  55                  60

Val Thr Cys Glu Pro Ser Pro Cys Gln Ser Gly Cys Thr Ser Ser Cys
 65                  70                  75                  80

Thr Pro Ser Cys Cys Gln Gln Ser Ser Cys Gln Pro Ala Cys Cys Thr
                 85                  90                  95

Ser Ser Pro Cys Gln Gln Ala Cys Cys Val Pro Val Cys Cys Lys Thr
            100                 105                 110

Val Cys Cys Lys Pro Val Cys Cys Met Pro Val Cys Cys Gly Pro Ser
        115                 120                 125

Ser Ser Cys Cys Gln Gln Ser Ser Cys Gln Pro Ala Cys Cys Ile Ser
    130                 135                 140

Ser Pro Cys Gln Gln Ser Cys Cys Val Pro Val Cys Cys Lys Pro Ile
145                 150                 155                 160

```
Cys Cys Val Pro Val Cys Ser Gly Ala Ser Ser Leu Cys Cys Gln Gln
            165                 170                 175
Ser Ser Cys Gln Pro Ala Cys Cys Thr Thr Ser Cys Cys Arg Pro Ser
        180                 185                 190
Ser Ser Val Ser Leu Leu Cys Arg Pro Val Cys Arg Pro Ala Arg Arg
    195                 200                 205
Val Pro Val Pro Ser Cys Cys Val Pro Thr Ser Ser Cys Gln Pro Ser
    210                 215                 220
Cys Gly Arg Leu Ala Ser Cys Gly Ser Leu Leu Cys Arg Pro Thr Cys
225                 230                 235                 240
Ser Arg Leu Ala Cys
                245

<210> SEQ ID NO 33
<211> LENGTH: 2808
<212> TYPE: DNA
<213> ORGANISM: Homo sapiens
<220> FEATURE:
<221> NAME/KEY: CDS
<222> LOCATION: (2001)..(2528)

<400> SEQUENCE: 33
```

| | | | | | |
|---|---|---|---|---|---|
| gaatccactt | ttgaactgtt | aaggctactc | tagttttgtt | ctgcttttc | tgcctttcag | 60 |
| atggacacat | ttattagcat | ttgggagttg | ttcattagca | tttgtacaaa | gtgcacaaat | 120 |
| aactcctaat | aaaaagtgtt | aacccaatta | ggaatgggtg | gagggactgt | taattggaac | 180 |
| tgacttactc | ccaagttatt | ttagtgttta | ttcccagaca | tagggagctg | gtctagaaag | 240 |
| gcaagaactt | ttggatatta | gtaagttttt | tgttttcttt | tttttgagca | gaatcaacct | 300 |
| gtagtaagaa | agaaaaata | tttctcattt | taaaggtgtt | aaaagctgcc | attataagga | 360 |
| atcccatgtg | ttggggggtgg | tgcatacttt | ttggtgaatt | taataggtgt | ccattcataa | 420 |
| agcacagctt | attttacttc | agtgaatcag | agtgatggtt | taagtattgc | acaagggcac | 480 |
| ttcatgtgat | gcatgccaca | ctttggattc | tgcatgggag | agataatcat | aaaacaaagt | 540 |
| aactaagtgc | tctgaaacag | tgtgctttgg | aatgaaggaa | gttaattttc | aggtagttaa | 600 |
| gaggctctct | tttcgataac | cattgtgaat | gccatttccc | ttagttaaac | caaataaaat | 660 |
| gtcaaattca | aagaagaag | aatagacaca | gataagaagc | ctcttccccc | cattaatcta | 720 |
| aacatggatt | accaatattc | tttctctttc | ttgggctagg | aagtgaaata | tacttcaaat | 780 |
| gtatgaagat | cagtaaggca | tagaattccc | cagttgaaca | ctattcagtg | tgaatattgt | 840 |
| taggaaaagt | aaataaggct | tgttaggct | tttatatctt | agtataaata | agcttaatag | 900 |
| tttcttttct | gagacaagtt | aaagttgaat | ttacttttat | atttgcaagg | tatttgcaac | 960 |
| ttgactctga | ataagaaaac | cataattaaa | gcttcaattt | tgcttctatc | ttactgagaa | 1020 |
| attagggaa | agttaaagct | ctctgagagg | taatttttcc | atgtatgggt | tgaacagggg | 1080 |
| atgtttaaag | acccatataa | ctctaatact | tcaagttaaa | agcttcagaa | aaatgttaac | 1140 |
| aattcctcaa | agtttaagta | taaattaata | attgcagcta | agaatctgtc | cttttatcca | 1200 |
| gaaaaaaaa | ttgaaacata | aaacaaaata | aaatttatga | gttgatttag | agcataacca | 1260 |
| tagaatagtg | cttgctacaa | gataggttca | tcagaaaata | tctgaaaaac | ttcaatttaa | 1320 |
| agtcttacta | aaaagtttgt | gtttattgtt | tcctaagtga | gcattgtcta | agtagcctc | 1380 |
| ttgttaagga | agatgcctga | tatggacacc | caacataatg | ctgcactcct | cagttctgat | 1440 |
| cctgagctct | taaggtacta | gtaaaaggtt | taactgacag | attgctgagg | ctactgaata | 1500 |

```
cagttagtat ttggagaaat cctccgtttc tggtaacaaa taatatgctt gtgttaaaaa    1560
gaaggacaat ctattttgag tagtaaccac tgatgctcct gataacttaa gggaagtaaa    1620
gaaagaattt tgtgtaattc catttggtac aataaggact cactgtactc aaataataag    1680
aggcaagata ctcataaatg tgatgacata taacattgaa ggtcaaacca cagtgaattc    1740
caggaaaaaa aaaaactgag tggcttcctt ctaagtgttc cagagtgact aaagtacaag    1800
taagtatatg aagatgtgat aaattaaaca ataacctagg gaagcattct tataataaaa    1860
agtgagcaag gagaagggag tgtcgagaca gtggacacac ccaggtctaa gagcatatat    1920
aacttggagt ccagactatg acattcaaac tcagagaatc tttccactat aactcagctg    1980
aactcacatc tcccgtcaac atg tcc tac aac tgc tgc tct gga aac ttc tcc    2033
                      Met Ser Tyr Asn Cys Cys Ser Gly Asn Phe Ser
                       1               5                      10 tcc cgc tcc tgt ggt gac tac ctg cgc tac cca gca tcc tca cgt ggc       2081
Ser Arg Ser Cys Gly Asp Tyr Leu Arg Tyr Pro Ala Ser Ser Arg Gly
             15                  20                  25 ttt tcc tac ccc agc aat ctg gtc tac agc act gac ctc tgc tct ccc       2129
Phe Ser Tyr Pro Ser Asn Leu Val Tyr Ser Thr Asp Leu Cys Ser Pro
         30                  35                  40 agc acc tgc cag ctg ggt tcc tct ctc tat agg ggc tgt cag gag atc       2177
Ser Thr Cys Gln Leu Gly Ser Ser Leu Tyr Arg Gly Cys Gln Glu Ile
     45                  50                  55 tgc tgg gag ccc acc agc tgc cag acg tcc tat gtg gag tcc agc ccc       2225
Cys Trp Glu Pro Thr Ser Cys Gln Thr Ser Tyr Val Glu Ser Ser Pro
 60                  65                  70                  75 tgc cag acc tcc tgc tac cgc ccc aga acc tcc ttg ctc tgc agt cct       2273
Cys Gln Thr Ser Cys Tyr Arg Pro Arg Thr Ser Leu Leu Cys Ser Pro
                 80                  85                  90 tgc aag acg act tac tct ggg tct cta ggc ttt gga tcc agc agc tgc       2321
Cys Lys Thr Thr Tyr Ser Gly Ser Leu Gly Phe Gly Ser Ser Ser Cys
             95                 100                 105 cgc tcc ctg ggc tat gga tcg agg agc tgc tac tca gtg ggc tgt ggg       2369
Arg Ser Leu Gly Tyr Gly Ser Arg Ser Cys Tyr Ser Val Gly Cys Gly
         110                 115                 120 tcc agt ggt gtc aga tcc ctg ggt tat gga agc tgt ggc ttc cct tcc       2417
Ser Ser Gly Val Arg Ser Leu Gly Tyr Gly Ser Cys Gly Phe Pro Ser
     125                 130                 135 ctc ggc tat gga tct gga ttc tgc cgc cca acc tac ttg gct tct agg       2465
Leu Gly Tyr Gly Ser Gly Phe Cys Arg Pro Thr Tyr Leu Ala Ser Arg
140                 145                 150                 155 agc tgc cag tct cct tgt tac aga cca gcc tat gga tca acc ttc tgc       2513
Ser Cys Gln Ser Pro Cys Tyr Arg Pro Ala Tyr Gly Ser Thr Phe Cys
                 160                 165                 170 aga tca act tgc tga atttccagac ctttaagca aagtgtctca gtctctacgt        2568
Arg Ser Thr Cys
             175 agagctgtta tcataggcat ttccagcaat gtgagctaac ccctcttact actagctctt    2628 catcctttct ctggcatcaa gtactggctg gacaggctag ttctttcaga ctgtgaaatt    2688 aatgaatgag caaaatatag agtcaaatgt ctataatttt gaaacaagtg attcgttatc    2748 acgtaagttc atcttataaa gtatatggaa gttcagtttt gtttcacgta ataaattcat    2808
```

<210> SEQ ID NO 34
<211> LENGTH: 175
<212> TYPE: PRT
<213> ORGANISM: Homo sapiens

<400> SEQUENCE: 34

```
Met Ser Tyr Asn Cys Cys Ser Gly Asn Phe Ser Arg Ser Cys Gly
  1               5                  10                  15
Asp Tyr Leu Arg Tyr Pro Ala Ser Ser Arg Gly Phe Ser Tyr Pro Ser
             20                  25                  30
Asn Leu Val Tyr Ser Thr Asp Leu Cys Ser Pro Ser Thr Cys Gln Leu
         35                  40                  45
Gly Ser Ser Leu Tyr Arg Gly Cys Gln Glu Ile Cys Trp Glu Pro Thr
     50                  55                  60
Ser Cys Gln Thr Ser Tyr Val Glu Ser Pro Cys Gln Thr Ser Cys
 65                  70                  75                  80
Tyr Arg Pro Arg Thr Ser Leu Leu Cys Ser Pro Cys Lys Thr Thr Tyr
                 85                  90                  95
Ser Gly Ser Leu Gly Phe Gly Ser Ser Cys Arg Ser Leu Gly Tyr
                100                 105                 110
Gly Ser Arg Ser Cys Tyr Ser Val Gly Cys Gly Ser Ser Gly Val Arg
            115                 120                 125
Ser Leu Gly Tyr Gly Ser Cys Gly Phe Pro Ser Leu Gly Tyr Gly Ser
        130                 135                 140
Gly Phe Cys Arg Pro Thr Tyr Leu Ala Ser Arg Ser Cys Gln Ser Pro
145                 150                 155                 160
Cys Tyr Arg Pro Ala Tyr Gly Ser Thr Phe Cys Arg Ser Thr Cys
                165                 170                 175
```

<210> SEQ ID NO 35
<211> LENGTH: 2721
<212> TYPE: DNA
<213> ORGANISM: Homo sapiens
<220> FEATURE:
<221> NAME/KEY: CDS
<222> LOCATION: (2001)..(2519)

<400> SEQUENCE: 35

```
gcctaggagt ccctcgtggc atcctcaggc tgtgggtgta tccggagagc tgcctgcact     60
acttctaata tatctagtcc ccagggtcaa ccttataaac cttagaaagt tttccttttt    120
tttttttttt ttttttttg aaacagagtc tcactctgtc gcccaggctg gagtgcagtg    180
gcgccatctc ggctcactgc aagctctgtc tccggggttc acgccattct ccagcctcag    240
cctcccgagt agctgggact acaggcgccc gccaccacat ccagctaatt ttttgtattt    300
ttagtaaaga cagggtttca ccgtgttagc caggatggtc tctatctcct gacattgtga    360
tccgcccgcc tcggcctccc aaagtgttgg gattacaggc gtgagccaca gccccggcc     420
catagttttc cttttaagaa gaaggattgg aacgaggata ctgctctgcc acaaactaga    480
agaccctac aaccctggat ccacagctgt ttgcagccga tcctcatgca aattgccaac     540
agatacaggt gggaggtgaa ccaggacat ctggacaaga ggcgcacaat ctcaggcttg     600
aagcactgct gaaatgaaat gacagagggt gttacagctg tggcgttgct cacaacaaat    660
ggcaatgtta aaaaaaaaaa acttttctgt gtcataaaaa ataattcaag tattttgat     720
gtactattc taaagaaac accaagtttt acttccattt gttctacaga aaatcatgtg      780
gacaaaacca ttgtcatgtg tagagatgat caaagaccga ctatgcaacc aaaaaatgta    840
gaaaagatt atagatgagg atgatgataa aggtatatta ttgtcttgat tttgtgacat    900
cttgggtttt gttaactatg gaagttttta ttctaagtta atatccatgt ttatatctat    960
tattatattc ctaatattgt gtttttaatg aggatctcca aattatactt ttcaacacca  1020
```

```
caaaacctaa atccacctct ttaaagaggg ctgggacaga gtcacgaaaa acatagaagc    1080
tggtgttacc ccgcaaatgc tcagaaggca gtcaacattt tgaggtgggg gtttagaggt    1140
gttgtagaca ggtaggctcc agaacactta caaatatgaa tgcatcatac aaaagtcatc    1200
aaataagttt atttgaaagc attttgattt gcttttagga tggagtcctg agcatccttc    1260
tgctattgtg actactctga cttgtttcct acctcatctc agcagtgtct tctactttcc    1320
tttttttcac atgggtcctt attgttgtat ttgtatttat ttatttttg cttttgtttt     1380 gatttctttt ttctaaatac taatttttta aaaaatttg ttcaagatga tatctatgtc     1440
tagttatctc tcaattcctt tggcttactt ttatataggc cctcgagact ggacttacaa    1500
gcactgatta tagtaaataa cagatggcaa actattttgg agagtgtgaa caataagatt    1560
tctgcctcta ggccactgac aaaaaaagat gaatacattg ctatccccac ccaagacaga    1620
aagaatttcc cagccaaaac aggagcagat gtataaatca tgggcagaga aaataagagg    1680
ggttttcctg gacataatgg agtagggact aatcacatac tgtcatagca tttgtaacat    1740
aaatgcattt cattgacgca gagctgtaaa acaaaagga gttcttccat aaatataaga    1800
tgaagggtgt tagttaactg caatgacaaa gaagattact aagttgctta tatgaaatgt    1860
gggagcttaa atgtgtgaag gatgacccctg taaggtgcca cacccacggc tgaacgtata    1920
taaatggtcc tgtccagatg tggcatgcaa actcagaatc ttctcagtgt aactcagctg    1980
aactcacatc tcccatcaac atg tcc tac aac tgc tgc tct gga aac ttc tcc   2033
               Met Ser Tyr Asn Cys Cys Ser Gly Asn Phe Ser
                 1               5                  10 tcc cgc tcc tgt ggt ggc tac ctg cac tac cca gcc tcc tcc tgt ggc      2081
Ser Arg Ser Cys Gly Gly Tyr Leu His Tyr Pro Ala Ser Ser Cys Gly
         15                  20                  25 ttt tcc tac ccc agc aac cag gtc tac agc act gac ctc tgc tct ccc      2129
Phe Ser Tyr Pro Ser Asn Gln Val Tyr Ser Thr Asp Leu Cys Ser Pro
     30                  35                  40 agc acg tgc cag ctg ggt tcc tct ctc tat agg ggc tgt cag cag acc      2177
Ser Thr Cys Gln Leu Gly Ser Ser Leu Tyr Arg Gly Cys Gln Gln Thr
 45                  50                  55 tgc tgg gag ccc acc agc tgc cag aca tcc tat gtg gag tcc agc ccc      2225
Cys Trp Glu Pro Thr Ser Cys Gln Thr Ser Tyr Val Glu Ser Ser Pro
 60                  65                  70                  75 tgc cag acc tcc tgc tac cgt ccc aga acc tcc ttg ctc tgc agt ccc      2273
Cys Gln Thr Ser Cys Tyr Arg Pro Arg Thr Ser Leu Leu Cys Ser Pro
             80                  85                  90 tgc cag aca act tac tct ggg tct cta ggc ttt gga tcc agc agc tgc      2321
Cys Gln Thr Thr Tyr Ser Gly Ser Leu Gly Phe Gly Ser Ser Ser Cys
             95                 100                 105 cgc tcc ctg ggc tat gga tcg agg agc tgc tac tca gtg ggc tgt ggg      2369
Arg Ser Leu Gly Tyr Gly Ser Arg Ser Cys Tyr Ser Val Gly Cys Gly
         110                 115                 120 tcc agt ggc ttc aga tcc ctg ggt tat gga ggc tgt ggc ttc cct tcc      2417
Ser Ser Gly Phe Arg Ser Leu Gly Tyr Gly Gly Cys Gly Phe Pro Ser
 125                 130                 135 ctg ggc tat ggc gtt gga ttc tgc cgc cca acc tac ttg gct tct agg      2465
Leu Gly Tyr Gly Val Gly Phe Cys Arg Pro Thr Tyr Leu Ala Ser Arg
140                 145                 150                 155 agc tgc cag tct tct tgc tac aga cca act tgt gga tca ggc ttc tac      2513
Ser Cys Gln Ser Ser Cys Tyr Arg Pro Thr Cys Gly Ser Gly Phe Tyr
             160                 165                 170 tat tga tcatcttgtt aaattgctga ttttgttggc taatgccttc aatgcctcta       2569
Tyr
```

-continued

| | |
|---|---|
| ctcataacct ttattgtctt catcatgtac agaaagaatt agcctcttat tctataatta | 2629 |
| tcaagttctc agtttgtctt tgtccccaaa tactggctgg caggcttcat ctgaaaaact | 2689 |
| gtaattggag aactagctca aaataaatct tg | 2721 |

<210> SEQ ID NO 36
<211> LENGTH: 172
<212> TYPE: PRT
<213> ORGANISM: Homo sapiens

<400> SEQUENCE: 36

Met Ser Tyr Asn Cys Cys Ser Gly Asn Phe Ser Arg Ser Cys Gly
1               5                   10                  15

Gly Tyr Leu His Tyr Pro Ala Ser Ser Cys Gly Phe Ser Tyr Pro Ser
            20                  25                  30

Asn Gln Val Tyr Ser Thr Asp Leu Cys Ser Pro Ser Thr Cys Gln Leu
        35                  40                  45

Gly Ser Ser Leu Tyr Arg Gly Cys Gln Gln Thr Cys Trp Glu Pro Thr
    50                  55                  60

Ser Cys Gln Thr Ser Tyr Val Glu Ser Ser Pro Cys Gln Thr Ser Cys
65                  70                  75                  80

Tyr Arg Pro Arg Thr Ser Leu Leu Cys Ser Pro Cys Gln Thr Thr Tyr
                85                  90                  95

Ser Gly Ser Leu Gly Phe Gly Ser Ser Cys Arg Ser Leu Gly Tyr
            100                 105                 110

Gly Ser Arg Ser Cys Tyr Ser Val Gly Cys Gly Ser Ser Gly Phe Arg
        115                 120                 125

Ser Leu Gly Tyr Gly Gly Cys Gly Phe Pro Ser Leu Gly Tyr Gly Val
    130                 135                 140

Gly Phe Cys Arg Pro Thr Tyr Leu Ala Ser Arg Ser Cys Gln Ser Ser
145                 150                 155                 160

Cys Tyr Arg Pro Thr Cys Gly Ser Gly Phe Tyr Tyr
                165                 170

<210> SEQ ID NO 37
<211> LENGTH: 2885
<212> TYPE: DNA
<213> ORGANISM: Homo sapiens
<220> FEATURE:
<221> NAME/KEY: CDS
<222> LOCATION: (2001)..(2519)

<400> SEQUENCE: 37

| | |
|---|---|
| atatgtaatg tagttaaaaa gtgtaccttg cttataattg gaatctaagc aaaagaaaga | 60 |
| tgagaggatg gggcagaagc aatatttgaa gagagtacag ttgggaattt accaatcttg | 120 |
| ataaaagaca tcaactcaca cgtgaaataa taggagaatg gtgtagatct agtctaacta | 180 |
| aggtggagat ggctgaaaaa atgagtttta gcagatatta cctggagaca gtctgaacat | 240 |
| aagctccaaa actaaactca aaagtttgtt tattgtttct ctaaatcatt gaacaactga | 300 |
| aataattttt tttttgttta ccctgattgg catactcaag ataaaatgtt cagtttaaat | 360 |
| ttttgctat ccttcaaaaa attggtttac tttttgtatt agtctattct cacactgcta | 420 |
| taaactacta cctgtgactg ggtaatttat aaagagaaga ggtttaattg actcacagtt | 480 |
| ctgcaggctg tacacgaagc acggctgggg aggcttcagg gaacttacaa tcatggcaga | 540 |
| aaatgaagga gaagcaggca gtcctacaag ggaagcagta gaaagagtga aggggaagt | 600 |

-continued

```
gctacacatt tttaaacaac cagatctcat gagagctaac tcactagcac gagaacagca    660 aggggggaaat ccaccccat gatccaatca tctcccacca ggccttcccc aacactgggg    720
attacaattt ggcctgagat ttgggcaggg acacaaatcc aaacagtatc acttttttaaa   780 aagtataaac aagattaaat atttacagat tttctgcatt ttttctcttt ccagagtctc    840
ccctgagaga ggctgggaga gttgtaagat ttggacatag gtctggccca agtgaaggag    900
aaagagaaag aagtgcttga gacctatgca ggagacagta gttctttaag gccgttgagg    960
aaaccctgag tcaaagctgg ccgtcaattg tcttccagga attcctatat cccactgtgc   1020
tcagtctttg cttgggagca gcccagagaa agcaagcctt ccccaaaaat gcagtgttaa   1080
cttttagaac acagcaggta ggaccactgg ttatttaagc ctcctgtaat ttaagatccg   1140
agatgagaat tctccaggct gccacacata tgaatgagaa tctcttagga ccatgggcct   1200
catattagat gcattgaatc taaaattcat ttatttttt ctgtcatttc aatggtgtgt    1260
gtttatttaa cactttaatt ctcttcataa ggccccagaa ttgttttttca tttgtgattg   1320 tctcagttcc atcccttgct gtcaccatgt ctccaaataa ttgtccaggt ttccttctgg   1380
tcataggcat caatgttatt caatttgtct tggctcatac ttttccctct acactggatg   1440
tgagacacag tgagtaacag tacataatag atgaaggaaa cttttgtgga atgagaaagg   1500
atggtgacat gtaggtttag ttttcagcag gtttctcatt aaggccaaag ttgtgtctct   1560
aatccattga caaaaaagac atgtaacttt atctcatttc tcactgttta gggaaaatta   1620
ttgcccataa cagccaataa caagacacat gaaaattatg ctaggaggaa aaggaggtgc   1680
tttcctagac ataataaaat aaatattaat acgaaacagt catagcattt ctggcataag   1740
tgcagttcat tggctttgtg ctataacacc aaaattatag cacgcataaa tacaacatgt   1800
ggaaaagtat tcaaatgcaa ttacaggcaa gattgctgag ctacacatat gtaaatgagg   1860
gagcacaaaa atgtgaggga tgactctgct gtgcaccaca cctattgctg agaggatata   1920
aatgacactg tccaggatgc cacgttaaaa ctcagaatct tcccaggtac actcagctga   1980
actcacatct tcccgtcaac atg tcc tac aac tgt tgc tct aga aac ttc tcc   2033
                      Met Ser Tyr Asn Cys Cys Ser Arg Asn Phe Ser
                       1               5                  10 tcc tgc tcc cac ggg ggt tac ttg cac tac cca ggc tcc tcc tgt ggc    2081
Ser Cys Ser His Gly Gly Tyr Leu His Tyr Pro Gly Ser Ser Cys Gly
         15                  20                  25 tct tcc tac ccc agc aac ctg gtc tac agc act gac ctc tgc tct ccc    2129
Ser Ser Tyr Pro Ser Asn Leu Val Tyr Ser Thr Asp Leu Cys Ser Pro
     30                  35                  40 agc acc tgc cag ctg ggt tcc tct ctc tat agg ggc tgt cag gag acc    2177
Ser Thr Cys Gln Leu Gly Ser Ser Leu Tyr Arg Gly Cys Gln Glu Thr
 45                  50                  55 tgc tgg agg ccc aac agc tgt cag aca ttg tgt gtt gag tcc agc ccc    2225
Cys Trp Arg Pro Asn Ser Cys Gln Thr Leu Cys Val Glu Ser Ser Pro
 60                  65                  70                  75 tgc cac acc tcc tgc tac tac ccc agg act cac atg ctc tgc aat tct    2273
Cys His Thr Ser Cys Tyr Tyr Pro Arg Thr His Met Leu Cys Asn Ser
             80                  85                  90 tgc ctg act atg cat gtt ggg tct cgg ggt ttt gga tcc aat agc tgc    2321
Cys Leu Thr Met His Val Gly Ser Arg Gly Phe Gly Ser Asn Ser Cys
                 95                 100                 105 tgc tcc ctg agc tgt gga tcc agg agc tgc tcc tca ctg ggc tgt gga    2369
Cys Ser Leu Ser Cys Gly Ser Arg Ser Cys Ser Ser Leu Gly Cys Gly
         110                 115                 120 tcc aat ggc ttc aga tat ctg aat tat aga atc cat acc tcc cct tcc    2417
```

```
                Ser Asn Gly Phe Arg Tyr Leu Asn Tyr Arg Ile His Thr Ser Pro Ser
                    125                 130                 135 cag agt tat aga tcc aga ttc tgc cat cca atc tat ttt cca cct aga         2465
Gln Ser Tyr Arg Ser Arg Phe Cys His Pro Ile Tyr Phe Pro Pro Arg
140                 145                 150                 155 agg tgg ttc cat tca tct tgt tat cag cca ttc tgt aga tct ggt ttc         2513
Arg Trp Phe His Ser Ser Cys Tyr Gln Pro Phe Cys Arg Ser Gly Phe
                160                 165                 170 tac tga ctaatgtggt gactggtaaa actcatttga gaaatgcata ttctttagta          2569
Tyr aggtcatctg ttaatttctt cctttgagaa gtattctaat attattgatc accaggtctt       2629
ccttactttc cagccctcaa aaactgggtt gtatgttagt tctgtcaaac tgcagtttgg       2689
atcaatgaat aatctataac tggatcaatc tggatctata actctgggaa gggaaggcat      2749 ggatttttata attcagatat ctgaagccat tggatcaatg agtgatccaa actgcattat     2809
agatataatt tatagttttt gtatttcttt ccaaaagaga taggaagtga aaaagatttt     2869 atttaataa actctt                                                        2885
```

<210> SEQ ID NO 38
<211> LENGTH: 172
<212> TYPE: PRT
<213> ORGANISM: Homo sapiens

<400> SEQUENCE: 38

```
Met Ser Tyr Asn Cys Cys Ser Arg Asn Phe Ser Ser Cys Ser His Gly
  1               5                  10                  15

Gly Tyr Leu His Tyr Pro Gly Ser Ser Cys Gly Ser Ser Tyr Pro Ser
                 20                  25                  30

Asn Leu Val Tyr Ser Thr Asp Leu Cys Ser Pro Ser Thr Cys Gln Leu
             35                  40                  45

Gly Ser Ser Leu Tyr Arg Gly Cys Gln Glu Thr Cys Trp Arg Pro Asn
         50                  55                  60

Ser Cys Gln Thr Leu Cys Val Glu Ser Pro Cys His Thr Ser Cys
 65                  70                  75                  80

Tyr Tyr Pro Arg Thr His Met Leu Cys Asn Ser Cys Leu Thr Met His
                 85                  90                  95

Val Gly Ser Arg Gly Phe Gly Ser Asn Ser Cys Cys Ser Leu Ser Cys
                100                 105                 110

Gly Ser Arg Ser Cys Ser Ser Leu Gly Cys Gly Ser Asn Gly Phe Arg
            115                 120                 125

Tyr Leu Asn Tyr Arg Ile His Thr Ser Pro Ser Gln Ser Tyr Arg Ser
        130                 135                 140

Arg Phe Cys His Pro Ile Tyr Phe Pro Pro Arg Arg Trp Phe His Ser
145                 150                 155                 160

Ser Cys Tyr Gln Pro Phe Cys Arg Ser Gly Phe Tyr
                165                 170
```

<210> SEQ ID NO 39
<211> LENGTH: 2734
<212> TYPE: DNA
<213> ORGANISM: Homo sapiens
<220> FEATURE:
<221> NAME/KEY: CDS
<222> LOCATION: (2001)..(2483)

<400> SEQUENCE: 39
gaggctccat attaaacaga acaaataata tgatctccaa gatgaagtga gtccaaagtt         60

-continued

| | |
|---|---|
| gtggcattta caagttcttc ttaaacttct atcaaattaa tgtggacaaa gttttagaga | 120 |
| tttagaggca gagagaaggg aagaacacct cttttcacaa taactggttc agagaaggat | 180 |
| ttttgaataa ggagcctgga ttaactgaag acaaattcac taaatccctt agttttgcct | 240 |
| gaataaattc atgctctcca tttaactcat aagttttgta ttcaagatta ttttaaagag | 300 |
| ttacatttga aacaaaagaa aatggggaag gaatagtttc caaacctact tactaaggta | 360 |
| caaggttagg ggaaatcaac tgccattgaa aaatagaaag taactcactg aatagatatt | 420 |
| tgaattggcc atatttgctt cttcttcat tcttccttct ggaaggccta tattaagtta | 480 |
| cttttcaata ttgccataca ttttaattga gaaaatttaa tcgagaaaat gtctaacatt | 540 |
| attgttgtaa gtttattata ttttattata aaataaaatg tcatcaacca tgacagtaca | 600 |
| ctttctttgg tcctgaatat aatttaacta cttgtatttc aacatagaat attttgtgaa | 660 |
| tgaacttaca aagtggctat cctcaaagaa tacgacaaag ctgtccaatt tttatttttc | 720 |
| aacatggaat ctataattca gcagaggcaa acaaacacat gaacaaaaca taaaatataa | 780 |
| caagtaaaaa aaagaaaaaa gataaaatca aacttaagca cagaaaaaag aaagaaaaat | 840 |
| agagggaaag aaagtcagag gaagagagag agaaaataag agagaaacat tcatatacca | 900 |
| tgcagaggaa aagaggactg gggaacaaag aaacttcaca ttttcacagg aaaatgtagg | 960 |
| atggtacctg gttctacaag tggcaaaaag acactgaaag ccagtaatat ggaaagctag | 1020 |
| agccattcta agaaggtaga agtcctgtat aattacaaaa gtagatgata aatatatcaa | 1080 |
| agttcataag atttgctaat tttgaaaatt tttgctcata aagacattga gacaagacac | 1140 |
| atgacagctg gaatgcaata ggaaaaaaaa ttctgaaatt cctgagcttt ctctttgttt | 1200 |
| ctctttcact tgtttcctcc cttcagcaga caagcattcg ggctctttgg ctgaagagac | 1260 |
| atgacctcaa attgatcttc tctgtgactg tgtttcaatc gagcttcttt ttgttatctc | 1320 |
| gtctttaaat aaatggcaag gtttctttca atttctagcc atttctttct atctctttgc | 1380 |
| tttgcctgtt cttgatcttt cttcactgga tatgagacag actttataac tgtagtactt | 1440 |
| aatgtattaa tttactctta ccgccctaaa aaatcaccac aaagtaattt tggagtatag | 1500 |
| caatcaatgg tgacaagatg gatcatttc acaaggttc tcatccaggt ggaaattgca | 1560 |
| ccagaaagaa actaacgtta tctcattccc cactcttaag aggaaaacat ctactagcaa | 1620 |
| agccagatgt gaatacacag gaaaagaggc agttagcatg tgccaaagaa ataggaagag | 1680 |
| cttccttgt catgatgagc tagacattaa tataaaacag tcatagcatt tctgacataa | 1740 |
| gtacagttca ttggctttgt gctataacac gaaaattata gcacccataa atacaataca | 1800 |
| tggaaaacta ttcaaatgca attacagaca agattacgca gttacacata tgtaaatgag | 1860 |
| ggatcacaaa tatgtaaagg atgaccctgt tgggcaccac acctattgct gagaggatat | 1920 |
| aaatgccctt gtccaggatg cgacattaaa actcagaatc ttcttaggta cactcagctg | 1980 |

| | | |
|---|---|---|
| aactcccatc tctcatcagc atg tcc tac aac tgc tgc tct aga aac ttc tcc | | 2033 |
| Met Ser Tyr Asn Cys Cys Ser Arg Asn Phe Ser | | |
| 1 5 10 | | |
| tcc cgc tcc ttt ggg ggc tac ctg tac tac cca ggc tcc tac ccc agc | | 2081 |
| Ser Arg Ser Phe Gly Gly Tyr Leu Tyr Tyr Pro Gly Ser Tyr Pro Ser | | |
| 15 20 25 | | |
| agc ctg gtc tac agc act gcc ctc tgc tct ccc agc acc tgc cag ctg | | 2129 |
| Ser Leu Val Tyr Ser Thr Ala Leu Cys Ser Pro Ser Thr Cys Gln Leu | | |
| 30 35 40 | | |
| cgt tcc tct ctc tac agg gac tgt cag aag acc tgc tgg gag ccc gcc | | 2177 |
| Arg Ser Ser Leu Tyr Arg Asp Cys Gln Lys Thr Cys Trp Glu Pro Ala | | |

-continued

```
                45                  50                  55
agc tgc cag aaa tcc tgc tac cgc ccc agg acc tcc atc ctc tgc tgt        2225
Ser Cys Gln Lys Ser Cys Tyr Arg Pro Arg Thr Ser Ile Leu Cys Cys
 60                  65                  70                  75 ccc tgt cag acg act tgc tct gga tct cta ggc ttt cgg tcc agc agc        2273
Pro Cys Gln Thr Thr Cys Ser Gly Ser Leu Gly Phe Arg Ser Ser Ser
                 80                  85                  90 tgt cgc tcc cag ggc tat gga tct agg tgc tgc tac tcg ctg gga aat        2321
Cys Arg Ser Gln Gly Tyr Gly Ser Arg Cys Cys Tyr Ser Leu Gly Asn
             95                 100                 105 gga tcc agt ggc ttc aga ttc ctg aaa tat gga ggc tgt ggt ttt cct        2369
Gly Ser Ser Gly Phe Arg Phe Leu Lys Tyr Gly Gly Cys Gly Phe Pro
        110                 115                 120 tcc ctg agt tac gga tcc aga ttc tgc tac cca aac tac ttg gct tct        2417
Ser Leu Ser Tyr Gly Ser Arg Phe Cys Tyr Pro Asn Tyr Leu Ala Ser
    125                 130                 135 gga gcc tgg cag tct tct tgt tac aga cca atc tgt gga tct cgc ttc        2465
Gly Ala Trp Gln Ser Ser Cys Tyr Arg Pro Ile Cys Gly Ser Arg Phe
140                 145                 150                 155 tat caa ttc acc tgc taa atttctagat cctttgagt attgggatca                2513
Tyr Gln Phe Thr Cys
                160 aagtctctac tgaatgcagc cattatttc attcttgcca gatcccaata tcttttatt       2573 cttccaccac cagcttcttg catgaccaac ttctggcaga ctgcgaaatt aatgagtaac       2633 ctaatattaa cttctaatat ctttaccatt gatcgaatat atgctatctg attttcatcc       2693 aaaaactgtt gaaatggaa attttaatct aataaatgta t                           2734
```

<210> SEQ ID NO 40
<211> LENGTH: 160
<212> TYPE: PRT
<213> ORGANISM: Homo sapiens

<400> SEQUENCE: 40

```
Met Ser Tyr Asn Cys Cys Ser Arg Asn Phe Ser Ser Arg Ser Phe Gly
 1               5                  10                  15

Gly Tyr Leu Tyr Tyr Pro Gly Ser Tyr Pro Ser Ser Leu Val Tyr Ser
            20                  25                  30

Thr Ala Leu Cys Ser Pro Ser Thr Cys Gln Leu Arg Ser Ser Leu Tyr
        35                  40                  45

Arg Asp Cys Gln Lys Thr Cys Trp Glu Pro Ala Ser Cys Gln Lys Ser
    50                  55                  60

Cys Tyr Arg Pro Arg Thr Ser Ile Leu Cys Cys Pro Cys Gln Thr Thr
 65                  70                  75                  80

Cys Ser Gly Ser Leu Gly Phe Arg Ser Ser Ser Cys Arg Ser Gln Gly
                85                  90                  95

Tyr Gly Ser Arg Cys Cys Tyr Ser Leu Gly Asn Gly Ser Ser Gly Phe
           100                 105                 110

Arg Phe Leu Lys Tyr Gly Gly Cys Gly Phe Pro Ser Leu Ser Tyr Gly
        115                 120                 125

Ser Arg Phe Cys Tyr Pro Asn Tyr Leu Ala Ser Gly Ala Trp Gln Ser
    130                 135                 140

Ser Cys Tyr Arg Pro Ile Cys Gly Ser Arg Phe Tyr Gln Phe Thr Cys
145                 150                 155                 160
```

<210> SEQ ID NO 41
<211> LENGTH: 3122

-continued

```
<212> TYPE: DNA
<213> ORGANISM: Homo sapiens
<220> FEATURE:
<221> NAME/KEY: CDS
<222> LOCATION: (2001)..(2414)

<400> SEQUENCE: 41
```

| | | | | |
|---|---|---|---|---|
| attcaatatt ttattgacaa acacaacagg aagatttgga atctactaga atgcttttg | | | | 60 |
| gctattaata attgagaagc ctaataaata agaattgttt attccagaaa cacagaacaa | | | | 120 |
| actatgttac ttaataaatg aaacatgatt ggagatcaat ttgtctcctc aaaagtttag | | | | 180 |
| acttataaag tctacaattt ggaaggaagt tgagcaatta tctccagcct cctgtcagat | | | | 240 |
| tggaattcca cttacaacat cctaattaga ttttcccagg gccctcagta tggaaatatc | | | | 300 |
| attaattgca agagcaactc atttagatt tttagctgaa tcttcccta aaacttttac | | | | 360 |
| ctagtaatcc tgattcttca tagaagggag tctcagttca cttccattgt agaatacatc | | | | 420 |
| agttctgaag atggatgtct taagaggttt gcccattccc acaggttaag gcatttcctg | | | | 480 |
| catccgtgcc atatatctat ttacagtttg ctctgatgaa cttctgagc gaatccagaa | | | | 540 |
| aaatcctcat tactctagta ctctaggcag aatatatatg tcagctgata catcagaggt | | | | 600 |
| cacaaaggca ttcactctca attacacatt atcatcatgt atccttccca cccctttatt | | | | 660 |
| tcaatttata aagtcatttg ttactatgaa ttctttacat attttatctt tctgtaata | | | | 720 |
| ctacatggga tagacatttc cctcatttct tgcttttctt ttccctctct ggtaaaaatg | | | | 780 |
| tcaccctctg agagaaaaga aaggaaaaga ttaacgattt acatttttact tatagtgctt | | | | 840 |
| attattttcc tctcagtaac atcaacatga ccaaaaatta cttataccttt atgggataa | | | | 900 |
| acggtttttt ataatcaaac ttattgatga cttctatgaa gaagcaaatc aacctttgag | | | | 960 |
| taagggatt ctttagtagt tttacaatgt aaacttcaaa gcacttgttc aaaaatttca | | | | 1020 |
| cccttcattc ttaactcttc atgtgcacaa gagtgactta gctacttgtg ttataagaaa | | | | 1080 |
| tctaaactta aatatgttag gcactcattt agcatgtcta ccaaataagg attgttattg | | | | 1140 |
| ggttatttct tctaatggtt caagaattg aaagaaggaa tagatattga aattttttt | | | | 1200 |
| ctgttctcaa ttgaatttat aaaattggag caagatcaaa gtcccttcca gattacaagg | | | | 1260 |
| tatttttcag atctttacaa ataccagaac tctcagtgtc ttagccgttt gatccaattt | | | | 1320 |
| ctagaaggac aggatgaatg aagcatcaag tttttttctt tgttttttg tttctttgtt | | | | 1380 |
| tgtttgtttg ttttggagat ggaatcttgc tctgtctccc aggctggagt gcagtggtac | | | | 1440 |
| gatctcggct cactgcaaac tccgcctccc gggttcaagc aattctcctg cctcagcctc | | | | 1500 |
| ctgagtagct gggattacag ccgcccacca ccatgcccgg ctaattttg tattttagt | | | | 1560 |
| agagacggag tttcaccatg ttggtcaggc tggtctggaa ctcctgacct cgtgatatgc | | | | 1620 |
| ctgcctcagc ctcccaaagt gctggaatta caagtgtgag cctccgcgcc cgacccttg | | | | 1680 |
| aagcatcagt cttataggta caattatggt ggttttcatt ctacctaagc aagatgaatg | | | | 1740 |
| agaaatggca ttttgtttc atgaacaatt gctttgaaaa actaatgaaa ttctttcatg | | | | 1800 |
| tagaagtcta cgttcataaa taaaattctt tgagtgttaa tatatttcat tttgactgca | | | | 1860 |
| gcctaattaa gtgttctcat tagaatgggc acttgtgact acacctattg ctagagtatg | | | | 1920 |
| tcagtgtcca gtatagaagg taacattcac acacacgc tcctcactgc aaatcacctg | | | | 1980 |
| agctcagaac tcctgttaac atg tct tac aac tgc agc tct gga aac ttc tcc | | | | 2033 |
| | Met Ser Tyr Asn Cys Ser Ser Gly Asn Phe Ser | | | |
| | 1 5 10 | | | |
| tcc tgc tgt ttt gga agt tac ctg agg tat cca gtt tcc act tat aat | | | | 2081 |

```
Ser Cys Cys Phe Gly Ser Tyr Leu Arg Tyr Pro Val Ser Thr Tyr Asn
            15                  20                  25 ttg ttc tac ccc agc aat gcc atc tat tct cca aat acc tgc caa ctg    2129
Leu Phe Tyr Pro Ser Asn Ala Ile Tyr Ser Pro Asn Thr Cys Gln Leu
        30                  35                  40 ggc tcc tct ctc tac aat ggc tgt cag gag acc tac tgt gag ccc acc    2177
Gly Ser Ser Leu Tyr Asn Gly Cys Gln Glu Thr Tyr Cys Glu Pro Thr
            45                  50                  55 agc tgc cag aca tcc tgc act ttg gcc aga tcc tat cag aca tcc tgt    2225
Ser Cys Gln Thr Ser Cys Thr Leu Ala Arg Ser Tyr Gln Thr Ser Cys
 60                  65                  70                  75 tac tgc cca aag aat tcc atc ttc tgc agt ccc cgc cag act aac tac    2273
Tyr Cys Pro Lys Asn Ser Ile Phe Cys Ser Pro Arg Gln Thr Asn Tyr
                80                  85                  90 ata aga tcc ctt gga tgt gga aac act ggc ctt gga tct ctt ggt tgt    2321
Ile Arg Ser Leu Gly Cys Gly Asn Thr Gly Leu Gly Ser Leu Gly Cys
                    95                 100                 105 gga agc act ggc ttc caa tct ctg gac tgt ggg tcc agc ttc tac cac    2369
Gly Ser Thr Gly Phe Gln Ser Leu Asp Cys Gly Ser Ser Phe Tyr His
            110                 115                 120 cca act acc ttt tca tcc agg aat ttc cag gca act tgt tac taa        2414
Pro Thr Thr Phe Ser Ser Arg Asn Phe Gln Ala Thr Cys Tyr
        125                 130                 135 ccagcctttg ggtctcgcct ttttggatca tcttactgaa tattctccat tctctcatga   2474
ttatttctgt actctatgga actgcaacac tcagcctgtc caatatctgt gattgttgac   2534
catctacatc agtaggactc agcatcctag ccctcttgga agtatatgat tgaacacgga   2594
caaattaatc ttgacctagg acccttccta aatctgacag gagatatatc ttgaatttca   2654
atttttgtgc caatgctcag gatcatttct gttatcatct ttctaaaatc cttctctcat   2714
tattttccca gaactcttcc actcaaatat atttcaaata gttacaatat tttaaataag   2774
cttatttctt tggcatgaat tctggcattc cattttattt tgttaataca atacacttag   2834
gctgggcatg atggctcaca cctgtaatcc cagcactttg ggagactgag gctggcggat   2894
cactttaggt caagagtttg aggccatcct ggccaacaca gtgaaaaccc atttctacta   2954
aaaatacaaa aattagcaag gcctggtgtg cacctataat cccagctact caggaggctg   3014
aggcaggcga atcacttgaa tctgagagac ggaggttgta gtcagctgag atcatgccac   3074
tacactccag cctgggcaac aaagtgggac tctgtgtcaa aaataaa               3122
```

<210> SEQ ID NO 42
<211> LENGTH: 137
<212> TYPE: PRT
<213> ORGANISM: Homo sapiens

<400> SEQUENCE: 42

```
Met Ser Tyr Asn Cys Ser Ser Gly Asn Phe Ser Ser Cys Cys Phe Gly
 1               5                  10                  15

Ser Tyr Leu Arg Tyr Pro Val Ser Thr Tyr Asn Leu Phe Tyr Pro Ser
            20                  25                  30

Asn Ala Ile Tyr Ser Pro Asn Thr Cys Gln Leu Gly Ser Ser Leu Tyr
        35                  40                  45

Asn Gly Cys Gln Glu Thr Tyr Cys Glu Pro Thr Ser Cys Gln Thr Ser
    50                  55                  60

Cys Thr Leu Ala Arg Ser Tyr Gln Thr Ser Cys Tyr Cys Pro Lys Asn
 65                  70                  75                  80

Ser Ile Phe Cys Ser Pro Arg Gln Thr Asn Tyr Ile Arg Ser Leu Gly
```

```
                85                  90                  95
Cys Gly Asn Thr Gly Leu Gly Ser Leu Gly Cys Gly Ser Thr Gly Phe
            100                 105                 110
Gln Ser Leu Asp Cys Gly Ser Ser Phe Tyr His Pro Thr Thr Phe Ser
        115                 120                 125
Ser Arg Asn Phe Gln Ala Thr Cys Tyr
    130                 135
```

<210> SEQ ID NO 43
<211> LENGTH: 2601
<212> TYPE: DNA
<213> ORGANISM: Homo sapiens
<220> FEATURE:
<221> NAME/KEY: CDS
<222> LOCATION: (2001)..(2273)

<400> SEQUENCE: 43

| | | | | | |
|---|---|---|---|---|---|
| atgcttcatt | caaataatat | ttttgaatgc | caactaaata | tgagactttg | ttttgacact | 60 |
| cagcaggtca | gagaaacacc | gcattgtaaa | aaaaaaaaaa | gtgtgacttg | aacagaaagt | 120 |
| cattatgttt | agggaaataa | acaggcacac | aaagagaggt | atcacatgtt | ctcactcata | 180 |
| agtgggagat | aaaaaagtta | atcttatgaa | tgtagagaaa | agagtgatag | atatcagatg | 240 |
| ctggaatggg | tgtgtgggtg | caggagagat | aaaagttgga | tgaaaggtat | aagttctatt | 300 |
| gcagagtgac | tatagttaac | aacaatatac | tgtatatttc | aaagtagctg | aagagagag | 360 |
| cttgatttat | tcccaacata | agaaatgat | aaatatttaa | agtgatggat | atttcaatta | 420 |
| ctctaccttg | aacattatac | attctatgca | tgcaattaaa | tatcatatgt | atctaataag | 480 |
| tatgtaaaat | atgtatcaat | aaaaaattta | ataaaaataa | aaattttaaa | atgtgtcatt | 540 |
| cggttactca | taaatctcaa | aaaaatctta | gtagtatgat | tatagtcata | taaaactgat | 600 |
| acctttctgg | agttccaagt | ttcaagatat | aggtacatct | ggatgaggct | taatcaggta | 660 |
| tgaggtaagc | cttgggcatt | tctaactcta | tgggctgagc | tgagggactc | actggtcaac | 720 |
| tctccctaca | gagctactcc | ttcttttcta | tattttcac | aattgtccct | acatttaga | 780 |
| gaatttcgtg | ttaatctaag | ttgcacaaat | attttttaa | atttcagata | atttgaagag | 840 |
| ttgaaaaatg | ttttaaacaa | gaaacaccat | aatcaatatc | ttagaagatc | tagttgatt | 900 |
| ctcaggaaaa | gataactaga | aagcggttaa | acaaagcac | aacaaaaaac | atgggcacag | 960 |
| aataggcaaa | gacaagggca | atattgact | atggagatct | aaatggaaag | aatgaatgtt | 1020 |
| gatttgagta | aataggttgt | agccagaaca | ttttacctac | ttcaaacttt | tacctggtta | 1080 |
| tagtaatgaa | ttgtggagga | aaagaagttg | ggtgaaattt | gaagtgagat | cagcaaaaga | 1140 |
| tgcaagaggg | atgaattaat | gacaaaaggt | agagaaagaa | aaacaattct | gtatgaaggc | 1200 |
| agattataat | cttcattttt | tggtaacagt | gaggttagaa | catataatgg | agaagggact | 1260 |
| tgagatataa | atagaaaact | ctggaaagac | cagatgagat | gggctttga | tccctgtaag | 1320 |
| agtctctcca | cttatgacta | caattgtgct | atgttcttaa | acaaaacaa | atattttgta | 1380 |
| tgctgttgtg | caaagcccaa | aataaatata | acaattgtgc | atgatcaaag | ttttaaaagt | 1440 |
| ctacaaatta | ggtgacattt | gtttctttca | ggtacataca | cagatgaatc | aaatctttct | 1500 |
| tgcttctcac | tctacaaaat | atgtgtgttt | tatgaagaaa | ctgatgaaag | taagagtctt | 1560 |
| gaccttggct | atttcttgaa | attttgtgga | atcaactata | accacgtcca | aaaatgctag | 1620 |
| tgatgagaat | atatttgaat | agaaattcaa | gaatttttaa | tgtgactgat | gttaagtgac | 1680 |
| tggtaataaa | gaattctatt | taaggtttgg | tatgttttag | actttgaaga | agcagcaatc | 1740 |

-continued

```
ccttctaata aaattaaagc agcaagctca gggacaacct aactaggtag ccaaacaagc    1800
tcaggcaatc ttactgagtg ttgtcagggg acaatagatt aacgagctgc ctcaggcaag    1860
tataattcat ggaatgacac aaaaagaggg gcacatgttt atcacatgct ctgaccaggg    1920
tatataaacc tcctatacat gctggcattc acactcagga tcttgcctga caacaaacc     1980 aactcaccac tcctgacacc atg agt cac tac ggc agc tac tac gga ggc ctg    2033
                      Met Ser His Tyr Gly Ser Tyr Tyr Gly Gly Leu
                        1               5                  10 ggc tac agc tgt gga ggc ttc ggt ggc ctg ggc tat ggc tat ggc tgt      2081
Gly Tyr Ser Cys Gly Gly Phe Gly Gly Leu Gly Tyr Gly Tyr Gly Cys
             15                  20                  25 gga tgt ggc agc ttc tgc aga cgg ggt tct ggc tgt ggc tat gga ggc      2129
Gly Cys Gly Ser Phe Cys Arg Arg Gly Ser Gly Cys Gly Tyr Gly Gly
         30                  35                  40 tac gga tat ggc tct ggc ttt gga agc tac gga tat ggc tct ggc ttt      2177
Tyr Gly Tyr Gly Ser Gly Phe Gly Ser Tyr Gly Tyr Gly Ser Gly Phe
     45                  50                  55 gga ggc tac gga tat ggc tct ggc ttt gga ggc tat gga tat ggc tgc      2225
Gly Gly Tyr Gly Tyr Gly Ser Gly Phe Gly Gly Tyr Gly Tyr Gly Cys
 60                  65                  70                  75 tgc cgc cca tcg tac aat gga gga tac gga ttc tct ggc ttt tat taa      2273
Cys Arg Pro Ser Tyr Asn Gly Gly Tyr Gly Phe Ser Gly Phe Tyr
                 80                  85                  90 atgaattgct gaaattggaa gcagaggaga aacctccaaa tgtgtttggt cctgtcccgt    2333
gctttcattc caaaaatcca ttctattgcc ttcagcatca atggagagat atttagctat    2393
gttaaatctt taaatagat ttaagctgct tctgtgaata tttgttgtct ttttactttc     2453
ggagtccgtc acctgaaatc atattcatgt ataactactc taggttgttc ttctaaattt    2513
gctttatttt tcttaccacc attaccttga tgttatctat caagatccta gcaaaaactt    2573
gtattttgct tttatctaat aaatgaag                                       2601
```

<210> SEQ ID NO 44
<211> LENGTH: 90
<212> TYPE: PRT
<213> ORGANISM: Homo sapiens

<400> SEQUENCE: 44

```
Met Ser His Tyr Gly Ser Tyr Tyr Gly Gly Leu Gly Tyr Ser Cys Gly
  1               5                  10                  15

Gly Phe Gly Gly Leu Gly Tyr Gly Tyr Gly Cys Gly Cys Gly Ser Phe
             20                  25                  30

Cys Arg Arg Gly Ser Gly Cys Gly Tyr Gly Gly Tyr Gly Tyr Gly Ser
         35                  40                  45

Gly Phe Gly Ser Tyr Gly Tyr Gly Ser Gly Phe Gly Gly Tyr Gly Tyr
     50                  55                  60

Gly Ser Gly Phe Gly Gly Tyr Gly Tyr Gly Cys Cys Arg Pro Ser Tyr
 65                  70                  75                  80

Asn Gly Gly Tyr Gly Phe Ser Gly Phe Tyr
                 85                  90
```

<210> SEQ ID NO 45
<211> LENGTH: 2480
<212> TYPE: DNA
<213> ORGANISM: Homo sapiens
<220> FEATURE:
<221> NAME/KEY: CDS
<222> LOCATION: (2001)..(2246)

<400> SEQUENCE: 45

```
ataggttatt tgttcctcta agaaagaaa gctatttgag ctaatttctc ttttaaattc      60
ttattgttgg atacattcgt agtattgttc atttctatga gatgtaagat ttttacctgt    120
aagaactaga attcattcat ctattcaaca cttatatatt gagtttctat tgcatgctgg    180
tcattgaact gcagccagca aatctatctg gagaaatgca caatttcaaa attgcttata    240
aactcatcaa agcttaaca gtatattcaa agtaataaaa attaaacaag aaattatata    300
tttaagctta aagttaaggg catatgtggg tggggtttgg ggtcagcctt gggtctaggt    360
gactaaattc ttagagtcag ctgaggtact ctttgtcttt aattattatt tccttcatcc    420
tgtcttttta tattatacat attttaggg gattcctaag acattcacaa tgctaacagt    480
ctcttactga attccccagg gtctttggcg atggcatcta ttaacatcta acactttaat    540
aaatacctaa catcttagta aagcttagtt agctattttc ttttaggaaa aaaagaaac    600
acacaatagg taaggtaac ataaaggcaa aaatatctga aaaatcgaag attttatta    660
tatatatata tgaatttaag taagtattaa atgaaaatgg atgggaggca aaagaattg    720
catatatttc accatctcac ctagtcccag accctaatgg gaactgaaag aatatattga    780
aaagaggagg ccgggcgctg tggctcatgc ctgtaatccc agcactgtgg gaggccgaga    840
cgggtggatc acgaggtcag gagatcgaga ccatccgggc taacacggtg aaaccccgtc    900
tctactaaaa atacaaaaaa aaattagccg ggcgtggtgg cgggtgcctg tagtcccagc    960
taatccggag gctgaggccg gagaatggcg tgaacccggg tggtggagct tgcagtgagc   1020
cgagacagcg ccactgcact ccagcctggg cgaaagagcg agattctgtc tcagaaaaaa   1080
aaaaaaaaag aaaagaaaag aggataattg tgtggatcag gaaaaggaa tgaatgggag   1140
gagggcaata caatctgtat ttttggtagc accttggatg tctaatatgc cagtaaggga   1200
gtcgggatgt gaaaacaatt tgaacagtt tgtaaagctg cttaggaaat agattttga   1260
ttactgtgat ttgactttaa tgtttgagca atatactgtt gtgttgttaa atcaaaatgg   1320
ttttttatttt ttaaacgagt aaaaccaaaa aaagagaata ttggttatga tggccaatgt   1380
tctagagtaa tagaagaatg atggctttat tttaactttt ttaaccccat gaaattcttt   1440
actgttaggc atagcaggtg agcagatggc tccagtcttt caaatgtttg cttctcttta   1500
aaaagggacc tcacctgagg taatagatac ctctggaaga atataataaa tttcagagca   1560
ttgaatttaa ccaaagtctg ttatttaatc ataaatgagt aaaacaattc aaggaaagcc   1620
agagatgaag caatatttaa tttcaaaaca tagcattacc aactatgtaa tgcaatatgc   1680
ctacgaagaa gtctatttaa ggtctggtat gcacagactt tgaagctaca gcaatttctt   1740
ctcataaaag tgatgcaata tgttaaaggg acagcatgag aagacagcaa tgcaagctca   1800
aacactttaa tgagtttgag ggcctcttca gatgtcagga ttgggtcagg taagtgtaac   1860
atacacaact acactaaaat aggcagcaag tgttttgtta cgtgatgtgt cagggtatat   1920
aagcatgcct gcacagatgt caacattcac actcaggacc ttgccttgag cagcaaacca   1980
aactcactac ccctgacacc atg agc tac tac ggc agc tac tat gga ggc ctg   2033
                        Met Ser Tyr Tyr Gly Ser Tyr Tyr Gly Gly Leu
                          1               5                   10
ggc tat ggc tgt gga ggc ttt ggt ggc ctg ggc tat ggc tat ggc tgt     2081
Gly Tyr Gly Cys Gly Gly Phe Gly Gly Leu Gly Tyr Gly Tyr Gly Cys
             15                  20                  25
gga tgt ggc agc ttc cgc aga ctg ggt tct ggc tgt ggc tat gga ggc     2129
Gly Cys Gly Ser Phe Arg Arg Leu Gly Ser Gly Cys Gly Tyr Gly Gly
```

```
                30              35              40
tac gga tat ggc tct ggc ttt gga ggc tat gga tat ggc tct ggc ttc      2177
Tyr Gly Tyr Gly Ser Gly Phe Gly Gly Tyr Gly Tyr Gly Ser Gly Phe
         45                  50                  55 gga ggc tac gga tat ggc tgc tac cgc cca tca tac tat gga gga tat      2225
Gly Gly Tyr Gly Tyr Gly Cys Tyr Arg Pro Ser Tyr Tyr Gly Gly Tyr
 60                  65                  70                  75 gga ttc tct gga ttc tat taa actactgccc cagcaacaca atgtgtgaaa         2276
Gly Phe Ser Gly Phe Tyr
                 80 ttataagagg actttcccag agctgacttc aatcattgga caacaaagat catgctggag    2336 ctatttgcac aaaagaattt aacatctcag aatttcaggc aattttttt ctctgtatac     2396 ccacatctct ataataatcc tagtattctc tactttgct tttaaagctg attgaattat     2456 ctgtttatct tccaataaaa catt                                           2480

<210> SEQ ID NO 46
<211> LENGTH: 81
<212> TYPE: PRT
<213> ORGANISM: Homo sapiens

<400> SEQUENCE: 46

Met Ser Tyr Tyr Gly Ser Tyr Tyr Gly Gly Leu Gly Tyr Gly Cys Gly
 1               5                   10                  15

Gly Phe Gly Gly Leu Gly Tyr Gly Tyr Gly Cys Gly Cys Gly Ser Phe
                 20                  25                  30

Arg Arg Leu Gly Ser Gly Cys Gly Tyr Gly Gly Tyr Gly Tyr Gly Ser
             35                  40                  45

Gly Phe Gly Gly Tyr Gly Tyr Gly Ser Gly Phe Gly Gly Tyr Gly Tyr
         50                  55                  60

Gly Cys Tyr Arg Pro Ser Tyr Tyr Gly Gly Tyr Gly Phe Ser Gly Phe
 65                  70                  75                  80

Tyr

<210> SEQ ID NO 47
<211> LENGTH: 2450
<212> TYPE: DNA
<213> ORGANISM: Homo sapiens
<220> FEATURE:
<221> NAME/KEY: CDS
<222> LOCATION: (2001)..(2219)

<400> SEQUENCE: 47
aatacttata aatctcacaa aaactcacca gcatgttcaa agtcatgtaa attaaatgaa     60
tttttagttg tcgaagccaa gagacaggtg ctgcatggag attaatcaag agtggtctca   120
atgttgtatc tgtttcacta attcaacaaa gtcagctgag gaactctatg aagcccaggg   180
caaatttctt tacatatgtt tctctattct gtgccatttc accatggtgc ctttattttg   240
aaaactttga agacaatttc tattttagga tacctttaa atttcagaaa gccataggag    300
ttggagtaca tttaaaaaa cccatcccct caagtattta tctgttgagt taacaaacag    360
tctaatttta ctcaagacat tttaaaatgt acaattaagt tgttattgac tatagtcact   420
ctattgtgct atcaaatagt aggtcttatt cattatttct aagtattttt gctggggtgg   480
ggagttgagg atgtttagta agtacaaaaa atagaaagct ttaaaaatga tattttaatg   540
aactattaac agatcagtag gcagtggtta gaaattacct cagaataaat gagtacagga   600
tagacataga agaacatcag aatcacgcct gtaatcctag cactttgcgg ggccgaggcg   660
```

```
ggcagatcac gagatcagga gatcaagacc attctggcta acatggtgaa accccgtctg    720
tactaaaaat ccaaaaaaaa tagccaggcg tggtggcggg cgcctgtagt cccagctact    780
ggggaggttg aggcaggaga atggcgtgaa cccgggaggc ggagcttgta gtaagccgag    840
atggtgccac tgcactccag actgggcgac agagtgagac tccgtctcaa aaacaaaca    900 aacaaaaaaa tcaggaaaga tgttacagtg aatacaaaga ggagatagaa aaaaaaagc    960 gttgagataa gtcgatggaa gacagaggga atgtatgcaa taaacttcta cctggctgtt   1020
tctatagaca ttaagaaaat gggaagaaga ataaaagctg aaatgagaaa ggaaatagag   1080
gtcatatata cactactgaa aaatgataaa gaaagaaagt aattgactag aatgtgcaaa   1140
acagaggcag atgcaatctg caattttacc aggactttga ataaaaccaa ttataaagga   1200
gagttttagg acttgaatgg aaaactaaag tgctactctg ataagtctgc gtaggagatg   1260
gattttgtgc cctcaatttc tgaaattaat tcttatgtat tttgcaacca aaaggttctg   1320
aagctggtgt gcaaagtcaa aaatagtata aaagttattg tgaataaaat gctaaaaatc   1380
agcatacact ctcttttttt gagtcctttg gcgattgtac acagcagggc attaaaatca   1440
ttttgatttc aaatgttttc ctgtattgtg catataggca ctttctgaag acctcacctt   1500
gataaataag tttgcttttt aaaactatag atttaacatc tgtaaattga aaaacagct    1560 gtaaatttag ttgaatatga agttatcagt ttggaagatg acggacaaag gaaattattc   1620
attataaaag gaataccata aagtgtagat gatgtaatac acctggtaat aggcaattct   1680
gttgagcatt tggaatgtgc atattttgaa cagtaagccc tttcttttca taaagcaaa    1740 gcagtaagtt caatcgtgtc ctgaataaga cattaagtaa gctgaaatat tttaatgaga   1800
atgagggcat ctccctacat cagaagacaa tagataaatg agttgtaaca tcaaacgtaa   1860
tacaaataac tatagcaaag gagggtatac agatgactca tcacacgctc tgaccagggt   1920
atataagcct cctacacatg ctggtgttca cactcaggat cttgccttga gcagcatacc   1980
aactcaccac tcctgacacc atg aac tac tac ggc aac tac tat gga ggc ctg   2033
                       Met Asn Tyr Tyr Gly Asn Tyr Tyr Gly Gly Leu
                        1               5                       10 ggc tac ggc tac gga ggc ttc gat gac ctg ggc tat ggc tat ggc tgt    2081
Gly Tyr Gly Tyr Gly Gly Phe Asp Asp Leu Gly Tyr Gly Tyr Gly Cys
             15                  20                      25 gga tgt ggc agc ttc cgc aga ctg ggc tat ggc ggt ggc tac gga ggc    2129
Gly Cys Gly Ser Phe Arg Arg Leu Gly Tyr Gly Gly Gly Tyr Gly Gly
         30                  35                  40 tac gga tac ggc tct ggc ttc gga ggc tat gga tac cgc agc tgc cgt    2177
Tyr Gly Tyr Gly Ser Gly Phe Gly Gly Tyr Gly Tyr Arg Ser Cys Arg
     45                  50                  55 cca tca tgc tat gga gga tat gga ttc tct gga ttt tat tga            2219
Pro Ser Cys Tyr Gly Gly Tyr Gly Phe Ser Gly Phe Tyr
 60                  65                  70 aatccttccc tgacaaccta acatgagggg acataagaag atcacccaaa cctgactgca   2279
ataacaaaca aacgaggtca ccctggatca agccaagatc aagagcagtt agcatctaag   2339
aggtttaaga ataccctatca ttccataatt ctttgcttta tgtctctgga tgtgtcttac   2399
ttgtaccttt ataactgtgg ggtttctctg ttccttttag aataaattat g            2450
```

<210> SEQ ID NO 48
<211> LENGTH: 72
<212> TYPE: PRT
<213> ORGANISM: Homo sapiens

<400> SEQUENCE: 48

```
Met Asn Tyr Tyr Gly Asn Tyr Tyr Gly Gly Leu Gly Tyr Gly Tyr Gly
 1               5                   10                  15

Gly Phe Asp Asp Leu Gly Tyr Gly Tyr Gly Cys Gly Cys Gly Ser Phe
            20                  25                  30

Arg Arg Leu Gly Tyr Gly Gly Gly Tyr Gly Gly Tyr Gly Tyr Gly Ser
        35                  40                  45

Gly Phe Gly Gly Tyr Gly Tyr Arg Ser Cys Arg Pro Ser Cys Tyr Gly
    50                  55                  60

Gly Tyr Gly Phe Ser Gly Phe Tyr
65                  70
```

<210> SEQ ID NO 49
<211> LENGTH: 2421
<212> TYPE: DNA
<213> ORGANISM: Homo sapiens
<220> FEATURE:
<221> NAME/KEY: CDS
<222> LOCATION: (2001)..(2177)

<400> SEQUENCE: 49

| | |
|---|---|
| gggcattggt ctcagcaaaa attccttgag taagattcca caagcacagg ccaccaaagc | 60 |
| aaaaatggac acataggatt acatcacgtt aaaaagcttc tgcacagcaa aggaagcaat | 120 |
| caacaaaatg aagagacaac ccacagaatg aagaaaata tttgtaaact atgcatctga | 180 |
| caagggatta ataaccagaa tatataagga gctcaaacaa atctgtacgg aaaaaaaaaa | 240 |
| tctaataatc tgattagaaa tggacaaaag aaccaaatag atgttttgga atcctcattc | 300 |
| gctattagtg gggatggaaa ttagtacaac cactatggag aacagtttgg aggtttctca | 360 |
| aaaaacaaag aatgaagcta ccatatgaca cagaaatccc actgctggtg ctaaactcat | 420 |
| ctttagcatc aaacctaatc tctagtccct gacaccatga gctactacag cagctactat | 480 |
| ggaggcctgg tatacatcca aggaaggga aaacagtata tcaaagagat atgtgcactc | 540 |
| ccatgtttgt tgcagcactg ttcataatag caaagatttg gaagcaacct aattttccac | 600 |
| caacagatga atggataaag aaaatgtggt atgtatacac aatggagtac tagtcaacca | 660 |
| taaaaaataa tgagatcctg tcatttgcaa cagaatggat ggaactggtc gtcattatgc | 720 |
| taagtgaaat aagtcaggca cagaaaaaca actttgtat gttctcactt atttgtggga | 780 |
| gctaaaaatt gaaacaatt gaactcatgg agatagagac tagaaggatg gttaacagag | 840 |
| aatggaaagg ggagtaggtg ggtgcagggt aggggtgggg agggatgtga gtgatggagg | 900 |
| agtaggggtg gttaatgggt acaaaggaat agaaatgatg aataagacct agtatttgat | 960 |
| agcacaaaag tgtggccata ctaagttata ctctcttagt tattttaaaa tgtataatta | 1020 |
| aattgcattt aaattaaatt attgatttaa tcgaacattt taaaataaga gagtgtaatt | 1080 |
| gaattgcttt aacacaaagg ataaatgctt gaggggatgg atacccatt tatcatttac | 1140 |
| cagtgattat tactccatta accagtgatt agtatgcatt gtcatgtctg tataaaagta | 1200 |
| tttcatatac cccatagata tatatactct actatgtatt cttaaaaata aaatttgaaa | 1260 |
| aaagaaaaat aatatttaat ggaacttcat gggaaaagtg tatgcagagg aaaaggtaca | 1320 |
| cttttgaagt taatggatga ataaaaaatt gggaagaagc ctaacaaaaa attggcagag | 1380 |
| gaagctaatt gaaggtttct catagaaatt aaggcaagaa agctttacaa agaatgaat | 1440 |
| ggatggaagg ttagcaatgt caaggtcaa ttaaagttca aatgagtcaa aaaccaaggt | 1500 |
| ttcctctaaa tttgactact ggaaatcact aatgactttg tgactatgcc ctgactacca | 1560 |

-continued

```
tgaagagaag tccttgggtt ctgggaatga agtaaccaag acgatggact gcaaattaaa    1620
aagaaaagca atatgaggtt atgtaattac agcgttactg gaagctatca acccgattag    1680 accatttaa ttacaacacc agcctggcct ttgaagtggc tataatcatt tttcatcttc    1740
```

```
aaaatattt gttcttagga atgcaaacta aagactaaaa gtctttaaat aatagtttgg    1800 acccttgtt acataagaaa agaaaaaaaa taaacaattg ttagacttaa aattattctg    1860
ttatgtggaa ataagatcac ctgtcattgt tgttcatgac acccactact tagagtataa    1920
aatcattctg agaagttaga gacacctaca ctcaggaaac tcatcattag cattgaactg    1980
aatctctagt ccctgacacc atg aga tac tat ggc agc tac tac aga ggc ctg    2033
                       Met Arg Tyr Tyr Gly Ser Tyr Tyr Arg Gly Leu
                        1               5                  10 gga tat ggc tgt gga ggc ttt ggt ggt ctg ggc tat ggc tgt ggc tgt    2081
Gly Tyr Gly Cys Gly Gly Phe Gly Gly Leu Gly Tyr Gly Cys Gly Cys
         15                  20                  25 gga ggc tac aga tat ggc tct ggc tat gga ggc tat aga tat ggc tgc    2129
Gly Gly Tyr Arg Tyr Gly Ser Gly Tyr Gly Gly Tyr Arg Tyr Gly Cys
     30                  35                  40 tgc cgc cca tca tgc cgt gaa gga tat gga ttc tct gga ttc tac taa    2177
Cys Arg Pro Ser Cys Arg Glu Gly Tyr Gly Phe Ser Gly Phe Tyr
 45                  50                  55 aaaacttgct gattctcata ctctaactcc aagatcttgc ccgtatgctt cagcaaggcg    2237 aacactttc tcaatgtaga gaaataccct accatttttt ggcttcatgc tccagaagga    2297
actagccatc agtttttatg gaagaatctg gaatcattac attgaatcag gtttcacct    2357 attattattt agtcactgac atctgttgtg acatgtattt taaaatagtt ttaaataaac    2417
acgt                                                                 2421
```

<210> SEQ ID NO 50
<211> LENGTH: 58
<212> TYPE: PRT
<213> ORGANISM: Homo sapiens

<400> SEQUENCE: 50

```
Met Arg Tyr Tyr Gly Ser Tyr Tyr Arg Gly Leu Gly Tyr Gly Cys Gly
 1               5                  10                  15

Gly Phe Gly Gly Leu Gly Tyr Gly Cys Gly Cys Gly Gly Tyr Arg Tyr
             20                  25                  30

Gly Ser Gly Tyr Gly Gly Tyr Arg Tyr Gly Cys Cys Arg Pro Ser Cys
         35                  40                  45

Arg Glu Gly Tyr Gly Phe Ser Gly Phe Tyr
     50                  55
```

<210> SEQ ID NO 51
<211> LENGTH: 2511
<212> TYPE: DNA
<213> ORGANISM: Homo sapiens
<220> FEATURE:
<221> NAME/KEY: CDS
<222> LOCATION: (2001)..(2192)

<400> SEQUENCE: 51

```
agtcctatca gtgccaagtg ggaggtcgtg tgagctgaga atgagaagag gcagatgact      60
tgatgcttcg tggacaggca agttcacat acgtgttagc ttcactttta ggaatcaaat     120
aaagcagagg accctagaaa ataattccta gattggaggt tctgggatct tctattcctg    180
ataataatat tttccctacc aagcaaatat atctggtttt atctggattg tgacaagtgc    240
```

-continued

```
taaagataat agtcttttta aaaaattacc taaaattata ttgaacctac attttcttaa      300
ctgaagcaaa ttcaaataca gcaattcttt accattaata attcccttca acttgtagtt      360
tgcaaagttc cctcaggatg gaaatatgtt aagtacctag ttatgtagca cttttaataa      420
actggtaaag gaaataagtt taatcagtat aaatgaagtt caaaaataac ctgtattctt      480
tgaggttcct ggataaagaa aatgtggcac atatatacca tggaatactc tgcagccata      540
aaaaaggatg agttcatgtc ctttgcaggg acatggatga agctggaacc accattctca      600
gcaaactaac acaagaacag aaaagcaaac accacatgtt ctcactcata agtgggagtt      660
aatcaatgag aacacatgga cacagggagg ggaacatcac acaccagggc ctgtcagggg      720
gtgggggact aggggaggga cagcattagg agaaatacct aacatagacg atgggtcgat      780
gggtgcagca aaccaccatg gcacatgtat acctatgtaa caaacctgcg cgttttgcac      840
atttacctca gtacttaaag tgtatatata catacataca tgtatatata tatatataca      900
tatatatata tatatagcag gagtagctga gcatatatgc ttactggttt catgtcattt      960
gcttttattt atattgatga tatgaaacaa aaatataagg cagctgggca ttgtgggaga     1020
agatataccc taacctgcaa tctttgattt caaatgcatc tgctgaacta aggccaataa     1080
tcaaagtact taggttttag tcctaatctg ccactaagtt tcactgttgc gtaactctgc     1140
ttgtctctct gaatccattt ttctcatcag taacaagaac actgaaataa atgatgactc     1200
aagtctcttt aattctataa ttatatgatc ctatgatagt acgaaattta gaatctagac     1260
taagattaaa tttggggaga ggaaactatt cataagggat tggcagggac tttatgcaca     1320
ctttaatggt atctactaag caggctggct ctacatgaag cataatattt gagaaattcc     1380
tttgacatta atttgtgact cttttaaaaa ttaaatatca tcattccact ataaaatgtg     1440
gttcccagct gactttaaaa gcacattgta taaagacata catcatagtt gattgccatt     1500
tcagagaaca ataatgtttc aattttgtg aattcttggc agaataaaga taacatcctt      1560
ggcttagaaa aggctcagca gccatggact gtcaaaggaa agagtgcaat cagaggataa     1620
atgtaattgc atgagatgca atttgaagaa tacttgaagc tatagagatt tgtttatggc     1680
atttgaaact cagaaactca tacatgtaca gtgaatataa atgcaactac attttattag     1740
aggcaaaaca cttatctaga aatccaaata aagcagaaaa taaaacatgt tgtataattt     1800
ctaaataact agcttcataa acaaggaaga gagtgggatg ggtgttacaa aacaagatag     1860
ttggcatagt tttcaggtaa cacgttctaa gggatgacat ttaaaggtgt ggctttccac     1920
atgcatcaga gtatatataa atgttcctgt ccagtcacag tcaccaaact gacctacaac     1980
agctaaccac ttctgacaac atg agc tac tcc ggc agc tac tat gga ggc cta    2033
                      Met Ser Tyr Ser Gly Ser Tyr Tyr Gly Gly Leu
                        1               5                      10 ggc tac ggc tgt gga gga ttc ggt ggc ctg ggc tat ggc tat agc tgt       2081
Gly Tyr Gly Cys Gly Gly Phe Gly Gly Leu Gly Tyr Gly Tyr Ser Cys
             15                  20                  25 gga tgt ggc agc ttc cgc aga ctg ggc tat ggc tgt ggc tat gga ggc       2129
Gly Cys Gly Ser Phe Arg Arg Leu Gly Tyr Gly Cys Gly Tyr Gly Gly
         30                  35                  40 tac aga tac agc tgc tgc cac cca tca tgc tat ggg gga tac tgg tct       2177
Tyr Arg Tyr Ser Cys Cys His Pro Ser Cys Tyr Gly Gly Tyr Trp Ser
         45                  50                  55 tct gga ttc tat tga ataaatactt gaaatatagt cttctgtgag attcccaatt       2232
Ser Gly Phe Tyr
 60
```

```
cttccaagaa actttattcc ataaccatat ggaattccat attccataac aaaacagctg    2292
cttggatcac ctgccttttg acaatagtgt gaagaaaact tgatcaacta gatattggca    2352
tttgattagt gatgttctcc agatattcac ttttttattg gctggagagc cattatactc    2412
taagaaagat tgtctttcaa tatctgatat ctaaccatga acttttctc atgtggtaaa     2472 tgtgttttga gcctcaaatt tttatcacaa taaatgtgc                           2511
```

<210> SEQ ID NO 52
<211> LENGTH: 63
<212> TYPE: PRT
<213> ORGANISM: Homo sapiens

<400> SEQUENCE: 52

Met Ser Tyr Ser Gly Ser Tyr Tyr Gly Gly Leu Gly Tyr Gly Cys Gly
 1               5                  10                  15

Gly Phe Gly Gly Leu Gly Tyr Gly Tyr Ser Cys Gly Cys Gly Ser Phe
                20                  25                  30

Arg Arg Leu Gly Tyr Gly Cys Gly Tyr Gly Gly Tyr Arg Tyr Ser Cys
            35                  40                  45

Cys His Pro Ser Cys Tyr Gly Gly Tyr Trp Ser Ser Gly Phe Tyr
        50                  55                  60

<210> SEQ ID NO 53
<211> LENGTH: 2400
<212> TYPE: DNA
<213> ORGANISM: Homo sapiens
<220> FEATURE:
<221> NAME/KEY: CDS
<222> LOCATION: (2001)..(2138)

<400> SEQUENCE: 53

```
gtgaatcaga acatagcgtg cccctgcaaa aatatctcta aaggcctttc attgtgctga      60
gaagttctgg cccttacgta tctctctgat tcatatcct gctactctcc tccatttatc      120
tataatgctc aaactctgct ggcttttgt cttttaaaat gcagcaggtt tcttctcaca      180
ataaggccct ggcctctgca cttactgatt tctctttctt aaaataatac caggaatatt     240
tgactcattt tctatttcaa ttgaaatgtt cacttcccag agagactttt aatggccacc     300
ttatattaat tagtctacct ccagtaactg aacttaatgt aactcactga gttttattat     360
tctcacagga ttcttcactg ttagaatcta tttcattcat ttttaaaatc agtctctcta    420
tcccttctgt ctcattgtaa cctgcagaaa gtagagactt tgtctatttt gttcatctgc     480
tcaatctgca tttcttataa cggtgcctga tacagcagat tcttaataaa gatttgatga    540
attagtgaaa aaataaccaa atgaatgaca tgatgcaact ttctatactc aaattctgtg     600
tagaataatc acaatctttg ttctatgctt ggggtaactg gggataaatt catgtactct    660
gggatccttt tggatcatat gcaaaccagt ggaggaattt atcatggtga ttttttttctg   720 gtttgagaat ccatgccttt tccgattgtt aaggtggtgg tatatatcca ctaaagttta    780
tgaactactg tgtgcagttc cgaaattctg actaaatgtt ctacttgcct cttattgata    840
tgatactttg ccagtctcac attgatctac aaagtatgat ccctaggttg atcattggta    900
gttctgctac atttaagagt agcaaatgaa ttaaatatgta ctattatttg tttatatttt   960
attctaattg ctttatcata ataaatgact aataattcat taataatatt taataagtgg    1020
atggaataaa cgtgacaaat tatcacaggg agcttcatag aaagtcagct ctcataatta    1080
aggctatcac cagaatgcat ttgggccaga aatgtggttt gctgatgtta ttctatccaa    1140
```

```
gtcaccactt taaaaaatag taacaggaat tctgctagaa gatgaaaagt atttttacaa      1200
tacttttgga aatttggaat taatatattt taaaataagc aaattcatta aatataaaaa      1260
gaaggtaaaa tatgtgaata ttatgtgtca ggagaggaaa acatgaattt tgagatacgg      1320
tgggtaattg tttctaattg ctttctcaga tgcaaagaga acaccacaac taataatata      1380
accaaagtga ggatgatgga agagaaaaaa ctttactact ccaagaacat aagctacata      1440
tgaacttgga agaaaatttt tagtcccatt gattaagaaa taaattagtc aaaacataca      1500
ggcatatttg caagtaaata aagacatttt catcggcttc ctcactgcat agccaacctt      1560
ccctaaccat tcctggccac tctgtggttt aaggactgca tttatggagg tagaggagga      1620
tattgaaaaa gaaaaaagaa atgtttcaag aggcaggaaa tataagctta atgtgatcac      1680
agagaagcta atcatcaagt ttaaattggg attttaagta agcaaaagcc acaaaattaa      1740
gagaatatct ccttaaggct catgatttta cttgttggca tcctgacaca tagcaatatt      1800 aatatttcc tggacatatg gctaagagat tcttgagggt ttttttaatc ttaatgcaaa       1860
ttagttgtga gaatgagtcc aatgtagatt gtggtttcct tcacatataa ctcaggttgg      1920
ataaaataat ttgtacaaat caggagagtc aaatttcaga aactactatc tgcctcaatt      1980
gaactccatc ttctgacacc atg tgc tac tac cac aac tat tat ggt agc ctg     2033
                        Met Cys Tyr Tyr His Asn Tyr Tyr Gly Ser Leu
                          1               5                      10 gac tat ggt tgc agc tat ggc tct gaa tat ggt aac tct gga tat gcc       2081
Asp Tyr Gly Cys Ser Tyr Gly Ser Glu Tyr Gly Asn Ser Gly Tyr Ala
             15                  20                  25 tgc aac ttt ccg tgc tcc tat gga aga ttc cta ttg gct cct aga aag       2129
Cys Asn Phe Pro Cys Ser Tyr Gly Arg Phe Leu Leu Ala Pro Arg Lys
         30                  35                  40 aaa ttc tga ttgctgatca ctttgagcca ttttcttgtg atgcactaat               2178
Lys Phe
    45 tgcatcaaca gggttatttta tggattcgtt attgtctctc caattttaac taactctaat    2238 tattgattac cacaggtcat atttgcattg gattagtgga atttcctacc agttagtggg     2298 aaaatccttt gatattttgt tagttttatg tgtttatgtc tgttataata ttaacaattt     2358 ccatgcagga aaacttataa atttgcattt taataaatat aa                        2400

<210> SEQ ID NO 54
<211> LENGTH: 45
<212> TYPE: PRT
<213> ORGANISM: Homo sapiens

<400> SEQUENCE: 54

Met Cys Tyr Tyr His Asn Tyr Tyr Gly Ser Leu Asp Tyr Gly Cys Ser
  1               5                  10                  15

Tyr Gly Ser Glu Tyr Gly Asn Ser Gly Tyr Ala Cys Asn Phe Pro Cys
             20                  25                  30

Ser Tyr Gly Arg Phe Leu Leu Ala Pro Arg Lys Lys Phe
         35                  40                  45

<210> SEQ ID NO 55
<211> LENGTH: 2619
<212> TYPE: DNA
<213> ORGANISM: Homo sapiens
<220> FEATURE:
<221> NAME/KEY: CDS
<222> LOCATION: (2001)..(2333)

<400> SEQUENCE: 55
```

-continued

```
ttattttatc caacctgagt tatatgtgaa ggaaaccaca atctacattg gactcattct      60
cacaactaat ttgcattaag attaaaaaaa ccctcaagaa tctcttagcc atatgtccag     120
gaaaatatta atattgctat gtgtcaggat gccaacaagt aaaatcatga gccttaagga    180
gatattctct taattttgtg gcttttgctt acttaaaatc ccaatttaaa cttgatgatt    240
agcttctctg tgatcacatt aagcttatat ttcctgcctc ttgaaacatt tctttttct     300 ttttcaatat cctcctctac ctccataaat gcagtcctta aaccacagag tggccaggaa    360
tggttaggga aggttggcta tgcagtgagg aagccgatga aaatgtcttt atttacttgc    420
aaatatgcct gtatgttttg actaatttat ttcttaatca atgggactaa aaattttctt    480
ccaagttcat atgtagctta tgttcttgga gtagtaaagt tttttctctt ccatcatcct    540
cactttggtt atattattag ttgtggtgtt ctctttgcat ctgagaaagc aattagaaac    600
aattacccac cgtatctcaa aattcatgtt ttcctctcct gacacataat attcacatat    660
tttaccttct ttttatattt aatgaatttg cttattttaa aatatattaa ttccaaattt    720
ccaaaagtat tgtaaaaata cttttcatct tctagcagaa ttcctgttac tatttttttaa   780 agtggtgact tggatagaat aacatcagca aaccacattt ctggcccaaa tgcattctgg    840
tgatagcctt aattatgaga gctgactttc tatgaagctc cctgtgataa tttgtcacgt    900
ttattccatc cacttattaa atattattaa tgaattatta gtcatttatt atgataaagc    960
aattagaata aaatataaac aaataatagt acatattaat tcatttgcta ctcttaaatg   1020
tagcagaact accaatgatc aacctaggga tcatactttg tagatcaatg tgagactggc   1080
aaagtatcat atcaataaga ggcaagtaga acatttagtc agaatttcgg aactgcacac   1140
agtagttcat aaactttagt ggatatatac caccaccta acaatcggaa aaggcatgga    1200
ttctcaaacc agaaaaaaat caccatgata aattcctcca ctggtttgca tatgatccaa    1260
aaggatccca gagtacatga atttatcccc agttacccca agcatagaac aaagattgtg   1320
attattctac acagaatttg agtatagaaa gttgcatcat gtcattcatt tggttatttt   1380
ttcactaatt catcaaatct ttattaagaa tctgctgtat caggcaccgt tataagaaat   1440
gcagattgag cagatgaaca aaatagacaa agtctctact ttctgcaggt tacaatgaga   1500
cagaagggat agagagactg attttaaaaa tgaatgaaat agattctaac agtgaagaat   1560
cctgtgagaa taataaaact cagtgagtta cattaagttc agttactgga ggtagactaa   1620
ttaatataag gtggccatta aaagtctctc tgggaagtga acatttcaat tgaaatagaa   1680
aatgagtcaa atattcctgg tattatttta agaaagagaa atcagtaagt gcagaggcca   1740
gggccttatt gtgagaagaa acctgctgca ttttaaaaga caaaaagcca gcagagtttg   1800
agcattatag ataaatggag gagagtagca ggatatgaaa tcagagagat acgtaagggc   1860
cagaacttct cagcacaatg aaaggccttt agagatattt ttgcaggggc acgctatgtt   1920
ctgattcact gaggcatata aaaggccctc tgcggagaag tgtccatact gaagtcacct   1980
acactccttc ctacccaagg atg acc tca aca acc aac acc atg tgt ggc agc   2033
                     Met Thr Ser Thr Thr Asn Thr Met Cys Gly Ser
                      1               5                  10 tac tac aga aac tac aat ggt ggc cat ggc tat ggg tgc tgt ggc tac    2081
Tyr Tyr Arg Asn Tyr Asn Gly Gly His Gly Tyr Gly Cys Cys Gly Tyr
            15                  20                  25 gga ggc ctg ggc tgt ggt tat ggc ggc tgt ggc tat ggg tgc tgt ggc    2129
Gly Gly Leu Gly Cys Gly Tyr Gly Gly Cys Gly Tyr Gly Cys Cys Gly
        30                  35                  40
```

-continued

```
tac gga ggc ctg ggc ttt ggc tat gga ggc ctg gac tgt ggc tat gga      2177
Tyr Gly Gly Leu Gly Phe Gly Tyr Gly Gly Leu Asp Cys Gly Tyr Gly
             45                  50                  55 ggc ctg ggc tgt ggc tat ggc tcc ttc tgt ggc tgt ggc tac aga ggc      2225
Gly Leu Gly Cys Gly Tyr Gly Ser Phe Cys Gly Cys Gly Tyr Arg Gly
 60                  65                  70                  75 ctg gac tgt ggc tat ggc tgt ggc tat ggc tat gtc tcc cac tcc ttc      2273
Leu Asp Cys Gly Tyr Gly Cys Gly Tyr Gly Tyr Val Ser His Ser Phe
                 80                  85                  90 tgt ggc tgt ggc tat agg tgc ggc tct ggc tat ggc tcc agc ttt ggc      2321
Cys Gly Cys Gly Tyr Arg Cys Gly Ser Gly Tyr Gly Ser Ser Phe Gly
             95                 100                 105 tac tac tat tga ggacaccatg ggagactctc accctctatc ctgtgacatt          2373
Tyr Tyr Tyr
        110 gcaattcacc aattctgaag cccacatgct ctgagccttt ccttgattg atgatatcct     2433 gcagtggaag tctaatatga tctgttgttg atctaccatc taaccaaaa atacctgag      2493 tttccatcat gaagtgggat aaggtgaagt tcacctgtca cttctccttt tatcaggatg    2553 atggtgtcac agtgactcct ttgatgactt tcatgctgta gtttgtttct ctgctgacct    2613 aataaa                                                                2619

<210> SEQ ID NO 56
<211> LENGTH: 110
<212> TYPE: PRT
<213> ORGANISM: Homo sapiens

<400> SEQUENCE: 56

Met Thr Ser Thr Thr Asn Thr Met Cys Gly Ser Tyr Tyr Arg Asn Tyr
 1               5                  10                  15

Asn Gly Gly His Gly Tyr Gly Cys Cys Gly Tyr Gly Gly Leu Gly Cys
             20                  25                  30

Gly Tyr Gly Gly Cys Gly Tyr Gly Cys Cys Gly Tyr Gly Gly Leu Gly
         35                  40                  45

Phe Gly Tyr Gly Gly Leu Asp Cys Gly Tyr Gly Gly Leu Gly Cys Gly
     50                  55                  60

Tyr Gly Ser Phe Cys Gly Cys Gly Tyr Arg Gly Leu Asp Cys Gly Tyr
 65                  70                  75                  80

Gly Cys Gly Tyr Gly Tyr Val Ser His Ser Phe Cys Gly Cys Gly Tyr
                 85                  90                  95

Arg Cys Gly Ser Gly Tyr Gly Ser Ser Phe Gly Tyr Tyr Tyr
            100                 105                 110

<210> SEQ ID NO 57
<211> LENGTH: 2410
<212> TYPE: DNA
<213> ORGANISM: Homo sapiens
<220> FEATURE:
<221> NAME/KEY: CDS
<222> LOCATION: (2001)..(2189)

<400> SEQUENCE: 57
ataatgaaat aatgtacctt taataagaga tccatctcct attttgatga ctcgtttatt     60
tcagatgtca aatttaaact acattaccag caaccaagag taaccacat ggcttccact     120 tgttgttgtt gttgttgttg ttgttgtgag acagagacta gctctgttgc ctggctggag    180
tgcagtggca caatctcact gcaacctcca cctcctggtt tcaagtgatt ctcctggatt    240
ctctgcctca gccttatgaa tagctggtgc gtgccaccac gcccagctaa ttttttgtatt   300
```

-continued

```
tttagtagag atggggtttc gccatgttgg ccaggatggt cttgatctcc tgacctcaag    360
atccgcccgc ctcggcctcc caaagcctgg ggttatggac gtgatggctt ccatttttta    420
aaaatcctac tttcacccaa taatatcctt cagcctaaat acatatatgc agacttggga    480
ataagagtgt agctccaaag tgataaggaa ggatgataag cgtgtaagag aagtcatggt    540
ggcagcattc acttgtaaaa tgttgagtga taaggtgttt catcactttt tgtggagcaa    600
tatcattctc tttggtttat acttcacatg tagctatcat tttatatatg attctaaacc    660
gtggcaaaga ctttgatttt tgacttcgtt gattctgggt atatagtaag aaaaggactt    720
ctattaaaaa tctgaatttt aaaacaattc agaattact  caaagattta ttggcatcat    780
gactccctga gatggcacaa gacaagagtt acatctcttc ccaaatgtat aacctcaatc    840
tacatatgag gaaaccttag acagattcaa ttggggaata ttccacaaaa tatctggctc    900
tctaaaattg taaggtcata aaagccaaga aaagacgaat gaaccatgag caattggagg    960
tgactaagaa gtataaaaac caaatgcaat gtgaattgga tccaagaaca gaaaaaaaga    1020
acattaaaat aaatatgtga atagtgctac aatgaaccat ggtcctagaa cttaaaataa    1080
aataagttaa taataacaga aaaatggtaa ataaagtct  gcagtttagt taagaatact    1140
gtacacagtt aatttctttg gtgtgataag tggattatgg ttatgaaaga tattaatatt    1200
agggatgttg aatgatggat atatggaaat tttctatact attttgacaa ctatctctat    1260
gcctgagatt attttaagat aagaagttaa aagagaatat aaaactattg ttccatttca    1320
ttgacttggt cacttattaa ttcttttata aatcaagaaa ataacttaca tttcttgtt    1380 cttccgtaga ggttgaacat aaaggaaaat tagactcact ggtataagta gaaaaataca    1440
acaaattttt ctcagatctg gttttctaga atttttaatt agttgaatta ttatcaacat    1500
catggcttta gtatagaaaa gacactaaat ccctgaaaaa agtattattt ggataaagag    1560
agcagaaata ctaaaagggc aaagttattg tttgctgaat gttgtgcaaa agagtacaat    1620
taattggggc ctagagcaaa taagagtgta actaacaaaa gtctttcttg atgtaaagga    1680
tggctataga aagtctagtt tgaggcagga ttatatgagt gtgagtgtgt gaggtctcct    1740
ttcatcagag ccctcaatca gataagggga gcccaaattg caaggccaaa caaaacaagc    1800
ctccttaata cctctgcagc attatcttac aattgagaaa aaacaaacta attatattag    1860
tcaaaaaatt agccagtggt atgctacctc tgctggatca ttcccatcct gaggcatata    1920
aaaggacttc tacaggaagt atccatactg aagtcaccta cactccttcc tacccaagga    1980
caacctccac aaccatcacg atg tgc ggc agc tac tac gga aac tac tac ggc    2033
                      Met Cys Gly Ser Tyr Tyr Gly Asn Tyr Tyr Gly
                        1               5                  10 gac cat ggc tat ggg tgc tgt gga tac gaa ggc cta ggc tat ggc tat     2081
Asp His Gly Tyr Gly Cys Cys Gly Tyr Glu Gly Leu Gly Tyr Gly Tyr
        15                  20                  25 gga agc ctg cgc tgt ggc tat agc tcc tgc tgt ggc tat ggt cat ggc     2129
Gly Ser Leu Arg Cys Gly Tyr Ser Ser Cys Cys Gly Tyr Gly His Gly
    30                  35                  40 tac ggc tcc cgc ttc ttc tgt ggc tgt ggc tat gga tgc ggc tct ggc     2177
Tyr Gly Ser Arg Phe Phe Cys Gly Cys Gly Tyr Gly Cys Gly Ser Gly
    45                  50                  55 tac tac tat tga ggacaccgtg ggagactcat cctctatcct gtgacatcgg         2229
Tyr Tyr Tyr
 60 gattcaccaa ttctgaaccc cgtatgctct gagctcgggg ctggatgaag attatcttat    2289
```

-continued

| | | |
|---|---|---|
| attaaaagtt tctgatgtga tttatctgaa gactgacccc cccaccccca gtaccctctg | 2349 |
| gatctagtat tttcaacttc cttttctgca tttaatgcat gaaaattaaa ataatgtaaa | 2409 |
| a | 2410 |

<210> SEQ ID NO 58
<211> LENGTH: 62
<212> TYPE: PRT
<213> ORGANISM: Homo sapiens

<400> SEQUENCE: 58

Met Cys Gly Ser Tyr Tyr Gly Asn Tyr Tyr Gly Asp His Gly Tyr Gly
1               5                   10                  15

Cys Cys Gly Tyr Glu Gly Leu Gly Tyr Gly Tyr Gly Ser Leu Arg Cys
            20                  25                  30

Gly Tyr Ser Ser Cys Cys Gly Tyr Gly His Gly Tyr Gly Ser Arg Phe
        35                  40                  45

Phe Cys Gly Cys Gly Tyr Gly Cys Gly Ser Gly Tyr Tyr Tyr
    50                  55                  60

<210> SEQ ID NO 59
<211> LENGTH: 2361
<212> TYPE: DNA
<213> ORGANISM: Homo sapiens
<220> FEATURE:
<221> NAME/KEY: CDS
<222> LOCATION: (2001)..(2147)

<400> SEQUENCE: 59

| | | |
|---|---|---|
| agggctctga tgaaaggaga cctcacacac tcacactcat ataatcctgc ctcaaactag | 60 |
| actttctata gccatccttt acatcaagaa agacttttgt tagttacact cttatttgct | 120 |
| ctaggcccca attaattgta ctcttttgca caacattcag caaacaataa ctttgcccct | 180 |
| ttagtatttc tgctctcttt atccaaataa tactttttc agggattag tgtcttttct | 240 |
| atactaaagc catgatgttg ataataattc aactaattaa aaattctaga aaaccagatc | 300 |
| tgagaaaaat ttgttgtatt tttctactta taccagtgag tctaattttc ctttatgttc | 360 |
| aacctctacg gaagaacaag aaaatgtaag ttatttctt gatttataaa agaattaata | 420 |
| agtgaccaag tcaatgaaat ggaacaatag ttttatattc tcttttaact tcttatctta | 480 |
| aaataatctc aggcatagag atagttgtca aaatagtata gaaaatttcc atatatccat | 540 |
| cattcaacat ccctaatatt aatatctttc ataaccataa tccacttatc acaccaaaga | 600 |
| aattaactgt gtacagtatt cttaactaaa ctgcagactt tattttacca ttttttctgtt | 660 |
| attattaact tattttattt taagttctag gaccatggtt cattgtagca ctattcacat | 720 |
| atttatttta atgttctttt tttctgttct tggatccaat tcacattgca tttggttttt | 780 |
| atacttctta gtcacctcca attgctcatg gttcattcgt cttttcttgg cttttatgac | 840 |
| cttacaattt tagagagcca gatattttgt ggaatattcc ccaattgaat ctgtctaagg | 900 |
| tttcctcata tgtagattga ggttatacat ttgggaagag atgtaactct tgtcttgtgc | 960 |
| catctcaggg agtcatgatg ccaataaatc tttgagtaat tctggaattg ttttaaaatt | 1020 |
| cagatttta atagaagtcc ttttcttact atatacccag aatcaacgaa gtcaaaaatc | 1080 |
| aaagtctttg ccacggttta gaatcatata taaaatgata gctacatgtg aagtataaac | 1140 |
| caaagagaat gatattgctc cacaaaaagt gatgaaacac cttatcactc aacattttac | 1200 |
| aagtgaatgc tgccaccatg acttctctta cacgcttatc atccttcctt atcactttgg | 1260 |

```
agctacactc ttattcccaa gtctgcatat atgtatttag gctgaaggat attattgggt    1320
gaaagtagga ttttttaaaaa atggaagcca tcacgtccat aaccccaggc tttgggaggc   1380
cgaggcgggc ggatcttgag gtcaggagat caagaccatc ctggccaaca tggcgaaacc    1440
ccatctctac taaaaataca aaaattagct gggcgtggtg gcacgcacca gctattcata    1500
aggctgaggc agagaatcca ggagaatcac ttgaaaccag gaggtggagg ttgcagtgag    1560
attgtgccac tgcactccag ccaggcaaca gagctagtct ctgtctcaca acaacaacaa    1620
caacaacaac aacaagtgga agccatgtgg gttactcttg gttgctggta atgtagttta    1680
aatttgacat ctgaaataaa cgagtcatca aaataggaga tggatctctt attaaaggta    1740
cattatttca ttatattcaa cattcctgag aaacagcaaa gttgtcttgg atgtattggt    1800
tacaaggaat attttagatg gtttcaatgc taattagtgt ggaatgtgaa ctaacagtg    1860 cctgtgattt gtcccacata ccattcatgt ggcatttaag gcccttatta taagcttaaa    1920
actttaaact taaaactcta taaacttaaa actctagaat ctgatcctgc tatacaactg    1980
agcctacctt tcttgaaacc atg agc ttt gat aac aac tac cat ggt ggc cag    2033
                       Met Ser Phe Asp Asn Asn Tyr His Gly Gly Gln
                         1               5                  10 ggc tat gcc aaa gga ggc ctg ggc tgc agc tat ggc tgt ggt ctt agc     2081
Gly Tyr Ala Lys Gly Gly Leu Gly Cys Ser Tyr Gly Cys Gly Leu Ser
             15                  20                  25 ggc tat ggc tat gcc tgc tac tgc cca tgg tgt tat gaa aga tct tgg     2129
Gly Tyr Gly Tyr Ala Cys Tyr Cys Pro Trp Cys Tyr Glu Arg Ser Trp
         30                  35                  40 ttt tct ggc tgc ttc tga gaaattagag attgctgatc tgtttaggcc             2177
Phe Ser Gly Cys Phe
     45 attctcttat gagctatgtt ttcttcccgt gttttttttct gttcaaagag tgacaactaa   2237 aatttagccc acattgccaa gtcagaattt atttgatcaa ttagctggaa tttccaacaa    2297 tttaatcaaa cgaaaaaaga acctttgatg ttgtgttact agtatatgat taagtacaaa   2357 taat                                                                 2361

<210> SEQ ID NO 60
<211> LENGTH: 48
<212> TYPE: PRT
<213> ORGANISM: Homo sapiens

<400> SEQUENCE: 60

Met Ser Phe Asp Asn Asn Tyr His Gly Gly Gln Gly Tyr Ala Lys Gly
  1               5                  10                  15

Gly Leu Gly Cys Ser Tyr Gly Cys Gly Leu Ser Gly Tyr Gly Tyr Ala
             20                  25                  30

Cys Tyr Cys Pro Trp Cys Tyr Glu Arg Ser Trp Phe Ser Gly Cys Phe
         35                  40                  45

<210> SEQ ID NO 61
<211> LENGTH: 2507
<212> TYPE: DNA
<213> ORGANISM: Homo sapiens
<220> FEATURE:
<221> NAME/KEY: CDS
<222> LOCATION: (2001)..(2216)

<400> SEQUENCE: 61
actttaaata cataagtcag gtaacatttt tacaggatac aactttacaa acgtacaaat    60
gcactttatt ttactgttat accaaattct atcttgattc attatttcca ctaaatggca   120
```

```
aaacatttat tcttgtccct ttcaggtaaa ctcaacaaaa ttcaatcact ttctggttgt      180
cagtattaaa atacaattgc aataaagaca ttaccactcc tcattctctg cctgaggtgt      240
gcttcgatgt gcagtgatat gctgttggtt ttgaggagga ccatacctgt tctgcactga      300
cacctttgga tggcataaca catattgcca ttttccactg ccacaaaaat aaaactctgt      360
tcaatccatt acctagcatg aagtgttaca tccttgggtc tctacagcca gaacagtctt      420
tggttgtagt aaggaaatca atgagtctcc actcagatcc acctgggtga gaaccaatca      480
ttgtatctcc ccctgcttgt gctatgtgtg tggggaact tggtaggact ttccccttct       540
cagtaaaacc aggatgtgac tttctctgtt gttagatgta catcctcaat gcagagtttc      600
tcttcccttc agcttcaagg acataatgcc cctaaatgag aacttaagca tgcctgagtt      660
ctcttattca attgatcaac tctctactga agcttctatc cagaaaaaca gggatgggat      720
gaaataagta aagacagcaa aatttattct agtattctgg ttcctactat gaaccaaaca      780
ctattcaaag tgtctggtat gtatcaaaag atttgatttt ctaaatttcc ttgtggggta      840
ggtatcatta ttacaatccc atttgcagat agggcagctg aagcatgtag ttaacagtgg      900
tcagacagct atggatagta gaggtaaaat ttgagcctag aaagcacatt acagatattt      960
tactcttatt tactatattc aactcactct tataaagtca tcttactaag aatataagtc     1020
cagagggcta cttgacttaa tcattcaatt tagctctgat cttcactgct ttgaaaaaag     1080
attaggctat agtaacatgt tcctcatagt ctcatatttt gccaaagact tcttgtttga     1140
tggtggaaat atagtaggtt gcatgaaaag atacttctgc cagtatattt gttttaaata     1200 tgaaatacc tatacttact tttgagccag aacacaaata taacaaatgc cttgaaattt       1260
caggaaaatt tttataaaaa tacaatttta taaataaaat gaaacctcat tgattacgaa     1320
tttgaaacta tgggaaagaa ctattgtttt aaaacagtca caaaggaaa tattgatgtg      1380 agaaagaaaa gtatagtttt ctcatgcctg gtatttttaga atttcaaact attggctttg    1440
tgtcaacagt ctctggaagc tgagtgacac tttctggctt ttaaaagaaa accatctctc     1500
atgtgaaaat gagaagaatt cctaaaggaa acaatgggg ttggagcagc aggaaagaga      1560
tggagaaact caagctcaag ggagattacc atgacctgtt gaatgtcagc aaaaataagg     1620
taaaattatt ggttgtttag aacaggtcag tttgtttact aaaatgctat ttcttgccat     1680
aaaggctggt tggaaaatgg taatttgaat gtctggtgtg agtagagttt taaagatcag     1740
acagttgatg ctcattaaag atgcacaaat gtttcagatg tggctgaaca atagaaaatg     1800
ttctaaatgc cacaaggcca cgattgaaaa ccaagagtca acaaattact catgctggtc     1860
cttcaaatta gccaatggca tgacttgtgt atggttccca cccacactga ggcatataaa     1920
aggccctctg caggggaagt gttcatactg aagtcaccta cacttcctcc tacccaagga    1980
caacctccac aaccaacacc atg tgt ggc agc tac tac gga aac tac tat ggc    2033
                        Met Cys Gly Ser Tyr Tyr Gly Asn Tyr Tyr Gly
                         1               5                   10 acc cct ggc tat ggg ttc tgt ggc tat gga ggc ctg ggc tat ggc tat     2081
Thr Pro Gly Tyr Gly Phe Cys Gly Tyr Gly Gly Leu Gly Tyr Gly Tyr
            15                  20                  25 gga ggc ctg ggc tgt ggc tat ggc tcc tgc tgt ggc tgt ggc ttc cgc     2129
Gly Gly Leu Gly Cys Gly Tyr Gly Ser Cys Cys Gly Cys Gly Phe Arg
        30                  35                  40 aga ctg ggc tgt ggc tat ggc tat ggc tcc cgc tcc ctc tgt ggc tat     2177
Arg Leu Gly Cys Gly Tyr Gly Tyr Gly Ser Arg Ser Leu Cys Gly Tyr
    45                  50                  55
```

```
ggc tat gga tgc ggc tct ggc tct ggc tac tat tat tga ggatgccatg    2226
Gly Tyr Gly Cys Gly Ser Gly Ser Gly Tyr Tyr Tyr
 60              65                  70 ggagactctc accctctatc ctgtgatact gagattcact aattctgaag cccacatgtt   2286
ctgagatttt cccttgagtg atgatatcct gcaatggaag tctaatatgg tctgttgttg   2346
agctaccatc taacctacaa atatcttgaa tttccatcat gaaacgggat aaggtaaaat   2406
tcacctgtca gttctccttt catcagaatg atggtgtcac atcatctgcc ttgatgactt   2466
ttatgatgga gcttttttct ctgttcacct aataaacaca t                       2507
```

<210> SEQ ID NO 62
<211> LENGTH: 71
<212> TYPE: PRT
<213> ORGANISM: Homo sapiens

<400> SEQUENCE: 62

Met Cys Gly Ser Tyr Tyr Gly Asn Tyr Tyr Gly Thr Pro Gly Tyr Gly
 1               5                  10                  15

Phe Cys Gly Tyr Gly Gly Leu Gly Tyr Gly Tyr Gly Gly Leu Gly Cys
                20                  25                  30

Gly Tyr Gly Ser Cys Cys Gly Cys Gly Phe Arg Arg Leu Gly Cys Gly
            35                  40                  45

Tyr Gly Tyr Gly Ser Arg Ser Leu Cys Gly Tyr Gly Tyr Gly Cys Gly
        50                  55                  60

Ser Gly Ser Gly Tyr Tyr Tyr
 65                  70

<210> SEQ ID NO 63
<211> LENGTH: 2385
<212> TYPE: DNA
<213> ORGANISM: Homo sapiens
<220> FEATURE:
<221> NAME/KEY: CDS
<222> LOCATION: (2001)..(2171)

<400> SEQUENCE: 63

```
actgttgaca caaagccaat agtttgaaat tctaaaatac caggcatgag aaaactatac     60
ttttctttct cacatcaata tttccttttg tgactgtttt aaaacaatag ttctttccca    120
tagtttcaaa ttcgtaatca atgaggtttc atttttattta taaaattgta tttttataaa   180
aattttcctg aaatttcaag gcatttgtta tatttgtgtt ctggctcaaa agtaagtata    240
ggtattttca tatttaaaac aataatactg gcagaagtat ctttttcatgc aacctactat   300 atttccacca tcaaacaaga agtctttggc aaaatatgag actatgagga acatgttact   360
atagcctaat cttttttcaa agcagtgaag atcagagcta aattgaatga ttaagtcaag   420
tagccctctg gacttatatt cttagtaaga tgactttata agagtgagtt gaatatagta   480
aataagagta aaatatctgt aatgtgcttt ctaggctcaa attttacctc tactatccat   540
agctgtctga ccactgttaa ctacatgctt cagctgccct atctgcaaat gggattgtaa   600
taatgatacc taccccacaa ggaaatttag aaaatcaaat cttttgatac ataccagaca   660
ctttgaatag tgtttggttc atagtaggaa ccagaatact agaataaatt ttgctgtctt   720
tacttatttc atcccatccc tgttttttctg gatagaagct tcagtagaga gttgatcaat   780
tgaataagag aactcaggca tgcttaagtt ctcatttagg ggcattatgt ccttgaagct   840
gaagggaaga gaaactctgc attgaggatg tacatctaac aacagagaaa gtcacatcct   900
ggttttactg agaaggggaa agtcctacca agttccccaa cacacatagc acaagcaggg   960
```

-continued

```
ggagatacaa tgattggttc tcacccaggt ggatctgagt ggagactcat tgatttcctt    1020
actacaacca aagactgttc tggctgtaga gacccaagga tgtaacactt catgctaggt    1080
aatggattga acagagtttt attttttgtgg cagtggaaaa tggcaatatg tgttatgcca   1140
tccaaaggtg tcagtgcaga acaggtatgg tcctcctcaa accaacagc atatcactgc    1200 acatcgaagc acacctcagg cagagaatga ggagtggtaa tgtctttatt gcaattgtat   1260
tttaatactg acaaccagaa agtgattgaa ttttgttgag tttacctgaa agggacaaga   1320
ataaatgttt tgccatttag tggaaataat gaatcaagat agaatttggt ataacagtaa   1380
aataaagtgc atttgtacgt ttgtaaagtt gtatcctgta aaaatgttac ctgacttatg   1440
tatttaaagt gaaataaact gttctatctc tgaagaaata ttgggcaata ttacagatct   1500
catactcgaa agacttgccc cttaggcaca tctgtctccc caaagccatg cagacagact   1560
tcttcaactg caactggtag atgaatgtaa aggaattaac aagccaaaac caatttgaat   1620
cagatgagat ttgcatagtt tctgttattt catagaatct catcatgaaa ttttagtatg   1680
tgctctcagg aaaaaggat gttaaaacca ggttaaaaaa aatctgtcat tcaaatcaca    1740
ttctttgatt gtgaaaatct tgacacaaca ctagaggaat cctagctatg aaggcttcac   1800
tatgcctaat gaaataagag atttatgaga gtgttgcctt ggcggtgtta gcggtcaacc   1860
caaaataatt cataataaga gcaacattgc ctgtgatttg ccacacctac tactgaggaa   1920
gtataaaaga cctgtgaaga tggagatgtt caaattcaag aacatcctct tctacacctg   1980
aaccatccat ttctgacacc atg att tac tac agc aac tat tat ggt ggc tat  2033
                     Met Ile Tyr Tyr Ser Asn Tyr Tyr Gly Gly Tyr
                      1               5                  10 ggg tat ggt ggg ctt ggc tgt ggc tat ggc tgt ggt tat cgt ggc tat    2081
Gly Tyr Gly Gly Leu Gly Cys Gly Tyr Gly Cys Gly Tyr Arg Gly Tyr
             15                  20                  25 gga tgt ggt tat ggt ggc tat gga ggc tat gga aat ggc tac tac tgc    2129
Gly Cys Gly Tyr Gly Gly Tyr Gly Gly Tyr Gly Asn Gly Tyr Tyr Cys
         30                  35                  40 cca tct tgc tat gga aga tat tgg tca tat ggt ttc tac tga            2171
Pro Ser Cys Tyr Gly Arg Tyr Trp Ser Tyr Gly Phe Tyr
         45                  50                  55 acaattctag agctcaccag atttgtctgc ttgtgaaacc tggattctca tgctgctctt   2231
gttcatctga tcctgtgtct tcaaaacagc agaaacctaa actaggctat tatcaaagaa   2291
ctacagatgc tgtctttctc tggttctgtt gtgcaagatg ataaagaata ggttttaaaa   2351
tgcaattctt tgattcttaa gtcctttaaa taaa                              2385
```

<210> SEQ ID NO 64
<211> LENGTH: 56
<212> TYPE: PRT
<213> ORGANISM: Homo sapiens

<400> SEQUENCE: 64

```
Met Ile Tyr Tyr Ser Asn Tyr Tyr Gly Gly Tyr Gly Tyr Gly Gly Leu
 1               5                  10                  15

Gly Cys Gly Tyr Gly Cys Gly Tyr Arg Gly Tyr Gly Cys Gly Tyr Gly
             20                  25                  30

Gly Tyr Gly Gly Tyr Gly Asn Gly Tyr Tyr Cys Pro Ser Cys Tyr Gly
         35                  40                  45

Arg Tyr Trp Ser Tyr Gly Phe Tyr
     50                  55
```

<210> SEQ ID NO 65
<211> LENGTH: 2491
<212> TYPE: DNA
<213> ORGANISM: Homo sapiens
<220> FEATURE:
<221> NAME/KEY: CDS
<222> LOCATION: (2001)..(2198)

<400> SEQUENCE: 65

| | | | | | |
|---|---|---|---|---|---|
| aattaaagac | ttaaatataa | agcctcaaac | tgtaaaacta | ttagaagaaa | acatagaaga | 60 |
| ttgttgatat | tggactgggc | aatgatttct | tagatacgat | gtagtgacta | cagtttacaa | 120 |
| tagtgcattg | tgcacttaaa | tatttagggt | gatgttatta | aaacatctat | gaggctggga | 180 |
| gtggtggctc | atgcctgtaa | ccccagcact | ttgggaggcc | aaggcaggca | gatcaccttg | 240 |
| agtcaggagt | tcacgaccag | cctagccaac | atggtgaaac | cccgtctcta | caaaaattaa | 300 |
| aaaattagct | gggtgtggtg | gtgcacatct | gtaatcccag | ctactcagga | ggctgaggca | 360 |
| cgaggatcgc | ttgaacgtgg | gaggtggagg | ttgcagtgag | cccagatcgc | atcactgcac | 420 |
| tccatgcact | ccagcctggg | caagacagag | actccgtcta | aaaagcaac | aacaaaaaaa | 480 |
| gtctatgagt | gcataagaat | gtttaagcat | attattttcg | caactgctaa | attatatact | 540 |
| cattctggaa | attgataaat | gaaaaaatca | actattttcc | tctcctgaat | aaactcatag | 600 |
| atgagaattt | tttttctctt | tataggtttc | tatcttctac | aggtagaagt | aatgatagaa | 660 |
| ttgtaaaatc | agcattttga | acttctggca | ataatgggtc | taggtaacta | ttactgaata | 720 |
| taaaaactg | tagctaaaaa | gtttatgggg | gagattgtaa | aatgaaccca | atccacaatc | 780 |
| ccagccttac | taaatgtgaa | gcaatgggcc | acccagacac | catttacatc | ctaatattat | 840 |
| gtaataaaat | gtcacagag | caactataaa | atatcactct | tgtcaacaaa | tagtaaaaat | 900 |
| aaccagaatc | acatcaacct | tgtcatcta | cctgtagatg | gtatgaggga | tagaggaaga | 960 |
| tatgaaaagg | gaaaacaaga | aagaaatcag | ccacgtctaa | aatgtaagaa | ttctatagga | 1020 |
| caataacaaa | gtttcctcga | acaataaaaa | tacattaaaa | aggaaaaaaa | agaaccatca | 1080 |
| catctctaaa | aagagttaaa | gacatgccta | aatgtaatga | atgcgtgtct | taatgtaaaa | 1140 |
| aaaagactat | gaaaatatat | ttgggaagca | atcaaggaaa | actgatcacg | aattaactat | 1200 |
| tagggatgc | caaataattt | tgtaatgtca | ttggtgtgat | aacggtattg | gggctctctc | 1260 |
| tatacatatt | tttttagact | tctgttgtga | tagagatatt | cactgaagta | cttataagaa | 1320 |
| aaatgttgtc | ttgcctggga | tttgttttaa | aatgttcagc | agaactaact | aactaactac | 1380 |
| aaaaaatgta | cagggagaga | aggaactgaa | gacagaatat | tgatgattat | taaattccag | 1440 |
| ggatgtgttt | ataaagcttc | aaaatacaat | tctatttact | tttatgtctg | aatgaaattt | 1500 |
| acttattaaa | gcaaataatg | aacaagaaaa | aaacttagct | gagtatgcta | ataaaactct | 1560 |
| attgttaaag | ttatttttct | ttgtagaaga | ttctcacata | atgtatgcac | aagtaatcac | 1620 |
| agaattttaa | acatcaacct | tttacaaccc | attcaatgat | taaattagac | acaaagttgt | 1680 |
| caaatatttt | aagctaaaca | aagtatgagt | aagggcttta | aaataagaat | aagaaaaaca | 1740 |
| cattaaaggc | atttgatcat | gagaaggctg | acacaatagc | aaagtcatct | tgtttataaa | 1800 |
| ggcttcacat | tgtttaataa | aacaaatatt | caggaagtat | actaatacaa | attaatagaa | 1860 |
| aatatgcaat | caacaggtcc | tgtggtgggt | cccacccacc | actgagggtg | tatataaaag | 1920 |
| gactgcctgg | gcatataggg | atattcaaac | tgaagaaact | gattccttgc | tcctcaacca | 1980 |
| aatcctccac | tcttgaaacc | atg tgc tac tac agc aac tac tat ggt ggt ctg | | | 2033 |
| | | Met Cys Tyr Tyr Ser Asn Tyr Tyr Gly Gly Leu | | | |

|  | 1 | | | | 5 | | | | | 10 | | | |
|---|---|---|---|---|---|---|---|---|---|---|---|---|---|
| cgt | tat | ggc | tat | gga | gtc | ctg | ggc | ggt | ggc | tat | ggc | tgt | ggc | tgt | ggt | 2081 |
| Arg | Tyr | Gly | Tyr | Gly | Val | Leu | Gly | Gly | Gly | Tyr | Gly | Cys | Gly | Cys | Gly |
|  |  | 15 |  |  |  |  | 20 |  |  |  |  | 25 |  |  |  |

```
cgt tat ggc tat gga gtc ctg ggc ggt ggc tat ggc tgt ggc tgt ggt    2081
Arg Tyr Gly Tyr Gly Val Leu Gly Gly Gly Tyr Gly Cys Gly Cys Gly
         15                  20                  25 tat ggc cat ggc tat gga ggc ctg ggc tgt ggc tat ggc cgt ggc tat    2129
Tyr Gly His Gly Tyr Gly Gly Leu Gly Cys Gly Tyr Gly Arg Gly Tyr
         30                  35                  40 ggt ggc tat gga tat ggc tgc tgc cgc cca tct tgc tat gga aga tac    2177
Gly Gly Tyr Gly Tyr Gly Cys Cys Arg Pro Ser Cys Tyr Gly Arg Tyr
         45                  50                  55 tgg tcc tgt ggc ttc tac tga gaaatatctg gcaactcaac ctcgtggtct       2228
Trp Ser Cys Gly Phe Tyr
 60              65 cttccacatg gacttcctaa atttgccttc ataattcttc atatgagtaa ttcattttc   2288 tgttgtaaaa tgtcaacatc atccttaagt atctggaaga aaaataggt cagatgctgc   2348 aagcctcatc tagagtaact gaaatcattt gacatgtttc acagattttt aaaaagcttt  2408
gttttgatat tgtactgtca ttaaattgtt gattttgat caacttatgt gagaagatgt   2468 aaatttctt ttaataaaca tct                                           2491
```

<210> SEQ ID NO 66
<211> LENGTH: 65
<212> TYPE: PRT
<213> ORGANISM: Homo sapiens

<400> SEQUENCE: 66

```
Met Cys Tyr Tyr Ser Asn Tyr Tyr Gly Gly Leu Arg Tyr Gly Tyr Gly
 1               5                  10                  15

Val Leu Gly Gly Gly Tyr Gly Cys Gly Cys Tyr Gly His Gly Tyr
                20                  25                  30

Gly Gly Leu Gly Cys Gly Tyr Gly Arg Gly Tyr Gly Tyr Gly Tyr
             35                  40                  45

Gly Cys Cys Arg Pro Ser Cys Tyr Gly Arg Tyr Trp Ser Cys Gly Phe
         50                  55                  60

Tyr
 65
```

<210> SEQ ID NO 67
<211> LENGTH: 2910
<212> TYPE: DNA
<213> ORGANISM: Homo sapiens
<220> FEATURE:
<221> NAME/KEY: CDS
<222> LOCATION: (2001)..(2135)

<400> SEQUENCE: 67

```
aagaatgctt gtgattttg cacattgatt ttgtatcctg agattttgct gaagttgcct     60
atcagcttaa agtatctcaa aataataaga gctagctatg acaaacccac agccaatatc   120
atactgaatg ggcaaaaact ggaagcattc cctttgaaaa ctggcacaag agagggatgc   180
cctctctcac cactcctatt taacatagtg ttggaagttc tggccaaggc aatcaggcag   240
gaaaaggaaa taagggtat tcagttagga aaagaggaag tcaaatgttc cctgtttgca    300
gatgacgtga ttgtatatct agaaaacccc atcatctcag cccaaatttt ctagccctct   360
tattcagaaa gttgagcata cacaccagct ctctgtcatc aagtgaaggt ggggaacata   420 aggtgggct taagggagtt gtgaaagcac aaacaactta cagaagcaat tggcttggat   480
tctcatggtt tcctctctgc tgagttgtct cttctttctc aacatacacc tatgaattta   540
```

-continued

```
tgctgatttt ccagttggag aaggaaaaat tagtcctgga ttatagatgg ttctgccaat    600
atggtagcac tgcctaaaag tggatgactg aagtacaaca gatcaaatcg gggattaccc    660
taaaggtcag tggtgaagga aaattttcaa ttattttta tcatcttaag aaatgatagt    720
atctagattc agcctgcctt tgagaactta agtctacata taagtacatg atacagacag    780
agtcaatatc cctacagaaa aattaatagt catgccttct gttatatttg ggtctcaaaa    840
atgtctactt tacgttcctg tgactttgga atcagataag attctcaatg ctttctttt    900
ctccgaagaa acatatctac attgcagtgc aggtacaaga taatcaacca acaactttt    960
taaagaatgc ttaaggtgtg gagaagaagg aactaaacag gcaagaaaag ggcactactt   1020
ttaagagagc atagcaatag gaaaactaca gaataatatg tgattggtgg gagtttgtac   1080
agaataaatc acagttgatc cttgaacaat gcagggatta ggagtgccaa cctccacgca   1140
gttgaaaatc tgagtataac ttttgactcc ccaaaaactt aactactaat agcctactgt   1200
tgaccagaag ccttaccaat aacataaaca gttgattaat acatgcttat gttacctgta   1260
atgagagatt atactcctat aataaagtag gctaaagaaa agaaaatttt attaagaaaa   1320
taaagaaaaa gagaaaatgg atttactatt cactaagtgg aagtggatca tcataaaggt   1380
cttcagcctt attgtcttca tgttgagtag gttgaggagg agaaggagga ggaggggttg   1440
gtcttgctgc cggagtggca gaggtgaaga aaatctgctt aatataagcg tatctgtgca   1500
gttcaaactc atggtattca agagtccact gtatttgcta ctaagttta tagcgataac   1560
atcacagctg tgttgattaa gatttaaata tgcatataag aagaaggta ttattagcaa   1620
agtgatcgga agaggatggc atttgcctcc tccacgtgat gtcatccaac atagctacaa   1680
aggttaaatt cggcatcagt gtgagtaagg tcatggaact cagtattttt ttttcctta   1740
aagtctatca gctgtttggc aggatcataa catactgaga agaaaatctc aattttatca   1800
ggatagggag tcttttttta aaatctaaag atacaagatt aatgagattt ttaaatacag   1860
gttggtctat atgacaatgt caggagtgcc tgtggtttgt cacacctcca ctgagactga   1920
taaaagaccc agtatttag tgttttatg cactaaaact tatgctggcc tctcaggcta   1980
gagacttaaa tcctgacaca atg agc tac tat ggc aac tac tac gga gga ctg   2033
                     Met Ser Tyr Tyr Gly Asn Tyr Tyr Gly Gly Leu
                      1               5                  10
ggc tat ggc tat gac tgt aaa tat agt tat acc tct ggc ttt ggt gcc      2081
Gly Tyr Gly Tyr Asp Cys Lys Tyr Ser Tyr Thr Ser Gly Phe Gly Ala
              15                  20                  25
ttt aga atc ctg gac tgt ggc tac aga tgt ggc tgt ggt ggg gta tgg      2129
Phe Arg Ile Leu Asp Cys Gly Tyr Arg Cys Gly Cys Gly Gly Val Trp
          30                  35                  40
att tga ctgctgccac caatatgatt atgctacatg cttattatca ggcactgact      2185
Ile
  45
gaataatatc tacaattggg tccatttcct tatgagacag gggtgctgtt ctactacact   2245
tttttaatt tgtttaaccc aattagaatt cttaatgatt ccctataatc ccagcacttt   2305
aggaggccga ggcgggtgga tcacctgggg ttaggagttc gagaccagcc tggccaacat   2365
ggcaaaatcc catctctact aaaagttaaa aaaatagcca ggtgtggtgg tgggtgcctg   2425
tagccccagc tactggggag gctgaggcag gaggatcact tgaacccaaa ggcagaggtt   2485
gcagtcagcc gagatggcac cactgcactc cagcctgagc aacaaaatga gattccatct   2545
caaaaaaaca aaaataatgc ttagttattc aatctaattc taggcaaaga acacacatca   2605
```

| | |
|---|---|
| ttaaattcac actaaatcca catcagtgcc ccagattaac tacattttc tcttccaaac | 2665 |
| tgatgtgttt tcataattta ccaagcaaat tactttttga tatgtttcag gagtagggag | 2725 |
| ctctaggttt attttaatt aaacttactt tggccaggcc aatgtcattc attttttaaa | 2785 |
| tttattaatt actcacttgt ttaataagtc ctcattaagt aatttctata tagggcttcc | 2845 |
| tgttaagtct tagtgttact tatgggagaa gagttttaa gcagaaaaac aaatgtttaa | 2905 |
| ataaa | 2910 |

<210> SEQ ID NO 68
<211> LENGTH: 44
<212> TYPE: PRT
<213> ORGANISM: Homo sapiens

<400> SEQUENCE: 68

Met Ser Tyr Tyr Gly Asn Tyr Tyr Gly Gly Leu Gly Tyr Gly Tyr Asp
 1               5                  10                  15

Cys Lys Tyr Ser Tyr Thr Ser Gly Phe Gly Ala Phe Arg Ile Leu Asp
                20                  25                  30

Cys Gly Tyr Arg Cys Gly Cys Gly Gly Val Trp Ile
            35                  40

<210> SEQ ID NO 69
<211> LENGTH: 2603
<212> TYPE: DNA
<213> ORGANISM: Homo sapiens
<220> FEATURE:
<221> NAME/KEY: CDS
<222> LOCATION: (2001)..(2252)

<400> SEQUENCE: 69

| | |
|---|---|
| gttgattttt gtatatggtg agagatgggg tccagtttca ttcgtctgca tatagcaatc | 60 |
| caattttccc agcatcattt attgaagagg atatccttc cccaatgtat gttcgtgttg | 120 |
| acttagtcaa agaacagctg gctataaata atatggcttt atttccgggt tctctcttct | 180 |
| ttttcaatga tctatttatc tatatttata ccactaccac actgttttgg tagcccctgtg | 240 |
| atgtgttcct tgattctgta tttttacaaa acattattgt ataaaatgct tcaggcaagg | 300 |
| taaactgagg tcaattacat ggaagttcat tttctgagag catttgctca cttttgaaag | 360 |
| tttattacga aaacattact tgacatatgt atatttacac atatgtatat cacatacttt | 420 |
| aaaaatagca aaattaaaat tcaaatctca aaatttagt acaacaaata gatcaataca | 480 |
| agtatataca gaaatttgaa aagctgttac tgtttaggaa tgcttatatt tgggcaaaag | 540 |
| aaaaggggaa aagaaagaaa aagttttgtc tccaccatgt atcagggtca ttgctacact | 600 |
| acttatattg cctgtgtatt ttctgtaggc ctcttaataa aattttaaat aaaagtaatt | 660 |
| attttttattc ccatttggca gttgcagaaa ctgaggttca tctaagttga ggacattttc | 720 |
| catggtcata taattaggaa aagactcagt caggaaatta accaatctgt tttccaggga | 780 |
| aagctatttc tactacagag cctctggaac atggaggaca ttgtactgat tatcaatttg | 840 |
| tggcccctca gcatctaatt catccttcag tatattctct gtgctgatag atgggattcc | 900 |
| tttaagtatt tctccttcac tgtgagcatg gcttcaagtt ttctcaggag aggatgcagc | 960 |
| agggacattg caggaggaaa cagagctcct gcattttgg gtgtggcaca gaagggcagt | 1020 |
| agaaggtatc agcagtgtgg gttaaggata tccaatgaag ctccacctca gttttgggtc | 1080 |
| caggatatgc tggaaattat tattcagtag aaagcaccga tgtacagcat aaacatcaga | 1140 |
| gtggtccaat tattatggat atccaattgt taattcggtt cttaaacaca aacaaacctg | 1200 |

-continued

```
tgtttaagaa cagaatttaa caactggaca tcaacaacaa agttgtgaac caaggaattc    1260
ccctcacttt aaatggaaaa atcaaaagtt tattctataa attttaaatg acacatatta    1320
cataactgac ctgtcagacg tttaacaaaa attttttttt caagcaagag aaggtcatag    1380
actgcctaga aaagggggga atggtcaaac ttttcttcag agagaaggag agggtttcaa    1440
gaagttgagg tagcacgtgg aaatacccaa ttctttgtcc aaaaaccatg atttagtaat    1500
ttttagtgac tatgataaga aaagaacacc aaggtattag gaaagaataa aagaaatga    1560 tgatgatgat ggtattaaga gcagtgagaa ctccttatta aatagataat tctcaagacc    1620
ttacaagaac agaaagataa acatacattt ataggtcaaa catattttgg tgatgtgtta    1680
tgtcatggct atgaaatgaa actatggaaa acaaaattat ggttgtataa gcttgtgtgt    1740
ttagaacttg tatatttgtt ttcttttcag gcataaaaat attcctaggg aagtcataag    1800
caaattatga attccaaaga aagtagatgt acacagaatg agctcatttt aggcagatga    1860
ttataaaatg agcaaataga gcccatgtga ggatgaccca tgcatccctg aagtatata    1920 aaggtcttag aagagtagag gacagtcaca cttcagaaat atcctcctac acctcaactg    1980
```
```
aaatctaacc tcctgaaatc atg tgt tgc aac tac tac aga aac tgc tgt ggg    2033
                      Met Cys Cys Asn Tyr Tyr Arg Asn Cys Cys Gly
                        1               5                  10 ggc tgt gga tat ggc tct ggc tgg agt tcc ggc tgt gga tat ggt tgt      2081
Gly Cys Gly Tyr Gly Ser Gly Trp Ser Ser Gly Cys Gly Tyr Gly Cys
            15                  20                  25 ggc tat ggc tgt gga tac ggc tct ggc tgt aga tat ggc tct ggc tat      2129
Gly Tyr Gly Cys Gly Tyr Gly Ser Gly Cys Arg Tyr Gly Ser Gly Tyr
        30                  35                  40 gga act ggc tgt ggc tat ggc tgt gga tac ggc tct ggc tgt gga tat      2177
Gly Thr Gly Cys Gly Tyr Gly Cys Gly Tyr Gly Ser Gly Cys Gly Tyr
        45                  50                  55 ggc tgt gga tac agc tct agc tgc tgt ggc tac cga cca ctt tgc tac      2225
Gly Cys Gly Tyr Ser Ser Ser Cys Cys Gly Tyr Arg Pro Leu Cys Tyr
        60                  65                  70                  75 aga aga tgc tat tcc tct tgc tac taa tcatcactac aggtcatcct             2272
Arg Arg Cys Tyr Ser Ser Cys Tyr
                80
```
```
tggctttgca atgacctctc caagatcaag ttcaattgaa atctcccta cccattatct     2332 tcacatctaa gtaaaggttg actatggtca cctgactatc tgaatgcata agagaagc      2392 tgttggcagt ggatggagac tgagtagttt catcacatcg ctgaagagag gagattttat     2452
tctgattaat tttctagtgt aattttctaa tgtaagctct tacatctttt tctgaatctt     2512
tgtgccatga ctatttgctg aaacacaaga ggactatata attggagcat actaaaatgg     2572
aaaaaaaata gaattttctt aataaaaggc c                                    2603
```

<210> SEQ ID NO 70
<211> LENGTH: 83
<212> TYPE: PRT
<213> ORGANISM: Homo sapiens

<400> SEQUENCE: 70

```
Met Cys Cys Asn Tyr Tyr Arg Asn Cys Cys Gly Gly Cys Gly Tyr Gly
  1               5                  10                  15

Ser Gly Trp Ser Ser Gly Cys Gly Tyr Gly Cys Gly Tyr Gly Cys Gly
             20                  25                  30

Tyr Gly Ser Gly Cys Arg Tyr Gly Ser Gly Tyr Gly Thr Gly Cys Gly
         35                  40                  45
```

Tyr Gly Cys Gly Tyr Gly Ser Gly Cys Gly Tyr Gly Cys Gly Tyr Ser
            50                  55                  60

Ser Ser Cys Cys Gly Tyr Arg Pro Leu Cys Tyr Arg Arg Cys Tyr Ser
65                  70                  75                  80

Ser Cys Tyr

<210> SEQ ID NO 71
<211> LENGTH: 2532
<212> TYPE: DNA
<213> ORGANISM: Homo sapiens
<220> FEATURE:
<221> NAME/KEY: CDS
<222> LOCATION: (2001)..(2240)

<400> SEQUENCE: 71

| | | | | | |
|---|---|---|---|---|---|
| ggtatcctct | tgcagaatca | ccatggccct | gctatgacta | taaagataaa | atttgtaaaa | 60 |
| atattagaga | aaataaagat | gccatacaca | ttagacaatt | ttggaatgtc | gtataaattt | 120 |
| tatggctcaa | caccaattcc | tgagttctga | ccatgttttc | agcctcagta | gaaaaaattt | 180 |
| tctttgtggc | accaatatca | tgtctacagt | cttacctaga | ctagacccaa | attgaagcta | 240 |
| cagtcatatc | tagactagac | ccaaattgaa | gctacagtgg | cttcagtttg | ggtctagtct | 300 |
| ttgactccta | ttgactctta | agttcctctt | atgtaaaatg | tggattgggt | ctcaggtttg | 360 |
| cctggaattt | ctactgtgaa | aggtatagtc | tctttcctca | agaatatcat | gcttttatta | 420 |
| gtaaacagga | taaagtttca | ccaaagcatg | acaaatctat | tatattcgtc | tgcatatagg | 480 |
| agcaaacaag | aggatccact | tgtgaagtag | aatttatagt | tttgaatttc | aaggatgaaa | 540 |
| aaacagaaag | aaactaaagg | aaaagaaaaa | attgagacag | agatctattt | atgctttttt | 600 |
| taagggacta | acatagcag | agaaatgaga | tgagacgagt | gacagatagc | agaaaaaaaa | 660 |
| ggaaagattt | ccaactgaag | ggaaaatgta | atccacagta | gcaatgagga | aaggcatcct | 720 |
| gtagaaagtg | attccagatc | tgacttttga | tgtataaaca | gaaggttttt | ttggttgata | 780 |
| attgagggtg | atgagaaaaa | tactaatggc | agaaaaaatg | atactaattt | tcctcttttg | 840 |
| tatcttgaaa | aggtaagtgt | gatagagagg | attgttggga | agaaggaggg | cacctcggat | 900 |
| ttcaaaatca | cgatgaatat | ttttgtagaa | gattgagaac | ttgtaataag | tgggtaattg | 960 |
| agaattttga | atgagtagtg | tgaaatgcgt | gtatggaaac | gggacaaaat | ttattttgt | 1020 |
| gctactttat | atcatagaag | ggttagttgt | taatggtggg | cttttgctgt | cagtaaccta | 1080 |
| aaattgtcca | ctatccttta | gcttctgaag | taaatgtcca | aggaatagta | gtgaaggag | 1140 |
| aagaaaaatg | gtttattaaa | ttctaggaat | gtatctgtat | ttcatcatgc | aaaactttga | 1200 |
| tgaaatctgt | attggaggaa | agaactgagt | ttctggtcga | atgaatttt | ttacttcctt | 1260 |
| atccaaatga | agctgtttag | ttttaaaaag | gctcctcaat | gacaattact | tatatagctg | 1320 |
| aagaaatggg | agacaaaagg | agggcttctc | tgcctcccca | gggtcttggt | ttgcctggtg | 1380 |
| gatggaagga | aaatgtagga | agcacttgca | gatagcatac | attctggctt | tgaatgatca | 1440 |
| gatgtgaata | tgtttcttgg | gatttgaggg | aggttggaca | aggggtaggt | gtggaagtgc | 1500 |
| agagtgagtt | ggagaaagaa | gtctggcaag | aagttgtaat | gactcaggaa | aggagatagg | 1560 |
| agtgtctcct | tccctatggg | tagaggtaga | cattttagga | aaaagagag | gaaaaaaggg | 1620 |
| ataaaatttt | gttattatcc | tcccaaaact | tgttatgtaa | gatataaatt | tactgatagg | 1680 |
| agattttgaa | aattagtatc | agctttatat | ttgggcacat | gatttcattg | aggcagttct | 1740 |
| ttggcagagc | agattaaaat | gatgttcctg | aaatgaaact | agagtctcca | aaataattgg | 1800 |

-continued

```
ctcattttaa gcaaatatt attgatggtc aacagtgact ggcacataat aattgattaa      1860
atatttgttg cctaagtcag ggaatgagtg atatgctttg caattactg acagtatata     1920 aaggtctcag ggaagtagaa gacatccaca cctcagaagc atcttcttga aacccatctc    1980
aattctctcc tcttgacaac atg tgt tgc aac tac tac ggc aac tcc tgt ggc   2033
                     Met Cys Cys Asn Tyr Tyr Gly Asn Ser Cys Gly
                      1               5                  10 tat ggc tcc ggc tgt ggc tgt ggc tat ggc tct ggc tct ggc tgt ggc     2081
Tyr Gly Ser Gly Cys Gly Cys Gly Tyr Gly Ser Gly Ser Gly Cys Gly
            15                  20                  25 tgt ggc tat gga act ggc tat ggc tgt ggg tat ggc tgt ggg ttt ggc     2129
Cys Gly Tyr Gly Thr Gly Tyr Gly Cys Gly Tyr Gly Cys Gly Phe Gly
        30                  35                  40 tcc cat tat ggc tgt ggt tat gga act ggc tat ggc tgt gga tat ggc     2177
Ser His Tyr Gly Cys Gly Tyr Gly Thr Gly Tyr Gly Cys Gly Tyr Gly
    45                  50                  55 tct ggc tct ggc tac tgt ggc tac cgg cca ttt tgc ttt aga aga tgc     2225
Ser Gly Ser Gly Tyr Cys Gly Tyr Arg Pro Phe Cys Phe Arg Arg Cys
60                  65                  70                  75 tat tct tcc tgc taa aacatcactg tcggaggacc atttgcttct aaaatgacac    2280
Tyr Ser Ser Cys
            80 gtctgaagat aatgctgatt caaggattcg tactccaaga tttctatatc caagaattac   2340 atgcttgaca gaatcttcga cctctagcct cacatttctt tgaatgaaat catggccata   2400 ggatccatgg tgtcatctga ctgttttcca aatgttatct tttgctccct taatctctga   2460 ttctctgtta tgactgtgtt aatgatcata acatctacag ttgcggaagt caatcatttg   2520 taataaaaat gg                                                        2532
```

<210> SEQ ID NO 72
<211> LENGTH: 79
<212> TYPE: PRT
<213> ORGANISM: Homo sapiens

<400> SEQUENCE: 72

```
Met Cys Cys Asn Tyr Tyr Gly Asn Ser Cys Gly Tyr Gly Ser Gly Cys
 1               5                  10                  15

Gly Cys Gly Tyr Gly Ser Gly Ser Gly Cys Gly Cys Gly Tyr Gly Thr
            20                  25                  30

Gly Tyr Gly Cys Gly Tyr Gly Cys Gly Phe Gly Ser His Tyr Gly Cys
        35                  40                  45

Gly Tyr Gly Thr Gly Tyr Gly Cys Gly Tyr Gly Ser Gly Ser Gly Tyr
    50                  55                  60

Cys Gly Tyr Arg Pro Phe Cys Phe Arg Arg Cys Tyr Ser Ser Cys
65                  70                  75
```

<210> SEQ ID NO 73
<211> LENGTH: 2863
<212> TYPE: DNA
<213> ORGANISM: Homo sapiens
<220> FEATURE:
<221> NAME/KEY: CDS
<222> LOCATION: (2001)..(2492)

<400> SEQUENCE: 73

```
ggaagagagt tgtgtgctta aaagacactc attttctttt ttcctgaagt gatggaagat      60
attttctagg atccttttat ctgtaatttc cagctttcaa tgggagagac acatcaagac     120
```

-continued

```
aaggtaataa cttatacaat tgtctgtcat tccaggaatg tggcagtagg cactgaaacg      180
ttctcctttg taactctact actcacttca gattttggga attgccacag ttaagtactc      240
ttccatagta gcctgtgaac ctgtggctgg gagaagcctg taaactagta atccatttta      300
caacatgcaa gccaggccct agggccaagg actcaggcct tcaaacacca actaagatac      360
cctctgtggt gggaagagca tagccacaac attgtggaaa gtagtcatct cattaatttc      420
accccgttcc tgggaacaca tggtgagtca ctgagggagg tcaggacat tgaggtctga       480 tatctgggaa tcatgctatt gctcacagca ccctcttctt tgggtgtgtc gttagtttcc      540
aattagggat ttctgatgag tcctgacata acgctgtttg ctttgtggat atttaaaaca      600
tagcttacct gtagccctca aatacatgga aatccatttt attcccttac gctccctcat      660
gtaagctagt ttaaaatga gtcagatgct acagctgttt gggacagaa ataccactga        720 ccacttgaag cgatgttgaa gttgcttatt ttgccagagt tgaggcagtt tattcatcta      780
tgttcaggtg gacccaaacg agccatcatt ctggtgttta aaattcatta tattgtagtg      840
agatgaaata aaatagagtg atatccctat agcttcccca agcataaaaa gaataattaa      900
atatagcaca ctcttcacac atctcttcat taccaaacat tgattaagtg cctgcttccc      960
ccagctctgc ctccccctta tccctgatgg agacaatgac cttgaagagc ctttagtttg     1020
tccataatta aaatgcattc tatctatatg tgtgaaaata aatatctttt gaacatattg     1080
aacaaattgg gagaaagaca ctgtacccct tcaaattaac attatgataa ttttaaaaat     1140
taactaagcc ttttccactg gcatattaat gagacccagg agtcactatt atccactgtt     1200
attaaattaa acattttagg aataaagctc atccaattta cttagaaaag gtcttggcta     1260
caaatacagt tgcacttagt tagcttctaa tttgctttgt tggttgaaca taaagggtgg     1320
gtcccactgc cctctagcct tcccacgggc atcttgtttg agtcagttga ttaattttga     1380
gagccagctc agactttgga tacaagtctc tgtgcccttt gttcctgtca agtgttgtca     1440
ctgttgtctt gaaacatatt caaggaggca ccttcccaat gaggagctcc gttaggtgtg     1500
gtagagtgac tgattaagtt atgtttaaaa gatattaagt ccagtgacaa atgaaacagg     1560
gcatgggctt gtaattggtc ctggtaggga gggagagagt gtgtgatggt aggatggtgg     1620
catctttggt aggatgagtg tcaggtcaac actcatcata agcaagatga atgagggaca     1680
acgtgtgggc tgggatgacc aatagctttg aagctgccaa ccagccttct taatcagact     1740
aagtacagta cagaagactt gtgatttagt taccaaacta ctaaactttc tttatgaggg     1800
tgaaggcttc ttaagagaca attaatgtgt agattcacaa gatgttctaa ggcaaactgg     1860
tctgagccaa agaagccacg gagaccaggg agagagcccc acccaccagc aaggatatat     1920
aaaagctcag gagtctggag tgacattcac aactcaggag gtaacttcag caagctacct     1980
```

| | | | |
|---|---|---|---|
| gcagccctct gtctgacatc atg tcc ttc aac tgc tcc aca aga aat tgc tct | | | 2033 |
| Met Ser Phe Asn Cys Ser Thr Arg Asn Cys Ser | | | |
| 1 5 10 | | | |
| tcc agg ccc att gga gga cgc tgc att gtt cca gtg gcc caa gtt acc | | | 2081 |
| Ser Arg Pro Ile Gly Gly Arg Cys Ile Val Pro Val Ala Gln Val Thr | | | |
| 15 20 25 | | | |
| acg act tcc acc act gat gct gac tgc ctg ggc ggc atc tgt ttg ccc | | | 2129 |
| Thr Thr Ser Thr Thr Asp Ala Asp Cys Leu Gly Gly Ile Cys Leu Pro | | | |
| 30 35 40 | | | |
| agt tcc ttc cag act ggc tct tgg ctc ctg gac cac tgt caa gag acc | | | 2177 |
| Ser Ser Phe Gln Thr Gly Ser Trp Leu Leu Asp His Cys Gln Glu Thr | | | |
| 45 50 55 | | | |
| tgc tgt gag ccc act gct tgc cag cca acc tgt tac cgg cga act tca | | | 2225 |

```
Cys Cys Glu Pro Thr Ala Cys Gln Pro Thr Cys Tyr Arg Arg Thr Ser
 60                  65                  70                  75 tgt gtc tcc aac cct tgc cag gtg act tgc tct cga caa act acc tgt    2273
Cys Val Ser Asn Pro Cys Gln Val Thr Cys Ser Arg Gln Thr Thr Cys
                 80                  85                  90 att tcc aac ccc tgc tca act acc tac agc cgg ccg ctc acc ttt gtc    2321
Ile Ser Asn Pro Cys Ser Thr Thr Tyr Ser Arg Pro Leu Thr Phe Val
             95                 100                 105 tct agt gga tgt cag ccc ctg gga ggc atc tcc agt gtc tgc caa cca    2369
Ser Ser Gly Cys Gln Pro Leu Gly Gly Ile Ser Ser Val Cys Gln Pro
        110                 115                 120 gtg ggc ggc atc tct act gtc tgc caa cca gtg gga gga gtc tct act    2417
Val Gly Gly Ile Ser Thr Val Cys Gln Pro Val Gly Gly Val Ser Thr
    125                 130                 135 gtc tgc cag cca gcc tgt ggg gtc tcc agg acg tat cag cag tcc tgc    2465
Val Cys Gln Pro Ala Cys Gly Val Ser Arg Thr Tyr Gln Gln Ser Cys
140                 145                 150                 155 gtg tcc agc tgc cga aga acc tgc taa gtgtgtagga gccagtgagc          2512
Val Ser Ser Cys Arg Arg Thr Cys
                160 gaatcaagac tccacgacct gccagctgtt tccaggatct tccagcatgc tgcttgtccc   2572 tgaatagctc ttcatagctg acccttcttg tgaccgcctg actgctggct actatccatg   2632 cacacgctgt ctttagcact ctaaaatttt tctggccagc cctaagcttg ttttaagggt   2692 tgctcactgg tgctgtgtat gcctctggat gtgtccagaa gctttaccat ccacacccca   2752 gtctctgatg cttttgacat gttttcacct tgctgctgta tctcctggcc tctgcttttg   2812 tgtctcacaa aaacagagct tgtctcacca tgtatttctc aataaacctg c            2863

<210> SEQ ID NO 74
<211> LENGTH: 163
<212> TYPE: PRT
<213> ORGANISM: Homo sapiens

<400> SEQUENCE: 74

Met Ser Phe Asn Cys Ser Thr Arg Asn Cys Ser Ser Arg Pro Ile Gly
  1               5                  10                  15

Gly Arg Cys Ile Val Pro Val Ala Gln Val Thr Thr Thr Ser Thr Thr
                 20                  25                  30

Asp Ala Asp Cys Leu Gly Gly Ile Cys Leu Pro Ser Ser Phe Gln Thr
             35                  40                  45

Gly Ser Trp Leu Leu Asp His Cys Gln Glu Thr Cys Cys Glu Pro Thr
         50                  55                  60

Ala Cys Gln Pro Thr Cys Tyr Arg Arg Thr Ser Cys Val Ser Asn Pro
 65                  70                  75                  80

Cys Gln Val Thr Cys Ser Arg Gln Thr Thr Cys Ile Ser Asn Pro Cys
                 85                  90                  95

Ser Thr Thr Tyr Ser Arg Pro Leu Thr Phe Val Ser Ser Gly Cys Gln
                100                 105                 110

Pro Leu Gly Gly Ile Ser Ser Val Cys Gln Pro Val Gly Gly Ile Ser
            115                 120                 125

Thr Val Cys Gln Pro Val Gly Gly Val Ser Thr Val Cys Gln Pro Ala
        130                 135                 140

Cys Gly Val Ser Arg Thr Tyr Gln Gln Ser Cys Val Ser Ser Cys Arg
145                 150                 155                 160

Arg Thr Cys
```

-continued

```
<210> SEQ ID NO 75
<211> LENGTH: 2509
<212> TYPE: DNA
<213> ORGANISM: Homo sapiens
<220> FEATURE:
<221> NAME/KEY: CDS
<222> LOCATION: (2001)..(2192)

<400> SEQUENCE: 75
agtttggcct acacccagga atgaacaagg acagcttaga ggttagaagc aagaaggaat      60
cggttagatc agatctcttt cactgttata attttctcag ttaaaattat tgcaaaggtg     120
atttcaatta gttgcagact gcggatctag gtttctgtag ctcccttttgc aagtccttct   180 taggtagatt accaccttcc ttggggatgt gagagctgtt gtcactgatg atacaggttc    240
tcagctaaaa ctgagtccca ttttacatct tgttttgctt taatatttat ctcttagtga    300
atacatatac ttttaactct aagacaagaa agagttgggc ttcaactttc cacttcaaaa    360
cttttgaacc tattttttgtt ctcccctctc agttttacat ctcttgaaca atcaatgcaa   420
caggcatctc cattgtaatc tcattgagaa taagtggatg tgactttcag tgtccacttg    480
ctaattttag tcctttgagt tctggcccaa aggaaaggaa cagaccaatc agcatataga    540
tcaaaaatca aaatgagaaa gctcaccaac cgagaaagca aaggagcatt ttcattcttc    600
tgttgtgata atacaatatt tcttgctttt gcctttgttg tacaacatct ataaaaatgt    660
gatgatgaaa aaaacaggt gaaagtgaat gatttaggtt ctagtctggg ttttgtcact    720
cactgggtga tctgaccaat cttctccaat tctgtttcat catctgtaaa gtaagagggt   780
tacaccagtt ctgatattat attattctat ctgaagtgat tattaatagt atatagaata    840
gtcgtactgc ttatgtgctt gaaattggtt ttgataccaa tggctaagta gaagtgattc    900
tgacccttat catgaacact tcagtgggct tcattcttca aaagaaaat gtcatatttta   960 agtattttta attttacata ttctgtaaa ttgtagttta attaaggttt ccttagagag    1020
cagaagatgg aatcccagaa tttggaaaac agcttttttaa aacctctttg ctgattgtgt   1080
taggaattta gtaaggcaga gagggctgcc tgcctacctg tgactgtgga gtcagatggg    1140
tagatccagt actcagatgt taatctcttt agaagattat ttttttaaaaa gaagattaca    1200 aagatgaaga atatggtatc actttgcaaa aatcacaccc acggctcttg cccctagtgt    1260
tatttcctat ataaacattg aataatgaaa aagtcttgca gtaagagcta agagctatca    1320
aaagtttcat aaacaacatt gagttaaaag ggtagtaatg tgtaaggaaa caaaattttt    1380
ccatttgggt ttttctctct ctcttaaaaa aataaatgtg atccttttgt gctatcagct    1440
acattttgtt ggatttatac agtaagtgta cctcttctat tacttcacta acttaaataa    1500
caaagatgaa gggaaaaac tcatgggatt gggaagggca gttcttattt acagccatat   1560
ctctagctct gagcatagtg cctgggatgc attagttggg cattaaatat ttgtgcaagg    1620
aatacattaa gaattggata ctgggaaggg gctgtaatga agaacaatt ttaggtgaca    1680 aaatgggagc tgattgctgc tcttatgtct gattatagag cattaactat gatggtcaaa    1740
gcaagagggc tttgaagaca gcataatcat cctgtggaat ccaaactgca cagaaatcga    1800
atgaaaacat ctttaattag tgtcaggaat tgtcctacag ttttaagatg agtgagtttt    1860
ttttcatgca attgaatcta cgccatgaga agtctacccc actaatcact gaggatgtat    1920
aaaagtccca gggaagctgg tgatagttgt actcaggaaa cttgcccttg acctccaaac    1980
acatctacag ttgctgaacc atg agc tac tac aga agc tat tat gga ggc ctg   2033
                      Met Ser Tyr Tyr Arg Ser Tyr Tyr Gly Gly Leu
```

```
                     1               5                    10
ggc tat ggc tat gga ggc ttt ggt ggc tgg ggc tat ggc tat ggc tgc       2081
Gly Tyr Gly Tyr Gly Gly Phe Gly Gly Trp Gly Tyr Gly Tyr Gly Cys
             15                  20                  25 ggc tat ggc agc ttc cgc agg ttg ggc tat ggc tgt ggc tac gga ggc       2129
Gly Tyr Gly Ser Phe Arg Arg Leu Gly Tyr Gly Cys Gly Tyr Gly Gly
             30                  35                  40 tat gga ttc agc tgt tgc cga cca tta tac tac gga gga tat gga ttc       2177
Tyr Gly Phe Ser Cys Cys Arg Pro Leu Tyr Tyr Gly Gly Tyr Gly Phe
         45                  50                  55 tct gcc ttc tac tga agagtgaact cattctttgg atcactagaa tctgtctatc       2232
Ser Ala Phe Tyr
 60 atcctgactt aattctcctt tcaggtcttt ttaccccctc tgtgaattgc gcagccactt    2292 tcttgataaa ccagacaaag cagcaaaggg tgccttgtga actcttcaaa gtcaagactc    2352 aattctggca acaaacacaa cagaatcagt ggcagcagca aggggagccc ttcctgtaga    2412 atgacctaga atcccacctt tcaagctgtg aatccctctc ttcccttatt aatatatcaa    2472 catggcacca actcttcttc tatttcaata aactaat                             2509

<210> SEQ ID NO 76
<211> LENGTH: 63
<212> TYPE: PRT
<213> ORGANISM: Homo sapiens

<400> SEQUENCE: 76

Met Ser Tyr Tyr Arg Ser Tyr Tyr Gly Gly Leu Gly Tyr Gly Tyr Gly
 1               5                  10                  15

Gly Phe Gly Gly Trp Gly Tyr Gly Tyr Gly Cys Gly Tyr Gly Ser Phe
             20                  25                  30

Arg Arg Leu Gly Tyr Gly Cys Gly Tyr Gly Gly Tyr Gly Phe Ser Cys
         35                  40                  45

Cys Arg Pro Leu Tyr Tyr Gly Gly Tyr Gly Phe Ser Ala Phe Tyr
     50                  55                  60

<210> SEQ ID NO 77
<211> LENGTH: 192
<212> TYPE: DNA
<213> ORGANISM: Homo sapiens
<220> FEATURE:
<221> NAME/KEY: CDS
<222> LOCATION: (1)..(192)

<400> SEQUENCE: 77 atg ctc tgc gac aac ttc ccc ggg gct gtc ttc cca gga tgc tac tgg         48
Met Leu Cys Asp Asn Phe Pro Gly Ala Val Phe Pro Gly Cys Tyr Trp
 1               5                  10                  15 ggc agc tat ggc tac ccg ctg gga tat agc gtt ggc tgt ggc tat ggc         96
Gly Ser Tyr Gly Tyr Pro Leu Gly Tyr Ser Val Gly Cys Gly Tyr Gly
             20                  25                  30 agc acc tac tct cca gtg ggc tat ggc ttc ggc tat ggc tac aac ggc        144
Ser Thr Tyr Ser Pro Val Gly Tyr Gly Phe Gly Tyr Gly Tyr Asn Gly
         35                  40                  45 tgt ggg gct ttc ggc tac agg aga tac tcg cca ttt gct ctc tac tga        192
Cys Gly Ala Phe Gly Tyr Arg Arg Tyr Ser Pro Phe Ala Leu Tyr
     50                  55                  60

<210> SEQ ID NO 78
<211> LENGTH: 63
<212> TYPE: PRT
```

<213> ORGANISM: Homo sapiens

<400> SEQUENCE: 78

```
Met Leu Cys Asp Asn Phe Pro Gly Ala Val Phe Pro Gly Cys Tyr Trp
 1               5                  10                  15
Gly Ser Tyr Gly Tyr Pro Leu Gly Tyr Ser Val Gly Cys Gly Tyr Gly
            20                  25                  30
Ser Thr Tyr Ser Pro Val Gly Tyr Gly Phe Gly Tyr Gly Tyr Asn Gly
        35                  40                  45
Cys Gly Ala Phe Gly Tyr Arg Arg Tyr Ser Pro Phe Ala Leu Tyr
    50                  55                  60
```

<210> SEQ ID NO 79
<211> LENGTH: 20
<212> TYPE: DNA
<213> ORGANISM: Artificial Sequence
<220> FEATURE:
<223> OTHER INFORMATION: Forward Primer P1

<400> SEQUENCE: 79
tcactcactc acacctcccg         20

<210> SEQ ID NO 80
<211> LENGTH: 20
<212> TYPE: DNA
<213> ORGANISM: Artificial Sequence
<220> FEATURE:
<223> OTHER INFORMATION: Reverse Primer P2

<400> SEQUENCE: 80
gagacacggg gacccgtcct         20

<210> SEQ ID NO 81
<211> LENGTH: 22
<212> TYPE: DNA
<213> ORGANISM: Artificial Sequence
<220> FEATURE:
<223> OTHER INFORMATION: Forward Primer P3

<400> SEQUENCE: 81
tcactcactc acacacctcc cc         22

<210> SEQ ID NO 82
<211> LENGTH: 22
<212> TYPE: DNA
<213> ORGANISM: Artificial Sequence
<220> FEATURE:
<223> OTHER INFORMATION: Reverse Primer P4

<400> SEQUENCE: 82
atccccaacc agcgaccagc ga         22

<210> SEQ ID NO 83
<211> LENGTH: 20
<212> TYPE: DNA
<213> ORGANISM: Artificial Sequence
<220> FEATURE:
<223> OTHER INFORMATION: Forward Primer P5

<400> SEQUENCE: 83
tcactcactc acgtctcccc         20

<210> SEQ ID NO 84
<211> LENGTH: 20

```
-continued

<212> TYPE: DNA
<213> ORGANISM: Artificial Sequence
<220> FEATURE:
<223> OTHER INFORMATION: Reverse Primer P6

<400> SEQUENCE: 84
aactctggag aaacgggacc                                              20

<210> SEQ ID NO 85
<211> LENGTH: 21
<212> TYPE: DNA
<213> ORGANISM: Artificial Sequence
<220> FEATURE:
<223> OTHER INFORMATION: Forward Primer P7

<400> SEQUENCE: 85
agctcaaccc ccagcacagc a                                            21

<210> SEQ ID NO 86
<211> LENGTH: 21
<212> TYPE: DNA
<213> ORGANISM: Artificial Sequence
<220> FEATURE:
<223> OTHER INFORMATION: Reverse Primer P8

<400> SEQUENCE: 86
gtcaaagtgc aggagcaatt c                                            21

<210> SEQ ID NO 87
<211> LENGTH: 20
<212> TYPE: DNA
<213> ORGANISM: Artificial Sequence
<220> FEATURE:
<223> OTHER INFORMATION: Forward Primer P9

<400> SEQUENCE: 87
ccagctcacg tcttccccac                                              20

<210> SEQ ID NO 88
<211> LENGTH: 20
<212> TYPE: DNA
<213> ORGANISM: Artificial Sequence
<220> FEATURE:
<223> OTHER INFORMATION: Reverse Primer P10

<400> SEQUENCE: 88
cctaacccga gtcaggacca                                              20

<210> SEQ ID NO 89
<211> LENGTH: 23
<212> TYPE: DNA
<213> ORGANISM: Artificial Sequence
<220> FEATURE:
<223> OTHER INFORMATION: Forward Primer P11

<400> SEQUENCE: 89
ctccaccagt tcaaccccag cat                                          23

<210> SEQ ID NO 90
<211> LENGTH: 22
<212> TYPE: DNA
<213> ORGANISM: Artificial Sequence
<220> FEATURE:
<223> OTHER INFORMATION: Reverse Primer P12

<400> SEQUENCE: 90
```

-continued taagacaaag agcctgcccc at                                              22

<210> SEQ ID NO 91
<211> LENGTH: 20
<212> TYPE: DNA
<213> ORGANISM: Artificial Sequence
<220> FEATURE:
<223> OTHER INFORMATION: Forward Primer P13

<400> SEQUENCE: 91
catctcctcc agttcaatcc                                                 20

<210> SEQ ID NO 92
<211> LENGTH: 22
<212> TYPE: DNA
<213> ORGANISM: Artificial Sequence
<220> FEATURE:
<223> OTHER INFORMATION: Reverse Primer P14

<400> SEQUENCE: 92
tcaggctttg gatgatctta ag                                              22

<210> SEQ ID NO 93
<211> LENGTH: 20
<212> TYPE: DNA
<213> ORGANISM: Artificial Sequence
<220> FEATURE:
<223> OTHER INFORMATION: Forward Primer P15

<400> SEQUENCE: 93
accacccagt ccagcaccca                                                 20

<210> SEQ ID NO 94
<211> LENGTH: 20
<212> TYPE: DNA
<213> ORGANISM: Artificial Sequence
<220> FEATURE:
<223> OTHER INFORMATION: Reverse Primer P16

<400> SEQUENCE: 94
aggacaggac cggagccggc                                                 20

<210> SEQ ID NO 95
<211> LENGTH: 22
<212> TYPE: DNA
<213> ORGANISM: Artificial Sequence
<220> FEATURE:
<223> OTHER INFORMATION: Forward Primer P17

<400> SEQUENCE: 95
tcacacactc acttacacct cc                                              22

<210> SEQ ID NO 96
<211> LENGTH: 22
<212> TYPE: DNA
<213> ORGANISM: Artificial Sequence
<220> FEATURE:
<223> OTHER INFORMATION: Reverse Primer P18

<400> SEQUENCE: 96
cgtccccaac cagcgaccag cg                                              22

<210> SEQ ID NO 97
<211> LENGTH: 22
<212> TYPE: DNA
<213> ORGANISM: Artificial Sequence

```
<220> FEATURE:
<223> OTHER INFORMATION: Forward Primer P19

<400> SEQUENCE: 97
tcactcactc acacacctcc cc                                              22

<210> SEQ ID NO 98
<211> LENGTH: 22
<212> TYPE: DNA
<213> ORGANISM: Artificial Sequence
<220> FEATURE:
<223> OTHER INFORMATION: Reverse Primer P20

<400> SEQUENCE: 98
caagacaaag agcctgcccc ac                                              22

<210> SEQ ID NO 99
<211> LENGTH: 22
<212> TYPE: DNA
<213> ORGANISM: Artificial Sequence
<220> FEATURE:
<223> OTHER INFORMATION: Forward Primer P21

<400> SEQUENCE: 99
acactcactt acacctcccc ca                                              22

<210> SEQ ID NO 100
<211> LENGTH: 22
<212> TYPE: DNA
<213> ORGANISM: Artificial Sequence
<220> FEATURE:
<223> OTHER INFORMATION: Reverse Primer P22

<400> SEQUENCE: 100
tcctgagact ggagaatcct gc                                              22

<210> SEQ ID NO 101
<211> LENGTH: 21
<212> TYPE: DNA
<213> ORGANISM: Artificial Sequence
<220> FEATURE:
<223> OTHER INFORMATION: Forward Primer P23

<400> SEQUENCE: 101
agaccagccc tgtcctctgc g                                               21

<210> SEQ ID NO 102
<211> LENGTH: 21
<212> TYPE: DNA
<213> ORGANISM: Artificial Sequence
<220> FEATURE:
<223> OTHER INFORMATION: Reverse Primer P24

<400> SEQUENCE: 102
ggagttcaga gagcctgctg g                                               21

<210> SEQ ID NO 103
<211> LENGTH: 22
<212> TYPE: DNA
<213> ORGANISM: Artificial Sequence
<220> FEATURE:
<223> OTHER INFORMATION: Forward Primer P25

<400> SEQUENCE: 103
cagacatcac catcctcctc cc                                              22
```

<210> SEQ ID NO 104
<211> LENGTH: 21
<212> TYPE: DNA
<213> ORGANISM: Artificial Sequence
<220> FEATURE:
<223> OTHER INFORMATION: Reverse Primer P26

<400> SEQUENCE: 104
tctgggggtc caccagatgc t                                              21

<210> SEQ ID NO 105
<211> LENGTH: 23
<212> TYPE: DNA
<213> ORGANISM: Artificial Sequence
<220> FEATURE:
<223> OTHER INFORMATION: Forward Primer P27

<400> SEQUENCE: 105
ttatccagcc acacgccacc atg                                            23

<210> SEQ ID NO 106
<211> LENGTH: 22
<212> TYPE: DNA
<213> ORGANISM: Artificial Sequence
<220> FEATURE:
<223> OTHER INFORMATION: Reverse Primer P28

<400> SEQUENCE: 106
ctgtcacatt ctcaatccag aa                                             22

<210> SEQ ID NO 107
<211> LENGTH: 23
<212> TYPE: DNA
<213> ORGANISM: Artificial Sequence
<220> FEATURE:
<223> OTHER INFORMATION: Forward Primer P29

<400> SEQUENCE: 107
ttatccagcc acacgccacc atg                                            23

<210> SEQ ID NO 108
<211> LENGTH: 22
<212> TYPE: DNA
<213> ORGANISM: Artificial Sequence
<220> FEATURE:
<223> OTHER INFORMATION: Reverse Primer P30

<400> SEQUENCE: 108
agggctccag atcattctat ta                                             22

<210> SEQ ID NO 109
<211> LENGTH: 20
<212> TYPE: DNA
<213> ORGANISM: Artificial Sequence
<220> FEATURE:
<223> OTHER INFORMATION: Forward Primer P31

<400> SEQUENCE: 109
ctgaacgttc ttgtgcagga                                                20

<210> SEQ ID NO 110
<211> LENGTH: 20
<212> TYPE: DNA
<213> ORGANISM: Artificial Sequence
<220> FEATURE:
<223> OTHER INFORMATION: Reverse Primer P32

<400> SEQUENCE: 110
gctgacattg tcttggtcag                                           20

<210> SEQ ID NO 111
<211> LENGTH: 21
<212> TYPE: DNA
<213> ORGANISM: Artificial Sequence
<220> FEATURE:
<223> OTHER INFORMATION: Forward Primer P33

<400> SEQUENCE: 111
agctcaaccc ccagcacggc t                                         21

<210> SEQ ID NO 112
<211> LENGTH: 21
<212> TYPE: DNA
<213> ORGANISM: Artificial Sequence
<220> FEATURE:
<223> OTHER INFORMATION: Reverse Primer P34

<400> SEQUENCE: 112
gagcagccga ggggccagta g                                         21

<210> SEQ ID NO 113
<211> LENGTH: 20
<212> TYPE: DNA
<213> ORGANISM: Artificial Sequence
<220> FEATURE:
<223> OTHER INFORMATION: Forward Primer P35

<400> SEQUENCE: 113
cagctcctgc acgcccttgt                                           20

<210> SEQ ID NO 114
<211> LENGTH: 23
<212> TYPE: DNA
<213> ORGANISM: Artificial Sequence
<220> FEATURE:
<223> OTHER INFORMATION: Reverse Primer P36

<400> SEQUENCE: 114
agtggatagg taagccgtgg ttg                                       23

<210> SEQ ID NO 115
<211> LENGTH: 26
<212> TYPE: DNA
<213> ORGANISM: Artificial Sequence
<220> FEATURE:
<223> OTHER INFORMATION: Forward Primer P37

<400> SEQUENCE: 115
tgaaggtcgg tgtgaacgga tttggc                                    26

<210> SEQ ID NO 116
<211> LENGTH: 24
<212> TYPE: DNA
<213> ORGANISM: Artificial Sequence
<220> FEATURE:
<223> OTHER INFORMATION: Reverse Primer P38

<400> SEQUENCE: 116
catgtaggcc atgaggtcca ccac                                      24

<210> SEQ ID NO 117

```
<211> LENGTH: 501
<212> TYPE: DNA
<213> ORGANISM: Mus musculus
<220> FEATURE:
<221> NAME/KEY: CDS
<222> LOCATION: (1)..(501)

<400> SEQUENCE: 117 atg tcc tgc aac agc tgc tct gga act ttc tcc cag tcc ttt ggg ggc      48
Met Ser Cys Asn Ser Cys Ser Gly Thr Phe Ser Gln Ser Phe Gly Gly
 1               5                  10                  15 caa ctg cag tat ccg atc tct tca tgc ggt tcc tcc tac ccc aac aac      96
Gln Leu Gln Tyr Pro Ile Ser Ser Cys Gly Ser Ser Tyr Pro Asn Asn
             20                  25                  30 gtc ttc tac agc act gac ctc caa act ccc atc acc cac cag ctg ggc     144
Val Phe Tyr Ser Thr Asp Leu Gln Thr Pro Ile Thr His Gln Leu Gly
         35                  40                  45 tct tct ctt cac agt ggg tgc cag gaa acc ttc tgt gag ccc acc aac     192
Ser Ser Leu His Ser Gly Cys Gln Glu Thr Phe Cys Glu Pro Thr Asn
     50                  55                  60 tgc cag aca gcc tat gtg gtc tcc aga ccc tgc cag agg ctt tct aca     240
Cys Gln Thr Ala Tyr Val Val Ser Arg Pro Cys Gln Arg Leu Ser Thr
 65                  70                  75                  80 gtc aga gga ttc gag ggc cct gca ggc tgc cag tca act ttc tcg gga     288
Val Arg Gly Phe Glu Gly Pro Ala Gly Cys Gln Ser Thr Phe Ser Gly
                 85                  90                  95 tcc ctg gga ttt ggt tcc agg ggt ttc cag tct ttt ggc tgt ggc tac     336
Ser Leu Gly Phe Gly Ser Arg Gly Phe Gln Ser Phe Gly Cys Gly Tyr
            100                 105                 110 cca tcc cag ggc ttt gga tcc cat ggt ttc cag tca gta gga tgt ggt     384
Pro Ser Gln Gly Phe Gly Ser His Gly Phe Gln Ser Val Gly Cys Gly
        115                 120                 125 acc cct act ttc tca tcc cta aat tgt gga tcc agc ttt tac cgc cca     432
Thr Pro Thr Phe Ser Ser Leu Asn Cys Gly Ser Ser Phe Tyr Arg Pro
    130                 135                 140 acc tgc ttc tct acc aaa agc tgc cag tct gtt tct tat cag cca acc     480
Thr Cys Phe Ser Thr Lys Ser Cys Gln Ser Val Ser Tyr Gln Pro Thr
145                 150                 155                 160 tgt ggg act ggc ttc ttc tga                                         501
Cys Gly Thr Gly Phe Phe
                165

<210> SEQ ID NO 118
<211> LENGTH: 166
<212> TYPE: PRT
<213> ORGANISM: Mus musculus

<400> SEQUENCE: 118

Met Ser Cys Asn Ser Cys Ser Gly Thr Phe Ser Gln Ser Phe Gly Gly
 1               5                  10                  15

Gln Leu Gln Tyr Pro Ile Ser Ser Cys Gly Ser Ser Tyr Pro Asn Asn
             20                  25                  30

Val Phe Tyr Ser Thr Asp Leu Gln Thr Pro Ile Thr His Gln Leu Gly
         35                  40                  45

Ser Ser Leu His Ser Gly Cys Gln Glu Thr Phe Cys Glu Pro Thr Asn
     50                  55                  60

Cys Gln Thr Ala Tyr Val Val Ser Arg Pro Cys Gln Arg Leu Ser Thr
 65                  70                  75                  80

Val Arg Gly Phe Glu Gly Pro Ala Gly Cys Gln Ser Thr Phe Ser Gly
                 85                  90                  95
```

-continued

```
Ser Leu Gly Phe Gly Ser Arg Gly Phe Gln Ser Phe Gly Cys Gly Tyr
            100                 105                 110

Pro Ser Gln Gly Phe Ser His Gly Phe Gln Ser Val Gly Cys Gly
        115                 120                 125

Thr Pro Thr Phe Ser Ser Leu Asn Cys Gly Ser Phe Tyr Arg Pro
        130                 135                 140

Thr Cys Phe Ser Thr Lys Ser Cys Gln Ser Val Ser Tyr Gln Pro Thr
145                 150                 155                 160

Cys Gly Thr Gly Phe Phe
                165
```

<210> SEQ ID NO 119
<211> LENGTH: 453
<212> TYPE: DNA
<213> ORGANISM: Mus musculus
<220> FEATURE:
<221> NAME/KEY: CDS
<222> LOCATION: (1)..(453)

<400> SEQUENCE: 119

```
atg tct tac act tgc aac tct gga aac tac tcc tca cag tct ttt gga      48
Met Ser Tyr Thr Cys Asn Ser Gly Asn Tyr Ser Ser Gln Ser Phe Gly
 1               5                  10                  15 ggt ttc ttg agg cag cca gtc tct acc tac aac tcc ttc tac ccc acc      96
Gly Phe Leu Arg Gln Pro Val Ser Thr Tyr Asn Ser Phe Tyr Pro Thr
             20                  25                  30 agc aat gta gtc tat tct cca aag aac ttc cag ctg gga tcc tct ttc     144
Ser Asn Val Val Tyr Ser Pro Lys Asn Phe Gln Leu Gly Ser Ser Phe
         35                  40                  45 tac aat gga cag cag gag acc ttc agt gag cca ctt gaa ggc cac ttg     192
Tyr Asn Gly Gln Gln Glu Thr Phe Ser Glu Pro Leu Glu Gly His Leu
     50                  55                  60 ccc tgt gtg ggg tct gca tcc ttc cac aca tcc tgt ttc cgg cct aag     240
Pro Cys Val Gly Ser Ala Ser Phe His Thr Ser Cys Phe Arg Pro Lys
 65                  70                  75                  80 caa tac ttc tcc agc ccc tgc cag gga ggc ttt acc gga tct ttt gga     288
Gln Tyr Phe Ser Ser Pro Cys Gln Gly Gly Phe Thr Gly Ser Phe Gly
                 85                  90                  95 tat ggc aat act ggc ttt gga gct ttt ggg ttt gga agc tct ggc att     336
Tyr Gly Asn Thr Gly Phe Gly Ala Phe Gly Phe Gly Ser Ser Gly Ile
            100                 105                 110 cgc tct cag ggc tgt gga tcc aac ttc tac cgt cca gga tac ttt tct     384
Arg Ser Gln Gly Cys Gly Ser Asn Phe Tyr Arg Pro Gly Tyr Phe Ser
        115                 120                 125 tct aag agt atc cag tca tct tac tac cag cca ggc tac agc tct ggc     432
Ser Lys Ser Ile Gln Ser Ser Tyr Tyr Gln Pro Gly Tyr Ser Ser Gly
    130                 135                 140 ttt tgc ggg tca aat ttc tga                                         453
Phe Cys Gly Ser Asn Phe
145                 150
```

<210> SEQ ID NO 120
<211> LENGTH: 150
<212> TYPE: PRT
<213> ORGANISM: Mus musculus

<400> SEQUENCE: 120

```
Met Ser Tyr Thr Cys Asn Ser Gly Asn Tyr Ser Ser Gln Ser Phe Gly
 1               5                  10                  15

Gly Phe Leu Arg Gln Pro Val Ser Thr Tyr Asn Ser Phe Tyr Pro Thr
             20                  25                  30
```

```
Ser Asn Val Val Tyr Ser Pro Lys Asn Phe Gln Leu Gly Ser Ser Phe
         35                  40                  45

Tyr Asn Gly Gln Gln Glu Thr Phe Ser Glu Pro Leu Glu Gly His Leu
 50                  55                  60

Pro Cys Val Gly Ser Ala Ser Phe His Thr Ser Cys Phe Arg Pro Lys
 65                  70                  75                  80

Gln Tyr Phe Ser Pro Cys Gln Gly Phe Thr Gly Ser Phe Gly
                 85                  90                  95

Tyr Gly Asn Thr Gly Phe Gly Ala Phe Gly Phe Gly Ser Ser Gly Ile
                100                 105                 110

Arg Ser Gln Gly Cys Gly Ser Asn Phe Tyr Arg Pro Gly Tyr Phe Ser
            115                 120                 125

Ser Lys Ser Ile Gln Ser Ser Tyr Tyr Gln Pro Gly Tyr Ser Ser Gly
        130                 135                 140

Phe Cys Gly Ser Asn Phe
145                 150

<210> SEQ ID NO 121
<211> LENGTH: 582
<212> TYPE: DNA
<213> ORGANISM: Mus musculus
<220> FEATURE:
<221> NAME/KEY: CDS
<222> LOCATION: (1)..(582)

<400> SEQUENCE: 121 atg tct ttc aac tgc tcc aca aga aat tgc tct tcc agg cca gtt gga      48
Met Ser Phe Asn Cys Ser Thr Arg Asn Cys Ser Ser Arg Pro Val Gly
 1               5                  10                  15 gga cgt tac act gct cca gtg ggc cca gtt acc aca gcc tca gcc cgt      96
Gly Arg Tyr Thr Ala Pro Val Gly Pro Val Thr Thr Ala Ser Ala Arg
             20                  25                  30 gac gca gac tgc ctg agt ggc ctc tac ttg ccc agt tct ttc caa act     144
Asp Ala Asp Cys Leu Ser Gly Leu Tyr Leu Pro Ser Ser Phe Gln Thr
         35                  40                  45 ggc tcc tgg ctc ctg gac cat tgt cag gag tca tac tgt gag cct act     192
Gly Ser Trp Leu Leu Asp His Cys Gln Glu Ser Tyr Cys Glu Pro Thr
 50                  55                  60 gtc tgc cag cca acg tgc tac cag aga act tct tgt atc tcc act cct     240
Val Cys Gln Pro Thr Cys Tyr Gln Arg Thr Ser Cys Ile Ser Thr Pro
 65                  70                  75                  80 gcc cag gta act tgc aat cga cag act acc tgc gtc tcc aat cct tgc     288
Ala Gln Val Thr Cys Asn Arg Gln Thr Thr Cys Val Ser Asn Pro Cys
             85                  90                  95 tct acg ccc tgt agc cgg cca ctc act ttt gtg tcc act ggc tgt cag     336
Ser Thr Pro Cys Ser Arg Pro Leu Thr Phe Val Ser Thr Gly Cys Gln
            100                 105                 110 ccc ctg gga ggg att tcc agc tcc tgc caa cca gtg gga ggc atc tct     384
Pro Leu Gly Gly Ile Ser Ser Ser Cys Gln Pro Val Gly Gly Ile Ser
        115                 120                 125 acc acc tgc caa cca gtg gga ggc atc tct acc acc tgc caa cca gtg     432
Thr Thr Cys Gln Pro Val Gly Gly Ile Ser Thr Thr Cys Gln Pro Val
    130                 135                 140 gga ggc atc tct acc acc tgc caa caa gtg gga ggc atc tct acc gtc     480
Gly Gly Ile Ser Thr Thr Cys Gln Gln Val Gly Gly Ile Ser Thr Val
145                 150                 155                 160 tgc caa cca gtg gga ggt atc tct act gtc tgc caa cca acc tgt gga     528
Cys Gln Pro Val Gly Gly Ile Ser Thr Val Cys Gln Pro Thr Cys Gly
                165                 170                 175
```

```
gtc tcc agg aca cac cag cag tcc tgt gta tcc agc tgc cga aga act      576
Val Ser Arg Thr His Gln Gln Ser Cys Val Ser Ser Cys Arg Arg Thr
            180                 185                 190 tgc taa                                                              582
Cys
```

<210> SEQ ID NO 122
<211> LENGTH: 193
<212> TYPE: PRT
<213> ORGANISM: Mus musculus

<400> SEQUENCE: 122

```
Met Ser Phe Asn Cys Ser Thr Arg Asn Cys Ser Ser Arg Pro Val Gly
 1               5                  10                  15

Gly Arg Tyr Thr Ala Pro Val Gly Pro Val Thr Thr Ala Ser Ala Arg
             20                  25                  30

Asp Ala Asp Cys Leu Ser Gly Leu Tyr Leu Pro Ser Ser Phe Gln Thr
         35                  40                  45

Gly Ser Trp Leu Leu Asp His Cys Gln Glu Ser Tyr Cys Glu Pro Thr
     50                  55                  60

Val Cys Gln Pro Thr Cys Tyr Gln Arg Thr Ser Cys Ile Ser Thr Pro
 65                  70                  75                  80

Ala Gln Val Thr Cys Asn Arg Gln Thr Thr Cys Val Ser Asn Pro Cys
                 85                  90                  95

Ser Thr Pro Cys Ser Arg Pro Leu Thr Phe Val Ser Thr Gly Cys Gln
            100                 105                 110

Pro Leu Gly Gly Ile Ser Ser Cys Gln Pro Val Gly Gly Ile Ser
        115                 120                 125

Thr Thr Cys Gln Pro Val Gly Gly Ile Ser Thr Thr Cys Gln Pro Val
    130                 135                 140

Gly Gly Ile Ser Thr Thr Cys Gln Gln Val Gly Gly Ile Ser Thr Val
145                 150                 155                 160

Cys Gln Pro Val Gly Gly Ile Ser Thr Val Cys Gln Pro Thr Cys Gly
                165                 170                 175

Val Ser Arg Thr His Gln Gln Ser Cys Val Ser Ser Cys Arg Arg Thr
            180                 185                 190

Cys
```

<210> SEQ ID NO 123
<211> LENGTH: 237
<212> TYPE: DNA
<213> ORGANISM: Mus musculus
<220> FEATURE:
<221> NAME/KEY: CDS
<222> LOCATION: (1)..(237)

<400> SEQUENCE: 123

```
atg tgt ggc tac tac gga aac tac tat ggc ggc aga ggc tat ggc tgc       48
Met Cys Gly Tyr Tyr Gly Asn Tyr Tyr Gly Gly Arg Gly Tyr Gly Cys
 1               5                  10                  15 tgt ggc tgt gga ggc ctg ggc tat ggc tat gga ggc ttg ggc tgt ggc       96
Cys Gly Cys Gly Gly Leu Gly Tyr Gly Tyr Gly Gly Leu Gly Cys Gly
             20                  25                  30 tat ggc tcc tac tat ggc tgt ggc tac cgt gga ctg ggc tgt ggc tat      144
Tyr Gly Ser Tyr Tyr Gly Cys Gly Tyr Arg Gly Leu Gly Cys Gly Tyr
         35                  40                  45 ggc tat ggc tgt ggc tat ggc tca cgc tct ctc tat ggc tgt ggc tat      192
Gly Tyr Gly Cys Gly Tyr Gly Ser Arg Ser Leu Tyr Gly Cys Gly Tyr
```

```
                    50                  55                  60
gga tgc ggt tct ggc tat ggc tct gga ttt ggc tac tac tac tga         237
Gly Cys Gly Ser Gly Tyr Gly Ser Gly Phe Gly Tyr Tyr Tyr
 65                  70                  75

<210> SEQ ID NO 124
<211> LENGTH: 78
<212> TYPE: PRT
<213> ORGANISM: Mus musculus

<400> SEQUENCE: 124

Met Cys Gly Tyr Tyr Gly Asn Tyr Tyr Gly Gly Arg Gly Tyr Gly Cys
  1               5                  10                  15

Cys Gly Cys Gly Gly Leu Gly Tyr Gly Tyr Gly Gly Leu Gly Cys Gly
             20                  25                  30

Tyr Gly Ser Tyr Tyr Gly Cys Gly Tyr Arg Gly Leu Gly Cys Gly Tyr
         35                  40                  45

Gly Tyr Gly Cys Gly Tyr Gly Ser Arg Ser Leu Tyr Gly Cys Gly Tyr
     50                  55                  60

Gly Cys Gly Ser Gly Tyr Gly Ser Gly Phe Gly Tyr Tyr Tyr
 65                  70                  75

<210> SEQ ID NO 125
<211> LENGTH: 237
<212> TYPE: DNA
<213> ORGANISM: Mus musculus
<220> FEATURE:
<221> NAME/KEY: CDS
<222> LOCATION: (1)..(237)

<400> SEQUENCE: 125 atg tgt ggc tac tac gga aac tac tat ggc ggc aga ggc tat ggc tgc          48
Met Cys Gly Tyr Tyr Gly Asn Tyr Tyr Gly Gly Arg Gly Tyr Gly Cys
  1               5                  10                  15 tgt ggc tat gga ggc ctg ggc tat ggc tat gga ggc ctg ggc tgt ggc          96
Cys Gly Tyr Gly Gly Leu Gly Tyr Gly Tyr Gly Gly Leu Gly Cys Gly
             20                  25                  30 tat ggc tcc tac tat ggc tgt ggc tac cgt gga ctg ggc tgt ggc tat         144
Tyr Gly Ser Tyr Tyr Gly Cys Gly Tyr Arg Gly Leu Gly Cys Gly Tyr
         35                  40                  45 ggc tat ggc tgt ggc tat ggc tca cgc tct ctc tat ggc tgt ggc tat         192
Gly Tyr Gly Cys Gly Tyr Gly Ser Arg Ser Leu Tyr Gly Cys Gly Tyr
     50                  55                  60 gga tgt ggc tct ggc tat ggg tct gga ttt ggc tac tac tac tga             237
Gly Cys Gly Ser Gly Tyr Gly Ser Gly Phe Gly Tyr Tyr Tyr
 65                  70                  75

<210> SEQ ID NO 126
<211> LENGTH: 78
<212> TYPE: PRT
<213> ORGANISM: Mus musculus

<400> SEQUENCE: 126

Met Cys Gly Tyr Tyr Gly Asn Tyr Tyr Gly Gly Arg Gly Tyr Gly Cys
  1               5                  10                  15

Cys Gly Tyr Gly Gly Leu Gly Tyr Gly Tyr Gly Gly Leu Gly Cys Gly
             20                  25                  30

Tyr Gly Ser Tyr Tyr Gly Cys Gly Tyr Arg Gly Leu Gly Cys Gly Tyr
         35                  40                  45

Gly Tyr Gly Cys Gly Tyr Gly Ser Arg Ser Leu Tyr Gly Cys Gly Tyr
     50                  55                  60
```

```
Gly Cys Gly Ser Gly Tyr Gly Ser Gly Phe Gly Tyr Tyr Tyr
 65                  70                  75
```

<210> SEQ ID NO 127
<211> LENGTH: 387
<212> TYPE: DNA
<213> ORGANISM: Mus musculus
<220> FEATURE:
<221> NAME/KEY: CDS
<222> LOCATION: (1)..(387)

<400> SEQUENCE: 127

```
atg tgc tgc aac tac tac gga aac tcc tgt gga ggc tgt gga tac ggc      48
Met Cys Cys Asn Tyr Tyr Gly Asn Ser Cys Gly Gly Cys Gly Tyr Gly
 1               5                  10                  15 tca aga tat ggc tat ggc tgt gga tac ggc tca ggc tat ggc tgt gga      96
Ser Arg Tyr Gly Tyr Gly Cys Gly Tyr Gly Ser Gly Tyr Gly Cys Gly
             20                  25                  30 tac ggc tct ggc tat ggc tgt gga tac ggc tca ggc tat ggc tgt gga     144
Tyr Gly Ser Gly Tyr Gly Cys Gly Tyr Gly Ser Gly Tyr Gly Cys Gly
         35                  40                  45 tac ggc tct ggc tat ggc tgt gga tat ggc tct ggc tat ggc tgt gga     192
Tyr Gly Ser Gly Tyr Gly Cys Gly Tyr Gly Ser Gly Tyr Gly Cys Gly
     50                  55                  60 tac ggc tct ggc tat ggc tgt gga tat ggc tct agc tat ggc tgt gga     240
Tyr Gly Ser Gly Tyr Gly Cys Gly Tyr Gly Ser Ser Tyr Gly Cys Gly
 65                  70                  75                  80 tat ggc tca ggc tat ggc tgt gga tat ggc tct gga tat ggc tgt gga     288
Tyr Gly Ser Gly Tyr Gly Cys Gly Tyr Gly Ser Gly Tyr Gly Cys Gly
                 85                  90                  95 tat ggc aca ggc tat ggc tgt gga tat ggc tcc agg tat ggc tgt gga     336
Tyr Gly Thr Gly Tyr Gly Cys Gly Tyr Gly Ser Arg Tyr Gly Cys Gly
            100                 105                 110 tgt ggc tct ggc tgc tgt agc tac aga aaa tgc tat tcc tct tgc tgc     384
Cys Gly Ser Gly Cys Cys Ser Tyr Arg Lys Cys Tyr Ser Ser Cys Cys
        115                 120                 125 tag                                                                  387
```

<210> SEQ ID NO 128
<211> LENGTH: 128
<212> TYPE: PRT
<213> ORGANISM: Mus musculus

<400> SEQUENCE: 128

```
Met Cys Cys Asn Tyr Tyr Gly Asn Ser Cys Gly Gly Cys Gly Tyr Gly
 1               5                  10                  15

Ser Arg Tyr Gly Tyr Gly Cys Gly Tyr Gly Ser Gly Tyr Gly Cys Gly
             20                  25                  30

Tyr Gly Ser Gly Tyr Gly Cys Gly Tyr Gly Ser Gly Tyr Gly Cys Gly
         35                  40                  45

Tyr Gly Ser Gly Tyr Gly Cys Gly Tyr Gly Ser Gly Tyr Gly Cys Gly
     50                  55                  60

Tyr Gly Ser Gly Tyr Gly Cys Gly Tyr Gly Ser Ser Tyr Gly Cys Gly
 65                  70                  75                  80

Tyr Gly Ser Gly Tyr Gly Cys Gly Tyr Gly Ser Gly Tyr Gly Cys Gly
                 85                  90                  95

Tyr Gly Thr Gly Tyr Gly Cys Gly Tyr Gly Ser Arg Tyr Gly Cys Gly
            100                 105                 110

Cys Gly Ser Gly Cys Cys Ser Tyr Arg Lys Cys Tyr Ser Ser Cys Cys
```

<210> SEQ ID NO 129
<211> LENGTH: 234
<212> TYPE: DNA
<213> ORGANISM: Mus musculus
<220> FEATURE:
<221> NAME/KEY: CDS
<222> LOCATION: (1)..(234)

<400> SEQUENCE: 129

| ctg | ggc | tac | ggc | tat | ggc | agc | agc | ttt | gga | ggc | ctg | ggc | tgt | gga | tgt | 48 |
|-----|-----|-----|-----|-----|-----|-----|-----|-----|-----|-----|-----|-----|-----|-----|-----|----|
| Leu | Gly | Tyr | Gly | Tyr | Gly | Ser | Ser | Phe | Gly | Gly | Leu | Gly | Cys | Gly | Cys | |
| 1   |     |     |     | 5   |     |     |     |     | 10  |     |     |     |     | 15  |     | |

| aac | agc | atc | cgc | aga | ctg | ggc | tgt | ggc | tct | ggc | tat | gga | ggc | ttc | gga | 96 |
|-----|-----|-----|-----|-----|-----|-----|-----|-----|-----|-----|-----|-----|-----|-----|-----|----|
| Asn | Ser | Ile | Arg | Arg | Leu | Gly | Cys | Gly | Ser | Gly | Tyr | Gly | Gly | Phe | Gly | |
|     |     |     | 20  |     |     |     |     | 25  |     |     |     |     | 30  |     |     | |

| tat | ggc | tct | ggc | tat | ggg | ggc | tat | gga | tat | ggc | tct | gac | tat | gga | ggc | 144 |
|-----|-----|-----|-----|-----|-----|-----|-----|-----|-----|-----|-----|-----|-----|-----|-----|-----|
| Tyr | Gly | Ser | Gly | Tyr | Gly | Gly | Tyr | Gly | Tyr | Gly | Ser | Asp | Tyr | Gly | Gly | |
|     |     | 35  |     |     |     |     | 40  |     |     |     |     | 45  |     |     |     | |

| tat | gga | tat | gac | tct | agc | tat | gga | ggc | tat | gga | tgt | ggc | tgc | cgc | cgc | 192 |
|-----|-----|-----|-----|-----|-----|-----|-----|-----|-----|-----|-----|-----|-----|-----|-----|-----|
| Tyr | Gly | Tyr | Asp | Ser | Ser | Tyr | Gly | Gly | Tyr | Gly | Cys | Gly | Cys | Arg | Arg | |
|     | 50  |     |     |     |     | 55  |     |     |     |     | 60  |     |     |     |     | |

| cct | tca | tgc | tgt | gga | aga | tat | ggg | ttc | tcc | aac | ttc | tac | tga |     |     | 234 |
|-----|-----|-----|-----|-----|-----|-----|-----|-----|-----|-----|-----|-----|-----|-----|-----|-----|
| Pro | Ser | Cys | Cys | Gly | Arg | Tyr | Gly | Phe | Ser | Asn | Phe | Tyr |     |     |     | |
| 65  |     |     |     |     | 70  |     |     |     |     | 75  |     |     |     |     |     | |

<210> SEQ ID NO 130
<211> LENGTH: 77
<212> TYPE: PRT
<213> ORGANISM: Mus musculus

<400> SEQUENCE: 130

Leu Gly Tyr Gly Tyr Gly Ser Ser Phe Gly Gly Leu Gly Cys Gly Cys
1               5                   10                  15

Asn Ser Ile Arg Arg Leu Gly Cys Gly Ser Gly Tyr Gly Gly Phe Gly
            20                  25                  30

Tyr Gly Ser Gly Tyr Gly Gly Tyr Gly Tyr Gly Ser Asp Tyr Gly Gly
        35                  40                  45

Tyr Gly Tyr Asp Ser Ser Tyr Gly Tyr Gly Cys Gly Cys Arg Arg
    50                  55                  60

Pro Ser Cys Cys Gly Arg Tyr Gly Phe Ser Asn Phe Tyr
65                  70                  75

<210> SEQ ID NO 131
<211> LENGTH: 264
<212> TYPE: DNA
<213> ORGANISM: Mus musculus
<220> FEATURE:
<221> NAME/KEY: CDS
<222> LOCATION: (1)..(264)

<400> SEQUENCE: 131

| atg | agc | tac | tac | agc | ggc | tac | tcc | gga | ggc | ctg | ggc | tac | ggc | tat | ggc | 48 |
|-----|-----|-----|-----|-----|-----|-----|-----|-----|-----|-----|-----|-----|-----|-----|-----|----|
| Met | Ser | Tyr | Tyr | Ser | Gly | Tyr | Ser | Gly | Gly | Leu | Gly | Tyr | Gly | Tyr | Gly | |
| 1   |     |     |     | 5   |     |     |     |     | 10  |     |     |     |     | 15  |     | |

| agc | agc | ttt | gga | ggc | ccg | ggc | tgt | gga | tgt | aac | agc | atc | cgc | aga | ctg | 96 |
|-----|-----|-----|-----|-----|-----|-----|-----|-----|-----|-----|-----|-----|-----|-----|-----|----|
| Ser | Ser | Phe | Gly | Gly | Pro | Gly | Cys | Gly | Cys | Asn | Ser | Ile | Arg | Arg | Leu | |
|     |     |     | 20  |     |     |     |     | 25  |     |     |     |     | 30  |     |     | |

| ggc | tgt | ggc | tct | ggc | tat | gga | ggc | ttc | gga | tat | ggc | tct | ggc | tat | gga | 144 |
|-----|-----|-----|-----|-----|-----|-----|-----|-----|-----|-----|-----|-----|-----|-----|-----|-----|
| Gly | Cys | Gly | Ser | Gly | Tyr | Gly | Gly | Phe | Gly | Tyr | Gly | Ser | Gly | Tyr | Gly | |
|     |     | 35  |     |     |     |     | 40  |     |     |     |     | 45  |     |     |     | |

-continued

```
ggc tat gga tat ggc tct gac tat gga ggc tat gga tat ggc tct agc      192
Gly Tyr Gly Tyr Gly Ser Asp Tyr Gly Gly Tyr Gly Tyr Gly Ser Ser
 50                  55                  60 tat gga ggc tat gga tgt ggc tgc cgc cgc cct tca tgc tgt gga aga      240
Tyr Gly Gly Tyr Gly Cys Gly Cys Arg Arg Pro Ser Cys Cys Gly Arg
 65                  70                  75                  80 tat ggg ttc tcc aac ttc tac tga                                      264
Tyr Gly Phe Ser Asn Phe Tyr
                 85
```

<210> SEQ ID NO 132
<211> LENGTH: 87
<212> TYPE: PRT
<213> ORGANISM: Mus musculus

<400> SEQUENCE: 132

```
Met Ser Tyr Tyr Ser Gly Tyr Ser Gly Gly Leu Gly Tyr Gly Tyr Gly
 1               5                  10                  15

Ser Ser Phe Gly Gly Pro Gly Cys Gly Cys Asn Ser Ile Arg Arg Leu
                 20                  25                  30

Gly Cys Gly Ser Gly Tyr Gly Gly Phe Gly Tyr Gly Ser Gly Tyr Gly
             35                  40                  45

Gly Tyr Gly Tyr Gly Ser Asp Tyr Gly Gly Tyr Gly Tyr Gly Ser Ser
         50                  55                  60

Tyr Gly Gly Tyr Gly Cys Gly Cys Arg Arg Pro Ser Cys Cys Gly Arg
 65                  70                  75                  80

Tyr Gly Phe Ser Asn Phe Tyr
                 85
```

<210> SEQ ID NO 133
<211> LENGTH: 426
<212> TYPE: DNA
<213> ORGANISM: Mus musculus
<220> FEATURE:
<221> NAME/KEY: CDS
<222> LOCATION: (1)..(426)

<400> SEQUENCE: 133

```
atg agc tac tac agc ggc tac tcc gga ggc ctg ggc tac ggc tat ggc       48
Met Ser Tyr Tyr Ser Gly Tyr Ser Gly Gly Leu Gly Tyr Gly Tyr Gly
 1               5                  10                  15 agc agc ttt gga ggc ctg ggc tgt gga tgt aac agc atc cgc aga ctg       96
Ser Ser Phe Gly Gly Leu Gly Cys Gly Cys Asn Ser Ile Arg Arg Leu
                 20                  25                  30 ggc tgt ggc tct ggc tat gga ggc ttc gga tat ggc tct ggc tat gga      144
Gly Cys Gly Ser Gly Tyr Gly Gly Phe Gly Tyr Gly Ser Gly Tyr Gly
             35                  40                  45 ggc ttt gga ggc ttt gga tat ggc tct ggc tat gga ggc tac gga tac      192
Gly Phe Gly Gly Phe Gly Tyr Gly Ser Gly Tyr Gly Gly Tyr Gly Tyr
         50                  55                  60 ggc tct ggc tat gga ggc ttt gga ggc ttt gga tat ggc tct ggc tat      240
Gly Ser Gly Tyr Gly Gly Phe Gly Gly Phe Gly Tyr Gly Ser Gly Tyr
 65                  70                  75                  80 gga ggc ttc gga tat ggc tct ggc tat gga ggc ttt gga ggc ttt gga      288
Gly Gly Phe Gly Tyr Gly Ser Gly Tyr Gly Gly Phe Gly Gly Phe Gly
                 85                  90                  95 tat ggc tct ggc tat gga ggc tat gga tat ggc tct ggc ttt gga ggc      336
Tyr Gly Ser Gly Tyr Gly Gly Tyr Gly Tyr Gly Ser Gly Phe Gly Gly
            100                 105                 110 tat gga tat ggc tct ggc ttc aga ggc tat gga tgt ggc tgc cgc cgc      384
Tyr Gly Tyr Gly Ser Gly Phe Arg Gly Tyr Gly Cys Gly Cys Arg Arg
```

```
                  115                 120                 125
tct tca tgc tgt gga gga tat ggg ttc tcc agt ttc tac tga                426
Ser Ser Cys Cys Gly Gly Tyr Gly Phe Ser Ser Phe Tyr
    130                 135                 140

<210> SEQ ID NO 134
<211> LENGTH: 141
<212> TYPE: PRT
<213> ORGANISM: Mus musculus

<400> SEQUENCE: 134

Met Ser Tyr Tyr Ser Gly Tyr Ser Gly Gly Leu Gly Tyr Gly Tyr Gly
  1               5                  10                  15

Ser Ser Phe Gly Gly Leu Gly Cys Gly Cys Asn Ser Ile Arg Arg Leu
             20                  25                  30

Gly Cys Gly Ser Gly Tyr Gly Gly Phe Gly Tyr Gly Ser Gly Tyr Gly
         35                  40                  45

Gly Phe Gly Gly Phe Gly Tyr Gly Ser Gly Tyr Gly Gly Tyr Gly Tyr
     50                  55                  60

Gly Ser Gly Tyr Gly Gly Phe Gly Gly Phe Gly Tyr Gly Ser Gly Tyr
 65                  70                  75                  80

Gly Gly Phe Gly Tyr Gly Ser Gly Tyr Gly Gly Phe Gly Gly Phe Gly
             85                  90                  95

Tyr Gly Ser Gly Tyr Gly Gly Tyr Gly Tyr Gly Ser Gly Phe Gly Gly
            100                 105                 110

Tyr Gly Tyr Gly Ser Gly Phe Arg Gly Tyr Gly Cys Gly Cys Arg Arg
            115                 120                 125

Ser Ser Cys Cys Gly Gly Tyr Gly Phe Ser Ser Phe Tyr
    130                 135                 140

<210> SEQ ID NO 135
<211> LENGTH: 264
<212> TYPE: DNA
<213> ORGANISM: Mus musculus
<220> FEATURE:
<221> NAME/KEY: CDS
<222> LOCATION: (1)..(264)

<400> SEQUENCE: 135 atg agc cac tac agc agc tac tat gga ggc ctg ggc tac ggc tat ggc     48
Met Ser His Tyr Ser Ser Tyr Tyr Gly Gly Leu Gly Tyr Gly Tyr Gly
  1               5                  10                  15 agc ttt gga ggc ccg ggc tgt gga tgt aac agc atc cgc aga ctg gtg    96
Ser Phe Gly Gly Pro Gly Cys Gly Cys Asn Ser Ile Arg Arg Leu Val
             20                  25                  30 ggc ttt ggc tct ggc tat gga ggc ttt gga tat ggc tct ggc ttc gga   144
Gly Phe Gly Ser Gly Tyr Gly Gly Phe Gly Tyr Gly Ser Gly Phe Gly
         35                  40                  45 ggc ttc gga tat ggc tct gga tat gga ggc tat gga tat ggc tct ggc   192
Gly Phe Gly Tyr Gly Ser Gly Tyr Gly Gly Tyr Gly Tyr Gly Ser Gly
     50                  55                  60 ttc aga ggc tat gga tgt ggc tgc cgc cgc cct tca tgc tgt gga gga   240
Phe Arg Gly Tyr Gly Cys Gly Cys Arg Arg Pro Ser Cys Cys Gly Gly
 65                  70                  75                  80 tat ggg ttc tcc agt ttc tac tga                                   264
Tyr Gly Phe Ser Ser Phe Tyr
             85

<210> SEQ ID NO 136
<211> LENGTH: 87
```

```
<212> TYPE: PRT
<213> ORGANISM: Mus musculus

<400> SEQUENCE: 136

Met Ser His Tyr Ser Tyr Tyr Gly Gly Leu Gly Tyr Gly Tyr Gly
 1               5                  10                  15

Ser Phe Gly Gly Pro Gly Cys Gly Cys Asn Ser Ile Arg Arg Leu Val
                20                  25                  30

Gly Phe Gly Ser Gly Tyr Gly Gly Phe Gly Tyr Gly Ser Gly Phe Gly
            35                  40                  45

Gly Phe Gly Tyr Gly Ser Gly Tyr Gly Gly Tyr Tyr Gly Ser Gly
     50                  55                  60

Phe Arg Gly Tyr Gly Cys Gly Cys Arg Arg Pro Ser Cys Cys Gly Gly
65                  70                  75                  80

Tyr Gly Phe Ser Ser Phe Tyr
                85

<210> SEQ ID NO 137
<211> LENGTH: 181
<212> TYPE: DNA
<213> ORGANISM: Mus musculus
<220> FEATURE:
<221> NAME/KEY: CDS
<222> LOCATION: (2)..(181)

<400> SEQUENCE: 137 c cgc aga ctg gtg ggc ttt ggc tct ggc tat gga ggc ttt gga tat ggc      49
  Arg Arg Leu Val Gly Phe Gly Ser Gly Tyr Gly Gly Phe Gly Tyr Gly
   1               5                  10                  15 tct ggc ttc gga ggc ttc gga tat ggc tct gga tat gga ggc tat gga        97
Ser Gly Phe Gly Gly Phe Gly Tyr Gly Ser Gly Tyr Gly Gly Tyr Gly
                20                  25                  30 tat ggc tct ggc ttc aga ggc tat gga tgt ggc tgc cgc cgc cct tca       145
Tyr Gly Ser Gly Phe Arg Gly Tyr Gly Cys Gly Cys Arg Arg Pro Ser
            35                  40                  45 tgc tgt gga gga tat ggg ttc tcc agc ttc tac tga                        181
Cys Cys Gly Gly Tyr Gly Phe Ser Ser Phe Tyr
     50                  55                  60

<210> SEQ ID NO 138
<211> LENGTH: 59
<212> TYPE: PRT
<213> ORGANISM: Mus musculus

<400> SEQUENCE: 138

Arg Arg Leu Val Gly Phe Gly Ser Gly Tyr Gly Gly Phe Gly Tyr Gly
 1               5                  10                  15

Ser Gly Phe Gly Gly Phe Gly Tyr Gly Ser Gly Tyr Gly Gly Tyr Gly
                20                  25                  30

Tyr Gly Ser Gly Phe Arg Gly Tyr Gly Cys Gly Cys Arg Arg Pro Ser
            35                  40                  45

Cys Cys Gly Gly Tyr Gly Phe Ser Ser Phe Tyr
     50                  55

<210> SEQ ID NO 139
<211> LENGTH: 243
<212> TYPE: DNA
<213> ORGANISM: Mus musculus
<220> FEATURE:
<221> NAME/KEY: CDS
<222> LOCATION: (1)..(243)
```

```
<400> SEQUENCE: 139 atg gag gct tgg gct acg gct atg gca gca gct ttg gag gcc tgg gct     48
Met Glu Ala Trp Ala Thr Ala Met Ala Ala Leu Glu Ala Trp Ala
 1               5                  10                  15 tgt gga tgt aac agc atc cgc aga ctg ggc tgt ggc tct ggc tat gga     96
Cys Gly Cys Asn Ser Ile Arg Arg Leu Gly Cys Gly Ser Gly Tyr Gly
             20                  25                  30 agc tat gga tat ggc tct ggc ttc gga ggc ttt gga tat ggc tct ggc    144
Ser Tyr Gly Tyr Gly Ser Gly Phe Gly Gly Phe Gly Tyr Gly Ser Gly
         35                  40                  45 ttt gga ggc tac gga tac ggc tct gac tac gga ggc tat gga tat ggc    192
Phe Gly Gly Tyr Gly Tyr Gly Ser Asp Tyr Gly Gly Tyr Gly Tyr Gly
     50                  55                  60 tgt ggc cgc cct tca tgc tgt gga gga tat ggg ttc tcc agc ttc tac    240
Cys Gly Arg Pro Ser Cys Cys Gly Gly Tyr Gly Phe Ser Ser Phe Tyr
 65                  70                  75                  80 tga                                                                 243

<210> SEQ ID NO 140
<211> LENGTH: 80
<212> TYPE: PRT
<213> ORGANISM: Mus musculus

<400> SEQUENCE: 140

Met Glu Ala Trp Ala Thr Ala Met Ala Ala Leu Glu Ala Trp Ala
 1               5                  10                  15

Cys Gly Cys Asn Ser Ile Arg Arg Leu Gly Cys Gly Ser Gly Tyr Gly
             20                  25                  30

Ser Tyr Gly Tyr Gly Ser Gly Phe Gly Gly Phe Gly Tyr Gly Ser Gly
         35                  40                  45

Phe Gly Gly Tyr Gly Tyr Gly Ser Asp Tyr Gly Gly Tyr Gly Tyr Gly
     50                  55                  60

Cys Gly Arg Pro Ser Cys Cys Gly Gly Tyr Gly Phe Ser Ser Phe Tyr
 65                  70                  75                  80

<210> SEQ ID NO 141
<211> LENGTH: 255
<212> TYPE: DNA
<213> ORGANISM: Mus musculus
<220> FEATURE:
<221> NAME/KEY: CDS
<222> LOCATION: (1)..(255)

<400> SEQUENCE: 141 atg agt tac tac aac agc tac tac gga ggc ctg ggc tat ggc tct gga     48
Met Ser Tyr Tyr Asn Ser Tyr Tyr Gly Gly Leu Gly Tyr Gly Ser Gly
 1               5                  10                  15 ggc tat ggg ggc ctg ggc tat ggc tat ggc tgt ggc tgt ggc agt ttc     96
Gly Tyr Gly Gly Leu Gly Tyr Gly Tyr Gly Cys Gly Cys Gly Ser Phe
             20                  25                  30 cgc aga ctg ggc tat ggt tgt ggc ttt ggt ggc tac gga ggc ttt gga    144
Arg Arg Leu Gly Tyr Gly Cys Gly Phe Gly Gly Tyr Gly Gly Phe Gly
         35                  40                  45 tat ggc tct ggc tat gga ggc ttc agc tct ggc tct ggc tat gga ggc    192
Tyr Gly Ser Gly Tyr Gly Gly Phe Ser Ser Gly Ser Gly Tyr Gly Gly
     50                  55                  60 ttc gga tat ggc tac agg cgc ccc ctt tcc tat ggg gga tat gga ttc    240
Phe Gly Tyr Gly Tyr Arg Arg Pro Leu Ser Tyr Gly Gly Tyr Gly Phe
 65                  70                  75                  80 tcc acc ttc tac tga                                                 255
```

```
Ser Thr Phe Tyr
            85

<210> SEQ ID NO 142
<211> LENGTH: 84
<212> TYPE: PRT
<213> ORGANISM: Mus musculus

<400> SEQUENCE: 142

Met Ser Tyr Tyr Asn Ser Tyr Tyr Gly Gly Leu Gly Tyr Gly Ser Gly
  1               5                  10                  15

Gly Tyr Gly Gly Leu Gly Tyr Gly Tyr Gly Cys Gly Cys Gly Ser Phe
             20                  25                  30

Arg Arg Leu Gly Tyr Gly Cys Gly Phe Gly Gly Tyr Gly Gly Phe Gly
         35                  40                  45

Tyr Gly Ser Gly Tyr Gly Gly Phe Ser Ser Gly Ser Gly Tyr Gly Gly
     50                  55                  60

Phe Gly Tyr Gly Tyr Arg Arg Pro Leu Ser Tyr Gly Tyr Gly Phe
 65                  70                  75                  80

Ser Thr Phe Tyr

<210> SEQ ID NO 143
<211> LENGTH: 189
<212> TYPE: DNA
<213> ORGANISM: Mus musculus
<220> FEATURE:
<221> NAME/KEY: CDS
<222> LOCATION: (1)..(189)

<400> SEQUENCE: 143 atg agc tac tac ggc agc tac tac gga ggt ctg ggc tct ggc atc cga      48
Met Ser Tyr Tyr Gly Ser Tyr Tyr Gly Gly Leu Gly Ser Gly Ile Arg
  1               5                  10                  15 ggc ttt ggg aac ctg ggt tat ggc tat ggc tgt ggc tgt ggc ttt gga      96
Gly Phe Gly Asn Leu Gly Tyr Gly Tyr Gly Cys Gly Cys Gly Phe Gly
             20                  25                  30 ggt tac gga tat gga tct ggc tat ggc aga tat gga tat ggc tac ccg     144
Gly Tyr Gly Tyr Gly Ser Gly Tyr Gly Arg Tyr Gly Tyr Gly Tyr Pro
         35                  40                  45 cgc ccc ctt tat tat gga gga tat gga ttc tcc cga ttc tac tga        189
Arg Pro Leu Tyr Tyr Gly Gly Tyr Gly Phe Ser Arg Phe Tyr
     50                  55                  60

<210> SEQ ID NO 144
<211> LENGTH: 62
<212> TYPE: PRT
<213> ORGANISM: Mus musculus

<400> SEQUENCE: 144

Met Ser Tyr Tyr Gly Ser Tyr Tyr Gly Gly Leu Gly Ser Gly Ile Arg
  1               5                  10                  15

Gly Phe Gly Asn Leu Gly Tyr Gly Tyr Gly Cys Gly Cys Gly Phe Gly
             20                  25                  30

Gly Tyr Gly Tyr Gly Ser Gly Tyr Gly Arg Tyr Gly Tyr Gly Tyr Pro
         35                  40                  45

Arg Pro Leu Tyr Tyr Gly Gly Tyr Gly Phe Ser Arg Phe Tyr
     50                  55                  60

<210> SEQ ID NO 145
<211> LENGTH: 672
<212> TYPE: DNA
```

<213> ORGANISM: Mus musculus
<220> FEATURE:
<221> NAME/KEY: CDS
<222> LOCATION: (1)..(672)

<400> SEQUENCE: 145

| | | | | | | | | | | | | | | | | |
|---|---|---|---|---|---|---|---|---|---|---|---|---|---|---|---|---|
| atg | acc | tgc | tgt | ggc | tgt | tca | gga | ggc | tgt | ggc | tcc | agc | tgt | gga | ggc | 48 |
| Met | Thr | Cys | Cys | Gly | Cys | Ser | Gly | Gly | Cys | Gly | Ser | Ser | Cys | Gly | Gly | |
| 1 | | | | 5 | | | | | 10 | | | | | 15 | | |

| tgt | ggt | tcc | agc | tgc | tgc | aag | cct | gtg | tgc | tgc | gtg | cct | gtc | tgt | | 96 |
|---|---|---|---|---|---|---|---|---|---|---|---|---|---|---|---|---|
| Cys | Gly | Ser | Ser | Cys | Cys | Lys | Pro | Val | Cys | Cys | Val | Pro | Val | Cys | | |
| | | | 20 | | | | | 25 | | | | | 30 | | | |

| tcc | tgc | tct | agc | tgt | ggg | ggc | tgc | aag | gga | ggc | tgt | ggc | tcc | tgt | ggg | 144 |
|---|---|---|---|---|---|---|---|---|---|---|---|---|---|---|---|---|
| Ser | Cys | Ser | Ser | Cys | Gly | Gly | Cys | Lys | Gly | Gly | Cys | Gly | Ser | Cys | Gly | |
| | | 35 | | | | | 40 | | | | | 45 | | | | |

| ggc | tgc | aag | gga | ggc | tgt | ggt | tcc | tgt | ggg | ggc | tgc | aaa | gga | ggc | tgt | 192 |
|---|---|---|---|---|---|---|---|---|---|---|---|---|---|---|---|---|
| Gly | Cys | Lys | Gly | Gly | Cys | Gly | Ser | Cys | Gly | Gly | Cys | Lys | Gly | Gly | Cys | |
| 50 | | | | | 55 | | | | | 60 | | | | | | |

| ggc | tcc | tgt | ggg | ggc | tgc | aag | gga | ggc | tgt | tgt | caa | tcc | agt | tgc | tgt | 240 |
|---|---|---|---|---|---|---|---|---|---|---|---|---|---|---|---|---|
| Gly | Ser | Cys | Gly | Gly | Cys | Lys | Gly | Gly | Cys | Cys | Gln | Ser | Ser | Cys | Cys | |
| 65 | | | | 70 | | | | | 75 | | | | | 80 | | |

| aaa | ccc | tgc | tgc | tgc | cag | tcc | agc | tgc | tgc | aaa | ccc | tgt | tgc | tct | tca | 288 |
|---|---|---|---|---|---|---|---|---|---|---|---|---|---|---|---|---|
| Lys | Pro | Cys | Cys | Cys | Gln | Ser | Ser | Cys | Cys | Lys | Pro | Cys | Cys | Ser | Ser | |
| | | | 85 | | | | | 90 | | | | | 95 | | | |

| ggc | tgt | ggg | tct | tct | tgc | tgt | cag | tcc | agc | tgc | tgc | aaa | ccc | tgc | tgc | 336 |
|---|---|---|---|---|---|---|---|---|---|---|---|---|---|---|---|---|
| Gly | Cys | Gly | Ser | Ser | Cys | Cys | Gln | Ser | Ser | Cys | Cys | Lys | Pro | Cys | Cys | |
| | | 100 | | | | | 105 | | | | | 110 | | | | |

| tgc | cag | tcc | agc | tgc | tgc | aaa | ccc | tgt | tgc | tct | tca | ggc | tgt | ggg | tct | 384 |
|---|---|---|---|---|---|---|---|---|---|---|---|---|---|---|---|---|
| Cys | Gln | Ser | Ser | Cys | Cys | Lys | Pro | Cys | Cys | Ser | Ser | Gly | Cys | Gly | Ser | |
| | 115 | | | | | 120 | | | | | 125 | | | | | |

| tct | tgc | tgt | cag | tcc | agc | tgc | tgc | aaa | ccc | tgc | tgc | tgt | cag | tct | agc | 432 |
|---|---|---|---|---|---|---|---|---|---|---|---|---|---|---|---|---|
| Ser | Cys | Cys | Gln | Ser | Ser | Cys | Cys | Lys | Pro | Cys | Cys | Cys | Gln | Ser | Ser | |
| | 130 | | | | | 135 | | | | | 140 | | | | | |

| tgc | tgc | aag | ccc | tgc | tgc | cag | tcc | agc | tgc | tgc | aaa | ccc | tgt | tgc | | 480 |
|---|---|---|---|---|---|---|---|---|---|---|---|---|---|---|---|---|
| Cys | Cys | Lys | Pro | Cys | Cys | Gln | Ser | Ser | Cys | Cys | Lys | Pro | Cys | Cys | | |
| 145 | | | | | 150 | | | | | 155 | | | | | 160 | |

| tct | tca | ggc | tgt | ggg | tct | tct | tgc | tgc | cag | tcc | agc | tgc | tgt | aaa | ccc | 528 |
|---|---|---|---|---|---|---|---|---|---|---|---|---|---|---|---|---|
| Ser | Ser | Gly | Cys | Gly | Ser | Ser | Cys | Cys | Gln | Ser | Ser | Cys | Cys | Lys | Pro | |
| | | | 165 | | | | | 170 | | | | | 175 | | | |

| tgc | tgc | tgc | cag | tcc | agc | tgc | tgc | aag | ccc | tgc | tgc | tgc | cag | tcc | agc | 576 |
|---|---|---|---|---|---|---|---|---|---|---|---|---|---|---|---|---|
| Cys | Cys | Cys | Gln | Ser | Ser | Cys | Cys | Lys | Pro | Cys | Cys | Cys | Gln | Ser | Ser | |
| | | 180 | | | | | 185 | | | | | 190 | | | | |

| tgc | tgc | aag | ccc | tgc | tgc | cag | tcc | agc | tgc | tgc | aag | ccc | tgc | tgc | | 624 |
|---|---|---|---|---|---|---|---|---|---|---|---|---|---|---|---|---|
| Cys | Cys | Lys | Pro | Cys | Cys | Gln | Ser | Ser | Cys | Cys | Lys | Pro | Cys | Cys | | |
| | 195 | | | | | 200 | | | | | 205 | | | | | |

| tgc | cag | tcc | agc | tgc | tgt | gcc | cct | gtg | tgc | tgc | cag | tgt | aaa | atc | tga | 672 |
|---|---|---|---|---|---|---|---|---|---|---|---|---|---|---|---|---|
| Cys | Gln | Ser | Ser | Cys | Cys | Ala | Pro | Val | Cys | Cys | Gln | Cys | Lys | Ile | | |
| | 210 | | | | | 215 | | | | | 220 | | | | | |

<210> SEQ ID NO 146
<211> LENGTH: 223
<212> TYPE: PRT
<213> ORGANISM: Mus musculus

<400> SEQUENCE: 146

Met Thr Cys Cys Gly Cys Ser Gly Gly Cys Gly Ser Ser Cys Gly Gly
1               5                   10                  15

Cys Gly Ser Ser Cys Cys Lys Pro Val Cys Cys Val Pro Val Cys
            20                  25                  30

Ser Cys Ser Ser Cys Gly Gly Cys Lys Gly Gly Cys Gly Ser Cys Gly
        35                  40                  45

-continued

```
Gly Cys Lys Gly Gly Cys Gly Ser Cys Gly Gly Cys Lys Gly Gly Cys
 50                  55                  60
Gly Ser Cys Gly Gly Cys Lys Gly Gly Cys Cys Gln Ser Ser Cys Cys
 65                  70                  75                  80
Lys Pro Cys Cys Cys Gln Ser Ser Cys Cys Lys Pro Cys Cys Ser Ser
                 85                  90                  95
Gly Cys Gly Ser Ser Cys Cys Gln Ser Ser Cys Lys Pro Cys Cys
                100                 105                 110
Cys Gln Ser Ser Cys Cys Lys Pro Cys Cys Ser Ser Gly Cys Gly Ser
            115                 120                 125
Ser Cys Cys Gln Ser Ser Cys Cys Lys Pro Cys Cys Cys Gln Ser Ser
        130                 135                 140
Cys Cys Lys Pro Cys Cys Cys Gln Ser Ser Cys Cys Lys Pro Cys Cys
145                 150                 155                 160
Ser Ser Gly Cys Gly Ser Ser Cys Cys Gln Ser Ser Cys Cys Lys Pro
                165                 170                 175
Cys Cys Cys Gln Ser Ser Cys Cys Lys Pro Cys Cys Cys Gln Ser Ser
            180                 185                 190
Cys Cys Lys Pro Cys Cys Cys Gln Ser Ser Cys Cys Lys Pro Cys Cys
        195                 200                 205
Cys Gln Ser Ser Cys Cys Ala Pro Val Cys Cys Gln Cys Lys Ile
    210                 215                 220

<210> SEQ ID NO 147
<211> LENGTH: 693
<212> TYPE: DNA
<213> ORGANISM: Mus musculus
<220> FEATURE:
<221> NAME/KEY: CDS
<222> LOCATION: (1)..(693)

<400> SEQUENCE: 147 atg acc tgc tgt ggc tgt tca gga ggc tgt ggc tcc agc tgt ggg ggc      48
Met Thr Cys Cys Gly Cys Ser Gly Gly Cys Gly Ser Ser Cys Gly Gly
 1               5                  10                  15 tgt ggc tcc agc tgt ggg ggc tgt ggc tct ggc tgt ggg gga tgt ggc      96
Cys Gly Ser Ser Cys Gly Gly Cys Gly Ser Gly Cys Gly Gly Cys Gly
            20                  25                  30 tca aat tgt ggg ggc tgt ggc tcc agc tgc tgc aag cct gtg tgt tgc     144
Ser Asn Cys Gly Gly Cys Gly Ser Ser Cys Cys Lys Pro Val Cys Cys
        35                  40                  45 tgt aag cct gtg tgc tgt tgt gtt cct gtc tgt tcc tgc tcc agc tgt     192
Cys Lys Pro Val Cys Cys Cys Val Pro Val Cys Ser Cys Ser Ser Cys
 50                  55                  60 gga ggc tgt ggc tcc agc tgt ggt gga tgt ggc agc tgt ggc tcc agc     240
Gly Gly Cys Gly Ser Ser Cys Gly Gly Cys Gly Ser Cys Gly Ser Ser
 65                  70                  75                  80 tgt gga ggc tgt ggc tcc agc tgt tgc aag cct gtg tgc tgt tgt gtg     288
Cys Gly Gly Cys Gly Ser Ser Cys Cys Lys Pro Val Cys Cys Cys Val
                85                  90                  95 cct gtc tgt tcc tgc tcc agc tgt gga ggc tgc aag ccc tgc tgc tgc     336
Pro Val Cys Ser Cys Ser Ser Cys Gly Gly Cys Lys Pro Cys Cys Cys
                100                 105                 110 cag tcc agc tgc tgc aaa ccc tgc tgc tct tca ggc tgt ggg tct tcc     384
Gln Ser Ser Cys Cys Lys Pro Cys Cys Ser Ser Gly Cys Gly Ser Ser
            115                 120                 125 tgc tgt cag tcc agc tgc tgc aag ccc tgc tgc tgt cag tcc agc tgc     432
Cys Cys Gln Ser Ser Cys Cys Lys Pro Cys Cys Cys Gln Ser Ser Cys
```

```
            130                 135                 140
tgc aag ccc tgc tgc tgt cag tcc agc tgc tgc aag ccc tgt tgc tct    480
Cys Lys Pro Cys Cys Cys Gln Ser Ser Cys Cys Lys Pro Cys Cys Ser
145                 150                 155                 160 tca ggc tgt ggg tct tcc tgc tgt cag tcc agc tgc tgt aag ccc tgc    528
Ser Gly Cys Gly Ser Ser Cys Cys Gln Ser Ser Cys Cys Lys Pro Cys
                165                 170                 175 tgc tgt cag tct agc tgc tgc aag ccc tgc tgt tgt cag tct agc tgc    576
Cys Cys Gln Ser Ser Cys Cys Lys Pro Cys Cys Cys Gln Ser Ser Cys
            180                 185                 190 tgc aag ccc tgc tgc tgt cag tct agc tgc tgc aag ccc tgc tgc tgt    624
Cys Lys Pro Cys Cys Cys Gln Ser Ser Cys Cys Lys Pro Cys Cys Cys
        195                 200                 205 cag tcc agc tgc tgc aag ccc tgc tgt tca tca ggc tgc ggg tct tcc    672
Gln Ser Ser Cys Cys Lys Pro Cys Cys Ser Ser Gly Cys Gly Ser Ser
    210                 215                 220 tgc tgt cag gac agc tgc tga                                        693
Cys Cys Gln Asp Ser Cys
225                 230

<210> SEQ ID NO 148
<211> LENGTH: 230
<212> TYPE: PRT
<213> ORGANISM: Mus musculus

<400> SEQUENCE: 148

Met Thr Cys Cys Gly Cys Ser Gly Gly Cys Gly Ser Ser Cys Gly Gly
1               5                   10                  15

Cys Gly Ser Ser Cys Gly Gly Cys Gly Ser Gly Cys Gly Gly Cys Gly
                20                  25                  30

Ser Asn Cys Gly Gly Cys Gly Ser Cys Cys Lys Pro Val Cys Cys
            35                  40                  45

Cys Lys Pro Val Cys Cys Val Pro Val Cys Ser Cys Ser Ser Cys
    50                  55                  60

Gly Gly Cys Gly Ser Ser Cys Gly Gly Cys Gly Ser Cys Gly Ser Ser
65                  70                  75                  80

Cys Gly Gly Cys Gly Ser Ser Cys Cys Lys Pro Val Cys Cys Val
            85                  90                  95

Pro Val Cys Ser Cys Ser Ser Cys Gly Gly Cys Lys Pro Cys Cys
        100                 105                 110

Gln Ser Ser Cys Cys Lys Pro Cys Cys Ser Ser Gly Cys Gly Ser Ser
    115                 120                 125

Cys Cys Gln Ser Ser Cys Cys Lys Pro Cys Cys Gln Ser Ser Cys
130                 135                 140

Cys Lys Pro Cys Cys Cys Gln Ser Ser Cys Cys Lys Pro Cys Cys Ser
145                 150                 155                 160

Ser Gly Cys Gly Ser Ser Cys Cys Gln Ser Ser Cys Cys Lys Pro Cys
                165                 170                 175

Cys Cys Gln Ser Ser Cys Cys Lys Pro Cys Cys Cys Gln Ser Ser Cys
            180                 185                 190

Cys Lys Pro Cys Cys Cys Gln Ser Ser Cys Cys Lys Pro Cys Cys Cys
        195                 200                 205

Gln Ser Ser Cys Cys Lys Pro Cys Cys Ser Ser Gly Cys Gly Ser Ser
    210                 215                 220

Cys Cys Gln Asp Ser Cys
225                 230
```

<210> SEQ ID NO 149
<211> LENGTH: 561
<212> TYPE: DNA
<213> ORGANISM: Mus musculus
<220> FEATURE:
<221> NAME/KEY: CDS
<222> LOCATION: (1)..(561)

<400> SEQUENCE: 149

| | | | | | | | | | | | | | | | | |
|---|---|---|---|---|---|---|---|---|---|---|---|---|---|---|---|---|
| atg | acc | aac | tcc | tgc | tgc | tcc | cct | tgc | tgc | cag | ccc | acc | tgc | tgc | agg | 48 |
| Met | Thr | Asn | Ser | Cys | Cys | Ser | Pro | Cys | Cys | Gln | Pro | Thr | Cys | Cys | Arg | |
| 1 | | | | 5 | | | | | 10 | | | | | 15 | | |

| acc | acc | tgc | tgc | agg | acc | acc | tgc | tgg | aga | cca | agc | tgt | gtg | acc | agc | 96 |
|---|---|---|---|---|---|---|---|---|---|---|---|---|---|---|---|---|
| Thr | Thr | Cys | Cys | Arg | Thr | Thr | Cys | Trp | Arg | Pro | Ser | Cys | Val | Thr | Ser | |
| | | | 20 | | | | | 25 | | | | | 30 | | | |

| tgt | tgc | cag | ccc | tgc | tgc | cag | ccc | agc | tgc | tgt | ggc | tcc | agc | tgc | tgc | 144 |
|---|---|---|---|---|---|---|---|---|---|---|---|---|---|---|---|---|
| Cys | Cys | Gln | Pro | Cys | Cys | Gln | Pro | Ser | Cys | Cys | Gly | Ser | Ser | Cys | Cys | |
| | | 35 | | | | | 40 | | | | | 45 | | | | |

| cag | cct | tgc | tgt | caa | acc | acc | tgc | tgc | agg | acc | tgc | ttc | cag | cca | tgc | 192 |
|---|---|---|---|---|---|---|---|---|---|---|---|---|---|---|---|---|
| Gln | Pro | Cys | Cys | Gln | Thr | Thr | Cys | Cys | Arg | Thr | Cys | Phe | Gln | Pro | Cys | |
| 50 | | | | | 55 | | | | | 60 | | | | | | |

| tgt | gtg | agc | agc | tgc | tgc | cgc | aca | ccc | tgc | tgc | cag | ccc | tgc | tgc | tgt | 240 |
|---|---|---|---|---|---|---|---|---|---|---|---|---|---|---|---|---|
| Cys | Val | Ser | Ser | Cys | Cys | Arg | Thr | Pro | Cys | Cys | Gln | Pro | Cys | Cys | Cys | |
| 65 | | | | | 70 | | | | | 75 | | | | | 80 | |

| gtg | tcc | agc | tgc | tgc | cag | ccc | tgc | tgc | cag | ccc | agc | tgc | tgt | cag | tcc | 288 |
|---|---|---|---|---|---|---|---|---|---|---|---|---|---|---|---|---|
| Val | Ser | Ser | Cys | Cys | Gln | Pro | Cys | Cys | Gln | Pro | Ser | Cys | Cys | Gln | Ser | |
| | | | 85 | | | | | 90 | | | | | 95 | | | |

| agc | tgc | tgc | cag | cct | agg | tgc | tgt | gag | tcc | agc | tgc | tgc | cag | ccc | agg | 336 |
|---|---|---|---|---|---|---|---|---|---|---|---|---|---|---|---|---|
| Ser | Cys | Cys | Gln | Pro | Arg | Cys | Cys | Glu | Ser | Ser | Cys | Cys | Gln | Pro | Arg | |
| | | 100 | | | | | 105 | | | | | 110 | | | | |

| tgc | tgt | atc | tcc | agc | tgc | tgc | cag | ccc | tgc | tgc | agg | cct | agc | tgc | tgt | 384 |
|---|---|---|---|---|---|---|---|---|---|---|---|---|---|---|---|---|
| Cys | Cys | Ile | Ser | Ser | Cys | Cys | Gln | Pro | Cys | Cys | Arg | Pro | Ser | Cys | Cys | |
| | | 115 | | | | | 120 | | | | | 125 | | | | |

| cag | tct | agc | tgc | tgc | agg | ccc | tgc | tgc | cag | ccc | ttc | tgc | ctc | aac | ctg | 432 |
|---|---|---|---|---|---|---|---|---|---|---|---|---|---|---|---|---|
| Gln | Ser | Ser | Cys | Cys | Arg | Pro | Cys | Cys | Gln | Pro | Phe | Cys | Leu | Asn | Leu | |
| | 130 | | | | | 135 | | | | | 140 | | | | | |

| tgc | tgc | cag | cca | gcc | tgc | tct | gga | cct | gtg | acc | tgc | acc | agg | act | tgc | 480 |
|---|---|---|---|---|---|---|---|---|---|---|---|---|---|---|---|---|
| Cys | Cys | Gln | Pro | Ala | Cys | Ser | Gly | Pro | Val | Thr | Cys | Thr | Arg | Thr | Cys | |
| 145 | | | | 150 | | | | | 155 | | | | | 160 | | |

| tac | cag | cca | aca | tgt | gtt | tgt | gtg | cct | ggt | tgc | ctg | tcc | caa | ggc | tgt | 528 |
|---|---|---|---|---|---|---|---|---|---|---|---|---|---|---|---|---|
| Tyr | Gln | Pro | Thr | Cys | Val | Cys | Val | Pro | Gly | Cys | Leu | Ser | Gln | Gly | Cys | |
| | | | 165 | | | | | 170 | | | | | 175 | | | |

| ggg | tcc | agc | tgt | tgt | gag | ccc | tgt | ggc | tgt | tga | | | | | | 561 |
|---|---|---|---|---|---|---|---|---|---|---|---|---|---|---|---|---|
| Gly | Ser | Ser | Cys | Cys | Glu | Pro | Cys | Gly | Cys | | | | | | | |
| | | 180 | | | | | 185 | | | | | | | | | |

<210> SEQ ID NO 150
<211> LENGTH: 186
<212> TYPE: PRT
<213> ORGANISM: Mus musculus

<400> SEQUENCE: 150

Met Thr Asn Ser Cys Cys Ser Pro Cys Cys Gln Pro Thr Cys Cys Arg
 1               5                  10                  15

Thr Thr Cys Cys Arg Thr Thr Cys Trp Arg Pro Ser Cys Val Thr Ser
             20                  25                  30

Cys Cys Gln Pro Cys Cys Gln Pro Ser Cys Cys Gly Ser Ser Cys Cys
         35                  40                  45

Gln Pro Cys Cys Gln Thr Thr Cys Cys Arg Thr Cys Phe Gln Pro Cys
     50                  55                  60

```
Cys Val Ser Ser Cys Cys Arg Thr Pro Cys Cys Gln Pro Cys Cys
 65                  70                  75                  80

Val Ser Ser Cys Cys Gln Pro Cys Cys Gln Pro Ser Cys Cys Gln Ser
                 85                  90                  95

Ser Cys Cys Gln Pro Arg Cys Cys Glu Ser Ser Cys Cys Gln Pro Arg
                100                 105                 110

Cys Cys Ile Ser Ser Cys Cys Gln Pro Cys Cys Arg Pro Ser Cys Cys
            115                 120                 125

Gln Ser Ser Cys Cys Arg Pro Cys Cys Gln Pro Phe Cys Leu Asn Leu
130                 135                 140

Cys Cys Gln Pro Ala Cys Ser Gly Pro Val Thr Cys Thr Arg Thr Cys
145                 150                 155                 160

Tyr Gln Pro Thr Cys Val Cys Val Pro Gly Cys Leu Ser Gln Gly Cys
                165                 170                 175

Gly Ser Ser Cys Cys Glu Pro Cys Gly Cys
                180                 185

<210> SEQ ID NO 151
<211> LENGTH: 1044
<212> TYPE: DNA
<213> ORGANISM: Mus musculus
<220> FEATURE:
<221> NAME/KEY: CDS
<222> LOCATION: (53)..(640)

<400> SEQUENCE: 151
gagaatctca gaaactcctg tgaacacaac tcctccctcc acatccaaca cc atg acc      58
                                                          Met Thr
                                                            1 aac tcc tgc tgc tcc cct tgc tgc cag ccc acc tgc tgc agg acc acc      106
Asn Ser Cys Cys Ser Pro Cys Cys Gln Pro Thr Cys Cys Arg Thr Thr
      5                  10                  15 tgc tgc agg acc acc tgc tgg aga cca agc tgt gtg acc agc tgt tgc      154
Cys Cys Arg Thr Thr Cys Trp Arg Pro Ser Cys Val Thr Ser Cys Cys
 20                  25                  30 cag ccc tgc tgc cag ccc agc tgc tgt ggc tcc agc tgc tgc cag cct      202
Gln Pro Cys Cys Gln Pro Ser Cys Cys Gly Ser Ser Cys Cys Gln Pro
 35                  40                  45                  50 tgt tgt caa acc acc tgc tgc agg acc tgc ttc cag cca tgc tgt gtg      250
Cys Cys Gln Thr Thr Cys Cys Arg Thr Cys Phe Gln Pro Cys Cys Val
                 55                  60                  65 agc agc tgc tgc cgc aca ccc tgc tgc cag ccc tgc tgc tgt gtg tcc      298
Ser Ser Cys Cys Arg Thr Pro Cys Cys Gln Pro Cys Cys Cys Val Ser
             70                  75                  80 agc tgc tgc cag ccc tgc tgc cag ccc agc tgt tgt cag tcc agc tgt      346
Ser Cys Cys Gln Pro Cys Cys Gln Pro Ser Cys Cys Gln Ser Ser Cys
         85                  90                  95 tgc cag ccc agc tgt tgt cag tcc agc tgt tgc cag cct agc tgt tgt      394
Cys Gln Pro Ser Cys Cys Gln Ser Ser Cys Cys Gln Pro Ser Cys Cys
    100                 105                 110 cag tcc agc tgt tgt cag ccc agg tgt tgt atc tcc agc tgt tgc cag      442
Gln Ser Ser Cys Cys Gln Pro Arg Cys Cys Ile Ser Ser Cys Cys Gln
115                 120                 125                 130 ccc tgc tgc agg cct agc tgt tgt cag tcc agc tgc tgc aag ccc tgc      490
Pro Cys Cys Arg Pro Ser Cys Cys Gln Ser Ser Cys Cys Lys Pro Cys
                135                 140                 145 tgc cag ccc ttc tgc ctc aac ctg tgc tgc cag cca gcc tgc tct gga      538
Cys Gln Pro Phe Cys Leu Asn Leu Cys Cys Gln Pro Ala Cys Ser Gly
            150                 155                 160
```

-continued

```
cct gtg acc tgc acc agg act tgc tac cag cca aca tgt gtc tgt gtg      586
Pro Val Thr Cys Thr Arg Thr Cys Tyr Gln Pro Thr Cys Val Cys Val
        165                 170                 175 cct ggc tgc ctg tcc caa ggc tgt ggg tct aac tgc tcc caa tct tgc      634
Pro Gly Cys Leu Ser Gln Gly Cys Gly Ser Asn Cys Ser Gln Ser Cys
180                 185                 190 tgt tga taactctatc tcctgccaca tgccagcttg ccagcatcta accaaaattc       690
Cys
195 cccaacacaa tcatcctgtg tgctttgcca ttattaacta tcagtgagtc gtcttcttgt    750 gatggttgta tctgctggat gagagagact gttcttctca ttactcagtt gttaacctcc    810 tggtccattt catcttcttt tgagcttcag ttatgttctc agatgcagaa aagaagcttc    870 attctttctc ttcaaggaac ttaagcaaag caaaccttga ttcttctctt ttagccctcc    930 tcagtaataa ttatttcatt tcttagtggg tttctcttct tgtcactatt gggcttactt    990 taagttgtct tctgggttcc atgtgttctc aataaatctg catttgttct tctg          1044
```

<210> SEQ ID NO 152
<211> LENGTH: 195
<212> TYPE: PRT
<213> ORGANISM: Mus musculus

<400> SEQUENCE: 152

```
Met Thr Asn Ser Cys Cys Ser Pro Cys Cys Gln Pro Thr Cys Cys Arg
 1               5                  10                  15

Thr Thr Cys Cys Arg Thr Thr Cys Trp Arg Pro Ser Cys Val Thr Ser
            20                  25                  30

Cys Cys Gln Pro Cys Cys Gln Pro Ser Cys Cys Gly Ser Ser Cys Cys
        35                  40                  45

Gln Pro Cys Cys Gln Thr Thr Cys Cys Arg Thr Cys Phe Gln Pro Cys
    50                  55                  60

Cys Val Ser Ser Cys Cys Arg Thr Pro Cys Cys Gln Pro Cys Cys Cys
65                  70                  75                  80

Val Ser Ser Cys Cys Gln Pro Cys Cys Gln Pro Ser Cys Cys Gln Ser
                85                  90                  95

Ser Cys Cys Gln Pro Ser Cys Cys Gln Ser Ser Cys Cys Gln Pro Ser
            100                 105                 110

Cys Cys Gln Ser Ser Cys Cys Gln Pro Arg Cys Cys Ile Ser Ser Cys
        115                 120                 125

Cys Gln Pro Cys Cys Arg Pro Ser Cys Cys Gln Ser Ser Cys Cys Lys
    130                 135                 140

Pro Cys Cys Gln Pro Phe Cys Leu Asn Leu Cys Cys Gln Pro Ala Cys
145                 150                 155                 160

Ser Gly Pro Val Thr Cys Thr Arg Thr Cys Tyr Gln Pro Thr Cys Val
                165                 170                 175

Cys Val Pro Gly Cys Leu Ser Gln Gly Cys Gly Ser Asn Cys Ser Gln
            180                 185                 190

Ser Cys Cys
        195
```

<210> SEQ ID NO 153
<211> LENGTH: 1712
<212> TYPE: DNA
<213> ORGANISM: Mus musculus
<220> FEATURE:
<221> NAME/KEY: CDS
<222> LOCATION: (21)..(866)

<400> SEQUENCE: 153

```
cccacagttt tcgacgaaaa atg gcg ggg tct cct gag ttg gtg gtc ctt gac         53
                     Met Ala Gly Ser Pro Glu Leu Val Val Leu Asp
                      1               5                  10 cct cca tgg gac aag gag ctc gcg gct ggc aca gag agc cag gcc ttg          101
Pro Pro Trp Asp Lys Glu Leu Ala Ala Gly Thr Glu Ser Gln Ala Leu
             15                  20                  25 gtc tcc gcc act ccc cga gaa gac ttt cgg gtg cgc tgc acc tcg aag          149
Val Ser Ala Thr Pro Arg Glu Asp Phe Arg Val Arg Cys Thr Ser Lys
         30                  35                  40 cgg gct gtg acc gaa atg cta caa ctg tgc ggc cgc ttc gtg caa aag          197
Arg Ala Val Thr Glu Met Leu Gln Leu Cys Gly Arg Phe Val Gln Lys
     45                  50                  55 ctc ggg gac gct ctg ccg gag gag att cgg gag ccc gct ctg cga gat          245
Leu Gly Asp Ala Leu Pro Glu Glu Ile Arg Glu Pro Ala Leu Arg Asp
 60                  65                  70                  75 gcg cag tgg act ttt gaa tca gct gtg caa gag aat atc agc att aat          293
Ala Gln Trp Thr Phe Glu Ser Ala Val Gln Glu Asn Ile Ser Ile Asn
                 80                  85                  90 ggg caa gca tgg cag gaa gct tca gat aat tgt ttt atg gat tct gac          341
Gly Gln Ala Trp Gln Glu Ala Ser Asp Asn Cys Phe Met Asp Ser Asp
             95                 100                 105 atc aaa gta ctt gaa gat cag ttt gat gaa ata gta gat ata gcc              389
Ile Lys Val Leu Glu Asp Gln Phe Asp Glu Ile Ile Val Asp Ile Ala
         110                 115                 120 aca aaa cgt aag cag tat ccc aga aag atc ctg gaa tgt gtc atc aaa          437
Thr Lys Arg Lys Gln Tyr Pro Arg Lys Ile Leu Glu Cys Val Ile Lys
     125                 130                 135 acc ata aaa gca aaa caa gaa att ctg aag cag tac cac cct gtt gta          485
Thr Ile Lys Ala Lys Gln Glu Ile Leu Lys Gln Tyr His Pro Val Val
 140                 145                 150                 155 cat cca ctg gac cta aaa tat gac cct gat cca gcc cct cat atg gaa          533
His Pro Leu Asp Leu Lys Tyr Asp Pro Asp Pro Ala Pro His Met Glu
                 160                 165                 170 aat ttg aaa tgc aga ggg gaa aca gta gca aag gag atc agt gaa gcc          581
Asn Leu Lys Cys Arg Gly Glu Thr Val Ala Lys Glu Ile Ser Glu Ala
             175                 180                 185 atg aag tcc ttg cct gca tta att gaa caa gga gag gga ttt tcc caa          629
Met Lys Ser Leu Pro Ala Leu Ile Glu Gln Gly Glu Gly Phe Ser Gln
         190                 195                 200 gtt ctc agg atg cag cct gtt atc cac ctc cag agg att cac caa gaa          677
Val Leu Arg Met Gln Pro Val Ile His Leu Gln Arg Ile His Gln Glu
     205                 210                 215 gtc ttt tcc agt tgt cat agg aaa cca gat gct aaa cct gag aac ttt          725
Val Phe Ser Ser Cys His Arg Lys Pro Asp Ala Lys Pro Glu Asn Phe
220                 225                 230                 235 ata aca cag ata gaa acc aca cca aca gag act gct tcc agg aaa acc          773
Ile Thr Gln Ile Glu Thr Thr Pro Thr Glu Thr Ala Ser Arg Lys Thr
                 240                 245                 250 tct gac gtg gta ctg aaa aga aag caa act aaa gac tgc ccc cag aga          821
Ser Asp Val Val Leu Lys Arg Lys Gln Thr Lys Asp Cys Pro Gln Arg
             255                 260                 265 aaa tgg tat cca ttg cgg cca aag aaa att aat ctt gat aca tga              866
Lys Trp Tyr Pro Leu Arg Pro Lys Lys Ile Asn Leu Asp Thr
         270                 275                 280 gctctttctg tttattttgg gagttgaaaa taggcaccat caacatttag attacagcct        926
aattaatacc tagataagac ttcatttgaa ataagaaata actcttttac tagtgattca        986
```

-continued

```
tttatacaga tatagtatct ctgtgcgggg atatgatata atattgtatt tccttactgt      1046
tttatctatt gtaaataaaa agcattttaa aaagtattga cacaaagccc atcagtgggc      1106
attaaaaata ttaaaagtgc agacttttac tgtccttaag tgccatcaac tctcagctcc      1166
cttgtagctt ttgtgggatt taacaagtaa caaattctgt tgtgtttccc tggtatacat      1226
ctttctagga aaaaaaaaaa aagagagaga gctgtataat gattttcgt ttacatgctg       1286 aaaagtaatt atcagtttct gcacagcagc agatgcaggg ttttttttta aagatgtagt      1346
ttgatttatc aaattaatgt gctgatgata atactggctt tgactttgtt actccatgtt      1406
cagctaattt aggtttgtga gattaacttt aggattttt gttgtgtaag acaatgataa       1466
ctattatttg tgcaacatta ctctttgaaa taaaaattgg catgtagcca atgtttcctg      1526
cccacactca cttttttcta tagaccatta acataatttg acttggaact aatggtttct      1586
ttttagggtt tcttatttat ttctttacaa atcattccag ttcaaaatat atatcagatt      1646
aatacactga aaaaaagtg tcattgtggt ttattggaac ctattttcac cttggagggt       1706
ggttta                                                                 1712
```

<210> SEQ ID NO 154
<211> LENGTH: 281
<212> TYPE: PRT
<213> ORGANISM: Mus musculus

<400> SEQUENCE: 154

```
Met Ala Gly Ser Pro Glu Leu Val Val Leu Asp Pro Pro Trp Asp Lys
1               5                   10                  15

Glu Leu Ala Ala Gly Thr Glu Ser Gln Ala Leu Val Ser Ala Thr Pro
            20                  25                  30

Arg Glu Asp Phe Arg Val Arg Cys Thr Ser Lys Arg Ala Val Thr Glu
        35                  40                  45

Met Leu Gln Leu Cys Gly Arg Phe Val Gln Lys Leu Gly Asp Ala Leu
    50                  55                  60

Pro Glu Glu Ile Arg Glu Pro Ala Leu Arg Asp Ala Gln Trp Thr Phe
65                  70                  75                  80

Glu Ser Ala Val Gln Glu Asn Ile Ser Ile Asn Gly Gln Ala Trp Gln
                85                  90                  95

Glu Ala Ser Asp Asn Cys Phe Met Asp Ser Asp Ile Lys Val Leu Glu
            100                 105                 110

Asp Gln Phe Asp Glu Ile Ile Val Asp Ile Ala Thr Lys Arg Lys Gln
        115                 120                 125

Tyr Pro Arg Lys Ile Leu Glu Cys Val Ile Lys Thr Ile Lys Ala Lys
    130                 135                 140

Gln Glu Ile Leu Lys Gln Tyr His Pro Val Val His Pro Leu Asp Leu
145                 150                 155                 160

Lys Tyr Asp Pro Asp Pro Ala Pro His Met Glu Asn Leu Lys Cys Arg
                165                 170                 175

Gly Glu Thr Val Ala Lys Glu Ile Ser Glu Ala Met Lys Ser Leu Pro
            180                 185                 190

Ala Leu Ile Glu Gln Gly Glu Gly Phe Ser Gln Val Leu Arg Met Gln
        195                 200                 205

Pro Val Ile His Leu Gln Arg Ile His Gln Glu Val Phe Ser Ser Cys
    210                 215                 220

His Arg Lys Pro Asp Ala Lys Pro Glu Asn Phe Ile Thr Gln Ile Glu
225                 230                 235                 240
```

-continued

```
Thr Thr Pro Thr Glu Thr Ala Ser Arg Lys Thr Ser Asp Val Val Leu
            245                 250                 255

Lys Arg Lys Gln Thr Lys Asp Cys Pro Gln Arg Lys Trp Tyr Pro Leu
            260                 265                 270

Arg Pro Lys Lys Ile Asn Leu Asp Thr
            275                 280

<210> SEQ ID NO 155
<211> LENGTH: 978
<212> TYPE: DNA
<213> ORGANISM: Mus musculus
<220> FEATURE:
<221> NAME/KEY: CDS
<222> LOCATION: (55)..(561)

<400> SEQUENCE: 155
agatcctcaa atcactctct cagaaaccca cccagaacct ccacctctaa cacc atg      57
                                                            Met
                                                              1 gtc agc tcc tgt tgt ggc tct gtc tgc tct gag gag ggc tgt agc caa    105
Val Ser Ser Cys Cys Gly Ser Val Cys Ser Glu Glu Gly Cys Ser Gln
      5                   10                  15 ggc tgc tgc cag ccc agc tgc tgt gtg tcc agc tgc tgc agg cct cag    153
Gly Cys Cys Gln Pro Ser Cys Cys Val Ser Ser Cys Cys Arg Pro Gln
 20                  25                  30 tgc tgc cag tct gtg tgc tgc cag ccc acc tgc tgc cgc ccc agc tgc    201
Cys Cys Gln Ser Val Cys Cys Gln Pro Thr Cys Cys Arg Pro Ser Cys
 35                  40                  45 tgc atc tcc agc tgc tgt cgc ccc agc tgc tgt agg ccc agt tgc tgc    249
Cys Ile Ser Ser Cys Cys Arg Pro Ser Cys Cys Arg Pro Ser Cys Cys
 50                  55                  60                  65 agg ccc agc tgc tgt gtg tcc agc tgc tgc aga ccc cag tgc tgc cag    297
Arg Pro Ser Cys Cys Val Ser Ser Cys Cys Arg Pro Gln Cys Cys Gln
                 70                  75                  80 tct gcg tgc tgc cag ccc acc tgc tgc cgc ccc agc tgc tgc cgc ccc    345
Ser Ala Cys Cys Gln Pro Thr Cys Cys Arg Pro Ser Cys Cys Arg Pro
             85                  90                  95 agc tgc tgc atc tcc agc tgc tgc caa cca tct tgt ggt ggt tct agc    393
Ser Cys Cys Ile Ser Ser Cys Cys Gln Pro Ser Cys Gly Gly Ser Ser
            100                 105                 110 tgt tgt ggc tcc agc tgc tgc cgc cct tgc tgc cgc ccc tgt tgc cgc    441
Cys Cys Gly Ser Ser Cys Cys Arg Pro Cys Cys Arg Pro Cys Cys Arg
        115                 120                 125 ccc tgc tgc tgt ctg aga cca gtc tgc ggt cag gtc tgc tgc caa acc    489
Pro Cys Cys Cys Leu Arg Pro Val Cys Gly Gln Val Cys Cys Gln Thr
130                 135                 140                 145 act tgc tac cgc ccc act tgt gtc atc tcc acc tgc cct cgc ccc atg    537
Thr Cys Tyr Arg Pro Thr Cys Val Ile Ser Thr Cys Pro Arg Pro Met
                150                 155                 160 tgc tgt gcc acc ccc tgt tgc tga gcctccatgc cttgatccag cttctatttc    591
Cys Cys Ala Thr Pro Cys Cys
                165 atctttgtcc ccacagttgg cgacaggggc atacagagtc atatcgatgg atgttgtttt    651 gctgagtaac atctctatat ttcattggac ccaacaatgg ctattctagc ttcaatccac    711 attctttatg tggaccttcc cttcccatag aagtgtgaat tagcttctac tgcaccagct    771 gctgaattga atcatcccca gattcttaac acttaggtcc aagttacaac tctcaagggt    831 cctcaggttg acttcaatag ttctctactg ttgatcttca tagtccccga cttaattgtt    891 caatgaagat gctcttcggt cattcttatt cccccaggtg ccctgtgttg tgtcactgtg    951
```

-continued

```
tcaaaataaa ccactactttt cccactt                                              978
```

<210> SEQ ID NO 156
<211> LENGTH: 168
<212> TYPE: PRT
<213> ORGANISM: Mus musculus

<400> SEQUENCE: 156

```
Met Val Ser Ser Cys Cys Gly Ser Val Cys Ser Glu Glu Gly Cys Ser
  1               5                  10                  15
Gln Gly Cys Cys Gln Pro Ser Cys Cys Val Ser Cys Cys Arg Pro
             20                  25                  30
Gln Cys Cys Gln Ser Val Cys Cys Gln Pro Thr Cys Cys Arg Pro Ser
         35                  40                  45
Cys Cys Ile Ser Ser Cys Cys Arg Pro Ser Cys Cys Arg Pro Ser Cys
     50                  55                  60
Cys Arg Pro Ser Cys Cys Val Ser Ser Cys Cys Arg Pro Gln Cys Cys
 65                  70                  75                  80
Gln Ser Ala Cys Cys Gln Pro Thr Cys Cys Arg Pro Ser Cys Cys Arg
                 85                  90                  95
Pro Ser Cys Cys Ile Ser Ser Cys Cys Gln Pro Ser Cys Gly Gly Ser
            100                 105                 110
Ser Cys Cys Gly Ser Ser Cys Cys Arg Pro Cys Cys Arg Pro Cys Cys
        115                 120                 125
Arg Pro Cys Cys Leu Arg Pro Val Cys Gly Gln Val Cys Cys Gln
    130                 135                 140
Thr Thr Cys Tyr Arg Pro Thr Cys Val Ile Ser Thr Cys Pro Arg Pro
145                 150                 155                 160
Met Cys Cys Ala Thr Pro Cys Cys
                165
```

<210> SEQ ID NO 157
<211> LENGTH: 920
<212> TYPE: DNA
<213> ORGANISM: Mus musculus
<220> FEATURE:
<221> NAME/KEY: CDS
<222> LOCATION: (63)..(650)

<400> SEQUENCE: 157

```
gacttccaaa ccttccaacc catcttcttg taaacccatc cagaacctcc acctctgaca    60 cc atg gcc aac tct tgt tgt ggc tct gtc tgc tct gag gag agc tgt    107
   Met Ala Asn Ser Cys Cys Gly Ser Val Cys Ser Glu Glu Ser Cys
     1               5                  10                  15 ggc caa ggc tgc tgc cag ccc agc tgc tgc cag acc acc tgc tgt agg   155
Gly Gln Gly Cys Cys Gln Pro Ser Cys Cys Gln Thr Thr Cys Cys Arg
                 20                  25                  30 acc acc tgc tgc cgc ccc agc tgc tgt gtg tcc agc tgc tgc aga ccc   203
Thr Thr Cys Cys Arg Pro Ser Cys Cys Val Ser Ser Cys Cys Arg Pro
             35                  40                  45 cag tgc tgc cag tct ctg tgc tgc cag ccc acc tgc cgc ccc agc       251
Gln Cys Cys Gln Ser Leu Cys Cys Gln Pro Thr Cys Cys Arg Pro Ser
         50                  55                  60 tgc tgc att tcc agc tgc tgc agg ccc acc tgc cgc ccc acc tgc       299
Cys Cys Ile Ser Ser Cys Cys Arg Pro Thr Cys Cys Arg Pro Thr Cys
     65                  70                  75 tgt att tcc agc tgc tgc agg ccc acc tgc tgt cgc ccc agc tgc tgc   347
Cys Ile Ser Ser Cys Cys Arg Pro Thr Cys Cys Arg Pro Ser Cys Cys
```

```
att tcc agc tgc tgc agg ccc acc tgc cgc ccc agc tgc tgt att    395
Ile Ser Ser Cys Cys Arg Pro Thr Cys Arg Pro Ser Cys Cys Ile
            100                 105                 110 tcc agc tgc tgc agg cct tct tgc tgc cgc ccc agc tgc tgc att tcc    443
Ser Ser Cys Cys Arg Pro Ser Cys Cys Arg Pro Ser Cys Cys Ile Ser
            115                 120                 125 agc tgc tgc agg cct tcc tgc tgc cgc ccc agc tgc tgc aga cct agc    491
Ser Cys Cys Arg Pro Ser Cys Cys Arg Pro Ser Cys Cys Arg Pro Ser
            130                 135                 140 tgt tgc att tct agc tgc tgc cgc ccc agc tgc tgt gtg tcc agc tgc    539
Cys Cys Ile Ser Ser Cys Cys Arg Pro Ser Cys Cys Val Ser Ser Cys
        145                 150                 155 tgc aga ccc cag tgc tgc atc tcc agc tgc tgc cgc ccc atc tgt tgc    587
Cys Arg Pro Gln Cys Cys Ile Ser Ser Cys Cys Arg Pro Ile Cys Cys
160                 165                 170                 175 cag acc acc tgc tgc agg acc acc tgc tac cgc cca gcg tgc tct agt    635
Gln Thr Thr Cys Cys Arg Thr Thr Cys Tyr Arg Pro Ala Cys Ser Ser
                180                 185                 190 ggt tct tgc tgc tga gcaccttcat ccagtcttca tcaccccccc actcttaata    690
Gly Ser Cys Cys
            195 tagaccatga atgaggtgaa ccccaagagg tcaatcaaag cctctgttgg atcttgactt    750 aggctccaaa tgcactcagt tcttcccca actaggtctt ctctcaaata aaagcaaatt    810 tctagggttt ttttttaaa taatctatca ttttactccc acattgatgt ttatgtcata    870 tttatataag tatttttata tttcaaataa acctgaattt tagacatctg    920
```

<210> SEQ ID NO 158
<211> LENGTH: 195
<212> TYPE: PRT
<213> ORGANISM: Mus musculus

<400> SEQUENCE: 158

```
Met Ala Asn Ser Cys Cys Gly Ser Val Cys Ser Glu Glu Ser Cys Gly
1               5                   10                  15

Gln Gly Cys Cys Gln Pro Ser Cys Cys Gln Thr Thr Cys Cys Arg Thr
            20                  25                  30

Thr Cys Cys Arg Pro Ser Cys Cys Val Ser Ser Cys Cys Arg Pro Gln
        35                  40                  45

Cys Cys Gln Ser Leu Cys Cys Gln Pro Thr Cys Cys Arg Pro Ser Cys
    50                  55                  60

Cys Ile Ser Ser Cys Cys Arg Pro Thr Cys Cys Arg Pro Thr Cys Cys
65                  70                  75                  80

Ile Ser Ser Cys Cys Arg Pro Thr Cys Cys Arg Pro Ser Cys Cys Ile
                85                  90                  95

Ser Ser Cys Cys Arg Pro Thr Cys Cys Arg Pro Ser Cys Cys Ile Ser
            100                 105                 110

Ser Cys Cys Arg Pro Ser Cys Cys Arg Pro Ser Cys Cys Ile Ser Ser
        115                 120                 125

Cys Cys Arg Pro Ser Cys Cys Arg Pro Ser Cys Cys Arg Pro Ser Cys
    130                 135                 140

Cys Ile Ser Ser Cys Cys Arg Pro Ser Cys Cys Val Ser Ser Cys Cys
145                 150                 155                 160

Arg Pro Gln Cys Cys Ile Ser Ser Cys Cys Arg Pro Ile Cys Cys Gln
                165                 170                 175
```

-continued

```
Thr Thr Cys Cys Arg Thr Thr Cys Tyr Arg Pro Ala Cys Ser Ser Gly
        180                 185                 190
Ser Cys Cys
    195

<210> SEQ ID NO 159
<211> LENGTH: 950
<212> TYPE: DNA
<213> ORGANISM: Mus musculus
<220> FEATURE:
<221> NAME/KEY: CDS
<222> LOCATION: (34)..(642)

<400> SEQUENCE: 159
ggaaatctac tcagaacctc catctctgac atc atg gtc aac tcc tgt tgt ggc       54
                                   Met Val Asn Ser Cys Cys Gly
                                     1               5 tct gtc tgc tct gag cag ggc tgt gat caa agt ccc tgc cag gag agc      102
Ser Val Cys Ser Glu Gln Gly Cys Asp Gln Ser Pro Cys Gln Glu Ser
         10                  15                  20 tgc ggc cag ccc agc tgc agt cag ccc agc tgc agc cag cca agc tgc      150
Cys Gly Gln Pro Ser Cys Ser Gln Pro Ser Cys Ser Gln Pro Ser Cys
     25                  30                  35 tgc cag act acc tgc tgc agg act acc tgc tgc cgc ccc agc tgc tgt      198
Cys Gln Thr Thr Cys Cys Arg Thr Thr Cys Cys Arg Pro Ser Cys Cys
 40                  45                  50                  55 gtg tcc agc tgc tgc agg ccc acc tgc cag acc acc tgc tgc cgc cca      246
Val Ser Ser Cys Cys Arg Pro Thr Cys Gln Thr Thr Cys Cys Arg Pro
                 60                  65                  70 gtc tgc tgc cag acc acc tgc cgc ccc agc tgt gga gtg tcc agc tgc      294
Val Cys Cys Gln Thr Thr Cys Arg Pro Ser Cys Gly Val Ser Ser Cys
             75                  80                  85 tgc cgc cca gtc tgc tgc cag acc acc tgc cgc ccc agc tgt gga gtg      342
Cys Arg Pro Val Cys Cys Gln Thr Thr Cys Arg Pro Ser Cys Gly Val
         90                  95                 100 ccc agc tgc tgc cgc cca gtc tgc tgc cag acc acc tgc cgc ccc agc      390
Pro Ser Cys Cys Arg Pro Val Cys Cys Gln Thr Thr Cys Arg Pro Ser
    105                 110                 115 tgt gga gtg tcc agc tgc tgc cgc cca gtc tgc tgc caa acc acc tgc      438
Cys Gly Val Ser Ser Cys Cys Arg Pro Val Cys Cys Gln Thr Thr Cys
120                 125                 130                 135 cgc ccc agc tgt gga gtg tcc agc tgt tgc cgc cca gtc tgc tgc cag      486
Arg Pro Ser Cys Gly Val Ser Ser Cys Cys Arg Pro Val Cys Cys Gln
                140                 145                 150 acc acc tgc cgc ccc agc tgt gga gtg tcc agc tgc tgc cgc cca gtc      534
Thr Thr Cys Arg Pro Ser Cys Gly Val Ser Ser Cys Cys Arg Pro Val
            155                 160                 165 tgc tgc cag acc act tgc cgc ccc agc tgc gga gtg tcc agc tgc tgc      582
Cys Cys Gln Thr Thr Cys Arg Pro Ser Cys Gly Val Ser Ser Cys Cys
        170                 175                 180 cgc cca gtc tgc tgt cag acc act tgc tgc cgt aca act tgc tgt ggc      630
Arg Pro Val Cys Cys Gln Thr Thr Cys Cys Arg Thr Thr Cys Cys Gly
    185                 190                 195 ccc tct tgc taa atttcctctc taactaccaa tcccgaggca gccataatca          682
Pro Ser Cys
200 caatgctcta accttctcat ccatgttaac ttttcctgt actaaatgcc tcctaccttt     742 gttgtcctga caccagtaag aaactgccaa aagagagtgc tacattacgt accgctcata    802 tttcccaaag atctcacctc tacatgtctg tctcagctac atggtatagc tgatcatatc    862
```

```
tctcaagtct ctactaccat ccttcccttg gcctttacca ttctgtgtta actattcttc      922
aataaatatt gccttatttc agaagtat                                         950
```

<210> SEQ ID NO 160
<211> LENGTH: 202
<212> TYPE: PRT
<213> ORGANISM: Mus musculus

<400> SEQUENCE: 160

```
Met Val Asn Ser Cys Cys Gly Ser Val Cys Ser Glu Gln Gly Cys Asp
  1               5                  10                  15

Gln Ser Pro Cys Gln Glu Ser Cys Gly Gln Pro Ser Cys Ser Gln Pro
                 20                  25                  30

Ser Cys Ser Gln Pro Ser Cys Cys Gln Thr Thr Cys Cys Arg Thr Thr
             35                  40                  45

Cys Cys Arg Pro Ser Cys Cys Val Ser Ser Cys Cys Arg Pro Thr Cys
 50                  55                  60

Gln Thr Thr Cys Cys Arg Pro Val Cys Cys Gln Thr Thr Cys Arg Pro
 65                  70                  75                  80

Ser Cys Gly Val Ser Ser Cys Cys Arg Pro Val Cys Cys Gln Thr Thr
                 85                  90                  95

Cys Arg Pro Ser Cys Gly Val Pro Ser Cys Cys Arg Pro Val Cys Cys
                100                 105                 110

Gln Thr Thr Cys Arg Pro Ser Cys Gly Val Ser Ser Cys Cys Arg Pro
            115                 120                 125

Val Cys Cys Gln Thr Thr Cys Arg Pro Ser Cys Gly Val Ser Ser Cys
130                 135                 140

Cys Arg Pro Val Cys Cys Gln Thr Thr Cys Arg Pro Ser Cys Gly Val
145                 150                 155                 160

Ser Ser Cys Cys Arg Pro Val Cys Cys Gln Thr Thr Cys Arg Pro Ser
                165                 170                 175

Cys Gly Val Ser Ser Cys Cys Arg Pro Val Cys Cys Gln Thr Thr Cys
            180                 185                 190

Cys Arg Thr Thr Cys Cys Gly Pro Ser Cys
            195                 200
```

<210> SEQ ID NO 161
<211> LENGTH: 821
<212> TYPE: DNA
<213> ORGANISM: Mus musculus
<220> FEATURE:
<221> NAME/KEY: CDS
<222> LOCATION: (67)..(564)

<400> SEQUENCE: 161

```
tcctgacttc caaaccttcc aacctatctt cttgtaaacc catccagaac ctccacctct       60 gacacc atg gtc agc tcc tgc tgt ggc tct gtc tgc tct gag gag ggc        108
       Met Val Ser Ser Cys Cys Gly Ser Val Cys Ser Glu Glu Gly
         1               5                  10 tgt ggt caa agc tgc tgc cag ccc agc tgc tgc caa acc acc tgc tgc       156
Cys Gly Gln Ser Cys Cys Gln Pro Ser Cys Cys Gln Thr Thr Cys Cys
 15                  20                  25                  30 cgc ccc agc tgc tgt gtg tcc agc tgc tgc aga ccc agc tgc tgc cgc       204
Arg Pro Ser Cys Cys Val Ser Ser Cys Cys Arg Pro Ser Cys Cys Arg
                 35                  40                  45 ccc agc tgc tgt gta tcc agc tgc tgc agg cct cag tgc tgc cag tct       252
Pro Ser Cys Cys Val Ser Ser Cys Cys Arg Pro Gln Cys Cys Gln Ser
             50                  55                  60
```

```
gtg tgc tgc cag ccc act tgt tgc cgt cct agc tgc tgc att tcc agc    300
Val Cys Cys Gln Pro Thr Cys Cys Arg Pro Ser Cys Cys Ile Ser Ser
             65                  70                  75 tgc tgc agg ccc agc tgc tgc cgc ccc agc tgt tgt gtg tcc agc tgc    348
Cys Cys Arg Pro Ser Cys Cys Arg Pro Ser Cys Cys Val Ser Ser Cys
         80                  85                  90 tgc agg ccc cag tgc tgc cag tct gtg tgc tgc cag cct acc tgc tgc    396
Cys Arg Pro Gln Cys Cys Gln Ser Val Cys Cys Gln Pro Thr Cys Cys
     95                 100                 105                 110 cgc ccc agc tgt tgc cgc cct tgc tgt ggt agt tcc agc tgt tgt gtg    444
Arg Pro Ser Cys Cys Arg Pro Cys Cys Gly Ser Ser Ser Cys Cys Val
                115                 120                 125 tcc agc tgt tgc aga ccc cag tgc tgc atc tcc agc tgt tgt cgc ccc    492
Ser Ser Cys Cys Arg Pro Gln Cys Cys Ile Ser Ser Cys Cys Arg Pro
            130                 135                 140 atc tgt tgc cag acc acc tgc tgc agg acc act tgc tgc cgc cca gcc    540
Ile Cys Cys Gln Thr Thr Cys Cys Arg Thr Thr Cys Cys Arg Pro Ala
        145                 150                 155 tgt tct agt ggt tct tgc tgc tga gcaccttcat ccagtctcct gctcgtcatc   594
Cys Ser Ser Gly Ser Cys Cys
    160                 165 acacatagtt cctaatgtag tccatgtgtg ttctgagtcc caagaggctc attctaaagc   654
ctctgataca aatgagattg atttggacaa caactatttg ccacactcca gcctgcttag   714
tatctgttta aaatgaacac atttgagcat tctaatctct cataaaatgt gttctgtgct   774
atattaaaaa aacaaacatc ctaataataa attaaaagtt taaaggc                821

<210> SEQ ID NO 162
<211> LENGTH: 165
<212> TYPE: PRT
<213> ORGANISM: Mus musculus

<400> SEQUENCE: 162

Met Val Ser Ser Cys Cys Gly Ser Val Cys Ser Glu Glu Gly Cys Gly
 1               5                  10                  15

Gln Ser Cys Cys Gln Pro Ser Cys Cys Gln Thr Thr Cys Cys Arg Pro
            20                  25                  30

Ser Cys Cys Val Ser Ser Cys Cys Arg Pro Ser Cys Cys Arg Pro Ser
        35                  40                  45

Cys Cys Val Ser Ser Cys Cys Arg Pro Gln Cys Cys Gln Ser Val Cys
    50                  55                  60

Cys Gln Pro Thr Cys Cys Arg Pro Ser Cys Cys Ile Ser Ser Cys Cys
65                  70                  75                  80

Arg Pro Ser Cys Cys Arg Pro Ser Cys Cys Val Ser Ser Cys Cys Arg
                85                  90                  95

Pro Gln Cys Cys Gln Ser Val Cys Cys Gln Pro Thr Cys Cys Arg Pro
            100                 105                 110

Ser Cys Cys Arg Pro Cys Cys Gly Ser Ser Ser Cys Cys Val Ser Ser
        115                 120                 125

Cys Cys Arg Pro Gln Cys Cys Ile Ser Ser Cys Cys Arg Pro Ile Cys
    130                 135                 140

Cys Gln Thr Thr Cys Cys Arg Thr Thr Cys Cys Arg Pro Ala Cys Ser
145                 150                 155                 160

Ser Gly Ser Cys Cys
            165
```

<210> SEQ ID NO 163
<211> LENGTH: 963
<212> TYPE: DNA
<213> ORGANISM: Mus musculus
<220> FEATURE:
<221> NAME/KEY: CDS
<222> LOCATION: (62)..(565)

<400> SEQUENCE: 163

| | | |
|---|---|---|
| ggactagaca aggaactctc cccatcttgt aagcctaccc agaacctcca cctctgacac | | 60 |
| c atg gtc agc tct tgt ggc tct gtc tgc tct gaa aag ggc tgt ggc caa<br>  Met Val Ser Ser Cys Gly Ser Val Cys Ser Glu Lys Gly Cys Gly Gln<br>    1              5                10                15 | | 109 |
| ggc tgc tgc cag ccc agc tgc tgc caa acc acc tgc tgt agg acc acc<br>Gly Cys Cys Gln Pro Ser Cys Cys Gln Thr Thr Cys Cys Arg Thr Thr<br>            20                25                30 | | 157 |
| tgc tgc cgc ccc agc tgc tgt gtg tcc agc tgc tgc agg ccc agc tgc<br>Cys Cys Arg Pro Ser Cys Cys Val Ser Ser Cys Cys Arg Pro Ser Cys<br> 35                  40                45 | | 205 |
| tgt gtg tcc agc tgc tgc agg ccc agt tgc tgc agg ccc cag tgc tgc<br>Cys Val Ser Ser Cys Cys Arg Pro Ser Cys Cys Arg Pro Gln Cys Cys<br> 50                  55                60 | | 253 |
| cag tct gtg tgc tgc cag ccg acc tgc tgc cgc ccc agc tgc tgc att<br>Gln Ser Val Cys Cys Gln Pro Thr Cys Cys Arg Pro Ser Cys Cys Ile<br> 65                  70                75                80 | | 301 |
| tcc agc tgc tgt caa ccc tcc tgt ggt agc tcc agc tgc tgt ggt tct<br>Ser Ser Cys Cys Gln Pro Ser Cys Gly Ser Ser Ser Cys Cys Gly Ser<br>            85                90                95 | | 349 |
| agt tgc tgc cgc ccc tgc tgc cgc ccc tgc tgc agc cct tgc tgc agc<br>Ser Cys Cys Arg Pro Cys Cys Arg Pro Cys Cys Ser Pro Cys Cys Ser<br>           100                105               110 | | 397 |
| ccc tgt tgc cgt ccc tgc tgc cga ccc tgc tgc cgc ccc tgt tgc cgc<br>Pro Cys Cys Arg Pro Cys Cys Arg Pro Cys Cys Arg Pro Cys Cys Arg<br>           115                120               125 | | 445 |
| ccc tgc tgc tgt ctg aga cca gtc tgt ggt cag gtc tgc tgc caa acc<br>Pro Cys Cys Cys Leu Arg Pro Val Cys Gly Gln Val Cys Cys Gln Thr<br>130                  135                140 | | 493 |
| act tgc tac cgc ccc acc tgt gtc atc tcc acc tgc ccc cgc ccc atg<br>Thr Cys Tyr Arg Pro Thr Cys Val Ile Ser Thr Cys Pro Arg Pro Met<br>145                  150                155               160 | | 541 |
| tgc tgt gcc atc ccc tgc tgc taa atctctttga atatgccatt tatctcttca<br>Cys Cys Ala Ile Pro Cys Cys<br>           165 | | 595 |
| atctcagcag atgaagtcct tccttctaaa aagtgcatag tgtttgaggg acttgatctc | | 655 |
| ctgagtccca gaagtcagac ttgtttgcaa ttgttccgtg tgaacattct gacttctgtc | | 715 |
| caaaactctt gcttaaaatg attttatcaa atacctccaa atagcttaac agatctccca | | 775 |
| caacatgtct caccttgtat ttttatctat tcatcatgct ggaggaattt aaattatccc | | 835 |
| tggcacttag atgagtatgc attttaatc cccatgacat taaaatccac taattgtctt | | 895 |
| ttatagcttt tgcaaagatt tttcatactt tactacttct gtgtaacaaa ataaacatc | | 955 |
| cacacagg | | 963 |

<210> SEQ ID NO 164
<211> LENGTH: 167
<212> TYPE: PRT
<213> ORGANISM: Mus musculus

<400> SEQUENCE: 164

Met Val Ser Ser Cys Gly Ser Val Cys Ser Glu Lys Gly Cys Gly Gln

```
                  1               5              10              15
              Gly Cys Cys Gln Pro Ser Cys Cys Gln Thr Thr Cys Cys Arg Thr Thr
                              20                  25                  30

Cys Cys Arg Pro Ser Cys Cys Val Ser Ser Cys Cys Arg Pro Ser Cys
                          35                  40                  45

Cys Val Ser Ser Cys Cys Arg Pro Ser Cys Cys Arg Pro Gln Cys Cys
                      50                  55                  60

Gln Ser Val Cys Cys Gln Pro Thr Cys Cys Arg Pro Ser Cys Cys Ile
              65                  70                  75                  80

Ser Ser Cys Cys Gln Pro Ser Cys Gly Ser Ser Cys Cys Gly Ser
                              85                  90                  95

Ser Cys Cys Arg Pro Cys Cys Arg Pro Cys Cys Ser Pro Cys Cys Ser
                          100                 105                 110

Pro Cys Cys Arg Pro Cys Cys Arg Pro Cys Cys Arg Pro Cys Cys Arg
                      115                 120                 125

Pro Cys Cys Cys Leu Arg Pro Val Cys Gly Gln Val Cys Cys Gln Thr
                  130                 135                 140

Thr Cys Tyr Arg Pro Thr Cys Val Ile Ser Thr Cys Pro Arg Pro Met
              145                 150                 155                 160

Cys Cys Ala Ile Pro Cys Cys
                              165

<210> SEQ ID NO 165
<211> LENGTH: 763
<212> TYPE: DNA
<213> ORGANISM: Mus musculus
<220> FEATURE:
<221> NAME/KEY: misc_feature
<222> LOCATION: (8)..(8)
<223> OTHER INFORMATION: "n" can be any nucleotide
<220> FEATURE:
<221> NAME/KEY: misc_feature
<222> LOCATION: (17)..(17)
<223> OTHER INFORMATION: "n" can be any nucleotide
<220> FEATURE:
<221> NAME/KEY: misc_feature
<222> LOCATION: (20)..(20)
<223> OTHER INFORMATION: "n" can be any nucleotide
<220> FEATURE:
<221> NAME/KEY: misc_feature
<222> LOCATION: (22)..(22)
<223> OTHER INFORMATION: "n" can be any nucleotide
<220> FEATURE:
<221> NAME/KEY: CDS
<222> LOCATION: (55)..(465)

<400> SEQUENCE: 165
ggggaatnca gaaactnctn tnaactacac agctctcaac tcaacggtaa caca atg        57
                                                              Met
                                                                1 gcc tgc tgt gct aca agc ttc tgt ggc ttt ccc act tgc tcc aca ggt       105
Ala Cys Cys Ala Thr Ser Phe Cys Gly Phe Pro Thr Cys Ser Thr Gly
            5                  10                  15 ggc tcc agc tgc tgc cag ccc acc tgc acc cag tcc agc tgt tgc cag       153
Gly Ser Ser Cys Cys Gln Pro Thr Cys Thr Gln Ser Ser Cys Cys Gln
        20                  25                  30 ccc agc tgt tgt gag gcc agc tgc tgc cag cca agc tgt tgc gag act       201
Pro Ser Cys Cys Glu Ala Ser Cys Cys Gln Pro Ser Cys Cys Glu Thr
    35                  40                  45 ggc ttt ggg ggt ggc att ggc tgt ggc cag gag ggt ggc agt gga ggt       249
Gly Phe Gly Gly Gly Ile Gly Cys Gly Gln Glu Gly Gly Ser Gly Gly
50                  55                  60                  65
```

```
gtg agc tgc cgt gtt aaa tgg tgc cgc cct gac tgc cgc gtg gag ggc      297
Val Ser Cys Arg Val Lys Trp Cys Arg Pro Asp Cys Arg Val Glu Gly
            70                  75                  80 acc tgc ctg ccc ccc tgc tgt gtg agc tgc aca ccc cca acc tgc          345
Thr Cys Leu Pro Pro Cys Cys Val Val Ser Cys Thr Pro Pro Thr Cys
                85                  90                  95 tgc cag ctg cac cat gcc cag gcc tcc tgc tgc cgt cca tcc tac tgt      393
Cys Gln Leu His His Ala Gln Ala Ser Cys Cys Arg Pro Ser Tyr Cys
            100                 105                 110 gga cag tct tgc tgc cgc cca gca tgc tgc tgc tac tgc tgc cag ccc      441
Gly Gln Ser Cys Cys Arg Pro Ala Cys Cys Cys Tyr Cys Cys Gln Pro
            115                 120                 125 agc tgc ttt gag ccc agc tgt tga aagccttctg gcaagaatct taggaagatg     495
Ser Cys Phe Glu Pro Ser Cys
130                 135 acacttcaaa atgaactaat tacaacccctt aaataatct tttaaacttc agtattgata    555
actcagctat tgacacggct acataatttc ccaggaggta aattcatttg gggtggaaga    615
gccaacatct tgttggctt gaacaccaac aaaagaccca ctgtgtggaa aggagtgtat     675
actacattac tataaatatt accagaacta cttcaatagc caattgggat ttgtatttaa    735
taaaaagtat tttgtctctt caatggtg                                       763

<210> SEQ ID NO 166
<211> LENGTH: 136
<212> TYPE: PRT
<213> ORGANISM: Mus musculus

<400> SEQUENCE: 166

Met Ala Cys Cys Ala Thr Ser Phe Cys Gly Phe Pro Thr Cys Ser Thr
1               5                   10                  15

Gly Gly Ser Ser Cys Cys Gln Pro Thr Cys Thr Gln Ser Ser Cys Cys
                20                  25                  30

Gln Pro Ser Cys Cys Glu Ala Ser Cys Cys Gln Pro Ser Cys Cys Glu
            35                  40                  45

Thr Gly Phe Gly Gly Gly Ile Gly Cys Gly Gln Glu Gly Gly Ser Gly
        50                  55                  60

Gly Val Ser Cys Arg Val Lys Trp Cys Arg Pro Asp Cys Arg Val Glu
65                  70                  75                  80

Gly Thr Cys Leu Pro Pro Cys Cys Val Val Ser Cys Thr Pro Pro Thr
                85                  90                  95

Cys Cys Gln Leu His His Ala Gln Ala Ser Cys Cys Arg Pro Ser Tyr
            100                 105                 110

Cys Gly Gln Ser Cys Cys Arg Pro Ala Cys Cys Cys Tyr Cys Cys Gln
        115                 120                 125

Pro Ser Cys Phe Glu Pro Ser Cys
    130                 135

<210> SEQ ID NO 167
<211> LENGTH: 1035
<212> TYPE: DNA
<213> ORGANISM: Mus musculus
<220> FEATURE:
<221> NAME/KEY: CDS
<222> LOCATION: (54)..(422)

<400> SEQUENCE: 167
aaaaactcag aaactcatcc aacctactca acatccaacc aactcctgac aac atg      56
                                                            Met
                                                            1
```

```
gcc tgc tgt gct act agc ttc tgt ggc ttt ccc act tgc tcc act ggt      104
Ala Cys Cys Ala Thr Ser Phe Cys Gly Phe Pro Thr Cys Ser Thr Gly
            5                   10                  15 ggc acc tgt ggc tcc agc tgc tgc cag ccc agc tgt tgt gag acc agc      152
Gly Thr Cys Gly Ser Ser Cys Cys Gln Pro Ser Cys Cys Glu Thr Ser
        20                  25                  30 tgc ttc cag cca agc tgc tgt ggg aca ggc tat ggc ctt ggg ggt gga      200
Cys Phe Gln Pro Ser Cys Cys Gly Thr Gly Tyr Gly Leu Gly Gly Gly
        35                  40                  45 att ggc tgt ggc cag gag ggt ggc ttt gga ggt gtg agc tgc cgt gtt      248
Ile Gly Cys Gly Gln Glu Gly Gly Phe Gly Gly Val Ser Cys Arg Val
 50                  55                  60                  65 aga tgg tgc cgc cct gac tgc gcg gtg gag ggc acc tgc ctg ccc ccc      296
Arg Trp Cys Arg Pro Asp Cys Arg Val Glu Gly Thr Cys Leu Pro Pro
                70                  75                  80 tgc tgt gtg gtg agc tgt ata ccc tca acc tgc tgc cag ctg cac cac      344
Cys Cys Val Val Ser Cys Ile Pro Ser Thr Cys Cys Gln Leu His His
            85                  90                  95 gcc cag gcc tcc tgc tgc cgt cca tcc tac tgt gga cag tcc tgc tgc      392
Ala Gln Ala Ser Cys Cys Arg Pro Ser Tyr Cys Gly Gln Ser Cys Cys
            100                 105                 110 cgc cca gcc tgt tgc tgc tac tgc tgc taa tccacctatt aagagctaat       442
Arg Pro Ala Cys Cys Cys Tyr Cys Cys
        115                 120 tttttgattg cccagatcat ggtattcttg aattgtgcat ctccttaacc aactctggag   502
cagtaacaag ttctccaacc tttgcttcgt tgtcttttat gaggcctcag agtacaggcg   562
catcacagcc ctgtccgagt ctgttctata accaatacct tgaccctcta cagtggatcc   622
agaaatgctg agaacccaca ggctgaccac caaattgttc tggatgtatt gcatctgaaa   682
ctcttgcaga attgaaaatt gtcaaaatct tgaagaatat tttctttaga acaatctgta   742
atcctattct tcctgcttgg tgaccaactt ttatcttctg tttacttaaa gcttttctaa   802
catcaaagac accagcccac agctgagaga cattcttcag atgtcatcag agaaaaatgg   862
aagttcctta accaacttct ggctgctaag aaataggcca gaccattcta cacttttcca   922
ctggatcctt tccttatttt ttttggatca taattcgttt gcctgctggc cattccatta   982
tatctgtagc attgtgactt ctgatgtttc ttaataaagc ttatatcctg ggc          1035
```

<210> SEQ ID NO 168
<211> LENGTH: 122
<212> TYPE: PRT
<213> ORGANISM: Mus musculus

<400> SEQUENCE: 168

Met Ala Cys Cys Ala Thr Ser Phe Cys Gly Phe Pro Thr Cys Ser Thr
 1               5                   10                  15

Gly Gly Thr Cys Gly Ser Ser Cys Cys Gln Pro Ser Cys Cys Glu Thr
            20                  25                  30

Ser Cys Phe Gln Pro Ser Cys Cys Gly Thr Gly Tyr Gly Leu Gly Gly
        35                  40                  45

Gly Ile Gly Cys Gly Gln Glu Gly Gly Phe Gly Gly Val Ser Cys Arg
    50                  55                  60

Val Arg Trp Cys Arg Pro Asp Cys Arg Val Glu Gly Thr Cys Leu Pro
 65                  70                  75                  80

Pro Cys Cys Val Val Ser Cys Ile Pro Ser Thr Cys Cys Gln Leu His
                85                  90                  95

```
His Ala Gln Ala Ser Cys Cys Arg Pro Ser Tyr Cys Gly Gln Ser Cys
            100                 105                 110

Cys Arg Pro Ala Cys Cys Cys Tyr Cys Cys
        115                 120

<210> SEQ ID NO 169
<211> LENGTH: 1624
<212> TYPE: DNA
<213> ORGANISM: Mus musculus
<220> FEATURE:
<221> NAME/KEY: CDS
<222> LOCATION: (448)..(951)

<400> SEQUENCE: 169
ggtccgtgcg tagggtggct gaagaggggc tttggattgg cagtctttga ccggtggcta     60
taagagagtc ctgctgacct gggaaggagt gtcactgaca ttcagtaggg cgtccaacat    120
aaatctgccg ctgctttctt ctcaaaggac tgggtttgga agtcaggaac cctggcagca    180
ggcgatcggg tggtgaggag cctccggcgc ggcctcgcct ccccggtccg gctcccgcgt    240
cagcaccgtg gacagcacgg accacctttc agggaccctc cggtcggcag gagcgcgctt    300
caggtttcgg cgatctcatc agtaccgcgg acagcgccca ggccctcgct ggcctcggcc    360
agcccaccgg ctcttcctat cagcaccgcg gacagccccc ctgaaccagc ccagcgacag    420
ccaaggactg gtcagaacgc cctgaag atg gcc act gag gtc cac aat ctt cag    474
                                Met Ala Thr Glu Val His Asn Leu Gln
                                 1                 5 gag ctc agg cga agc gct tcg ctg gcc acc aag gtc ttt atc cag aga       522
Glu Leu Arg Arg Ser Ala Ser Leu Ala Thr Lys Val Phe Ile Gln Arg
 10                  15                  20                  25 gac tac agt gac ggc acc atc tgt cag ttc cag acc aaa ttc ccg cca       570
Asp Tyr Ser Asp Gly Thr Ile Cys Gln Phe Gln Thr Lys Phe Pro Pro
                 30                  35                  40 gag ctg gat agc cgg att gag cgg cag ctc ttt gag gag acg gtg aag       618
Glu Leu Asp Ser Arg Ile Glu Arg Gln Leu Phe Glu Glu Thr Val Lys
             45                  50                  55 acc ctc aat ggt ttt tat gcg gag gct gag aag atc ggg ggc agc tcc       666
Thr Leu Asn Gly Phe Tyr Ala Glu Ala Glu Lys Ile Gly Gly Ser Ser
         60                  65                  70 tat ctg gag ggc tgc ctg gcc tgc gcc acg gcc tac ttc atc ttc ctc       714
Tyr Leu Glu Gly Cys Leu Ala Cys Ala Thr Ala Tyr Phe Ile Phe Leu
     75                  80                  85 tgc atg gag acc cac tat gag aag gtt ctc aag aag att tcc cgt tac       762
Cys Met Glu Thr His Tyr Glu Lys Val Leu Lys Lys Ile Ser Arg Tyr
 90                  95                 100                 105 atc cag gag cag aat gag aag gtc ttt gct ccc cga ggg ctc ctg ctc       810
Ile Gln Glu Gln Asn Glu Lys Val Phe Ala Pro Arg Gly Leu Leu Leu
                 110                 115                 120 acg gat ccg gtg gaa cgc gga atg agg gtt atc gag atc tcc atc tat       858
Thr Asp Pro Val Glu Arg Gly Met Arg Val Ile Glu Ile Ser Ile Tyr
             125                 130                 135 gag gac cgg tgc agc agt ggt agt tcc agt agc ggc agc agc agc ggc       906
Glu Asp Arg Cys Ser Ser Gly Ser Ser Ser Ser Gly Ser Ser Ser Gly
         140                 145                 150 agc ggc agc agc agc gct ggc ggg gga ggg gcg ggg gcc cgg tga           951
Ser Gly Ser Ser Ser Ala Gly Gly Gly Gly Ala Gly Ala Arg
     155                 160                 165 ctggccgaga gtccctgtag ggaggtgtac agccggagcg aggggctggc agatctacgg   1011
aggctgcgct accagagcac ccgcttctga gtctttctct gggcccaccc tgccatgtgg   1071
```

-continued

```
tgcggaaggg agggtgcctg cccgctgttc cctgtcccca gacctttgct ccttggcagg    1131
atcttcttct ttctgaccct ggaccttttt tttttttttt tttttttctc ccatgaggct    1191
gatctgagtc atcagaccca gaccgtccta ggatgtctgg ggtgggggtg ggggacccag    1251
cttggacaaa ccctatcttt cctgcctcct tcctcactct aaggagggcc tggagaattc    1311
ccaccctgca tgatacttca ccctcaaaga ctctttctaa ggcccaacgc tactatgggc    1371
tcctgcttgt cagtggtccc atctcttcac tggagatctg gggagatggg tgccctggga    1431
gctattcagc cgctccaaag gcagtgactt tcctgtcctc agagccgaaa gttctttcag    1491
ccttgccaag aagcacccaa ctctgagact ttgcacccca ccaggaactg attttagggg    1551
ttcagcctag gactctgatg ggctccactg gggtatggga aactttgga cgaatgaagc    1611
tggacagagc ttg                                                       1624
```

<210> SEQ ID NO 170
<211> LENGTH: 167
<212> TYPE: PRT
<213> ORGANISM: Mus musculus

<400> SEQUENCE: 170

```
Met Ala Thr Glu Val His Asn Leu Gln Glu Leu Arg Arg Ser Ala Ser
 1               5                  10                  15
Leu Ala Thr Lys Val Phe Ile Gln Arg Asp Tyr Ser Asp Gly Thr Ile
            20                  25                  30
Cys Gln Phe Gln Thr Lys Phe Pro Pro Glu Leu Asp Ser Arg Ile Glu
        35                  40                  45
Arg Gln Leu Phe Glu Glu Thr Val Lys Thr Leu Asn Gly Phe Tyr Ala
    50                  55                  60
Glu Ala Glu Lys Ile Gly Gly Ser Ser Tyr Leu Glu Gly Cys Leu Ala
65                  70                  75                  80
Cys Ala Thr Ala Tyr Phe Ile Phe Leu Cys Met Glu Thr His Tyr Glu
                85                  90                  95
Lys Val Leu Lys Lys Ile Ser Arg Tyr Ile Gln Glu Gln Asn Glu Lys
           100                 105                 110
Val Phe Ala Pro Arg Gly Leu Leu Leu Thr Asp Pro Val Glu Arg Gly
       115                 120                 125
Met Arg Val Ile Glu Ile Ser Ile Tyr Glu Asp Arg Cys Ser Ser Gly
   130                 135                 140
Ser Ser Ser Ser Gly Ser Ser Gly Ser Gly Ser Ser Ser Ala Gly
145                 150                 155                 160
Gly Gly Gly Ala Gly Ala Arg
               165
```

<210> SEQ ID NO 171
<211> LENGTH: 717
<212> TYPE: DNA
<213> ORGANISM: Mus musculus
<220> FEATURE:
<221> NAME/KEY: CDS
<222> LOCATION: (3)..(545)

<400> SEQUENCE: 171

```
at gtg aag tgc cca gca cca tgc cag acg acc tgt gtg aaa tgc cca      47
   Val Lys Cys Pro Ala Pro Cys Gln Thr Thr Cys Val Lys Cys Pro
    1               5                  10                  15 gcc cca tgc cag aag acc tat gtg aaa tgt ccc gcc cca tgc cag aca    95
Ala Pro Cys Gln Lys Thr Tyr Val Lys Cys Pro Ala Pro Cys Gln Thr
               20                  25                  30
```

```
act aat gtg aag tgc cca gct ccg tgt cag acg acc tct gtc aag tgt        143
Thr Asn Val Lys Cys Pro Ala Pro Cys Gln Thr Thr Ser Val Lys Cys
            35                  40                  45 cca gct ccc tgc cag gct cag aca tat tat gtc cag tat cag gtt cct        191
Pro Ala Pro Cys Gln Ala Gln Thr Tyr Tyr Val Gln Tyr Gln Val Pro
        50                  55                  60 tat cag acc tac tat act cag gct tct tca agt ggc tca gga cct cag        239
Tyr Gln Thr Tyr Tyr Thr Gln Ala Ser Ser Ser Gly Ser Gly Pro Gln
65                  70                  75 ggc tgt gtt cct gac ccg tgc tct gcc cct tgt tcc acc agc tac tgc        287
Gly Cys Val Pro Asp Pro Cys Ser Ala Pro Cys Ser Thr Ser Tyr Cys
                85                  90                  95
            80 tgt ttg gct ccc cgg agc ttt ggg gtg agt cct ctg aga cgc tgg atc        335
Cys Leu Ala Pro Arg Ser Phe Gly Val Ser Pro Leu Arg Arg Trp Ile
                100                 105                 110 cag cgg cct caa gga tgg aat aca gga tct tct agc tgc tgt gag gat        383
Gln Arg Pro Gln Gly Trp Asn Thr Gly Ser Ser Ser Cys Cys Glu Asp
            115                 120                 125 tct ggg tgc tgc agt tct gga ggc tgc ggg ggc tgc ggg ggc tgc ggg        431
Ser Gly Cys Cys Ser Ser Gly Gly Cys Gly Gly Cys Gly Gly Cys Gly
        130                 135                 140 ggt tgc ggc ggc tgc aac agc tgc tgt ggc tct ggg tgt tgc tgt ttg        479
Gly Cys Gly Gly Cys Asn Ser Cys Cys Gly Ser Gly Cys Cys Cys Leu
145                 150                 155 gga att att ccc atg aga tcc aga ggt cct gca tgc tgt gat cat gag        527
Gly Ile Ile Pro Met Arg Ser Arg Gly Pro Ala Cys Cys Asp His Glu
160                 165                 170                 175 gat gat tgc tgc tgt tag acacaaaaga acgttatgc ttccaaaatg                575
Asp Asp Cys Cys Cys
                180 tccctcctgc tatgtcttct ggtcttaccc aaaccggaca actgcttccc tagttcttaa      635 ctttgctctt ttatcaatgc atcctgccag agttagcgca accccccaaa ctgtggcaag      695 aataaagctc tgaatgcaag gc                                               717

<210> SEQ ID NO 172
<211> LENGTH: 180
<212> TYPE: PRT
<213> ORGANISM: Mus musculus

<400> SEQUENCE: 172

Val Lys Cys Pro Ala Pro Cys Gln Thr Thr Cys Val Lys Cys Pro Ala
  1               5                  10                  15

Pro Cys Gln Lys Thr Tyr Val Lys Cys Pro Ala Pro Cys Gln Thr Thr
                20                  25                  30

Asn Val Lys Cys Pro Ala Pro Cys Gln Thr Thr Ser Val Lys Cys Pro
            35                  40                  45

Ala Pro Cys Gln Ala Gln Thr Tyr Tyr Val Gln Tyr Gln Val Pro Tyr
        50                  55                  60

Gln Thr Tyr Tyr Thr Gln Ala Ser Ser Ser Gly Ser Gly Pro Gln Gly
65                  70                  75                  80

Cys Val Pro Asp Pro Cys Ser Ala Pro Cys Ser Thr Ser Tyr Cys Cys
                85                  90                  95

Leu Ala Pro Arg Ser Phe Gly Val Ser Pro Leu Arg Arg Trp Ile Gln
            100                 105                 110

Arg Pro Gln Gly Trp Asn Thr Gly Ser Ser Ser Cys Cys Glu Asp Ser
        115                 120                 125
```

| | | | | | | | | | | | | |
|---|---|---|---|---|---|---|---|---|---|---|---|---|
|Gly|Cys|Cys|Ser|Ser|Gly|Gly|Cys|Gly|Gly|Cys|Gly|Gly|
| |130| | | |135| | | |140| | | |

| | | | | | | | | | | | | |
|---|---|---|---|---|---|---|---|---|---|---|---|---|
|Cys|Gly|Gly|Cys|Asn|Ser|Cys|Cys|Gly|Ser|Gly|Cys|Cys|Cys|Leu|Gly|
|145| | | | |150| | | | |155| | | | |160|

Ile Ile Pro Met Arg Ser Arg Gly Pro Ala Cys Cys Asp His Glu Asp
                165                 170                 175

Asp Cys Cys Cys
        180

<210> SEQ ID NO 173
<211> LENGTH: 1550
<212> TYPE: DNA
<213> ORGANISM: Mus musculus
<220> FEATURE:
<221> NAME/KEY: CDS
<222> LOCATION: (69)..(530)

<400> SEQUENCE: 173

```
gtcgggagct gcagttcaga gagcggtgtc ctgctggaat ctgctggtgc cccacgctcc        60 aacccgag atg atg gcc agc aag cga gtg gcg aaa gag ctg gag agt ctt       110
         Met Met Ala Ser Lys Arg Val Ala Lys Glu Leu Glu Ser Leu
           1               5                  10 tcg aag gag ctg ccg cca tac ctt cgc caa ctg tct agt gac gat gcc        158
Ser Lys Glu Leu Pro Pro Tyr Leu Arg Gln Leu Ser Ser Asp Asp Ala
 15              20                  25                  30 aat gtg ctt gtg tgg cac atg ctc ctg ctg cca gac cag ctt ccc tat        206
Asn Val Leu Val Trp His Met Leu Leu Leu Pro Asp Gln Leu Pro Tyr
                 35                  40                  45 ggc ctc aaa gcc ttc caa gtg cgg att gat ttc ccc cgg gag tat cca        254
Gly Leu Lys Ala Phe Gln Val Arg Ile Asp Phe Pro Arg Glu Tyr Pro
             50                  55                  60 ttc aag cct ccc act ttg aga ttc acc acc aag atc tac cac ccc aac        302
Phe Lys Pro Pro Thr Leu Arg Phe Thr Thr Lys Ile Tyr His Pro Asn
         65                  70                  75 gtc agg gag gat ggt ctg gtg tgc ctg ccc ctc atc agc aat gag aac        350
Val Arg Glu Asp Gly Leu Val Cys Leu Pro Leu Ile Ser Asn Glu Asn
 80                  85                  90 tgg aag cct tac acc aag cct tat caa gtc ttg gag gcc ctc aat gtg        398
Trp Lys Pro Tyr Thr Lys Pro Tyr Gln Val Leu Glu Ala Leu Asn Val
 95                 100                 105                 110 ctg gtg agt aaa ccg aat ctg gaa gag cct gtg cgt ctg gaa ctt gct        446
Leu Val Ser Lys Pro Asn Leu Glu Glu Pro Val Arg Leu Glu Leu Ala
                115                 120                 125 gac ctc ctg act cag aac ccg gag atg ttc agg aag aag gca gaa gag        494
Asp Leu Leu Thr Gln Asn Pro Glu Met Phe Arg Lys Lys Ala Glu Glu
            130                 135                 140 ttc acc ctt aaa ttc gga gtg gac cgg ccc tct taa ttctgttctg            540
Phe Thr Leu Lys Phe Gly Val Asp Arg Pro Ser
        145                 150 aagcctggat cgtctgctta gcagatggat atcaccgact ggtgcccgag gccttgggaa       600
gctcaccctg tgcctaagtt ttcctttgta gttgctaatt atgaatcttg tacctggtgt       660
gtatgtatgt gatggaggtg gggggggcctg tgtgatgtgt gctccttccc tgagctgtct      720
ggctgtagat gtaccatccc cacatcctcc ttggcttcag agccagtggg agttaggtac       780
acacagtttc aggcctgctt tccagctctc tctgtcttag gccactgttc aggccaattg       840
gcagaaaatt gaatgcccca gggcccaggc accaagggt gagaaaggca ggactctgct        900
cagaaggcag agcctacaga aggtaccaaa tttactgttg agtgattgag attgaaagag       960
```

```
tagtaaactc agtgctccaa ggtatgctaa tcataaaaca gatagtgaca ttcctccacc      1020
cacccacttc ctgagttcaa ggagtattca ttcaaagaaa gtcaccttga ctttctttga      1080
atgaatactg caatgcaaat gtgctattgt tagaggctct tagaaactgt cttgagagtt      1140
aacaattacc aggtattcct tgtgacacct gtgactttgt acttccttgt gactcttatc      1200
tggtattttt ggtattttcc aacaacgccc ttcccacctc cttgagttgt gttttttttc      1260
ctttaaatac ccccttactc agctactcgg ggcgccacgg tcctctaccc ctgcgtggtg      1320
tatgaccgtg ggcccgagag cgctcttgaa taaaatcct cttgcaattt gcagcaagac       1380
cgtttctcgt gggtgatttt ggggtgtcgc ccctcctgag tcagaacgtg ggggagtcct      1440
cacgttgtgg gtctttcaag atcaacggcg cttgtcatag gcatgtccag atttaagtgt      1500
taaacatctt attttccact gatgaatctc aagataaaga gtctaacctc                 1550

<210> SEQ ID NO 174
<211> LENGTH: 153
<212> TYPE: PRT
<213> ORGANISM: Mus musculus

<400> SEQUENCE: 174

Met Met Ala Ser Lys Arg Val Ala Lys Glu Leu Glu Ser Leu Ser Lys
  1               5                  10                  15

Glu Leu Pro Pro Tyr Leu Arg Gln Leu Ser Ser Asp Asp Ala Asn Val
             20                  25                  30

Leu Val Trp His Met Leu Leu Leu Pro Asp Gln Leu Pro Tyr Gly Leu
         35                  40                  45

Lys Ala Phe Gln Val Arg Ile Asp Phe Pro Arg Glu Tyr Pro Phe Lys
     50                  55                  60

Pro Pro Thr Leu Arg Phe Thr Thr Lys Ile Tyr His Pro Asn Val Arg
 65                  70                  75                  80

Glu Asp Gly Leu Val Cys Leu Pro Leu Ile Ser Asn Glu Asn Trp Lys
                 85                  90                  95

Pro Tyr Thr Lys Pro Tyr Gln Val Leu Glu Ala Leu Asn Val Leu Val
            100                 105                 110

Ser Lys Pro Asn Leu Glu Glu Pro Val Arg Leu Glu Leu Ala Asp Leu
        115                 120                 125

Leu Thr Gln Asn Pro Glu Met Phe Arg Lys Lys Ala Glu Glu Phe Thr
    130                 135                 140

Leu Lys Phe Gly Val Asp Arg Pro Ser
145                 150

<210> SEQ ID NO 175
<211> LENGTH: 1934
<212> TYPE: DNA
<213> ORGANISM: Mus musculus
<220> FEATURE:
<221> NAME/KEY: CDS
<222> LOCATION: (252)..(1886)

<400> SEQUENCE: 175
gcggcactgc aaggtcccca ttggagccgg cggacaagtc ggacacgaca gagtcgaaat        60
ctgagtcggg atcggattcc agatcagagg aagacaagga gagtccggcc tcgattaagg       120
agataaaggc ggagacaccc caaccgaagg accgtcctgg cgtgcagatt aagctctcat       180
ggtcacagaa gataaagagc tggacagcaa aaagaaaag aaaactgtac cagctcgtca        240
tagacatcat c atg atg aac cga gtg tgt aag atg ttc cgt caa ggc ctc       290
             Met Met Asn Arg Val Cys Lys Met Phe Arg Gln Gly Leu
```

```
                    1               5                   10
agg gga ttt cgg gaa tat cag atc att gag cct gtt cac aag aag cat      338
Arg Gly Phe Arg Glu Tyr Gln Ile Ile Glu Pro Val His Lys Lys His
 15                  20                  25 cct gac ttc tcc ttc tgg gat aaa aag aag caa ggc cgt atc tcg ttt      386
Pro Asp Phe Ser Phe Trp Asp Lys Lys Lys Gln Gly Arg Ile Ser Phe
 30                  35                  40                  45 gtt acc gag gac ttt gct gca cag gag aag aag cca tcc tgg agg acc      434
Val Thr Glu Asp Phe Ala Ala Gln Glu Lys Lys Pro Ser Trp Arg Thr
                 50                  55                  60 cac cag gag atc caa gac ctc tgc aat att ctt cag gct cta gat tgc      482
His Gln Glu Ile Gln Asp Leu Cys Asn Ile Leu Gln Ala Leu Asp Cys
                     65                  70                  75 tac cgc agc tac aca gag tct cta cag ctg ctc ctg gcc aag gtc ata      530
Tyr Arg Ser Tyr Thr Glu Ser Leu Gln Leu Leu Leu Ala Lys Val Ile
                 80                  85                  90 cgc ttt gaa agg ttc ggt cgc cgg cgc gtc atc gtc aag aag ggg cag      578
Arg Phe Glu Arg Phe Gly Arg Arg Arg Val Ile Val Lys Lys Gly Gln
     95                 100                 105 atg ggc aat agc ttt tat ttc atc tac ctg ggc aca gtg gcc ata act      626
Met Gly Asn Ser Phe Tyr Phe Ile Tyr Leu Gly Thr Val Ala Ile Thr
110                 115                 120                 125 gag gac gag gat ggg agc agt gct ttc ctg gac cct cac cca aca ctg      674
Glu Asp Glu Asp Gly Ser Ser Ala Phe Leu Asp Pro His Pro Thr Leu
                130                 135                 140 ctg cac agg ggt ggc tcc ttc ggg gaa atg ggc ctt cta agc acc aca      722
Leu His Arg Gly Gly Ser Phe Gly Glu Met Gly Leu Leu Ser Thr Thr
                145                 150                 155 gta agg agt gcc acg gtg gtc tgc atg gag gag aca gag ttc ctg gtg      770
Val Arg Ser Ala Thr Val Val Cys Met Glu Glu Thr Glu Phe Leu Val
             160                 165                 170 gtc gac aga gag gat ttc gtt gca aat aag ctg ggt gac gaa gtt cag      818
Val Asp Arg Glu Asp Phe Val Ala Asn Lys Leu Gly Asp Glu Val Gln
175                 180                 185 aag gaa act cag tat cgg tac aat ttc ttt agg aac ttg gac ata ttc      866
Lys Glu Thr Gln Tyr Arg Tyr Asn Phe Phe Arg Asn Leu Asp Ile Phe
190                 195                 200                 205 cag tct tgg tct gaa gag aag ctc tgg aag ctg gtg gcc ttg ggg agg      914
Gln Ser Trp Ser Glu Glu Lys Leu Trp Lys Leu Val Ala Leu Gly Arg
                210                 215                 220 ata gag agg ttc tca tac gga cag atg gtg tct aaa gac ttt atg aat      962
Ile Glu Arg Phe Ser Tyr Gly Gln Met Val Ser Lys Asp Phe Met Asn
                225                 230                 235 tcg gca ttc atc aca ttt atc tgc cag ggc aac tgt gaa atc ctg cga     1010
Ser Ala Phe Ile Thr Phe Ile Cys Gln Gly Asn Cys Glu Ile Leu Arg
                240                 245                 250 ttg gta gcc ctg ggc gac tgc agt gcc tat tac aag tgg gtc tgg cag     1058
Leu Val Ala Leu Gly Asp Cys Ser Ala Tyr Tyr Lys Trp Val Trp Gln
255                 260                 265 caa ctg gag ctg ctg gat cac aaa cct ctg aga att cat gac aat gaa     1106
Gln Leu Glu Leu Leu Asp His Lys Pro Leu Arg Ile His Asp Asn Glu
270                 275                 280                 285 ata tct cca aag gag aga ttt aag gaa ctc cag atc aaa tcc tat cct     1154
Ile Ser Pro Lys Glu Arg Phe Lys Glu Leu Gln Ile Lys Ser Tyr Pro
                290                 295                 300 ctg cag gat ttc acg tat ttg aaa ctt ctg cgt ctc cag aaa gcc aga     1202
Leu Gln Asp Phe Thr Tyr Leu Lys Leu Leu Arg Leu Gln Lys Ala Arg
                305                 310                 315 gag caa cag gga ata gac ttc cac ggc aag atc aac aaa gta gaa aac     1250
```

```
Glu Gln Gln Gly Ile Asp Phe His Gly Lys Ile Asn Lys Val Glu Asn
            320                 325                 330 act ctc ccc aag ttg ctg ggc cca aag atc aaa tcc agg tac ggt cat      1298
Thr Leu Pro Lys Leu Leu Gly Pro Lys Ile Lys Ser Arg Tyr Gly His
        335                 340                 345 cca gtc aaa tgt tcc atg gtc aac acc aag ttt ggt gaa ctc ccc aag      1346
Pro Val Lys Cys Ser Met Val Asn Thr Lys Phe Gly Glu Leu Pro Lys
350                 355                 360                 365 gag gcc ata gtg ggg gtc tac atg aag atc cac aag aca gag gaa gga      1394
Glu Ala Ile Val Gly Val Tyr Met Lys Ile His Lys Thr Glu Glu Gly
                370                 375                 380 gag att gtg ggc ctt cac cag gcc ttt gtc ccg gaa atc cag cga gat      1442
Glu Ile Val Gly Leu His Gln Ala Phe Val Pro Glu Ile Gln Arg Asp
            385                 390                 395 tgc cgg ccc ttc atc ctt ctg agc ttg gga tca gag ttg ata caa gta      1490
Cys Arg Pro Phe Ile Leu Leu Ser Leu Gly Ser Glu Leu Ile Gln Val
        400                 405                 410 aga aaa gag aag ttt tat gac atg gtt gac gag gag aca aga gca aag      1538
Arg Lys Glu Lys Phe Tyr Asp Met Val Asp Glu Glu Thr Arg Ala Lys
    415                 420                 425 ata ata aag atg gat gtg gac tat ccc agc gat gaa gac ctg tgc cag      1586
Ile Ile Lys Met Asp Val Asp Tyr Pro Ser Asp Glu Asp Leu Cys Gln
430                 435                 440                 445 agt ttc ctg aag gaa aac gac tat att gtc ttt cgg aag gat ttg ctg      1634
Ser Phe Leu Lys Glu Asn Asp Tyr Ile Val Phe Arg Lys Asp Leu Leu
                450                 455                 460 cag tta ctg gtg gag ccc ctc aat aag tca cca ttc atc cca gtc cag      1682
Gln Leu Leu Val Glu Pro Leu Asn Lys Ser Pro Phe Ile Pro Val Gln
            465                 470                 475 acc aag aag aaa gag atc tac aac cac aag tct ttg ttc ctg gat cta      1730
Thr Lys Lys Lys Glu Ile Tyr Asn His Lys Ser Leu Phe Leu Asp Leu
        480                 485                 490 tgc agc ctt gaa aag aag gtg aag cag cac tat ccc att ttt ctg gcg      1778
Cys Ser Leu Glu Lys Lys Val Lys Gln His Tyr Pro Ile Phe Leu Ala
    495                 500                 505 ccc cag aaa tac ctg ccc ccc ttg agg gtt gtc caa gcc atc tca gca      1826
Pro Gln Lys Tyr Leu Pro Pro Leu Arg Val Val Gln Ala Ile Ser Ala
510                 515                 520                 525 ccc cgg cac aaa atc caa gaa ctc ctg cct caa tat aag aat gca ggg      1874
Pro Arg His Lys Ile Gln Glu Leu Leu Pro Gln Tyr Lys Asn Ala Gly
                530                 535                 540 gtc ctt att tag aacaaataaa gtaggttcgg attaaaaaaa aaaaaaaaaa          1926
Val Leu Ile
        545 aaaaaaaa                                                             1934

<210> SEQ ID NO 176
<211> LENGTH: 544
<212> TYPE: PRT
<213> ORGANISM: Mus musculus

<400> SEQUENCE: 176

Met Met Asn Arg Val Cys Lys Met Phe Arg Gln Gly Leu Arg Gly Phe
 1               5                  10                  15

Arg Glu Tyr Gln Ile Ile Glu Pro Val His Lys Lys His Pro Asp Phe
            20                  25                  30

Ser Phe Trp Asp Lys Lys Gln Gly Arg Ile Ser Phe Val Thr Glu
        35                  40                  45

Asp Phe Ala Ala Gln Glu Lys Lys Pro Ser Trp Arg Thr His Gln Glu
```

-continued

```
            50                  55                  60
Ile Gln Asp Leu Cys Asn Ile Leu Gln Ala Leu Asp Cys Tyr Arg Ser
 65                  70                  75                  80

Tyr Thr Glu Ser Leu Gln Leu Leu Ala Lys Val Ile Arg Phe Glu
                 85                  90                  95

Arg Phe Gly Arg Arg Val Ile Val Lys Gly Gln Met Gly Asn
            100                 105                 110

Ser Phe Tyr Phe Ile Tyr Leu Gly Thr Val Ala Ile Thr Glu Asp Glu
            115                 120                 125

Asp Gly Ser Ser Ala Phe Leu Asp Pro His Pro Thr Leu Leu His Arg
130                 135                 140

Gly Gly Ser Phe Gly Glu Met Gly Leu Leu Ser Thr Val Arg Ser
145                 150                 155                 160

Ala Thr Val Val Cys Met Glu Glu Thr Glu Phe Leu Val Val Asp Arg
            165                 170                 175

Glu Asp Phe Val Ala Asn Lys Leu Gly Asp Glu Val Gln Lys Glu Thr
            180                 185                 190

Gln Tyr Arg Tyr Asn Phe Phe Arg Asn Leu Asp Ile Phe Gln Ser Trp
            195                 200                 205

Ser Glu Glu Lys Leu Trp Lys Leu Val Ala Leu Gly Arg Ile Glu Arg
210                 215                 220

Phe Ser Tyr Gly Gln Met Val Ser Lys Asp Phe Met Asn Ser Ala Phe
225                 230                 235                 240

Ile Thr Phe Ile Cys Gln Gly Asn Cys Glu Ile Leu Arg Leu Val Ala
            245                 250                 255

Leu Gly Asp Cys Ser Ala Tyr Tyr Lys Trp Val Trp Gln Gln Leu Glu
            260                 265                 270

Leu Leu Asp His Lys Pro Leu Arg Ile His Asp Asn Glu Ile Ser Pro
            275                 280                 285

Lys Glu Arg Phe Lys Glu Leu Gln Ile Lys Ser Tyr Pro Leu Gln Asp
            290                 295                 300

Phe Thr Tyr Leu Lys Leu Leu Arg Leu Gln Lys Ala Arg Glu Gln Gln
305                 310                 315                 320

Gly Ile Asp Phe His Gly Lys Ile Asn Lys Val Glu Asn Thr Leu Pro
            325                 330                 335

Lys Leu Leu Gly Pro Lys Ile Lys Ser Arg Tyr Gly His Pro Val Lys
            340                 345                 350

Cys Ser Met Val Asn Thr Lys Phe Gly Glu Leu Pro Lys Glu Ala Ile
            355                 360                 365

Val Gly Val Tyr Met Lys Ile His Lys Thr Glu Glu Gly Glu Ile Val
            370                 375                 380

Gly Leu His Gln Ala Phe Val Pro Glu Ile Gln Arg Asp Cys Arg Pro
385                 390                 395                 400

Phe Ile Leu Leu Ser Leu Gly Ser Glu Leu Ile Gln Val Arg Lys Glu
            405                 410                 415

Lys Phe Tyr Asp Met Val Asp Glu Thr Arg Ala Lys Ile Ile Lys
            420                 425                 430

Met Asp Val Asp Tyr Pro Ser Asp Glu Asp Leu Cys Gln Ser Phe Leu
            435                 440                 445

Lys Glu Asn Asp Tyr Ile Val Phe Arg Lys Asp Leu Leu Gln Leu Leu
            450                 455                 460

Val Glu Pro Leu Asn Lys Ser Pro Phe Ile Pro Val Gln Thr Lys Lys
465                 470                 475                 480
```

```
Lys Glu Ile Tyr Asn His Lys Ser Leu Phe Leu Asp Leu Cys Ser Leu
                485                 490                 495
Glu Lys Lys Val Lys Gln His Tyr Pro Ile Phe Leu Ala Pro Gln Lys
            500                 505                 510
Tyr Leu Pro Pro Leu Arg Val Gln Ala Ile Ser Ala Pro Arg His
        515                 520                 525
Lys Ile Gln Glu Leu Leu Pro Gln Tyr Lys Asn Ala Gly Val Leu Ile
    530                 535                 540
```

<210> SEQ ID NO 177
<211> LENGTH: 763
<212> TYPE: DNA
<213> ORGANISM: Mus musculus
<220> FEATURE:
<221> NAME/KEY: CDS
<222> LOCATION: (57)..(386)

<400> SEQUENCE: 177

```
gagacctagg ggaagctcgg ccgcgttcct gacctgagac ctgaccggct gggacc atg       59
                                                                  Met
                                                                    1 gga tgc tgc ccg gga gac tgc ctc aat tgc tgc tcc cag gaa cag gac       107
Gly Cys Cys Pro Gly Asp Cys Leu Asn Cys Cys Ser Gln Glu Gln Asp
        5                  10                  15 tgc tgt gag gag tgt tgc tgc cag cag ggc tgc tgc ggc tgc tgt ggc       155
Cys Cys Glu Glu Cys Cys Cys Gln Gln Gly Cys Cys Gly Cys Cys Gly
         20                  25                  30 tgt tgt ggc tcc tgc tgt ggc tgc gga ggt tct agc tgc gga gga ggc       203
Cys Cys Gly Ser Cys Cys Gly Cys Gly Gly Ser Ser Cys Gly Gly Gly
 35                  40                  45 tgc tgc ggg tct ggc tgc ggg gga tgc gga ggc tgc ggg tct agc tgc       251
Cys Cys Gly Ser Gly Cys Gly Gly Cys Gly Gly Cys Gly Ser Ser Cys
 50                  55                  60                  65 tgc gga tct ggc tgc gga gga ggc tgc ggg ggc tgt gga ggc ggc tgc       299
Cys Gly Ser Gly Cys Gly Gly Gly Cys Gly Gly Cys Gly Gly Gly Cys
             70                  75                  80 tgt ggc ggc tcc gga tgc tgc ggt ggt ggc ggc ggg tgc tgt ggt cca       347
Cys Gly Gly Ser Gly Cys Cys Gly Gly Gly Gly Gly Cys Cys Gly Pro
         85                  90                  95 gtg tgc tgt cag ccc aca cct gtg tgt gag aca aaa tga agaccttccc       396
Val Cys Cys Gln Pro Thr Pro Val Cys Glu Thr Lys
100                 105                 110 ccctctaact gagacagtgt tgggacagc ctccgtccag tccactccag atggagacct      456
cctcatctcc tgactcgttt gcacctccaa gacagcgaca tgcctctcct gttatttctg    516
ataggagagc ttgccctggg gtctaaggca ctcaggccaa agagccatt tcctggcaag     576 aaattaaaag ctgggttcca atgaggtggt caccaagttc aatgttcctg acttcattta   636
catgaagtta cacgcctcgc agctatgagg cattctctta ctctttggac ctcttggtcc   696
atcccagttt tctgctcctt tgaaactttg tcaatctttt aataaattca agcatgctgg   756
ctacccc                                                              763
```

<210> SEQ ID NO 178
<211> LENGTH: 109
<212> TYPE: PRT
<213> ORGANISM: Mus musculus

<400> SEQUENCE: 178

Met Gly Cys Cys Pro Gly Asp Cys Leu Asn Cys Cys Ser Gln Glu Gln

```
                    1               5              10              15
Asp Cys Cys Glu Glu Cys Cys Cys Gln Gln Gly Cys Cys Gly Cys Cys
                   20              25              30
Gly Cys Cys Gly Ser Cys Cys Gly Cys Gly Ser Ser Cys Gly Gly
               35                  40              45
Gly Cys Cys Gly Ser Gly Cys Gly Gly Cys Gly Gly Cys Gly Ser Ser
           50              55              60
Cys Cys Gly Ser Gly Cys Gly Gly Cys Gly Cys Gly Gly Gly
 65              70              75              80
Cys Cys Gly Gly Ser Gly Cys Cys Gly Gly Gly Cys Cys Gly
                 85              90              95
Pro Val Cys Cys Gln Pro Thr Pro Val Cys Glu Thr Lys
              100             105

<210> SEQ ID NO 179
<211> LENGTH: 1097
<212> TYPE: DNA
<213> ORGANISM: Mus musculus
<220> FEATURE:
<221> NAME/KEY: CDS
<222> LOCATION: (71)..(439)

<400> SEQUENCE: 179
gatcatcacg tctccctctc ctctcctgag tctctctcct cactgcacct gagtcctctc      60
tactaacacc atg ggt tgc tgt ggc tgc gga ggc tgc gga ggc tgc ggc        109
            Met Gly Cys Cys Gly Cys Gly Gly Cys Gly Gly Cys Gly
              1               5              10 ggc tgt ggc ggc tgt ggc tgc ggt ggc tgt gga ggc tgc ggt ggc tgt      157
Gly Cys Gly Gly Cys Gly Cys Gly Gly Cys Gly Gly Cys Gly Gly Cys
         15              20              25 ggc tgc ggt ggc tgt ggc tgt ggt ggc tgt ggc tgt ggt ggc tgt ggc      205
Gly Cys Gly Gly Cys Gly Cys Gly Gly Cys Gly Cys Gly Gly Cys Gly
 30              35              40              45 tgc ggt ggc tgt ggc tgt ggt ggt tgt ggt ggc tgt ggc ggt tgt ggc      253
Cys Gly Gly Cys Gly Cys Gly Gly Cys Gly Cys Gly Gly Cys Gly
             50              55              60 tgc tgt ggt ggc tgc tgt ggc tgc tgt ggc tgc tgc aag cct acg gta      301
Cys Cys Gly Gly Cys Cys Gly Cys Cys Gly Cys Cys Lys Pro Thr Val
         65              70              75 gtc tgc tgc tgc cgc cgc tcc tgc tgc cgc tcc tgt ggt tgt ggc tcc      349
Val Cys Cys Cys Arg Arg Ser Cys Cys Arg Ser Cys Gly Cys Gly Ser
         80              85              90 tgt ggc tgt ggc tgt ggc tgt ggg aag ggc tgt tgc cag cag aag tgc      397
Cys Gly Cys Gly Cys Gly Cys Gly Lys Gly Cys Cys Gln Gln Lys Cys
 95             100             105 tgc tgc cag cag aag tgt ggc tgc aag aag tgc tgc tgc tag            439
Cys Cys Gln Gln Lys Cys Gly Cys Lys Lys Cys Cys Cys
110             115             120 acagaaaggg ttttcaggag ctgtgtgagt cctttgtccc attgcttcct atagctaaag      499
gcctcttaca caccatcatg tctgtctcca actggctttc tgtccccca acttctttta       559 tacctttctt ccttgatctt taaagtagtc tcattgacaa ctctcacaag gttctctaag      619
gcctaacata gaaacttcct gattgttctc tggttgctac aactcttggc aaaatcgctg      679
acttgggctg ccctcaggcc tggcctatgc ccttgggatc agggtaagta ctgcaggcta      739
ctcttgcctg ccactcctga ttaatgccct gctaatgaga ttgttctgga accttggcct      799
ttgtgcagtc ttctctctaa gccttcccag ttaaaagctg tctggactca cagtagttaa      859
```

```
atgtgagcat gtgagcatgt gagcatctct cagtgcctaa agcgtagatc agtaggatct      919
cagactcacg ggctacactg tctgtatttg attcccatca catgttcccg agttgctgtc      979
caccaatggc tgtcttccct ctctctgaga acagtggatt cccagtgtct cttctgctat     1039
gatgtagttg gttttcttca atgtcctcag tatctaataa actacataaa atgtcccc       1097

<210> SEQ ID NO 180
<211> LENGTH: 122
<212> TYPE: PRT
<213> ORGANISM: Mus musculus

<400> SEQUENCE: 180

Met Gly Cys Cys Gly Cys Gly Gly Cys Gly Gly Cys Gly Gly Cys Gly
 1               5                  10                  15

Gly Cys Gly Cys Gly Gly Cys Gly Gly Cys Gly Gly Cys Gly Cys Gly
             20                  25                  30

Gly Cys Gly Cys Gly Gly Cys Gly Cys Gly Gly Cys Gly Cys Gly Gly
         35                  40                  45

Cys Gly Cys Gly Gly Cys Gly Cys Gly Gly Cys Gly Cys Cys Gly
     50                  55                  60

Gly Cys Cys Gly Cys Cys Gly Cys Cys Lys Pro Thr Val Val Cys Cys
 65                  70                  75                  80

Cys Arg Arg Ser Cys Cys Arg Ser Cys Gly Cys Gly Ser Cys Gly Cys
                 85                  90                  95

Gly Cys Gly Cys Gly Lys Gly Cys Cys Gln Gln Lys Cys Cys Cys Gln
            100                 105                 110

Gln Lys Cys Gly Cys Lys Lys Cys Cys Cys
            115                 120

<210> SEQ ID NO 181
<211> LENGTH: 993
<212> TYPE: DNA
<213> ORGANISM: Mus musculus
<220> FEATURE:
<221> NAME/KEY: CDS
<222> LOCATION: (68)..(484)

<400> SEQUENCE: 181
gatcacactg ttctctcctc tcctgagtct ctcccctcac tgcacctgaa tcctctttac       60 tgacacc atg ggt tgc tgt ggc tgt gga ggc tgt ggc ggc tgc ggc ggc        109
        Met Gly Cys Cys Gly Cys Gly Gly Cys Gly Gly Cys Gly Gly
         1               5                  10 tgt ggt tgt ggc ggc tgt ggc tgt ggc ggc tgt ggc tgc ggt ggc tgt        157
Cys Gly Cys Gly Gly Cys Gly Cys Gly Gly Cys Gly Cys Gly Gly Cys
 15                  20                  25                  30 tgc tgc ggt ggc tgt ggc tgc ggt ggc tgt ggc tgc ggt ggc tgt ggc        205
Cys Cys Gly Gly Cys Gly Cys Gly Gly Cys Gly Cys Gly Gly Cys Gly
                 35                  40                  45 tgc cgt gcg ctg tgg cgg ctg cgg tgg ctg tgg cgg ctg tgt ctg tgg        253
Cys Arg Ala Leu Trp Arg Leu Arg Trp Leu Trp Arg Leu Cys Leu Trp
             50                  55                  60 ctg tgg tgg ctg tgg ctg tgg tgg ctg tgg tgg ctg tgg ctg ctg tgg        301
Leu Trp Trp Leu Trp Leu Trp Trp Leu Trp Trp Leu Trp Leu Leu Trp
 65                  70                  75 tgg ctg ctg tgg ttg ctg tgg cgt ccg cag acc tac ggt att ctg ctg        349
Trp Leu Leu Trp Leu Leu Trp Arg Pro Gln Thr Tyr Gly Ile Leu Leu
         80                  85                  90 cgc cgc cgc agc tgc tgc cgc tcc tgt ggc tgt ggc tcc tgt ggc tgc        397
Arg Arg Arg Ser Cys Cys Arg Ser Cys Gly Cys Gly Ser Cys Gly Cys
```

```
                        95                  100                 105                 110
ggc tgc ggc tgt ggc tgt ggg aag ggc tgt tgc cag cag aag tgc tgc     445
Gly Cys Gly Cys Gly Cys Gly Lys Gly Cys Cys Gln Gln Lys Cys Cys
                        115                 120                 125 tgc cag cag aag tgt gga tgc aag aag tgc tgc tgc tag cttgggatgt      494
Cys Gln Gln Lys Cys Gly Cys Lys Lys Cys Cys Cys
                130                 135 ctggcccctg agcaagtgct accagtaccg atctgttggt aagtcctgag tgcagaggat   554
ggaacaagtc accctgatct cgctgctaag gctttcctct gtcctagtct gagtataccc   614
tgctgtctcc ccagcatctg tctctctaga atccggactc tgaaactttg ttgcctgatt   674
tgaatactct gaagttcaag taaatttcct tatcatttta aatgcagtca tagtcaatgt   734
taagaaagga caaggtgca gggcatcttg gttactgatg tcaataagat tgtataatgg    794
tccccattgt gtttccttct tgaatttcta tctatgcttt aggtcagctt gtgtttaaca   854
atggcaatgt ctattctctg taatggtaat gtatattctc tgtttaacaa cggtaatata   914
gattctctgt agtcacagaa gtctttctag agtccagaca atgtgttaat cccctttaaa   974
taaaattaca aaataaaac                                                993

<210> SEQ ID NO 182
<211> LENGTH: 138
<212> TYPE: PRT
<213> ORGANISM: Mus musculus

<400> SEQUENCE: 182

Met Gly Cys Cys Gly Cys Gly Gly Cys Gly Gly Cys Gly Gly Cys Gly
 1               5                  10                  15

Cys Gly Gly Cys Gly Cys Gly Gly Cys Gly Cys Gly Gly Cys Cys Cys
                20                  25                  30

Gly Gly Cys Gly Cys Gly Gly Cys Gly Cys Gly Gly Cys Gly Cys Arg
            35                  40                  45

Ala Leu Trp Arg Leu Arg Trp Leu Trp Arg Leu Cys Leu Trp Leu Trp
        50                  55                  60

Trp Leu Trp Leu Trp Trp Leu Trp Trp Leu Trp Leu Leu Trp Trp Leu
    65                  70                  75                  80

Leu Trp Leu Leu Trp Arg Pro Gln Thr Tyr Gly Ile Leu Leu Arg Arg
                85                  90                  95

Arg Ser Cys Cys Arg Ser Cys Gly Cys Gly Ser Cys Gly Cys Gly Cys
                100                 105                 110

Gly Cys Gly Cys Gly Lys Gly Cys Cys Gln Gln Lys Cys Cys Cys Gln
            115                 120                 125

Gln Lys Cys Gly Cys Lys Lys Cys Cys Cys
        130                 135

<210> SEQ ID NO 183
<211> LENGTH: 938
<212> TYPE: DNA
<213> ORGANISM: Mus musculus
<220> FEATURE:
<221> NAME/KEY: CDS
<222> LOCATION: (66)..(635)

<400> SEQUENCE: 183
gctacacatc ttgtctctcc acctgctcct ctgacctact catccctcaa accaatacca    60 gaacc atg agc tgc tgt ggc tgt tca gga ggc tgt ggc tcc agc tgt ggg   110
      Met Ser Cys Cys Gly Cys Ser Gly Gly Cys Gly Ser Ser Cys Gly
       1               5                   10                  15
```

-continued

```
ggc tgt ggc tcc aac tgt tgc aag cct gtg tgc tgc aag cct gtg        158
Gly Cys Gly Ser Asn Cys Cys Lys Pro Val Cys Cys Lys Pro Val
                 20                  25                  30 tgc tgc tgt gtg cca gcc tgt tcc tgc tcc agc tgt ggg gac tgc aag    206
Cys Cys Cys Val Pro Ala Cys Ser Cys Ser Ser Cys Gly Asp Cys Lys
             35                  40                  45 gga ggc tgt ggc tcc tgt ggg ggc tgc aag gga ggc tgt ggc tcc tgt    254
Gly Gly Cys Gly Ser Cys Gly Gly Cys Lys Gly Gly Cys Gly Ser Cys
 50                  55                  60 ggt ggc tgc aag gga ggc tgt ggc tcc tgt gga ggc tgc aag gga ggc    302
Gly Gly Cys Lys Gly Gly Cys Gly Ser Cys Gly Gly Cys Lys Gly Gly
             65                  70                  75 tgt ggc tcc tgt gga ggc tgt ggc tcc tgt ggg ggc tgc aag gga ggc    350
Cys Gly Ser Cys Gly Gly Cys Gly Ser Cys Gly Gly Cys Lys Gly Gly
 80                  85                  90                  95 tgt agt tcc tgt gga ggc tgt ggc tcc tgt ggg ggc tgc aag gga ggc    398
Cys Ser Ser Cys Gly Gly Cys Gly Ser Cys Gly Gly Cys Lys Gly Gly
                100                 105                 110 tgt ggc tct tgt gga ggc tgt ggc tcc tgt ggg ggc tgt ggc tcc tgt    446
Cys Gly Ser Cys Gly Gly Cys Gly Ser Cys Gly Gly Cys Gly Ser Cys
             115                 120                 125 ggt tgc tgc cag tcc agc tgc tgc aag ccc tgt tgt tgc caa tcc agc    494
Gly Cys Cys Gln Ser Ser Cys Cys Lys Pro Cys Cys Cys Gln Ser Ser
 130                 135                 140 tgt tgc aag ccc tgc tgc tgc caa tcc agc tgc tgc cag tcc agc tgc    542
Cys Cys Lys Pro Cys Cys Cys Gln Ser Ser Cys Cys Gln Ser Ser Cys
             145                 150                 155 tgc aag ccc tgc tgc tgc cag tcc agc tgt tgc aag ccc tgc tgc tgt    590
Cys Lys Pro Cys Cys Cys Gln Ser Ser Cys Cys Lys Pro Cys Cys Cys
160                 165                 170                 175 cag tcc agc tgc tgt gct cct gta tgc tgc cag tgt aag atc tga        635
Gln Ser Ser Cys Cys Ala Pro Val Cys Cys Gln Cys Lys Ile
                 180                 185                 190 cactttccaa gaagtacctc tactattcct ttacttctgt agtctacctt ctttggaagc   695
tgtgggatta taatgacttt cctactcaag ttcaaggctt ccttctccag cccttgatgg   755
gaaggagcaa atcactgccc tgatgctttc ctgacaggct cacattgtaa cttagtcccc   815
agattcttta acctgtcttt ctcacattcc ctactatgtc taaccaggct tgccatcata   875
aagataatct gtgaagtttt gaaatgtatc caaaatttat taaataaatc ctcccccacc   935
atc                                                               938
```

<210> SEQ ID NO 184
<211> LENGTH: 189
<212> TYPE: PRT
<213> ORGANISM: Mus musculus

<400> SEQUENCE: 184

```
Met Ser Cys Cys Gly Cys Ser Gly Gly Cys Gly Ser Ser Cys Gly Gly
 1               5                  10                  15

Cys Gly Ser Asn Cys Cys Lys Pro Val Cys Cys Lys Pro Val Cys
                 20                  25                  30

Cys Cys Val Pro Ala Cys Ser Cys Ser Ser Cys Gly Asp Cys Lys Gly
             35                  40                  45

Gly Cys Gly Ser Cys Gly Gly Cys Lys Gly Gly Cys Gly Ser Cys Gly
 50                  55                  60

Gly Cys Lys Gly Gly Cys Gly Ser Cys Gly Gly Cys Lys Gly Gly Cys
 65                  70                  75                  80
```

```
Gly Ser Cys Gly Gly Cys Gly Ser Cys Gly Gly Cys Lys Gly Gly Cys
                85                  90                  95

Ser Ser Cys Gly Gly Cys Gly Ser Cys Gly Gly Cys Lys Gly Gly Cys
            100                 105                 110

Gly Ser Cys Gly Gly Cys Gly Ser Cys Gly Gly Cys Gly Ser Cys Gly
        115                 120                 125

Cys Cys Gln Ser Ser Cys Cys Lys Pro Cys Cys Gln Ser Ser Cys
    130                 135                 140

Cys Lys Pro Cys Cys Cys Gln Ser Ser Cys Cys Gln Ser Ser Cys
145                 150                 155                 160

Lys Pro Cys Cys Cys Gln Ser Ser Cys Cys Lys Pro Cys Cys Cys Gln
            165                 170                 175

Ser Ser Cys Cys Ala Pro Val Cys Cys Gln Cys Lys Ile
            180                 185

<210> SEQ ID NO 185
<211> LENGTH: 1076
<212> TYPE: DNA
<213> ORGANISM: Mus musculus
<220> FEATURE:
<221> NAME/KEY: CDS
<222> LOCATION: (66)..(656)

<400> SEQUENCE: 185
gacactcaca caccttcacc acctgctcct ctgacctgtt ccacctccaa ccaataacca      60 gaacc atg agc tgc tgt ggc tgt tgt gga ggc tgt ggc tcc agc tgc tgc     110
      Met Ser Cys Cys Gly Cys Cys Gly Gly Cys Gly Ser Ser Cys Cys
      1               5                   10                  15 aag cct gtg tgc tgt tgt gtg cct gtc tgt tcc tgc tcc agc tgt ggg       158
Lys Pro Val Cys Cys Cys Val Pro Val Cys Ser Cys Ser Ser Cys Gly
            20                  25                  30 ggc tgc aag gga ggc tgt agt tcc tgt gga ggc tgt ggc tcc tgt ggg       206
Gly Cys Lys Gly Gly Cys Ser Ser Cys Gly Gly Cys Gly Ser Cys Gly
        35                  40                  45 ggc tgc aag gga ggc tgt ggt tcc tgt gga ggc tgt ggt tcc tgt ggg       254
Gly Cys Lys Gly Gly Cys Gly Ser Cys Gly Gly Cys Gly Ser Cys Gly
    50                  55                  60 ggc tgc aag gga ggc tgt ggt tcc tgt gga ggc tgt ggc tcc tgt ggg       302
Gly Cys Lys Gly Gly Cys Gly Ser Cys Gly Gly Cys Gly Ser Cys Gly
65                  70                  75 ggc tgc aag gga ggc tgt ggt tcc tgt gga ggc tgt ggt tcc tgt ggg       350
Gly Cys Lys Gly Gly Cys Gly Ser Cys Gly Gly Cys Gly Ser Cys Gly
 80                 85                  90                  95 ggc tgc aag gga ggc tgt ggt tcc tgt gga ggc tgt ggc tcc tgt ggg       398
Gly Cys Lys Gly Gly Cys Gly Ser Cys Gly Gly Cys Gly Ser Cys Gly
            100                 105                 110 ggc tgc aag gga ggc tgt agt tcc tgt gga ggc tgt ggc tcc tgt ggt       446
Gly Cys Lys Gly Gly Cys Ser Ser Cys Gly Gly Cys Gly Ser Cys Gly
        115                 120                 125 gct gcc agt ccc agc tgt gta agc cct gct gct gcc agt cca gct gtt       494
Ala Ala Ser Pro Ser Cys Val Ser Pro Ala Ala Ala Ser Pro Ala Val
    130                 135                 140 caa gcc ctg ctg ctg cca gtc cag ctg ttg caa gcc ctg ctg ctg cca       542
Gln Ala Leu Leu Leu Pro Val Gln Leu Leu Gln Ala Leu Leu Leu Pro
145                 150                 155 gcc cag ctg ttg cta gtc cag ctg ctg tcc ttg ctg ctc ctc cat           590
Ala Gln Leu Leu Leu Val Gln Leu Leu Ser Leu Leu Leu His
160                 165                 170                 175
```

-continued

```
gac tgt ggg tct tca tgc tgt cca atg agc tgc tct ctt ccc att tac        638
Asp Cys Gly Ser Ser Cys Cys Pro Met Ser Cys Ser Leu Pro Ile Tyr
            180                 185                 190 tgc caa agg gag att tga gattctgctc agaggtccaa atcatcctat               686
Cys Gln Arg Glu Ile
        195 ctgtttgagg tttctgggga tgagtctaga ctgcacctca aagccctaaa gctctaatct      746 cactttgtga tccagaaggt gtttccttga tctacaaagc tggacatcca tttgtcaggc      806 aatagaggag tgcacagtcc tcctgcccat cacctctaat aggaaaccca gatccttttc      866 gatgccacct aggatggcag tactttctc agcatccaca ggccccttag agccccatcc       926 attcttccat gccaatagca ggaaggtcag ccctaccata aggtatgttc accacaggct      986 tctatgtctg ctttctttct ttttgctttt cttttcttcg tttggcccaa atgggacact     1046 gcaaaacatt aaataaacaa ataaacgccg                                     1076
```

```
<210> SEQ ID NO 186
<211> LENGTH: 196
<212> TYPE: PRT
<213> ORGANISM: Mus musculus

<400> SEQUENCE: 186
```

```
Met Ser Cys Cys Gly Cys Cys Gly Gly Cys Gly Ser Ser Cys Cys Lys
  1               5                  10                  15

Pro Val Cys Cys Val Pro Val Cys Ser Cys Ser Ser Cys Gly Gly
             20                  25                  30

Cys Lys Gly Gly Cys Ser Ser Cys Gly Gly Cys Gly Ser Cys Gly Gly
         35                  40                  45

Cys Lys Gly Gly Cys Gly Ser Cys Gly Gly Cys Gly Ser Cys Gly Gly
     50                  55                  60

Cys Lys Gly Gly Cys Gly Ser Cys Gly Gly Cys Gly Ser Cys Gly Gly
 65                  70                  75                  80

Cys Lys Gly Gly Cys Gly Ser Cys Gly Gly Cys Gly Ser Cys Gly Gly
                 85                  90                  95

Cys Lys Gly Gly Cys Gly Ser Cys Gly Gly Cys Gly Ser Cys Gly Gly
            100                 105                 110

Cys Lys Gly Gly Cys Ser Ser Cys Gly Gly Cys Gly Ser Cys Gly Ala
        115                 120                 125

Ala Ser Pro Ser Cys Val Ser Pro Ala Ala Ser Pro Ala Val Gln
    130                 135                 140

Ala Leu Leu Leu Pro Val Gln Leu Leu Gln Ala Leu Leu Leu Pro Ala
145                 150                 155                 160

Gln Leu Leu Leu Val Gln Leu Leu Leu Ser Leu Leu Leu Leu His Asp
                165                 170                 175

Cys Gly Ser Ser Cys Cys Pro Met Ser Cys Ser Leu Pro Ile Tyr Cys
            180                 185                 190

Gln Arg Glu Ile
        195
```

```
<210> SEQ ID NO 187
<211> LENGTH: 828
<212> TYPE: DNA
<213> ORGANISM: Mus musculus
<220> FEATURE:
<221> NAME/KEY: CDS
<222> LOCATION: (64)..(459)

<400> SEQUENCE: 187
```

-continued

| | |
|---|---|
| atcgtacctg tagactccca acctctcctc acttctcagc cccactccag cccagacacc | 60 |

| acc atg aca ggc tcc tgc tgt gga tcc ttc tcc tcc cag agc tgt gga<br>    Met Thr Gly Ser Cys Cys Gly Ser Phe Ser Ser Gln Ser Cys Gly<br>     1               5                    10                 15 | 108 |
| gga ggc tgc tgc cag ccc tgc tgc tgc agg gac ccc tgc tgc tgc cgc<br>Gly Gly Cys Cys Gln Pro Cys Cys Cys Arg Asp Pro Cys Cys Cys Arg<br>                 20                    25                   30 | 156 |
| cca gtg tcc tgc cag acc aca gtg tgt cgc cct gtg acc tgt gtg ccc<br>Pro Val Ser Cys Gln Thr Thr Val Cys Arg Pro Val Thr Cys Val Pro<br>                 35                    40                   45 | 204 |
| cac tgc acc agg ccc atc tgt gag ccc tgc cgc cgc ccc atc tgc tgt<br>His Cys Thr Arg Pro Ile Cys Glu Pro Cys Arg Arg Pro Ile Cys Cys<br>             50                    55                   60 | 252 |
| gac ccc tgc agc ctg cag cag ggc tgt cgc ccc atc acc tgc tgc<br>Asp Pro Cys Ser Leu Gln Gln Gly Cys Arg Pro Ile Thr Cys Cys<br>    65                70                    75 | 300 |
| ccc acc tct tgc aca gct gtg gtc tgc agg cct tgc tgc tgg gcc tcc<br>Pro Thr Ser Cys Thr Ala Val Val Cys Arg Pro Cys Cys Trp Ala Ser<br>80                    85                    90                   95 | 348 |
| acc tgc tgc cag ccc atc tca gtg cag gct ccc tgc tgc agg ccc ccc<br>Thr Cys Cys Gln Pro Ile Ser Val Gln Ala Pro Cys Cys Arg Pro Pro<br>                 100                 105                110 | 396 |
| tgc tgc cag cct gct ccc tgt cgc acc acc tgc agg acc tcc ccc tgt<br>Cys Cys Gln Pro Ala Pro Cys Arg Thr Thr Cys Arg Thr Ser Pro Cys<br>                 115                 120                125 | 444 |
| aac acc tgc tgc tga gccatcacat aggcagcttc tccgggtgaa cagaactcgt<br>Asn Thr Cys Cys<br>           130 | 499 |
| cctactcctg atggagcaga gagacaccac ttttgcagcc atctgtact tccccagttc | 559 |
| acccaaccgt aaaggcctat caagttctcc atatatatat tcagctagtc atctgcatag | 619 |
| ctctagacat attctagctc ccatcagcag aattcttggc atcaaaagca tatgtaagca | 679 |
| aatgttaagt tttttcatga agatccatcc cattgagtca ctgtaatttt tttttttttaa | 739 |
| tttcaaggtt cagatgggat atgttttcag catggtatcc ttgtgctatg gttttgcatg | 799 |
| ataaaaaaaa taaaattttta tttttggtg | 828 |

```
<210> SEQ ID NO 188
<211> LENGTH: 131
<212> TYPE: PRT
<213> ORGANISM: Mus musculus

<400> SEQUENCE: 188
```

Met Thr Gly Ser Cys Cys Gly Ser Phe Ser Ser Gln Ser Cys Gly
1               5                   10                  15

Gly Cys Cys Gln Pro Cys Cys Cys Arg Asp Pro Cys Cys Cys Arg Pro
            20                  25                  30

Val Ser Cys Gln Thr Thr Val Cys Arg Pro Val Thr Cys Val Pro His
        35                  40                  45

Cys Thr Arg Pro Ile Cys Glu Pro Cys Arg Arg Pro Ile Cys Cys Asp
    50                  55                  60

Pro Cys Ser Leu Gln Gln Gly Cys Cys Arg Pro Ile Thr Cys Cys Pro
65                  70                  75                  80

Thr Ser Cys Thr Ala Val Val Cys Arg Pro Cys Cys Trp Ala Ser Thr
                85                  90                  95

Cys Cys Gln Pro Ile Ser Val Gln Ala Pro Cys Cys Arg Pro Pro Cys
            100                 105                 110

Cys Gln Pro Ala Pro Cys Arg Thr Thr Cys Arg Thr Ser Pro Cys Asn
         115                 120                 125

Thr Cys Cys
    130

<210> SEQ ID NO 189
<211> LENGTH: 409
<212> TYPE: DNA
<213> ORGANISM: Mus musculus
<220> FEATURE:
<221> NAME/KEY: CDS
<222> LOCATION: (2)..(292)

<400> SEQUENCE: 189

```
t tgc tgt gtc gcc cgc tgc tgc agt gtc ccc acc ggc cct gcc acc acc        49
  Cys Cys Val Ala Arg Cys Cys Ser Val Pro Thr Gly Pro Ala Thr Thr
   1               5                  10                  15 atc tgc tcc tca gac aag tcc tgc cgc tgt gga gtc tgc ctg ccc agc          97
Ile Cys Ser Ser Asp Lys Ser Cys Arg Cys Gly Val Cys Leu Pro Ser
                 20                  25                  30 acc tgc cca cat gag atc agc ctc ctg cag ccc act tgc tgt gac ccc         145
Thr Cys Pro His Glu Ile Ser Leu Leu Gln Pro Thr Cys Cys Asp Pro
             35                  40                  45 tgc ccc cca ccc tgc tgc cag cct gaa gtg tac gtg cca acc tgc tgg         193
Cys Pro Pro Pro Cys Cys Gln Pro Glu Val Tyr Val Pro Thr Cys Trp
 50                  55                  60 ctg ctc aac tct tgc cac cca act ccc ggc ctg agt ggc atc aac ctg         241
Leu Leu Asn Ser Cys His Pro Thr Pro Gly Leu Ser Gly Ile Asn Leu
 65                  70                  75                  80 acc acc tac gtg cag ccc ggc tgt gag agt ccc tgt gag ccc tgc tgt         289
Thr Thr Tyr Val Gln Pro Gly Cys Glu Ser Pro Cys Glu Pro Cys Cys
                 85                  90                  95 taa gtcaagtctt cccaggttca gtggcctgtc tgctcagcat cctctctttc              342 ccccttccctt caataactgc ttctgcttgc atcaaagctc aatcaaaccc aattcccaga      402
aacaggg                                                                 409
```

<210> SEQ ID NO 190
<211> LENGTH: 96
<212> TYPE: PRT
<213> ORGANISM: Mus musculus

<400> SEQUENCE: 190

Cys Cys Val Ala Arg Cys Cys Ser Val Pro Thr Gly Pro Ala Thr Thr
 1               5                  10                  15

Ile Cys Ser Ser Asp Lys Ser Cys Arg Cys Gly Val Cys Leu Pro Ser
                 20                  25                  30

Thr Cys Pro His Glu Ile Ser Leu Leu Gln Pro Thr Cys Cys Asp Pro
             35                  40                  45

Cys Pro Pro Pro Cys Cys Gln Pro Glu Val Tyr Val Pro Thr Cys Trp
 50                  55                  60

Leu Leu Asn Ser Cys His Pro Thr Pro Gly Leu Ser Gly Ile Asn Leu
 65                  70                  75                  80

Thr Thr Tyr Val Gln Pro Gly Cys Glu Ser Pro Cys Glu Pro Cys Cys
                 85                  90                  95

<210> SEQ ID NO 191
<211> LENGTH: 300
<212> TYPE: DNA
<213> ORGANISM: Mus musculus

```
<220> FEATURE:
<221> NAME/KEY: CDS
<222> LOCATION: (1)..(300)

<400> SEQUENCE: 191 atg gct tgc tgt gtt gcc cgc tgc tgc agt gtc ccc acc ggc cct gcc      48
Met Ala Cys Cys Val Ala Arg Cys Cys Ser Val Pro Thr Gly Pro Ala
 1               5                  10                  15 acc acc atc tgc tcc tca gac aag tcc tgc cgc tgt gga gtc tgc ctg      96
Thr Thr Ile Cys Ser Ser Asp Lys Ser Cys Arg Cys Gly Val Cys Leu
            20                  25                  30 ccc agc acc tgc cca cac acc att tgg cag ctg gag ccc acc tgc tgt     144
Pro Ser Thr Cys Pro His Thr Ile Trp Gln Leu Glu Pro Thr Cys Cys
         35                  40                  45 gac aac tgc ccc cca ccc tgc cac atc cct cag ccc tgt gtg ccc acc     192
Asp Asn Cys Pro Pro Pro Cys His Ile Pro Gln Pro Cys Val Pro Thr
     50                  55                  60 tgc ttc ctg ctc aac tcc tgc cac cca acc cca gac ctg ctg act gtc     240
Cys Phe Leu Leu Asn Ser Cys His Pro Thr Pro Asp Leu Leu Thr Val
 65                  70                  75                  80 aac ctc acc acc tat gtg cag cca ggc tgt gag gag ccc tgt gtc cca     288
Asn Leu Thr Thr Tyr Val Gln Pro Gly Cys Glu Glu Pro Cys Val Pro
                 85                  90                  95 agg tgc tgc tga                                                     300
Arg Cys Cys
        100

<210> SEQ ID NO 192
<211> LENGTH: 99
<212> TYPE: PRT
<213> ORGANISM: Mus musculus

<400> SEQUENCE: 192

Met Ala Cys Cys Val Ala Arg Cys Cys Ser Val Pro Thr Gly Pro Ala
 1               5                  10                  15

Thr Thr Ile Cys Ser Ser Asp Lys Ser Cys Arg Cys Gly Val Cys Leu
            20                  25                  30

Pro Ser Thr Cys Pro His Thr Ile Trp Gln Leu Glu Pro Thr Cys Cys
         35                  40                  45

Asp Asn Cys Pro Pro Pro Cys His Ile Pro Gln Pro Cys Val Pro Thr
     50                  55                  60

Cys Phe Leu Leu Asn Ser Cys His Pro Thr Pro Asp Leu Leu Thr Val
 65                  70                  75                  80

Asn Leu Thr Thr Tyr Val Gln Pro Gly Cys Glu Glu Pro Cys Val Pro
                 85                  90                  95

Arg Cys Cys

<210> SEQ ID NO 193
<211> LENGTH: 352
<212> TYPE: DNA
<213> ORGANISM: Mus musculus
<220> FEATURE:
<221> NAME/KEY: CDS
<222> LOCATION: (2)..(94)

<400> SEQUENCE: 193 a aac tct tgc cac cca act ccc ggc ctg agt ggc atc aac ctg acc acc    49
  Asn Ser Cys His Pro Thr Pro Gly Leu Ser Gly Ile Asn Leu Thr Thr
   1               5                  10                  15 tac gtg cag ccc ggc tgt gag agt ccc tgt gag ccc tgc tgt taa          94
Tyr Val Gln Pro Gly Cys Glu Ser Pro Cys Glu Pro Cys Cys
```

-continued

```
                    20                  25                  30 gcagtcaagt cttcccaggt tcagtggcct gtctgctcag catcctctct ttcacctgcc      154
cttcaataac tgcttctgct tgcatcaaag ctcaatcacc ccaatgccca gaaacagggg      214
cccatggaca tgtttaaatt cttaatgctt tattcctttg ggaacagatg aatgatgtct      274
ctcttttaag ctcattcctg cttttttga gagataacca tttggactac ttattaataa       334
acttcattct ggcttagc                                                    352

<210> SEQ ID NO 194
<211> LENGTH: 30
<212> TYPE: PRT
<213> ORGANISM: Mus musculus

<400> SEQUENCE: 194

Asn Ser Cys His Pro Thr Pro Gly Leu Ser Gly Ile Asn Leu Thr Thr
 1               5                  10                  15

Tyr Val Gln Pro Gly Cys Glu Ser Pro Cys Glu Pro Cys Cys
             20                  25                  30

<210> SEQ ID NO 195
<211> LENGTH: 973
<212> TYPE: DNA
<213> ORGANISM: Mus musculus
<220> FEATURE:
<221> NAME/KEY: CDS
<222> LOCATION: (55)..(588)

<400> SEQUENCE: 195
gacattgtgt aaaactcatc tgggaacaga ctatcactct ccactccaga cacc atg       57
                                                             Met
                                                              1 acc cac acc tgt cag cca tgc tgc tgc aag acc gcc tcc tgc agg acc       105
Thr His Thr Cys Gln Pro Cys Cys Cys Lys Thr Ala Ser Cys Arg Thr
            5                  10                  15 tcc agc agc tct gaa tcc agc tct gaa tcc agc tgc cct gtg ttc atc      153
Ser Ser Ser Ser Glu Ser Ser Ser Glu Ser Ser Cys Pro Val Phe Ile
        20                  25                  30 tgc tgc gcc cca agt tgg tgc agc aca ccc tgt tgt tgc aag tct atc      201
Cys Cys Ala Pro Ser Trp Cys Ser Thr Pro Cys Cys Cys Lys Ser Ile
 35                  40                  45 tgc tgc cac agc acc aag act gtc aac agc tgt tcc cag ctg tgc tgt      249
Cys Cys His Ser Thr Lys Thr Val Asn Ser Cys Ser Gln Leu Cys Cys
 50                  55                  60                  65 cca cca acc tgc tgt gac cct gcc tcc tgt gac agc aac tgc tgc aag      297
Pro Pro Thr Cys Cys Asp Pro Ala Ser Cys Asp Ser Asn Cys Cys Lys
            70                  75                  80 cca acc tgt gtg acc atc tgc tgc agc aca cct tgc tgc cag ccc agc      345
Pro Thr Cys Val Thr Ile Cys Cys Ser Thr Pro Cys Cys Gln Pro Ser
        85                  90                  95 tgc tgc gtg ccc acc tgc tgc cag cct agc ctc ttc cag ctc tgc tgc      393
Cys Cys Val Pro Thr Cys Cys Gln Pro Ser Leu Phe Gln Leu Cys Cys
    100                 105                 110 caa cca act tgc tgt gaa acc agc tgc tgc aag acc acc tcc ttt aaa      441
Gln Pro Thr Cys Cys Glu Thr Ser Cys Cys Lys Thr Thr Ser Phe Lys
115                 120                 125 ccc tcc tgt gtg atc att ggt tgc agc aca ccc tgc tgc cag ccc tgc      489
Pro Ser Cys Val Ile Ile Gly Cys Ser Thr Pro Cys Cys Gln Pro Cys
    130                 135                 140                 145 tgt gtg tgc cca tct gcc gct gat aac cag ctc cca aag gaa caa agc      537
Cys Val Cys Pro Ser Ala Ala Asp Asn Gln Leu Pro Lys Glu Gln Ser
```

```
                    150                 155                 160
cat gct cct gcg aga gct ggc atg ccc tgt gtg cac gaa gcc acc tct    585
His Ala Pro Ala Arg Ala Gly Met Pro Cys Val His Glu Ala Thr Ser
            165                 170                 175 taa cctttgctgg ccaacttcat gttctcacca gggacctga caaatgtagg          638 ctttcttaag agatgaaatg tgttgaggaa ggatggagtc cctcaccctc tcatctccag  698
agactgtgga tcttgtacca tcttcatgtg tgactggcat gaagatctga tatcagctta  758
agttctgagg caggatcttt acatctctaa ccaaataact tacaaaggca cttcctccct  818
aagaataact ttatttaacc cgttatcttc ccaactgtat tttcttctgc ttctgaatta  878
ccccagattt tgtgtgtgcg atttccttct ttcttctcac tagtaagttg tgtacctaga  938
agcaaataat tttaataaac tttgtgctgc catcc                             973
```

<210> SEQ ID NO 196
<211> LENGTH: 177
<212> TYPE: PRT
<213> ORGANISM: Mus musculus
<400> SEQUENCE: 196

```
Met Thr His Thr Cys Gln Pro Cys Cys Cys Lys Thr Ala Ser Cys Arg
 1               5                  10                  15

Thr Ser Ser Ser Glu Ser Ser Glu Ser Ser Cys Pro Val Phe
            20                  25                  30

Ile Cys Cys Ala Pro Ser Trp Cys Ser Thr Pro Cys Cys Lys Ser
        35                  40                  45

Ile Cys Cys His Ser Thr Lys Thr Val Asn Ser Cys Gln Leu Cys
    50                  55                  60

Cys Pro Pro Thr Cys Cys Asp Pro Ala Ser Cys Asp Ser Asn Cys Cys
65                  70                  75                  80

Lys Pro Thr Cys Val Thr Ile Cys Cys Ser Thr Pro Cys Cys Gln Pro
                85                  90                  95

Ser Cys Cys Val Pro Thr Cys Cys Gln Pro Ser Leu Phe Gln Leu Cys
            100                 105                 110

Cys Gln Pro Thr Cys Cys Glu Thr Ser Cys Cys Lys Thr Thr Ser Phe
        115                 120                 125

Lys Pro Ser Cys Val Ile Ile Gly Cys Ser Thr Pro Cys Cys Gln Pro
    130                 135                 140

Cys Cys Val Cys Pro Ser Ala Ala Asp Asn Gln Leu Pro Lys Glu Gln
145                 150                 155                 160

Ser His Ala Pro Ala Arg Ala Gly Met Pro Cys Val His Glu Ala Thr
                165                 170                 175

Ser
```

<210> SEQ ID NO 197
<211> LENGTH: 684
<212> TYPE: DNA
<213> ORGANISM: Mus musculus
<220> FEATURE:
<221> NAME/KEY: CDS
<222> LOCATION: (1)..(684)

<400> SEQUENCE: 197

```
atg gct gcc tcc acc atg tct gtc tgt tct gac gct cgc acc aac tcc    48
Met Ala Ala Ser Thr Met Ser Val Cys Ser Asp Ala Arg Thr Asn Ser
 1               5                  10                  15 tcc tgg cag gtg gat gac tgc cca aag agc tgc tgt gag ccc tgc tgc    96
```

| | | |
|---|---|---|
| Ser Trp Gln Val Asp Asp Cys Pro Lys Ser Cys Cys Glu Pro Cys Cys<br>20 25 30 | | |
| tgt gcc ccc agc tgc tgc cag cca agc tgc tgc cag cca agc tgc tgt<br>Cys Ala Pro Ser Cys Cys Gln Pro Ser Cys Cys Gln Pro Ser Cys Cys<br>35 40 45 | | 144 |
| gtc ccc agt tgc tgt gcc ccc agc tgc tgt gtc ccc agc tgc tgc cag<br>Val Pro Ser Cys Cys Ala Pro Ser Cys Cys Val Pro Ser Cys Cys Gln<br>50 55 60 | | 192 |
| ccc agc tgc tgt gcc cca gcc ccc tgc ctg acc ctc atc tgc acc cca<br>Pro Ser Cys Cys Ala Pro Ala Pro Cys Leu Thr Leu Ile Cys Thr Pro<br>65 70 75 80 | | 240 |
| gta agc tgt gtg tcc agc ccc tgc tgc caa tct tcc tgc tgc aca ccc<br>Val Ser Cys Val Ser Ser Pro Cys Cys Gln Ser Ser Cys Cys Thr Pro<br>85 90 95 | | 288 |
| tca tgc tgc cag cag tct agc tgc cag cca gct tgc tgc acc tgc tcc<br>Ser Cys Cys Gln Gln Ser Ser Cys Gln Pro Ala Cys Cys Thr Cys Ser<br>100 105 110 | | 336 |
| ccc tgc cag cca tcc tgc tgt gta cct gtc tgc tgc act cct gtc tgc<br>Pro Cys Gln Pro Ser Cys Cys Val Pro Val Cys Cys Thr Pro Val Cys<br>115 120 125 | | 384 |
| tgc aca cct gtc tgc tgc aag cct gtg tgc tgc aca ccc atc tgc tct<br>Cys Thr Pro Val Cys Cys Lys Pro Val Cys Cys Thr Pro Ile Cys Ser<br>130 135 140 | | 432 |
| ggc tcc tcc tcc tgc tgc cag ccc tcc tgc tgt gct cct gtg tgc tgc<br>Gly Ser Ser Ser Cys Cys Gln Pro Ser Cys Cys Ala Pro Val Cys Cys<br>145 150 155 160 | | 480 |
| aag ccc ctg ctc cag cct gtc cct gct gtg tcg ccc agt gtg cag acc<br>Lys Pro Leu Leu Gln Pro Val Pro Ala Val Ser Pro Ser Val Gln Thr<br>165 170 175 | | 528 |
| tgc ctg ctg tgt gcc cac ctc ctc ctg tgc ctc ctc ctg cca gcc<br>Cys Leu Leu Cys Ala His Leu Leu Leu Cys Leu Leu Leu Pro Ala<br>180 185 190 | | 576 |
| cag ctg ctg tgg ccc aac ctc ctc tgt gtc cct gct gtg ccg ccc tgc<br>Gln Leu Leu Trp Pro Asn Leu Leu Cys Val Pro Ala Val Pro Pro Cys<br>195 200 205 | | 624 |
| ctc ctc cag aca ggc ctg ctg tgg aca gaa gtc cag ctg ctg aag gcc<br>Leu Leu Gln Thr Gly Leu Leu Trp Thr Glu Val Gln Leu Leu Lys Ala<br>210 215 220 | | 672 |
| tgt tcc tgg tga<br>Cys Ser Trp<br>225 | | 684 |

<210> SEQ ID NO 198
<211> LENGTH: 227
<212> TYPE: PRT
<213> ORGANISM: Mus musculus

<400> SEQUENCE: 198

Met Ala Ala Ser Thr Met Ser Val Cys Ser Asp Ala Arg Thr Asn Ser
1               5                   10                  15

Ser Trp Gln Val Asp Asp Cys Pro Lys Ser Cys Cys Glu Pro Cys Cys
            20                  25                  30

Cys Ala Pro Ser Cys Cys Gln Pro Ser Cys Cys Gln Pro Ser Cys Cys
        35                  40                  45

Val Pro Ser Cys Cys Ala Pro Ser Cys Cys Val Pro Ser Cys Cys Gln
    50                  55                  60

Pro Ser Cys Cys Ala Pro Ala Pro Cys Leu Thr Leu Ile Cys Thr Pro
65                  70                  75                  80

Val Ser Cys Val Ser Ser Pro Cys Cys Gln Ser Ser Cys Cys Thr Pro

-continued

```
            85                  90                  95
Ser Cys Cys Gln Gln Ser Ser Cys Gln Pro Ala Cys Cys Thr Cys Ser
                100                 105                 110

Pro Cys Gln Pro Ser Cys Cys Val Pro Val Cys Cys Thr Pro Val Cys
            115                 120                 125

Cys Thr Pro Val Cys Cys Lys Pro Val Cys Cys Thr Pro Ile Cys Ser
    130                 135                 140

Gly Ser Ser Ser Cys Cys Gln Pro Ser Cys Cys Ala Pro Val Cys Cys
145                 150                 155                 160

Lys Pro Leu Leu Gln Pro Val Pro Ala Val Ser Pro Ser Val Gln Thr
                165                 170                 175

Cys Leu Leu Cys Ala His Leu Leu Leu Cys Leu Leu Pro Ala
            180                 185                 190

Gln Leu Leu Trp Pro Asn Leu Leu Cys Val Pro Ala Val Pro Pro Cys
            195                 200                 205

Leu Leu Gln Thr Gly Leu Leu Trp Thr Glu Val Gln Leu Leu Lys Ala
    210                 215                 220

Cys Ser Trp
225

<210> SEQ ID NO 199
<211> LENGTH: 984
<212> TYPE: DNA
<213> ORGANISM: Mus musculus
<220> FEATURE:
<221> NAME/KEY: CDS
<222> LOCATION: (56)..(739)

<400> SEQUENCE: 199
cgacactcac acacattcat tcaacactca ctcaccctcc tccagcctac ccgcc atg        58
                                                            Met
                                                             1 gct gcc tcc acc atg tct gtc tgt tct gac gct cgc acc aac tcc tcc       106
Ala Ala Ser Thr Met Ser Val Cys Ser Asp Ala Arg Thr Asn Ser Ser
        5                  10                  15 tgg cag gtg gat gac tgc cca aag agc tgc tgt gag ccc tgc tgc tgt       154
Trp Gln Val Asp Asp Cys Pro Lys Ser Cys Cys Glu Pro Cys Cys Cys
            20                  25                  30 gcc ccc agc tgc tgc cag cca agc tgc tgc cag cca agc tgc tgt gtc       202
Ala Pro Ser Cys Cys Gln Pro Ser Cys Cys Gln Pro Ser Cys Cys Val
        35                  40                  45 ccc agt tgc tgt gcc ccc agc tgc tgt gtc ccc agc tgc tgc cag ccc       250
Pro Ser Cys Cys Ala Pro Ser Cys Cys Val Pro Ser Cys Cys Gln Pro
50                  55                  60                  65 agc tgc tgt gcc cca gcc ccc tgc ctg acc ctc atc tgc acc cca gta       298
Ser Cys Cys Ala Pro Ala Pro Cys Leu Thr Leu Ile Cys Thr Pro Val
                70                  75                  80 agc tgt gtg tcc agc ccc tgc tgc caa tct tcc tgc tgc aca ccc tca       346
Ser Cys Val Ser Ser Pro Cys Cys Gln Ser Ser Cys Cys Thr Pro Ser
            85                  90                  95 tgc tgc cag cag tct agc tgc cag cca gct tgc tgc acc tgc tcc ccc       394
Cys Cys Gln Gln Ser Ser Cys Gln Pro Ala Cys Cys Thr Cys Ser Pro
                100                 105                 110 tgc cag cca tcc tgc tgt gta cct gtc tgc tgc act cct gtc tgc tgc       442
Cys Gln Pro Ser Cys Cys Val Pro Val Cys Cys Thr Pro Val Cys Cys
            115                 120                 125 aca cct gtc tgc tgc aag cct gtg tgc tgc aca ccc atc tgc tct ggc       490
Thr Pro Val Cys Cys Lys Pro Val Cys Cys Thr Pro Ile Cys Ser Gly
130                 135                 140                 145
```

```
tcc tcc tcc tgc tgc cag ccc tcc tgc tgt gct cct gtg tgc tgc aag      538
Ser Ser Ser Cys Cys Gln Pro Ser Cys Cys Ala Pro Val Cys Cys Lys
                150                 155                 160 ccc ctg ctc cag cct gtc cct gct gtg tcg ccc agt gtg cag acc tgc      586
Pro Leu Leu Gln Pro Val Pro Ala Val Ser Pro Ser Val Gln Thr Cys
            165                 170                 175 ctg ctg tgt gcc cac ctc ctc ctg ctg tgc ctc ctc ctg cca gcc cag      634
Leu Leu Cys Ala His Leu Leu Leu Leu Cys Leu Leu Leu Pro Ala Gln
        180                 185                 190 ctg ctg tgg ccc aac ctc ctc tgt gtc cct gct gtg ccg ccc tgc ctg      682
Leu Leu Trp Pro Asn Leu Leu Cys Val Pro Ala Val Pro Pro Cys Leu
    195                 200                 205 ctc cag aca ggc ctg ctg tgg aca gaa gtc cag ctg ctg aag gcc tgt      730
Leu Gln Thr Gly Leu Leu Trp Thr Glu Val Gln Leu Leu Lys Ala Cys
210                 215                 220                 225 tcc tgg tga cagctgactt aggtcctggg gctcctctca gcttttccag              779
Ser Trp tctgactctg acctgggata gaaaatccac ccccaagatg tagcctccca acttgtccct    839
tgtgacttga tctctcctcc tgcttcctag gaggcctgct gatcctctgg gactctgcct    899
ttcctgtccc tttcttctgg ttgcttgccc ccaacgccag cctgtcagca gcccatggct    959
tcaataaacg ttttttaaca acctg                                         984

<210> SEQ ID NO 200
<211> LENGTH: 227
<212> TYPE: PRT
<213> ORGANISM: Mus musculus

<400> SEQUENCE: 200

Met Ala Ala Ser Thr Met Ser Val Cys Ser Asp Ala Arg Thr Asn Ser
1               5                   10                  15

Ser Trp Gln Val Asp Asp Cys Pro Lys Ser Cys Glu Pro Cys Cys
            20                  25                  30

Cys Ala Pro Ser Cys Cys Gln Pro Ser Cys Cys Gln Pro Ser Cys Cys
        35                  40                  45

Val Pro Ser Cys Cys Ala Pro Ser Cys Cys Val Pro Ser Cys Cys Gln
    50                  55                  60

Pro Ser Cys Cys Ala Pro Ala Pro Cys Leu Thr Leu Ile Cys Thr Pro
65                  70                  75                  80

Val Ser Cys Val Ser Pro Cys Cys Gln Ser Ser Cys Cys Thr Pro
                85                  90                  95

Ser Cys Cys Gln Gln Ser Ser Cys Gln Pro Ala Cys Cys Thr Cys Ser
            100                 105                 110

Pro Cys Gln Pro Ser Cys Cys Val Pro Val Cys Cys Thr Pro Val Cys
        115                 120                 125

Cys Thr Pro Val Cys Cys Lys Pro Val Cys Cys Thr Pro Ile Cys Ser
    130                 135                 140

Gly Ser Ser Ser Cys Cys Gln Pro Ser Cys Cys Ala Pro Val Cys Cys
145                 150                 155                 160

Lys Pro Leu Leu Gln Pro Val Pro Ala Val Ser Pro Ser Val Gln Thr
                165                 170                 175

Cys Leu Leu Cys Ala His Leu Leu Leu Leu Cys Leu Leu Leu Pro Ala
            180                 185                 190

Gln Leu Leu Trp Pro Asn Leu Leu Cys Val Pro Ala Val Pro Pro Cys
        195                 200                 205
```

```
Leu Leu Gln Thr Gly Leu Leu Trp Thr Glu Val Gln Leu Leu Lys Ala
    210                 215                 220

Cys Ser Trp
225

<210> SEQ ID NO 201
<211> LENGTH: 1281
<212> TYPE: DNA
<213> ORGANISM: Mus musculus
<220> FEATURE:
<221> NAME/KEY: CDS
<222> LOCATION: (139)..(531)

<400> SEQUENCE: 201
taacttggag gtcagaggaa gcaaacaagg aaggccagat gcattctggg taattggaac      60
actgagctgg gtataaaagc caccctggga aggagcttca gacatcctca ccttcttcca     120
aaccagccag cctctacc atg tgt cac acc agc tgc tct tca ggg tgc cag      171
                    Met Cys His Thr Ser Cys Ser Ser Gly Cys Gln
                     1               5                  10 cca tcc tgc tgt gtg tcc agc tcc tgc cag cca tcc tgt tgt gtg tct      219
Pro Ser Cys Cys Val Ser Ser Ser Cys Gln Pro Ser Cys Cys Val Ser
             15                  20                  25 agt ccc tgc cag gca tcc tgc ttt gtg tcc agc ccc tgc cag cca tcc      267
Ser Pro Cys Gln Ala Ser Cys Phe Val Ser Ser Pro Cys Gln Pro Ser
         30                  35                  40 tgc tgt gtg tcc agc tcc tgc cag tca gca tgc tgc agg cct gct ata      315
Cys Cys Val Ser Ser Ser Cys Gln Ser Ala Cys Cys Arg Pro Ala Ile
     45                  50                  55 tgc att cct gtt aga tac cag gta gcc tgc tgt gtg cct gtg agc tgt      363
Cys Ile Pro Val Arg Tyr Gln Val Ala Cys Cys Val Pro Val Ser Cys
 60                  65                  70                  75 ggg ccc act gtg tgc atg gct ccc tcc tgc cag tcc tct gtg tgt gtg      411
Gly Pro Thr Val Cys Met Ala Pro Ser Cys Gln Ser Ser Val Cys Val
                 80                  85                  90 cct gtg agc tgc cgg cct gtc tgt gtg acc tcc tcc tgc cag tca tct      459
Pro Val Ser Cys Arg Pro Val Cys Val Thr Ser Ser Cys Gln Ser Ser
             95                 100                 105 gga tgc tgc cag ccc tcc tgc ccc act ctg gtc tgc aag cct gtc acc      507
Gly Cys Cys Gln Pro Ser Cys Pro Thr Leu Val Cys Lys Pro Val Thr
        110                 115                 120 tgt agc aac ccc tct tgc tgt tga tcaggctctc aaaccagat cctgacagat     561
Cys Ser Asn Pro Ser Cys Cys
    125                 130 gggacacact tgctgtctca caacctgttc aacttgacct caggtttaga gttcgcacca     621
ggtgggaacc ctacctgtcc cacccgaac cttgaagaac agattccaga agtaggatct     681
gtatctgctg atctctcatg gatgtcctgg ctgcagggac cttctctaac cctgtgtact     741
aaataaacca gtttttttgag tttagctgca catgtctgtc ctgtttcatg cctaccttcc     801
tggttcctct tgaatcatga agaatgtgaa gttaatcaat ggtctctatg atccttggga     861
gatgaggtag ggtggaggac atggcctgat taaatgggtg tcttcaggtc cctgatattc     921
ctgtgcccag gggcccgcag aattggattt cctctttcat agctgcatcc tcttccctca     981
cccccttagc ccttcttttc cagtacagtg tccatatcca ctgcagacat tccgattatc    1041
cctggttgat ttttctctct ggtgcggtct tgtaatgctg ggttccttgt gacttttccc    1101
tacagggcac ttctaaaatg tttgactctt agttacataa catgattgat tgatcctgta    1161
acaccttccc ttcggcggtc acacatgccc atctttaatt gacaggtgat caactatgat    1221
```
gtagcaaaca tacatcattt gcaacttaga accagagagc atagttacat tctgctgact    1281

<210> SEQ ID NO 202
<211> LENGTH: 130
<212> TYPE: PRT
<213> ORGANISM: Mus musculus

<400> SEQUENCE: 202

Met Cys His Thr Ser Cys Ser Ser Gly Cys Gln Pro Ser Cys Cys Val
 1               5                  10                  15

Ser Ser Ser Cys Gln Pro Ser Cys Cys Val Ser Ser Pro Cys Gln Ala
            20                  25                  30

Ser Cys Phe Val Ser Ser Pro Cys Gln Pro Ser Cys Cys Val Ser Ser
        35                  40                  45

Ser Cys Gln Ser Ala Cys Cys Arg Pro Ala Ile Cys Ile Pro Val Arg
    50                  55                  60

Tyr Gln Val Ala Cys Cys Val Pro Val Ser Cys Gly Pro Thr Val Cys
65                  70                  75                  80

Met Ala Pro Ser Cys Gln Ser Ser Val Cys Val Pro Val Ser Cys Arg
                85                  90                  95

Pro Val Cys Val Thr Ser Ser Cys Gln Ser Ser Gly Cys Cys Gln Pro
            100                 105                 110

Ser Cys Pro Thr Leu Val Cys Lys Pro Val Thr Cys Ser Asn Pro Ser
        115                 120                 125

Cys Cys
    130

<210> SEQ ID NO 203
<211> LENGTH: 10
<212> TYPE: PRT
<213> ORGANISM: Mus musculus
<220> FEATURE:
<221> NAME/KEY: misc_feature
<222> LOCATION: (4)..(4)
<223> OTHER INFORMATION: "Xaa" can be Gln, Val, Arg, or Ile
<220> FEATURE:
<221> NAME/KEY: misc_feature
<222> LOCATION: (9)..(9)
<223> OTHER INFORMATION: "Xaa" can be Gln, Val, Arg, or Ile

<400> SEQUENCE: 203

Ser Cys Cys Xaa Pro Ser Cys Cys Xaa Pro
 1               5                  10

<210> SEQ ID NO 204
<211> LENGTH: 10
<212> TYPE: PRT
<213> ORGANISM: Mus musculus
<220> FEATURE:
<221> NAME/KEY: MISC_FEATURE
<222> LOCATION: (4)..(4)
<223> OTHER INFORMATION: "Xaa" can be Tyr, Leu or Phe

<400> SEQUENCE: 204

Tyr Gly Gly Xaa Gly Tyr Gly Ser Gly Tyr
 1               5                  10

HAIR KERATIN-ASSOCIATED PROTEINS

REFERENCE TO RELATED APPLICATIONS

This application is a continuation-in-part of International Application PCT/JP02/11851 filed on Nov. 13, 2002 and published as WO 03/042387 A1 on May 22, 2003, which application claims priority from Japanese Application No. 2001-348050 filed Nov. 13, 2001.

Each of the foregoing applications, and each document cited or referenced in each of the foregoing applications, including during the prosecution of each of the foregoing applications and ("application cited documents"), and any manufacturer's instructions or catalogues for any products cited or mentioned in each of the foregoing applications and articles and in any of the application cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

FIELD OF THE INVENTION

The present invention relates to a protein or a peptide having hair keratin binding activity, and a keratin-associated protein gene encoding the same; and a screening method and the like for substances promoting or suppressing hair keratin binding activity or the like by using said protein and peptide.

BACKGROUND OF THE INVENTION

Human hair fiber is produced in the hair follicles, which are composed of different particular epithelium and connective tissues and are one of the most active tissues in human body. It is well known that hair fiber is composed mainly of keratin-intermediate filaments (KIFs) and keratin-associated protein (KAPs), that KIFs are further classified into Type I and Type II, and forms a gene cluster on human chromosome 12 and 17 (Cytogenet. Cell Genet. 48, 148–151, 1988, Exp. Cell Res. 220, 357–362, 1995, Mol. Cell. Biol. 8, 722–736, 1988, Cytogenet. Cell Genet. 77, 169–174, 1997, Hum. Genet. 82, 109–112, 1989, Cytogenet. CellGenet. 57, 33–38, 1991, Genomics 24, 502–508, 1994). On the other hand, from the studies of animal other than human, it is reported that KAPs (keratin-associated protein) play a role as matrix embedding the space between KIFs and they are roughly classified into 3 groups based on their amino acid composition, that is ultra-high sulfur protein (cysteine content 30% or more), high sulfur protein (cysteine content 30% or less), and high Glycine/Tyrosine protein (glycine and tyrosine content 35–60%). As for KAPs, many cDNA are isolated from mice, rats, rabbits, sheep and the like, and for the present, proteins belonging to 17 sub-families have been identified (Powell, B. C., and Rogers, G. E. The role of keratin proteins and their genes in the growth, structure and properties of hair. In Formation and structure of human hair (ed. Jolles, P., Zahn, H., and Hocker, H.), pp. 59–148, Birkhauser Verlag, Basel., 1997; Genomics 54, 437–442, 1998; J. Invest. Dermatol. 111, 128–132, 1998; J. Invest. Dermatol. 111, 804–809, 1998; Mech. Dev. 86, 193–196, 1999; Development 128, 1547–1558, 2001; J. Biol. Chem. 276, 19440–19451, 2001). On the contrary, studies on human KAP have just begun.

Citation or identification of any document in this application is not an admission that such document is available as prior art to the present invention.

SUMMARY OF THE INVENTION

The object of the present invention relates to provide a protein group that binds to keratin, the main component of body hair and skin, and a gene encoding these, particularly to a protein strongly binding specifically to hair keratin that can be applied for the development of a novel hair restorer agent, a gene encoding the protein, or a screening method for substances promoting or suppressing hair keratin binding activity with the use of said protein and the like.

The present inventors have determined the base sequence of the euchromatic region of approximately 33.5 Mb of chromosome 21, with the international collaboration as a part of human genome project. A dot-matrix analysis of the base sequence of the long arm region of chromosome 21 (21q 22.3) was carried out, and the presence or the absence of low-frequency repetitive sequence was detected. As a result, they have found that 21 short sequences of approximately 0.05–1.2 kb being located spanning for approximately 163.5 kb and forming a cluster.

Further, a homology search was made for these repetitive sequences, and it was found that it is a KAP belonging to high sulfur protein having an amino acid composition rich in cysteine, among KAPs forming hair fiber, that the long-arm region of chromosome 21 (21g22.3) is a human KAP gene cluster. Moreover, by analyzing in detail the gene cluster, as 5 out of 21 were pseudogenes and 16 KAP genes were expressed only in hair root cells, it was found that it is a gene specifically related to hair. Furthermore, by masking the high-frequency repetitive sequences existing in the sequence spanning for approximately 1 Mb between CLDN8 gene and TIAM1 gene of the long arm region of chromosome 21 (21g22.11), and by searching the presence or the absence of short low frequency repetitive sequences, it was found that 5 genes and 3 pseudogenes form a cluster spanning for 95 kb, which belongs to a high sulfur type based on its amino acid composition; 18 genes and 3 pseudogenes form a cluster spanning for approximately 600 kb, belong to a high glycine tyrosine (G/Y) type based on its amino acid composition. Furthermore, the amino acid sequences being highly homologous to human KAPs were subjected to a data base search using Mouse whole genome shot-gun and BLAST. As a result, primary amino acid sequences comprising 14 mouse high G/Y type KAPs and 29 mouse high sulfur type KAPs were obtained, and after preparing an alignment from these primary amino acid sequences, repeat motif was searched and 2 functional peptides were found. Moreover, the present inventors determined that when KAPs are applied as hair growth agent, there is a possible problem of permeability into tissues in an intact size. Therefore, from the point of view of being a hair constituent element, the minimum repeat unit on KAPs sequence was searched to design a group of peptide targeting the crosslink within the tissues, and it was confirmed that these peptides have a hair growth/hair restoring effect.

The present invention was completed according to these knowledge.

In other words, the present invention relates to: a DNA that encodes keratin-associated protein which is (a) a protein comprising amino acid sequence shown in Seq. ID No. 2n (n shows any integer from 1 to 39), or (b) a protein comprising amino acid sequence shown in Seq. ID No. 2n (n shows any integer from 1 to 39), wherein one or several amino acids are deleted, substituted or added, and has hair-keratin binding activity ("1"); a DNA comprising a base sequence shown in Seq. ID Nos. 2n−1 (n shows any integer from 1 to 39) or its complementary sequence, or of a sequence containing a part or whole of these sequences ("2"); a DNA comprising a base sequence shown in Seq. ID Nos. 151, 155, 157, 159, 161, 163, 165, 167, 169, 171, 173, 175, 177, 179, 181, 183, 185, 187, 189, 193, 195, 197, 199 or 201 or its complementary sequence, or of a sequence containing a part or whole of theses sequences ("3"); a DNA that encodes a protein hybridizing under a moderate condition with the DNA according to "2" or "3", and has hair keratin binding activity ("4").

Furthermore, the present invention relates to: a protein comprising an amino acid sequence shown in Seq. ID No. 2n (n shows any integer from 1 to 39) ("5"); a protein comprising an amino acid sequence shown in Seq. ID No. 2n (n shows a integer from 1 to 39) wherein one or several amino acids are deleted, substituted or added, and has hair keratin binding activity ("6"); a protein comprising an amino acid sequence having hair keratin binding activity, shown in Seq. ID Nos. 152, 156, 158, 160, 162, 164, 166, 168, 170, 172, 174, 176, 178, 180, 182, 184, 186, 188, 190, 194, 196, 198, 200 or 202 ("7"); a protein comprising an amino acid sequence shown in Seq. ID Nos. 152, 156, 158, 160, 162, 164, 166, 168, 170, 172, 174, 176, 178, 180, 182, 184, 186, 188, 190, 194, 196, 198, 200 and 202, wherein one or several amino acids are deleted, substituted or added, and has hair keratin binding activity ("8").

Moreover, the present invention relates to: a peptide comprising a part of the protein according to any of "5" to "8", and binds specifically to keratin ("9"); a peptide comprising SCCXPSCCXP (X: Q, V, R, I) as set forth in Seq. ID No. 203, or whole or a part of SCCXPSCCXP (X: Q, V, R, I)("10"); a peptide comprising YGGXGYGSGY (X: Y, L, F) as set forth in Seq. ID No. 204, or whole or a part of YGGXGYGSGY (X: Y, L, F) ("11"); a fusion protein or a fusion peptide wherein the protein according to any of "5" to "8" or the peptide according to any of "9" to "11" is bound with a marker protein and/or a peptide tag ("12"); an antibody that binds specifically to the protein according to any of "5" to "8" or the peptide according to any of "9" to "11" ("13"); the antibody according to "13", wherein the antibody is a monoclonal antibody ("14"); a recombinant protein or peptide wherein the antibody according to "13" or "14" binds specifically ("15"); a recombinant vector comprising one or more DNA selected from the DNA that encodes the protein according to any of "5" to "8" or the peptide according to any of "9" to "11" ("16"); a host cell comprising an expressing system that can express one or more protein or peptide selected from the protein according to any of "5" to "8" or the peptide according to any of "9" to "11" ("17"); a preparation method of the protein according to any of "5" to "8" or the peptide according to any of "9" to "11", wherein the host cell according to "17" is cultured ("18"); a non-human animal wherein gene function that encodes the protein according to any of "5" to "8" or the peptide according to any of "9" to "11" is deleted on its chromosome ("19"); a non-human animal that overexpresses the protein according to any of "5" to "8" or the peptide according to any of "9" to "11" ("20"); the non-human animal according to any of "19" or "20", wherein the non-human animal is a mouse or a rat ("21").

Moreover, the present invention relates to: a screening method for substances promoting or suppressing hair keratin binding activity, wherein the protein according to any of "5" to "8" or the peptide according to any of "9" to "11", or the cell membrane expressing the protein according to any of "5" to "8" or the peptide according to any of "9" to "11", and a test substance are used ("22"); a screening method for substances promoting or suppressing hair keratin binding activity, or substances promoting or suppressing the expression of said protein or peptide, wherein the cells expressing the protein according to any of "5" to "8" or the peptide according to any of "9" to "11" and a test substance are used ("23"), the screening method for substances promoting or suppressing hair keratin binding activity or substances promoting or suppressing the expression of said protein or peptide according to "23", wherein the cells expressing the protein according to any of "5" to "8" or the peptide according to any of "9" to "11" are the host cell according to "17" ("24"); the screening method for substances promoting or suppressing hair keratin binding activity or for substances promoting or suppressing the expression of the protein according to any of "5" to "8" or the peptide according to any of "9" to "11", wherein the non-human animal according to any of "19" to "21" and a test substance are used ("25").

Furthermore, the present invention relates to a substance promoting hair keratin binding activity, obtained by the screening method according to any of "22" to "25" ("26"); a substance suppressing hair keratin binding activity obtained by the screening method according to any of "22" to "25" ("27"); a substance promoting the expression of the protein according to any of "5" to "8" or the peptide according to any of "9" to "11", obtained by the screening method according to any of "22" to "25" ("28"); a substance suppressing the expression of the protein according to any of "5" to "8" or the peptide according to any of "9" to "11", obtained by the screening method according to any of "22" to "25" ("29"); a cosmetic/therapeutic agent, wherein the active ingredients are one or more types selected from a group comprising the protein according to any of "5" to "8" or the peptide according to any of "9" to "11", the recombinant protein or peptide according to "15", the recombinant vector according to "16", the host cell according to "17", the substance promoting hair keratin binding activity according to "26", or the substance promoting the expression according to "28" ("30"); a cosmetic/therapeutic agent, wherein the active ingredients are one or more types selected from a group comprising the antibody according to "13" or "14", the substance suppressing hair keratin binding activity according to "27" or the substance suppressing the expression according to "29" ("31").

BRIEF DESCRIPTION OF DRAWINGS

FIG. 3 is a figure that shows the results of evaluating the identity between the KAP amino acid sequences in the 21q22.3 region of human chromosome.

FIG. 6 is a figure that compares the DNA (CDS) and the amino acid sequence encoding KAP02 (Seq. ID Nos. 2 and 3, respectively) and KAP09 (Seq. ID Nos. 17 and 18, respectively) of the present invention.

FIG. 7 is a picture that shows the estimated secondary structure of each KAP protein of the present invention.

FIG. 11 is a picture that shows the results of C.B.B. staining and Western Blot Analysis for the expression of 36 types of recombinant human KAPs, with the use of vectors pTriEx-1.1, pET-31b(+) and pFLAG-CTC.

FIG. 12 is a picture that shows the results of C.B.B. staining and Western Blot Analysis for the expression of 10 types of recombinant human KAPs, with the use of pET-32a.

FIG. 16 is a figure that shows the amino acid sequences of 3 KAP proteins (Seq. ID Nos. 118, 120, 122) belonging to Group 1 of mouse high G/Y type KAPs.

FIG. 17 is a figure that shows the amino acid sequences of 3 KAPs proteins (Seq. ID Nos. 124, 126, 128) belonging to Group 2 of mouse high G/Y type KAPs.

FIG. 18 is a figure that shows the amino acid sequences of 8 KAPs proteins (Seq. ID Nos. 130, 132, 134, 136, 138, 140, 142, 144) belonging to Group 3 of mouse high G/Y type KAPs.

Figure 19:
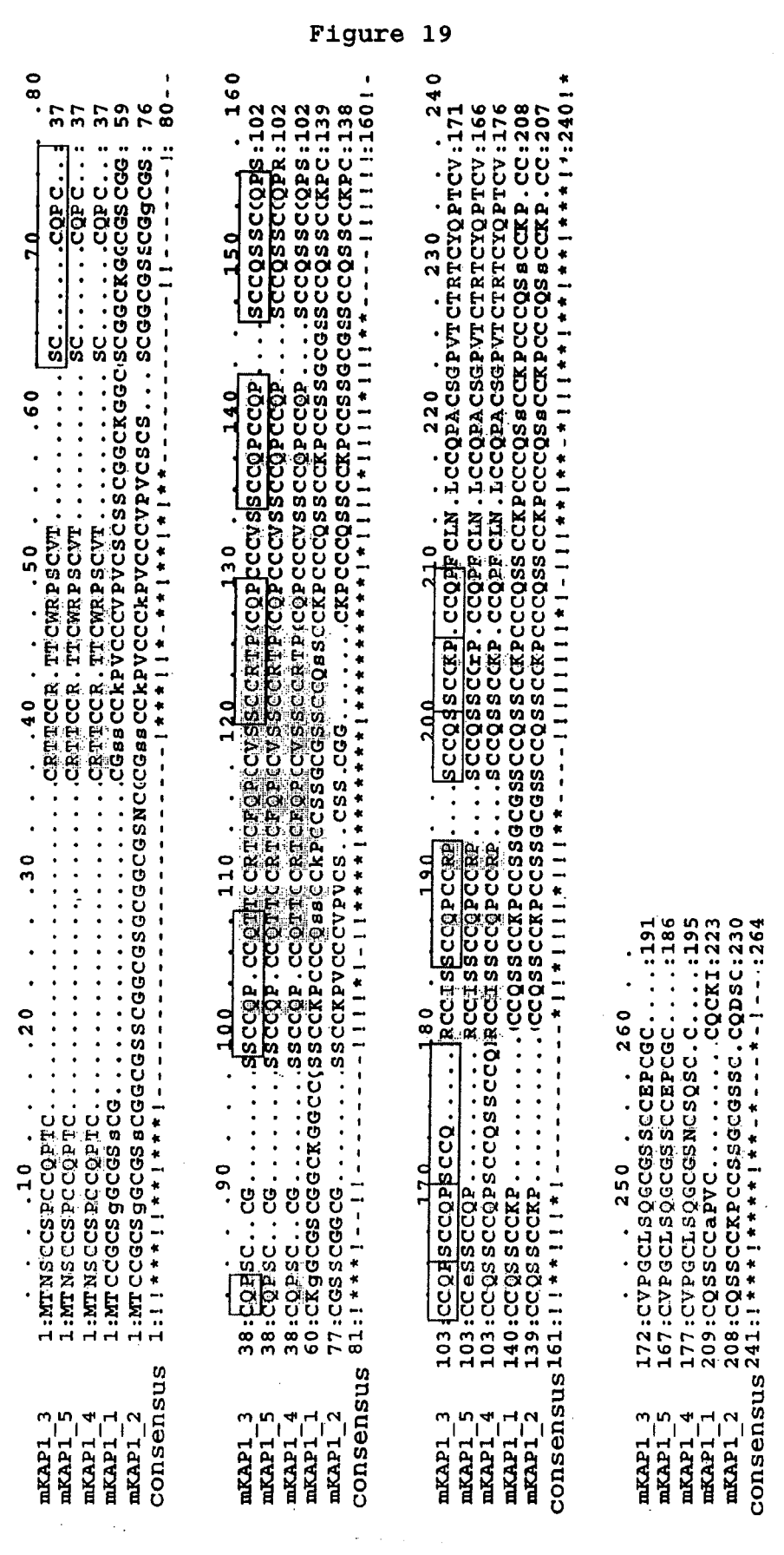

FIG. 19 is a figure that shows the amino acid sequences of 5 KAPs proteins (Seq. ID Nos. 146, 148, 150, 152, 154) belonging to Group 1 of mouse high sulfur type KAPs.

Figure 20:
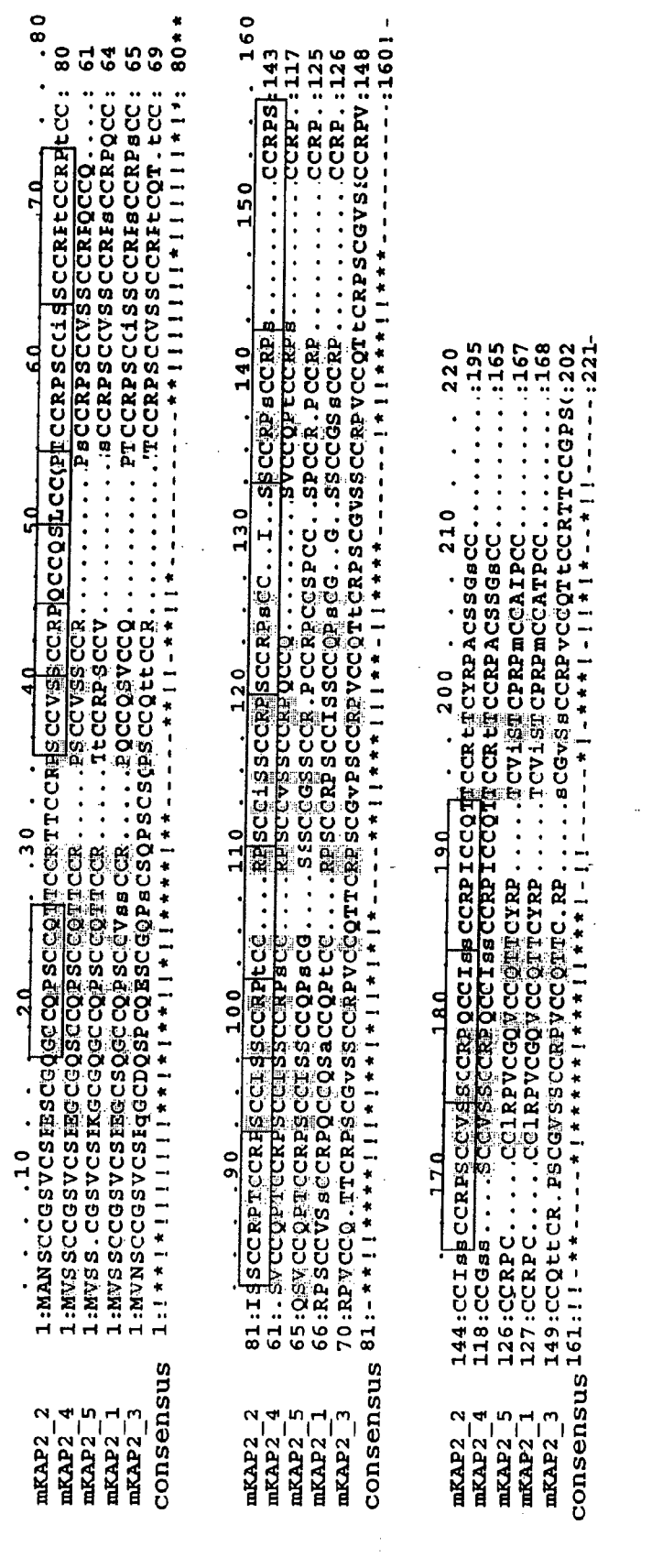

FIG. 20 is a figure that shows the amino acid sequences of 5 KAPs proteins (Seq. ID Nos. 156, 158, 160, 162, 164) belonging to Group 2 of mouse high sulfur type KAPs.

FIG. 21 is a figure that shows the amino acid sequences of 2 KAPs proteins (Seq. ID Nos. 166, 168) belonging to Group 3 of mouse high sulfur type KAPs.

Figure 22:
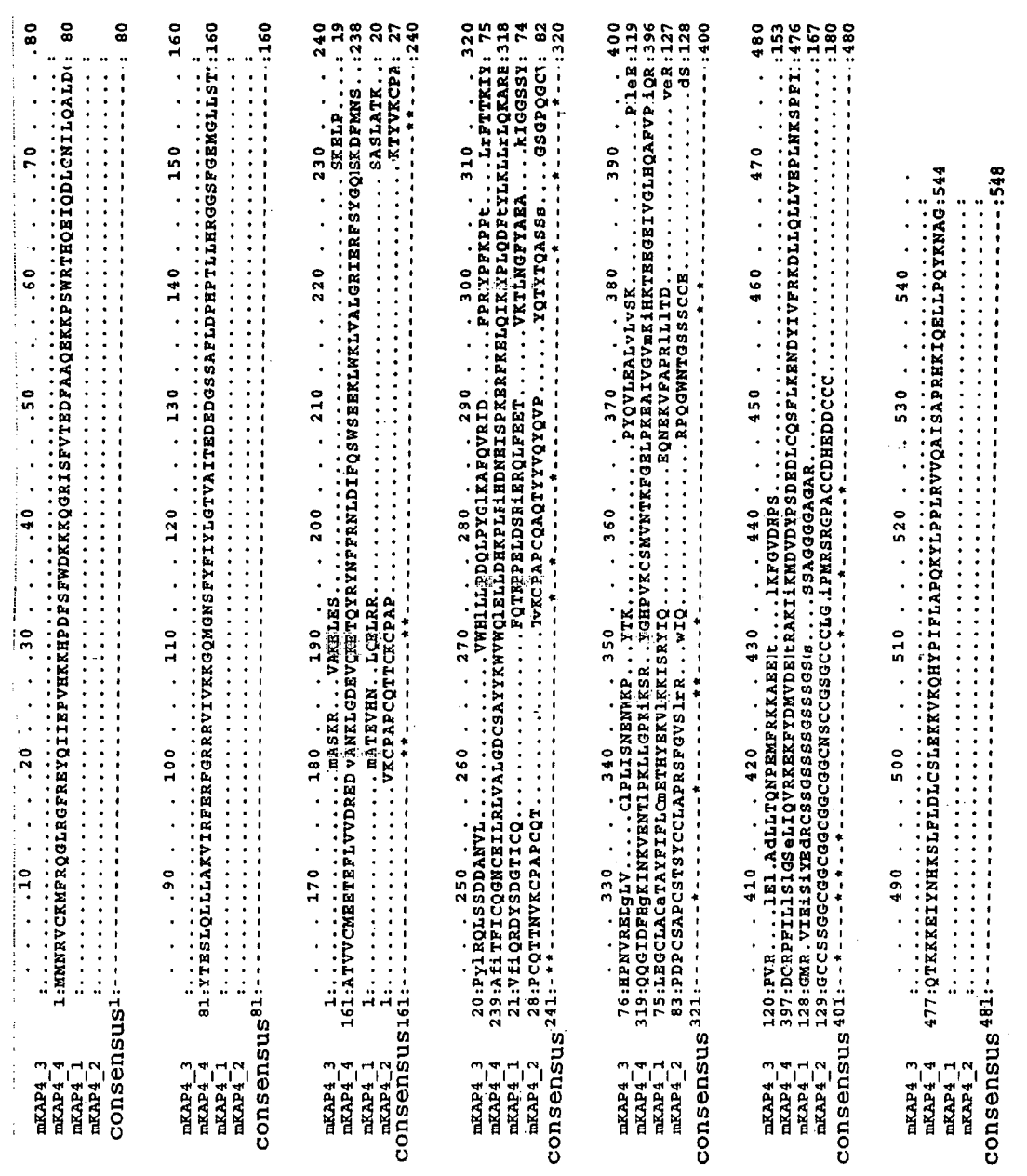

FIG. 22 is a figure that shows the amino acid sequences of 4 KAPs proteins (Seq. ID Nos. 170, 172, 174, 176) belonging to Group 4 of mouse high sulfur type KAPs.

FIG. 23 is a figure that shows the amino acid sequences of 5 KAPs proteins (Seq. ID Nos. 178, 180, 182, 184, 186) belonging to Group 5 of mouse high sulfur type KAPs.

FIG. 24 is a figure that shows the amino acid sequences of 5 KAPs proteins (Seq. ID Nos. 188, 190, 192, 194, 196) belonging to Group 6 of mouse high sulfur type KAPs.

Figure 25:
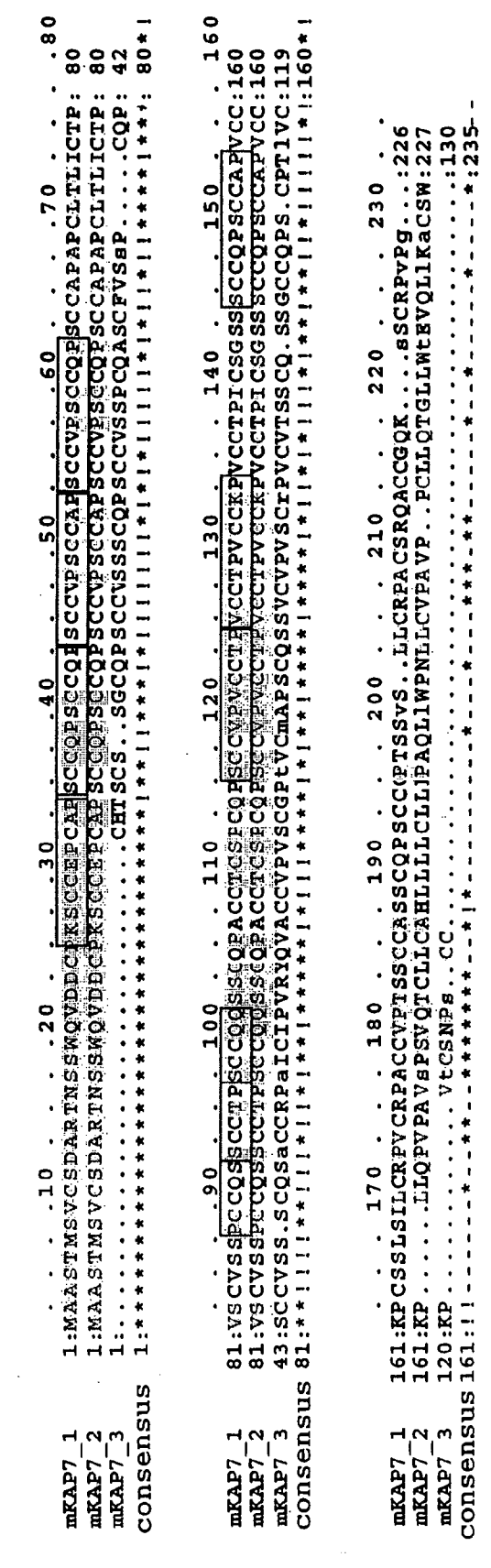

FIG. 25 is a figure that shows the amino acid sequences of 3 KAPs proteins (Seq. ID Nos. 198, 200, 202) belonging to Group 7 of mouse high sulfur type KAPs.

FIG. 26 is a figure that shows the GenBank Accession numbers of 29 mouse high sulfur type KAPs.

DETAILED DESCRIPTION

Figure 1:
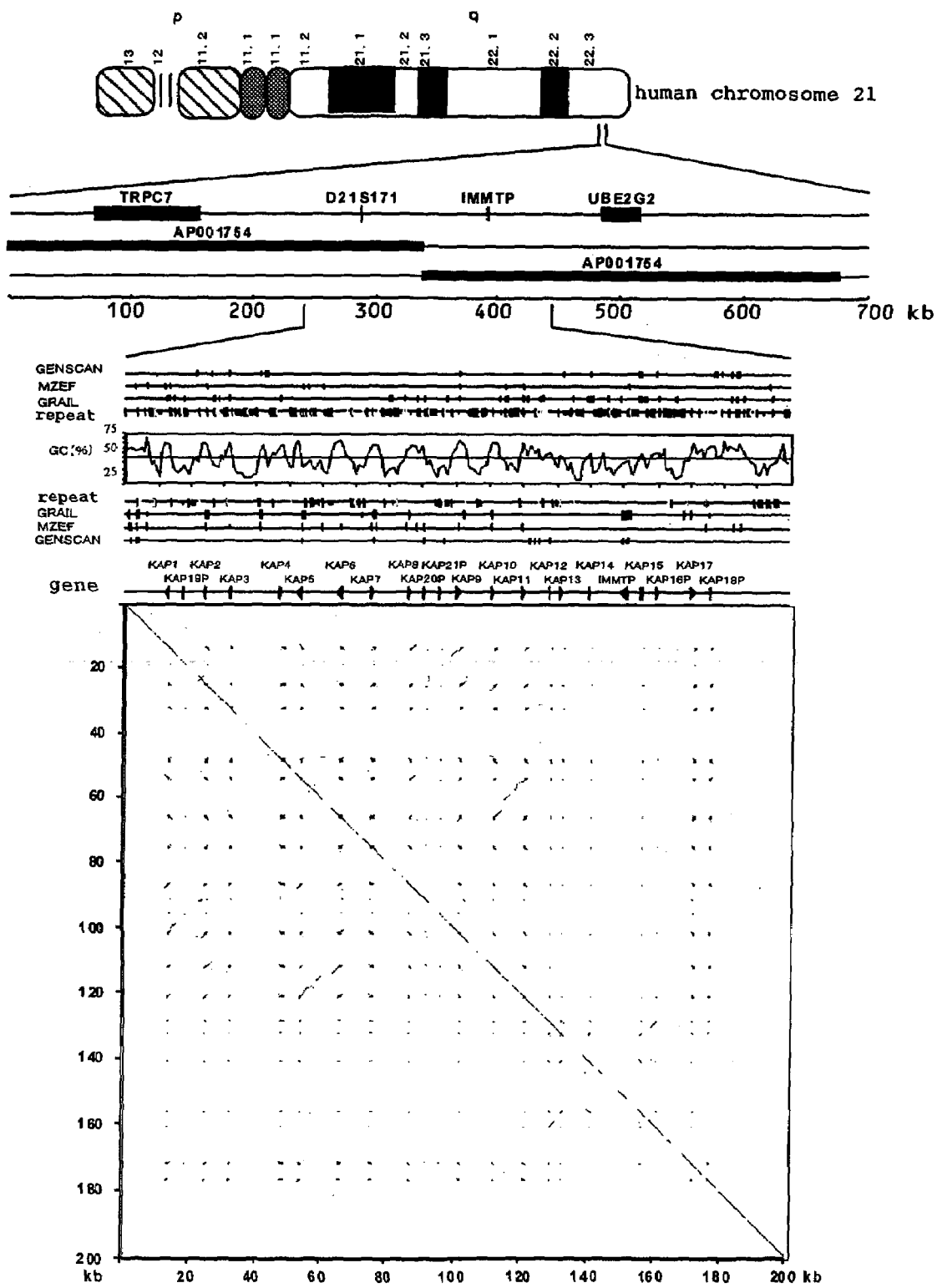
FIG. 1 is a picture that shows the results of evaluating the presence or the absence of the low frequency repetitive sequences in the 21q22.3 region of human chromosome.

As for the protein that is the object of the present invention, examples include: keratin-associated protein comprising an amino acid sequence shown in Seq. ID No. 2n (n shows any integer from 1 to 16), that can be identified from the amino acid sequence information encoded by the base sequence of the long arm region of human chromosome 21 (21q22.3); keratin-associated protein comprising an amino acid sequence shown as Seq. ID No. 2n (n shows any integer from 17 to 39), that can be identified from the amino acid sequence information encoded by the base sequence of the long arm region of human chromosome 21 (21q22.11), that is the keratin-associated protein (KAP) comprising the amino acid sequence shown in Seq. ID No. 2n (n shows any integer from 1 to 39); a protein comprising an amino acid sequence shown in Seq. ID No. 2n (n shows any integer from 1 to 39), wherein one or several amino acids are deleted, substituted or added, and having hair keratin binding activity, protein having hair keratin binding activity comprising an amino acid sequence shown in Seq. ID Nos. 152, 156, 158, 160, 162, 164, 166, 168, 170, 172, 174, 176, 178, 180, 182, 184, 186, 188, 190, 194, 196, 198, 200 and 202, protein comprising an amino acid sequence shown in Seq. ID Nos. 152, 156, 158, 160, 162, 164, 166, 168, 170, 172, 174, 176, 178, 180, 182, 184, 186, 188, 190, 194, 196, 198, 200 and 202, wherein one or several amino acids are deleted, substituted or added and having hair keratin binding activity, and recombinant protein of these, and the like. However, hair is not limited to head hair, but relates to all body hair.

Moreover, as for the part peptide of the above-mentioned keratin-associated protein, which is the object of the present invention, there is no specific limitation as long as it is composed of a part of the above-mentioned keratin-associated protein, and it is a peptide having an amino acid sequence binding specifically to hair keratin, a peptide comprising SCCXPSCCXP (X: Q, V, R, I) as set forth in Seq. ID No. 203, or whole or a part of SCCXPSCCXP (X: Q, V, R, I), or a peptide comprising YGGXGYGSGY (X: Y, L, F) as set forth in Seq. ID No. 204, or whole or a part of YGGXGYGSGY (X: Y, L, F). Among the above-mentioned peptides having an amino acid sequence binding specifically to hair keratin, SCCAP, SCCVP, SCCKP, SCCRP, SCCQQ, QQSSC can be preferably exemplified as a high sulfur type human peptide, and GGGYG, GYGCG, YGGGY, YGCGY, GYGYG, YGYGC can be preferably exemplified as a high G/Y type human peptide. All peptide sequences were derived from consensus motifs of each KAP amino acid sequence, respectively.

The keratin-associated protein and a part peptide of keratin-associated protein, and recombinant protein and peptide to which antibodies specifically binding to these proteins and peptides are bound specifically, that are the objects of the present invention may be related collectively as "protein/peptide of the present invention" hereinafter. In addition, the protein/peptide of the present invention can be prepared by publicly known methods, or by publicly known chemical synthesis method according to its DNA sequence information and the like, and there is no specific limitation for their origin.

As for DNA as an object of the present invention, there is no specific limitation as long as it encodes a protein/peptide of the present invention mentioned above, and examples include: a gene that encodes keratin-associated protein comprising an amino acid sequence shown in Seq. ID No. 2n (n shows any integer from 1 to 39), a gene that encode a protein comprising an amino acid sequence shown in Seq. ID No. 2n (n shows any integer from 1 to 39), wherein one or several amino acids are deleted, substituted or added, and that has hair keratin binding activity; DNA comprising an base sequence shown in Seq. ID No. 2n–1 (n shows any integer from 1 to 39) or its complementary sequence, or of a sequence containing a part or whole of these sequences; DNA comprising a base sequence shown in Seq. ID No. 151, 155, 157, 159, 161, 163, 165, 167, 169, 171, 173, 175, 177, 179, 181, 183, 185, 187, 189, 193, 195, 197, 199 and 201 that encode proteins having hair keratin binding activity or its complementary sequence, or of a sequence containing a part or whole of these sequences. These can be prepared by publicly known methods according to the DNA sequence information and the like, from gene library or from cDNA library and the like of human, mouse, rat, rabbit, sheep and the like. For example, DNA comprising a base sequence shown in Seq. ID No. 2n–1 (n shows any integer from 1 to 16) can be prepared from the long arm region of human genome chromosome 21 (21q22.3), and DNA comprising a base sequence shown in Seq. ID. No. 2n–1 (n shows any integer from 17 to 38) can be prepared from the long arm region of human genome chromosome 21 (21q22.11), by a common procedure according to its sequence information.

Moreover, as human KAP family shows almost no homology at DNA base level, although there is some correlation at amino acid level of protein, it is preferable to perform screening widely to find a novel KPA-related gene. From this point of view, as for DNA of the present invention, by making as a probe the DNA comprising a base sequence shown in Seq. ID No. 2n–1 (n shows any integer from 1 to 39) or its complementary sequence, or of a sequence comprising a sequence containing a part or whole of these sequences, it can be exemplified by a DNA that was hybridized under a moderate condition, preferably under stringent condition to various DNA library, and that encodes a protein having hair keratin binding activity. As for hybridization under moderate condition to obtain such DNA, it can be exemplified by hybridization at 42° C., and washing treatment at 42° C. with a buffer solution containing 0.1×SSC and 0.1% SDS. Furthermore, as for hybridization under stringent condition, it can be exemplified by hybridization at 65° C., and a washing treatment at 65° C. with a buffer solution containing 1×SSC and 0.1% SDS. Additionally, as for factors influencing the stringency of the hybridization, there are various factors besides the temperature condition above mentioned, and a person skilled in the art can realize a stringency equivalent to that for hybridization that was exemplified in the above, by combining appropriately various factors.

As for the fusion protein or fusion peptide of the present invention, there is no specific limitation as long as the protein/peptide of the present invention and the marker protein and/or peptide tag are bound. As for a marker protein, there is no specific limitation as long as it is a marker protein that is conventionally known, and it can be exemplified by alkali phosphataze, Fc region of an antibody, HRP, GFP and the like.

Moreover, as for an peptide tag of the present invention, peptide tags that are conventionally known such as HA tag, Myc tag, His tag, FLAG tag, GST tag and the like can be exemplified concretely. A fusion protein can be prepared by a common procedure, and it can be useful for purification of keratin-associated protein and the like by using the affinity of Ni-NTA and His tag, detection of keratin-associated protein, determination of antibody to keratin-associated protein and the like, or as a hair cosmetic/therapeutic agent and the like such as hair restorer agent for head hair, beard and the like, hair coloring agent, transforming agent of hair characteristics (curl and the like), substances promoting or suppressing hair keratin binding activity, substances promoting or suppressing the expression of the protein/peptide of the present invention, as well as a laboratory reagent of the art.

As for an antibody binding specifically to said protein or peptide of the present invention, immune specific antibody such as monoclonal antibody, polyclonal antibody, chimeric antibody, single-chain antibody, humanized antibody and the like can be exemplified concretely. These can be prepared by a common procedure with the use of a part or whole of protein/peptide of the present invention, fusion protein or fusion peptide and the like as an antigen, and among these, a monoclonal antibody is preferable from the point of view of its specificity. The antibodies such as said monoclonal antibody and the like are useful, for example, for detection/determination of protein/peptide of the present invention, as substances promoting or suppressing hair keratin binding activity, or as substances promoting or suppressing the expression of the protein/peptide of the present invention and the like, or to clarify the mechanism of the formation of hair fiber, and the like.

The antibodies of the present invention mentioned above, are generated with the use of conventional protocol, by administrating protein/peptide of the present invention, or cells expressing these on the surface of the membrane, to animals (preferably non-human animals). For example, as for preparation of monoclonal antibodies, any method such as hybridoma method (Nature 256, 495–497, 1975), trioma method, human B cells hydridoma method (Immunology Today 4, 72, 1983) and EBV-hybridoma method (MONOCLONAL ANTIBODIES AND CANCER THERAPY, pp. 77–96, Alan R. Liss, Inc., 1985) and the like that yield antibodies produced by culture of continuous cell system can be used.

As for producing a single-chain antibody against protein/peptide of the present invention mentioned above, the preparation method of a single-chain antibody can be applied (U.S. Pat. No. 4,946,778). Moreover, as for expressing humanized antibody, it is possible to use transgenic mice or other mammals and the like, to isolate/identify clones expressing protein/peptide of the present invention by using the above-mentioned antibodies, or to purify the polypeptide with an affinity chromatography. As for the antibodies against protein/peptide of the present invention, it is possible to use them for detection/determination of protein/peptide of the present invention, as a substance promoting or suppressing hair keratin binding activity, or as a substance promoting or suppressing the expression of the protein/peptide of the present invention, or to clarify the mechanism of the formation of hair fiber and the like. Moreover, the recombinant protein or peptide to which these antibodies bound specifically are also encompassed in the protein/peptide of the present invention, as mentioned above.

Moreover, the function of the protein/peptide of the present invention can be clarified by using fusion protein produced by labeling antibodies such as the monoclonal antibodies and the like mentioned above with, for example, fluorescent substances such as FITC (fluorescein isothiocyanate) or tetramethyl rhodamine isothiocyanate and the like, radioisotopes such as $^{125}I$ $^{32}P$ $^{14}C$ $^{35}S$ or $^{3}H$ and the like, or labeled with enzymes such as alkali phosphatase, peroxidase, β-galactosidase or phycoerythrin and the like, or a fusion protein fused with fluorescence luminescent protein such as green fluorescence protein (GFP) and the like. Furthermore, as for immunological assay method using antibodies of the present invention, it can be exemplified by RIA method, ELISA method, fluorescence antibody technique, plaque method, spotting method, hemagglutination method, ouchterlony method and the like.

As for a recombinant vectors of the present invention, there is no specific limitation as long as it is a vector that contains one or more DNA among DNA encoding the protein/peptide of the present invention, but it is preferable that it contains an expression system that can express in the host cells, one or more proteins or peptides among the protein/peptide of the present invention. Examples include expression systems derived from chromosome, episome and virus, more concretely vectors derived from bacterial plasmid, derived from yeast plasmid, vectors derived from papovavirus such as SV40, vaccinia vilus, adenovirus, fowl poxvirus, pseudorabies virus, retrovirus, or vectors derived from combinations thereof, such as those derived from plasmid and bacteriophage genetic elements, such as cosmids and phagemids. The expression system can contain regulatory sequence that not only promotes expression but also controls the expression.

The present invention further relates to host cells comprising an expression system that can express the protein/peptide of the present invention or to a preparation method of the protein/peptide of the present invention, wherein the host cells are cultured. The introduction of the genes that encodes the protein/peptide of the present invention to the host cells, can be preformed by methods described in many standard guidelines of laboratories such as Davis et al. (BASIC METHODS IN MOLECULAR BIOLOGY, 1986) and Sambrook et al. (MOLECULAR CLONING: A LABORATORY MANUAL, 2nd Ed., Cold Spring Harbor Laboratory Press, Cold Spring Harbor, N.Y., 1989), for example methods such as calcium phosphate transfection, DEAE-dextran mediated transfection, transvection, microinjection, cationic lipid mediated transfection, electroporation, transduction, scrape loading, ballistic introduction, infection and the like. Additionally, as for the host cells, examples include: bacteria prokaryotic cells such as *E. cola, streptomyces, Bacillus subtilis, streptococcus, staphylococcus* and the like, fungal cells such as yeast, *Aspergillus* and the like, insect cells such as *Drosophila* S2, *Spodoptera* Sf9 and the like, animal cells such as L cells, CHO cells, COS cells, NIH3T3 cells, HeLa cells, C127 cells, BALB/c3T3 cells (including mutants wherein dihydrofolate reductase or thymidine kinase and the like is deficient), BHK21 cells, HEK293 cells, Boewes malignant melanoma cells and the like, or plant cells and the like.

Furthermore, as for an expression system, there is no specific limitations as long as it is an expression system that can express the protein/peptide of the present invention in the host cells, and examples include expression systems derived from chromosome, episome, mammals and virus, for example vectors derived from bacterial plasmid, yeast plasmid, papovavirus such as SV40, vaccinia virus, adenovirus, fowl poxvirus, pseudorabies virus, retrovirus, vectors derived from bacteriophage, transposon or vectors derived from combinations thereof, such as those derived from plasmid and bacteriophage genetic elements, such as cosmids and phagemids can be exemplified. This expression system can include a regulatory sequence that not only promotes expression but controls the expression.

As for the host cells comprising the above-mentioned expression systems, and the protein/peptide of the present invention obtained by culturing the cell membrane of the cells, or the cells, they can be used for the screening method of the present invention as described hereinafter. For example, as for the method for obtaining the cell membrane, the method of F. Pietri-Rouxel et al. (Eur. J. Biochem., 247, 1174–1179, 1997) and the like can be used. Moreover, as for the method to recover and purify the protein/peptide of the present invention from the cell culture, publicly known methods including ammonium sulfate precipitation or ethanol precipitation, acid extraction, anion or cation exchange chromatography, phosphocellulose chromatography, hydrophobic interaction chromatography, affinity chromatography, hydroxyapatite chromatography and lectin chromatography, and preferably high performance liquid chromatography are used. Especially, as for the column to be used for affinity chromatography, column to which antibodies against the protein/peptide of the present invention or keratin are bound, or in case normal peptide tag is added to the protein/peptide of the present invention, the protein/peptide of the present invention can be obtained by using a column wherein a substance having affinity to the peptide tag. As for the purification method of the protein/peptide of the present invention, it can be also used for peptide synthesis.

In the present invention, a non-human animal wherein the gene function encoding the protein/peptide of the present invention is deleted on its chromosome, is related to a non-human animal wherein a part or whole of a gene encoding the protein/peptide of the present invention on the chromosome is inactivated by gene mutation such as disruption, deletion, substitution and the like, and thus has lost the function to express the protein/peptide of the present invention. Moreover, as for the non-human animal that overexpress the protein/peptide of the present invention, non-human animals that produce a large amount of the protein/peptide of the present invention compared to wild-type non-human animals can be exemplified concretely. Moreover, as for the non-human animal of the present invention, non-human animals such as rodents such as mice, rats and the like can be exemplified concretely, but they are not limited to these.

Meanwhile, as for homozygous non-human animals generated according to Mendel's law, deficient-type and overexpressing-type of the protein/peptide of the present invention, and their wild-type littermates are included. As it is possible to perform accurate comparative experiments at an individual level by using at the same time the deficient-type or overexpressing-type of the homozygous non-human animals and their wild-type littermates, it is preferable to use at the same time an wild-type non-human animal, in other words, an animal of the same species as the non-human animal wherein the gene function to encode the protein/peptide of the present invention is deleted or overexpressed on its chromosome or the littermates of these, at the time of the screening of the present invention that is described hereinafter. The preparation method of a non-human animal wherein the gene function encoding the protein/peptide of the present invention is deleted or overexpressed on its chromosome is explained in the following, by taking a KAP1 knockout mouse or human KAP1 transgenic mouse as example.

For example, mice wherein the gene function encoding KAP1 protein is deleted on its chromosome, that is KAP1 knockout mice, are determined by DNA sequencing. The process comprises the following step: the gene that encodes mouse KAP1 having homology with human KAP1 is screened by using gene fragments obtained from the mouse gene library by PCR and the like, and a gene encoding the screened mouse KAP1 is subcloned using viral vectors and the like. A part or whole of the gene that encodes mouse KAP1 in this clone is replaced by with pMCl neo gene cassette and the like, genes such as Difteria toxin A fragment (DT-A) genes, herpes simplex virus thymidine kinase (HSV-tk) genes and the like are introduced to 3' end side, to prepare a targeting vector.

The targeting vector thus prepared is linearized, and then introduced into ES cells by electoporation and the like to perform homologous recombination. Among the homologous recombinants, ES cells wherein homologous recombination occurred by antibiotics such as G418, Ganciclovir (GANC) and the like are selected. Moreover, it is preferable to confirm whether these ES cells are the targeted recombinants by Southern Blot Analysis and the like. Clones of the verified ES cells are microinjected into a mouse blastocyst, and the blastocyst is placed back to the host parent to generate a chimeric mouse. When this chimeric mouse is intercrossed with a wild-type mouse, heterozygous mouse can be obtained, and by intercrossing the heterozygous mouse, KAP1 knockout mouse of the present invention can be obtained. Moreover, as for a method to verify if the ability of expressing KAP1 is deleted in KAP1 knockout mouse, for example, it is possible to perform Northern Blot Analysis by isolating RNA from mouse prepared as above mentioned, or to observe directly KPAI expression in the mouse by Western Blot Analysis or the like.

The transgenic mouse of KAP1 is prepared as follows: a transgene is constructed by fusing promoters such as chicken β-actin, mouse neurofilament, SV40 and the like, polyA such as rabbit β-globin, SV40 and the like or intron, to cDNA that encodes KAP1 derived from human, mouse, rat, rabbit and the like, the transgene is microinjected to pronucleus of mouse fertilized egg, and after the obtained ovum is cultured, it is transplanted to the oviduct of the forest parent mouse. Afterwards, the transplanted animals are bred. By selecting among the generated mice baby mice having said cDNA, it is possible to generate transgenic mice. Furthermore, as for the selection of the baby mouse having cDNA, it can be done by Dot hybridization wherein the gene that encodes the introduced KAP1 is used as a probe, by extracting crude DNA from mouse tail and the like, or by PCR method using specific primers, or the like.

Moreover, the host cells and the like comprising genes or DNA that encode the protein/peptide of the present invention mentioned above, the protein/peptide of the present invention, the fusion protein wherein the protein/peptide of the present invention and marker protein and/or peptide tag are bound, an antibody against the protein/peptide of the present invention, and the expression system that can express the protein/peptide of the present invention, can not only be used as hair cosmetic/therapeutic agent and the like such as hair restorer for head hair, beard and the like, hair coloring agent, transforming agent of hair characteristics (curl and the like), or for screening of substance promoting or suppressing hair keratin binding activity or substance promoting or suppressing the expression of the protein/peptide of the present invention, but also to clarify the mechanism of the formation of hair fiber.

As for the screening of substance promoting or suppressing hair keratin binding activity, examples include a method using the protein/peptide of the present invention above mentioned or the cell membrane expressing the protein/peptide of the present invention and a test substance; a method using cells expressing the protein/peptide of the present invention and a test substance; a method using non-human animals such as knockout mouse or transgenic mouse of the protein/peptide of the present invention and the like and a test substance, and the like. Additionally, the method using the cells expressing the protein/peptide of the present invention and a test substance, the method using non-human animals such as knockout mouse or transgenic mouse of the protein/peptide of the present invention and the like and a test substance, can be used for the screening method for substances promoting or suppressing the expression of the protein/peptide of the present invention.

As for the screening method using the protein/peptide of the present invention mentioned above or the cell membrane expressing the protein/peptide of the present invention and a test substance, it can be exemplified concretely by a method wherein the protein/peptide of the present invention or the protein/peptide of the present invention that is expressed on the surface of the cell membrane, is contacted with a test substance, the hair keratin binding ability of the protein/peptide of the present invention is measured, to compare and estimate with those that are not contacted with the test substance. Moreover, as for the screening method using the cells expressing the protein/peptide of the present invention and a test substance, it can be exemplified concretely by a method wherein the cells expressing protein/peptide of the present invention are contacted with the test substance, the hair keratin binding ability of the protein/peptide of the present invention or the change in the expression level of the protein/peptide of the present invention is measured, to compare and estimate with those that are not contacted with the test substance.

As for the screening method using non-human animal wherein the gene function that encodes the protein/peptide of the present invention is deleted on its chromosome or non-human animal overexpressing the protein/peptide of the present invention and the test substance, it can be exemplified by the following examples: a method wherein the cells or tissues obtained from these non-human animals are contacted in vitro with the test substance, the keratin binding ability of the protein/peptide of the present invention or the change of the expression amount of the protein/peptide of the present invention is measured, and to compare and estimate with those that are not connected with the test substance, a method wherein the test substance is previously administered to non-human animal wherein the gene function that encodes the protein/peptide of the present invention is deleted on its chromosome or to non-human animal overexpressing the protein/peptide of the present invention, then the hair binding ability of the protein/peptide of the present invention in the cells, or tissues obtained from the non-human animals or from the non-human animal itself or the change in expression level of the protein/peptide of the present invention is measured, to compare and estimate with those wherein the test substances are not administered, and the like.

The present invention also provides for a method of transmitting data relating to the keratin associated protein nucleotide and protein sequences as well as substances promoting or suppressing hair keratin binding activity with the use of said protein and peptide fragments thereof identified by the screening methods of the present invention. The present invention also provides for a method of transmitting data comprises transmission of information from such methods herein discussed or steps thereof, e.g., via telecommunication, telephone, video conference, mass communication, e.g., presentation such as a computer presentation (e.g. POWERPOINT), internet, email, documentary communication such as a computer program (e.g. WORD) document and the like.

The invention further comprehends methods of doing business by providing access to such computer readable media and/or computer systems and/or sequence data to users; e.g., the media and/or sequence data can be accessible to a user, for instance on a subscription basis, via the Internet or a global communication/computer network; or, the computer system can be available to a user, on a subscription basis.

A "computer system" refers to the hardware means, software means and data storage means used to analyze the keratin associated protein nucleotide and protein sequences as well as substances promoting or suppressing hair keratin binding activity with the use of said protein and peptide fragments thereof identified by the screening methods of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT or IBM OS/2 operating systems.

Accordingly, the invention further comprehends methods of transmitting information obtained in any method or step thereof described herein or any information described herein, e.g., via telecommunications, telephone, mass communications, mass media, presentations, internet, email, etc.

Moreover, as for the substance promoting or suppressing hair keratin binding activity of the present invention or the substance promoting or suppressing the expression of the protein/peptide of the present invention obtained by the screening methods mentioned above, it can be used for the treatment and the like of the patients where the promotion of the hair keratin activity or the promotion of the expression of the protein/peptide of the present invention is necessary. Moreover, these promoting substances are useful as novel hair cosmetics/therapeutic agents such as hair restorer for head hair, beard and the like, natural hair coloring agent, transforming agent of hair characteristics (curl and the like) and the like, by using with the protein/peptide of the present invention, especially with the protein/peptide that binds most strongly with hair keratin. Moreover, as for the substance suppressing hair keratin binding activity of the present invention, or the substance suppressing the expression of the protein/peptide of the present invention obtained by the above-mentioned screening method, it can be used for the treatment and the like of the patients who need the suppression of hair keratin binding activity or the suppression of the expression of the protein/peptide of the present invention. These therapeutic agents can be administered orally or parenterally. As for the formulation for oral administration, it can be in the form of solid agent such as powder medicine, granules, capsules, tablets and the like, or liquid agent such as syrup, elixir and the like. As for the formulation for parenteral administration, it can be in the form of injectable solution, transdermal agent, suppository and the like. These formulations can be produced according to a conventional method by adding auxiliaries being pharmacologically and pharmaceutically acceptable to an active ingredient. As for the auxiliary, pharmaceutical ingredients including excipient such as soft silicic acid anhydride, starch, lactose, crystalline-cellulose, lactose calcium and the like; disintegrant such as carboxymethylcellulose and the like; lubricant such as magnesium stearate are used for oral form and formulation for mucous administration, pharmaceutical ingredients including solvent or solubilizing agent such as physiological saline, mannitol, propylene glycol and the like; suspending agent such as detergent and the like are used for injectable solution, and pharmaceutical ingredients including aqueous or oleaginous solvent or solubilizing agent, adhesive and the like are further used for external preparation. Further, the dosage can be decided according to the type of targeted diseases, the age, sex, body-weight, and symptoms of patients, and administration form.

The present invention will be described in detail with reference to the following examples, while the technical scope of the present invention will not be limited to these examples.

EXAMPLE 1

Identification of Low-Frequency Repetitive Sequences in the Base Sequence of Long Arm Region of Chromosome 21

As one of the project of human genome, with international collaboration, the base sequence of the euchromatic region of chromosome 21 which is approximately 33.5 Mb was determined, and the presence or the absence of low-frequency repetitive sequences in the base sequence of long arm region of chromosome 21 (21q22.3) was searched by dot-matrix analysis. The results are shown in FIG. 1. As a result, it has been clarified that 21 short sequences of approximately 0.05–1.2 kb are disseminated for 163.5 kb in 21q22.3, and form a cluster. By performing homology search to the above 21 repetitive sequences, it was observed that these genes had significant homology with mouse Krtapl2-1 and rabbit KAP4L, which are members of KAP, and further with mouse gUHS-SER-1 and gUHS-SER-2. From these results, it had been clarified that these genes are KAP that belongs to high sulfur protein which has an amino acid composition rich in cysteine, among KAP forming hair fiber. From the above mentioned, it was estimated that the region in the long arm region of chromosome 21 (21q22.3) is a human KAP gene cluster, and by examining it in detail, it has been clear that 21 genes form a cluster and that 5 genes out of them are pseudogenes.

EXAMPLE 2

Analysis of Each KAP Sequence in Long Arm Region of Human Chromosome 21

Figure 2:
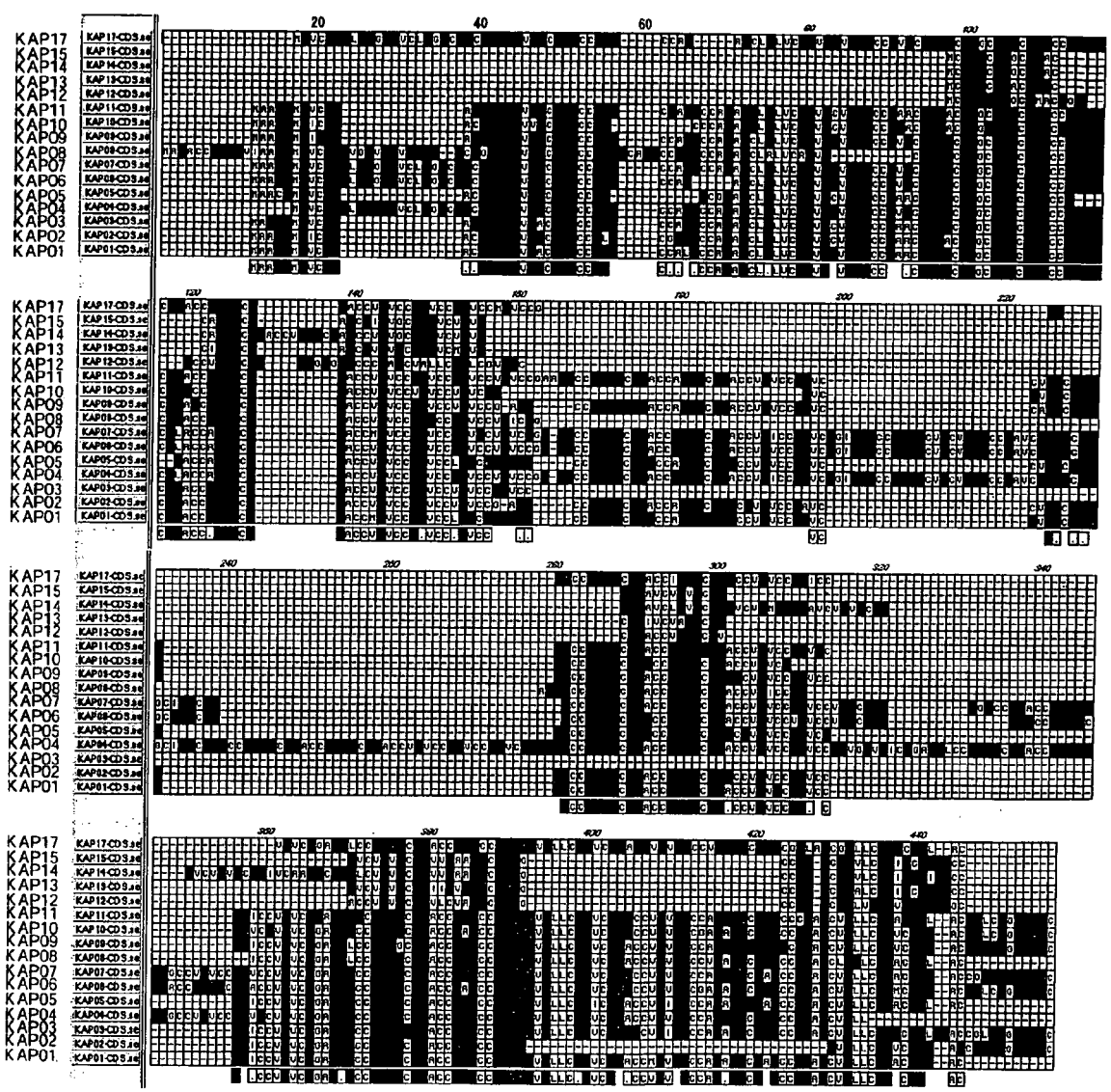
FIG. 2 is a picture that shows the list of amino-acid sequences of each KAP of the present invention, wherein KAP01-KAP015 and KAP17 are shown in Seq. ID Nos. 2, 4, 6, 8, 10, 12, 14, 16, 18, 20, 22, 24, 26, 28, 30, and 32, respectively.
Figure 4:
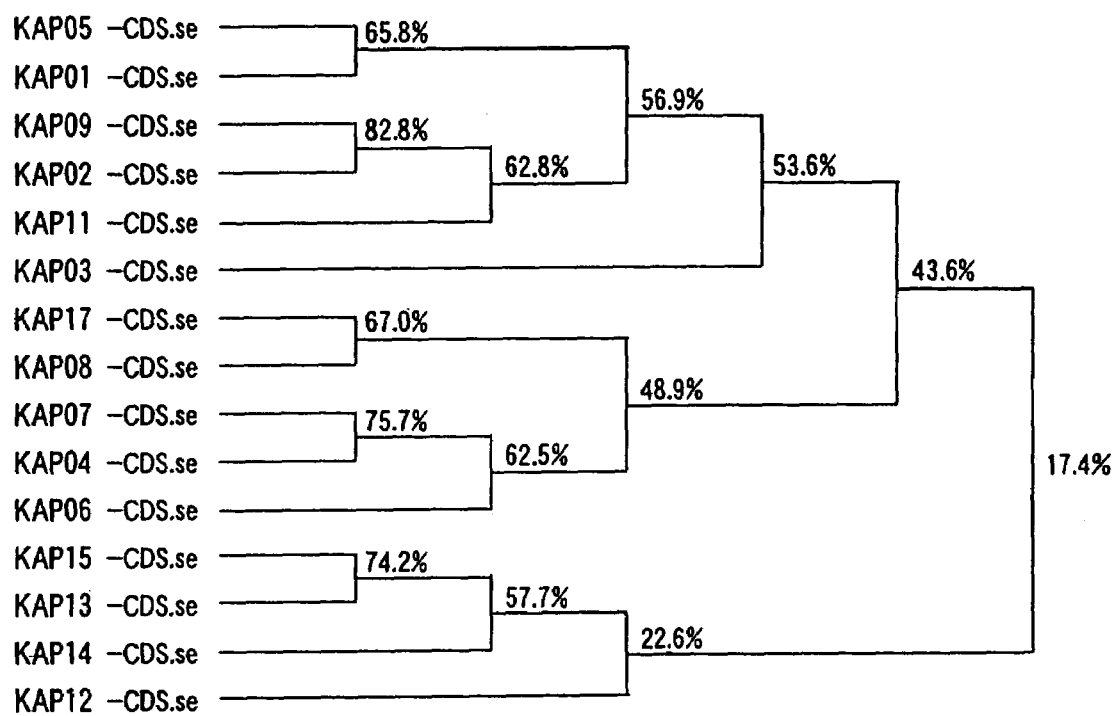
FIG. 4 is a figure that shows the phylogenetic tree of each KAP in the 21g22.3 region of human chromosome.
Figure 5:
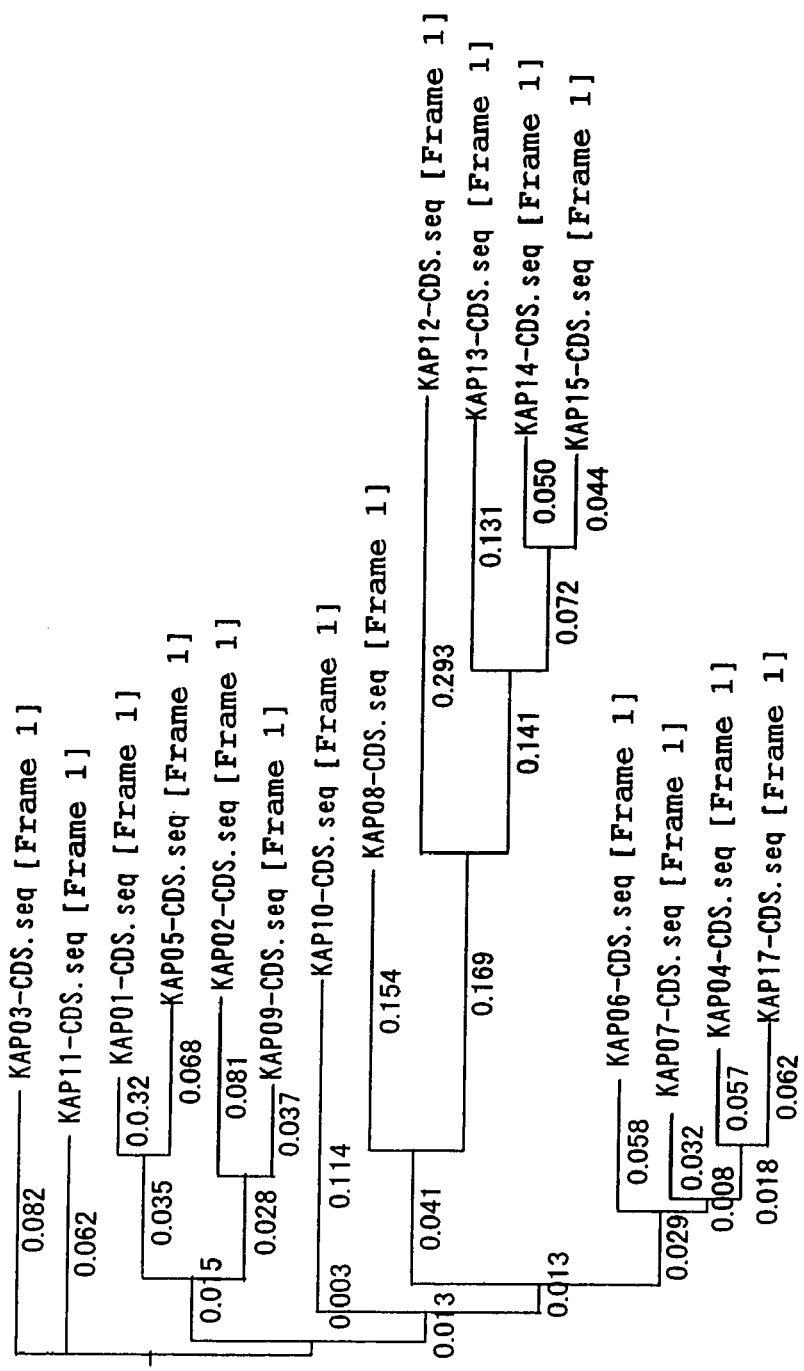
FIG. 5 is a figure that shows the phylogenetic tree of KAP in the 21g22.3 region of human chromosome.

From the results mentioned above, the amino acid sequence of each KAP protein that are encoded by 16 genes forming a cluster, comprising the base sequence shown in Seq. ID No. 2n−1 (n shows any integer from 1 to 16) were determined as shown in Seq. ID No. 2n (n shows any integer from 1 to 16), and the identity between amino acids was examined. The results are shown in FIGS. 2 and 3. Moreover, the phylogenetic tree of KAP gene cluster of 21q22.3 was constructed with the use of DNASIS V3.5 (HITACHI SOFTWARE ENGINEERING CO., LTD) and Clustal W VERSION 1.4 (Nucleic Acids Res. 22, 4673–4680, 1994), by the neighbor-joining method. These results are shown in FIGS. 4 and 5. From these results, it has been clear that human KAP can be classified in 2 sub-families (KAP01-11 and 17), (KAP12-15)], but no significant homology was observed among the families at DNA base level. However, it is very interesting from the point of view of genomic evolution that why such gene groups that show almost no homology at DNA base level although there are correlation at the amino acid level of protein, form a cluster in one single place. From these results, the comparison of the amino acid sequences of KAP 02 and KAP 09 and the genes encoding thereof, which showed a significant homology at amino acid level and DNA base level are shown in FIG. 6. The results of FIG. 6 show the sequences of the spliced transcripts of KAP 02 and KAP 09. From unspliced transcripts, proteins of 255 amino acids (KAP 02) and 292 amino acids (KPA 09) are produced, however as for spliced KAP02, only the first 26 amino acids and as for KAP 09, only the first 59 amino acids are the original sequences, and the remaining sequences are in a form that the part corresponding to 3'UTR is translated for unspliced transcripts. Therefore, it is estimated that protein generated from these spliced transcripts do not have function as keratin-associated protein.

Furthermore, the estimated secondary structure of each KAP protein was examined by using MacVector 6.5.3 Trial version (Accelrys Inc.). The results are shown in FIG. 7. It is known that the known keratin-associated protein of sheep or rabbit do not have a α-helix structure from the estimation of secondary structure. (Powell, B. C., and Rogers, G. E. The role of keratin proteins and their genes in the growth, structure and properties of hair. In Formation and structure of human hair (ed. Jolles, P., Zahn, H., and Hocker, H.), pp. 59–148, Birkhauser Verlag, Basel, 1997. Differentiation 58, 227–232, 1997). As it is clear from FIG. 7, it is estimated that KAPs found in 21q22.3 region did not have at all a a-helix structure. Therefore, it has been cleared that KAPs of 21q22.3 region had the same characteristics for the structure as keratin-associated protein as conventionally reported.

EXAMPLE 3

Gene Expression Site of Human KAP by RT-PCR)

Total RNA was extracted from human hair root or skin by guanidine-cesium chloride method, the extracted total RNA was treated with RNase-free DNase (Nippon Gene). 5 μg each of the obtained RNA was used, and a single-stranded cDNA (RT') was prepared with the use of reverse transcriptase (Invitrogen) and oligo dT18 primer, and was amplified by PCR. Those not performing reverse transcription reaction were used as negative control (RT). Primers P1–P38 used for PCR, as set forth in Seq. ID Nos. 79–116, respectively, and PCR conditions are shown in [Table 1].

TABLE 1

| | | forward primer | | reverse primer | annealing temp. (° C.) | enzyme* |
|---|---|---|---|---|---|---|
| KAP01 | P1 | TCACTCACTCACACCTCCCG | P2 | GAGACACGGGGACCCGTCCT | 55 | HF |
| KAP02 | P3 | TCACTCACTCACACACCTCCCC | P4 | ATCCCCAACCAGCGACCAGCGA | 55 | HF |
| KAP03 | P5 | TCACTCACTCACGTCTCCCC | P6 | AACTCTGGAGAAACGGGACC | 55 | HF |
| KAP04 | P7 | AGCTCAACCCCCAGCACAGCA | P8 | GTCAAAGTGCAGGAGCAATTC | 55 | HF |
| KAP05 | P9 | CCAGCTCACGTCTTCCCCAC | P10 | CCTAACCCGAGTCAGGACCA | 55 | HF |
| KAP06 | P11 | CTCCACCAGTTCAACCCCAGCAT | P12 | TAAGACAAAGAGCCTGCCCCAT | 65 | EL |
| KAP07 | P13 | CATCTCCTCCAGTTCAATCC | P14 | TCAGGCTTTGGATGATCTTAAG | 55 | HF |
| KAP08 | P15 | ACCACCCAGTCCAGCACCCA | P16 | AGGACAGGACCGGAGCCGGC | 55 | HF |
| KAP09 | P17 | TCACACACTCACTTACACCTCC | P18 | CGTCCCCAACCAGCGACCAGCG | 55 | HF |
| KAP10 | P19 | TCACTCACTCACACACCTCCCC | P20 | CAAGACAAAGAGCCTGCCCCAC | 55 | HF |
| KAP11 | P21 | ACACTCACTTACACCTCCCCCA | P22 | TCCTGAGACTGGAGAATCCTGC | 65 | EL |
| KAP12 | P23 | AGACCAGCCCTGTCCTCTGCG | P24 | GGAGTTCAGAGAGCCTGCTGG | 55 | HF |
| KAP13 | P25 | CAGACATCACCATCCTCCTCCC | P26 | TCTGGGGGTCCACCAGATGCT | 60 | EL |
| KAP14 | P27 | TTATCCAGCCACACGCCACCATG | P28 | CTGTCACATTCTCAATCCAGAA | 55 | EL |

TABLE 1-continued

| | forward primer | reverse primer | annealing temp. (° C.) | enzyme* |
|---|---|---|---|---|
| KAP15 | P29 TTATCCAGCCACACGCCACCATG | P30 AGGGCTCCAGATCATTCTATTA | 55 | EL |
| KAP16 | P31 CTGAACGTTCTTGTGCAGGA | P32 GCTGACATTGTCTTGGTCAG | 55 | EL |
| KAP17 | P33 AGCTCAACCCCCAGCACGGCT | P34 GAGCAGCCGAGGGGCCAGTAG | 55 | HF |
| KAP18 | P35 CAGCTCCTGCACGCCCTTGT | P36 AGTGGATAGGTAAGCCGTGGTTG | 65 | EL |
| G3PDH | P37 TGAAGGTCGGTGTGAACGGATTTGGC | P38 CATGTAGGCCATGAGGTCCACCAC | 60 | EL |

*HF: Expand High Fidelity enzyme (Roche) EL: Expand Long enzyme (Roche)
Condition for PCR reaction:
HF: 94° C. for 2 minutes × 1 cycle, followed by 39 cycles of 30 s at 94° C., 60 s at 55° C., 2 min at 72° C., and 5 min at 72° C. × 1 cycle.
EL: 94° C. for 2 minutes × 1 cycle, followed by 39 cycles of 30 s at 94° C., 60 s at xx° C. (any of the annealing temperature of the above table), 2 min at 68° C., and 5 min at 68° C. × 1 cycle.

Figure 8:
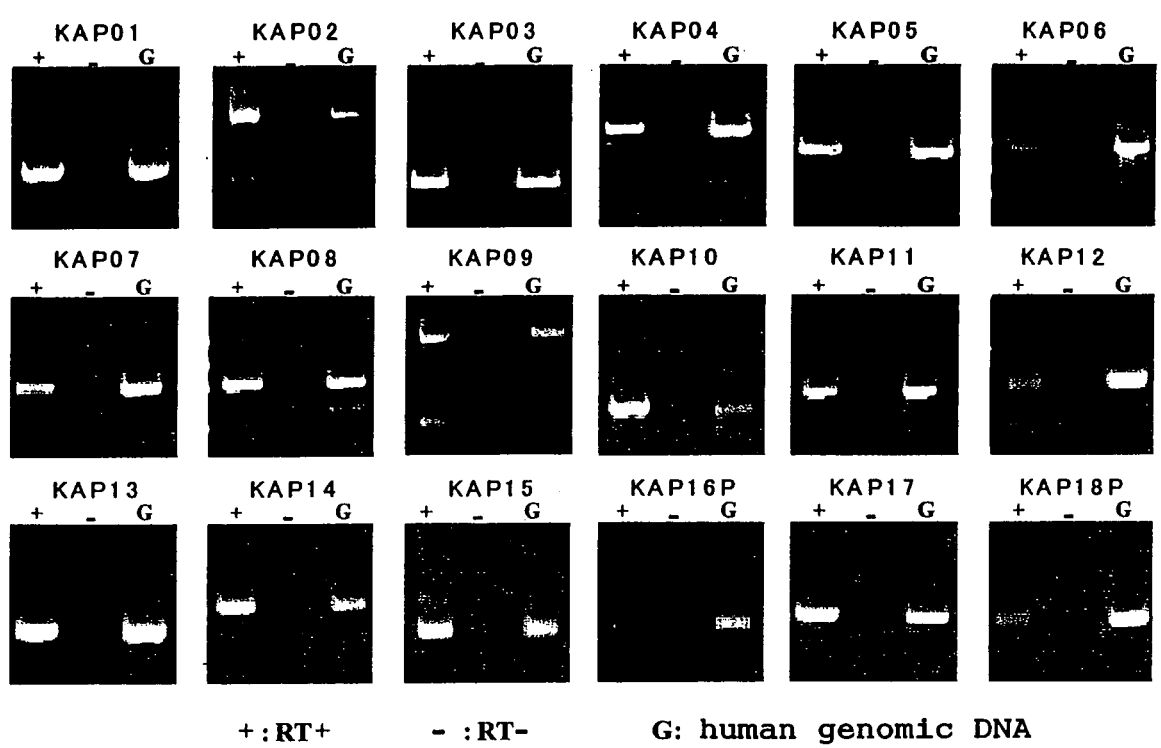
FIG. 8 is a figure that shows the results of examining the expression of each KAP in the q22.3 region of human chromosome 21 in the hair root, by RT-PCR.
Figure 9:
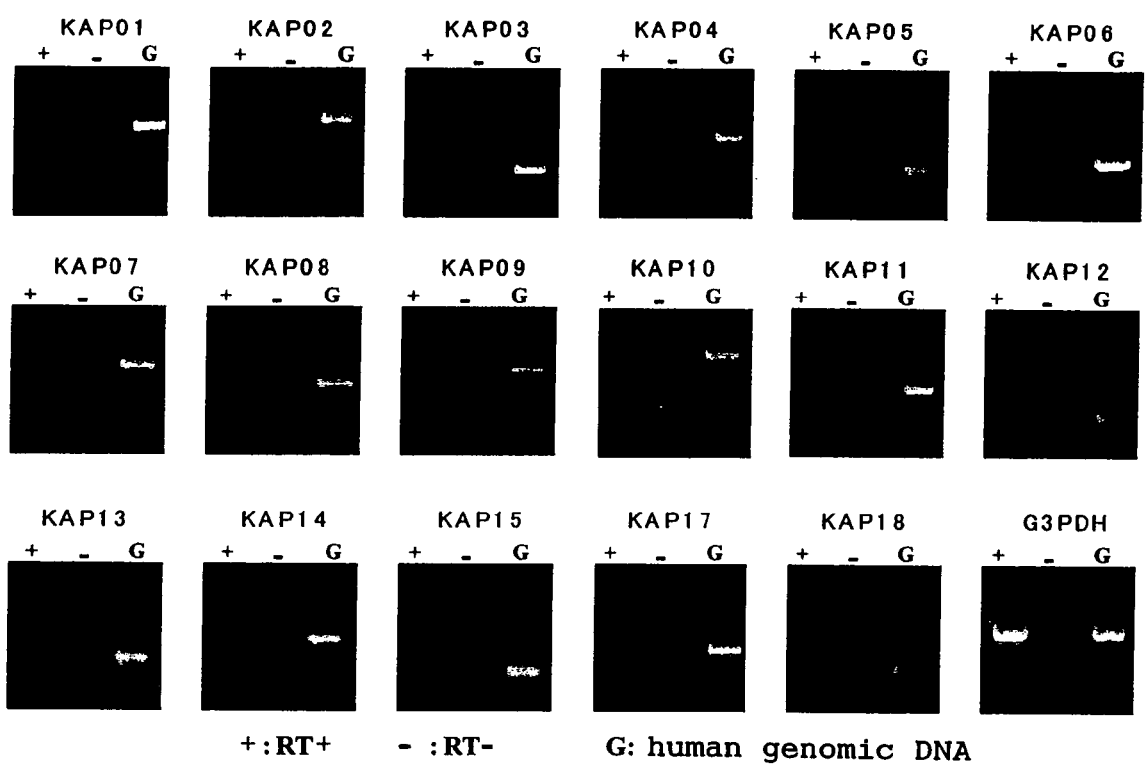
FIG. 9 is a figure that shows the results of KAP expression of the q22.3 region of human chromosome 21 in skin, which was investigated by RT-PCR.

The PCR products (cDNA) obtained by the above PCR were electrophoresed on agarose gel (1.5%), stained with ethidium bromide (EtBr), and bands were detected by 254 nm ultra-violet radiation. The results are shown in FIGS. 8 (hair root) and 9 (skin). Therefore, KAP gene is thought to be a gene related specifically to hair, because all KAP genes except pseudogene KAP16P were expressed in hair root but were not expressed in skin. Additionally, as shown in FIG. 8, as for KAP 02 and KAP 09, besides normal mRNA that are not spliced, shorter transcripts exist, and the latter was a spliced product wherein the site between the splicing donor site in KAP coding region and the splicing acceptor site in 3'UTR is eliminated. As a result, protein that does not function as KAP, as shown in FIG. 6 is generated. Meanwhile, as the short type transcripts that are generated by the above splicing are shorter than normal transcripts, it is possible that only short types amplify preferentially due to PCR conditions.

EXAMPLE 4

Identification of Novel KAP Gene Cluster in 21q22.11

Figure 10:
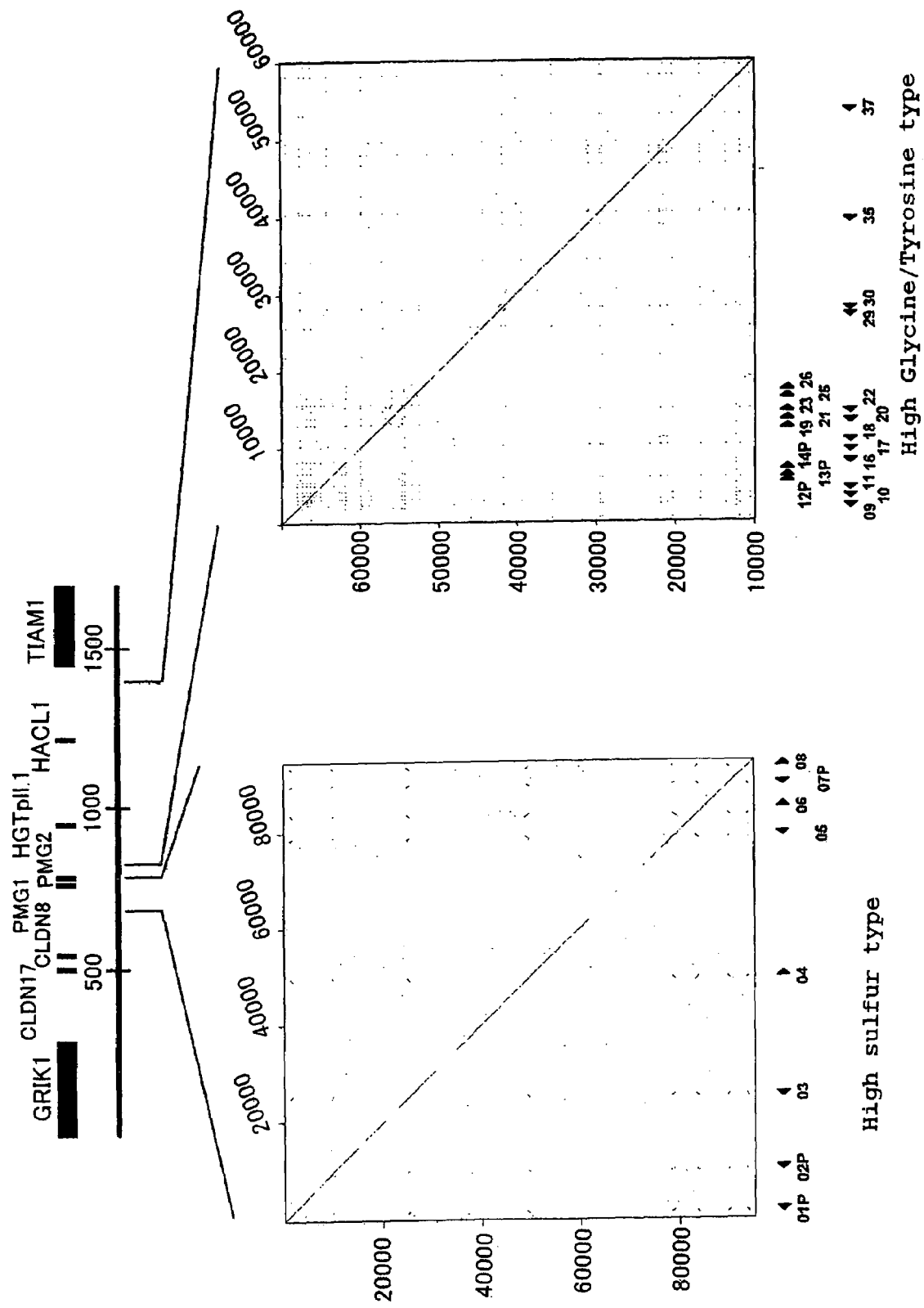
FIG. 10 is a figure that shows the result of examining the presence or the absence of a novel KAP gene cluster in the 21q22.11 region of human chromosome.

It was reported that there is apparently no gene in the region expanding for approximately 1 Mb between CLDN8 gene and TIAM1 gene of 21q22.11. Dot-matrix analysis was carried out similarly as to the 21q22.3 region in Example 1 but there was no low-frequency repetitive sequence that was detected in 21q22.3 region. Therefore, high-frequency repetitive sequences existing in the sequence of the region, were masked by Repeat Masker (http://ftp.genome.washington.edu: 80/cgi-bin/RepeatMasker), and an analysis was carried out again by taking attention not to pass by short low-frequency repetitive sequences. As a result, an image showing low-frequency repetitive sequences not primarily observed were detected (see FIG. 10). By making a homology search for these sequences, they showed significant homology with mouse Pmg-1, Pmg-2, HGTpII.1, and it has been clarified that these were KAP members. The sequence that showed homology with Pmg-1, Pmg-2 spanned for 95 kb, and it was clarified that 5 genes and 3 pseudogenes formed a cluster while belongs to high sulfur type based on its amino acid composition (FIG. 10, left). The amino acid sequence of each KAP protein encoded by 5 genes comprising the base sequence shown in Seq. ID No. 2n–1 (n shows any integer from 17 to 21) was determined to be shown in Seq. ID No. 2n (n shows any integer from 17 to 21). Moreover, the sequence that showed homology with HGTpII.1 spanned for approximately 600 kb, and it was clarified that 18 genes and 3 pseudogenes form a cluster, while belongs to high glycine tyrosine type based on its amino acid composition (FIG. 10, right). The amino acid sequence of each KAP protein encoded by 18 genes comprising the base sequence shown in Seq. ID No. 2n–1 (n shows any integer from 22 to 39) was determined as shown in Seq. ID No. 2n (n shows any integer from 22 to 39).

EXAMPLE 5

Preparation of Recombinant Human KAPs

Recombinant human high sulfur type KAPs and high G/Y type KAPs were prepared. As for human high sulfur type KAPs gene, KAP04 gene (Seq. ID No. 7), KAP05 gene (Seq. ID No. 9), KAP08 gene (Seq. ID No. 15), KAP11 gene (Seq. ID No. 21), KAP12 gene (Seq. ID No. 23), KAP15 gene (Seq. ID No. 29) were used. As for high G/Y type KAPs gene, pmg04 gene (Seq. ID No. 47), GY02 gene (Seq. ID No. 45), GY29 gene (Seq. ID No. 71), GY34 gene (Seq. ID No. 77) were used. Moreover, as for expression vectors, pET-31b(+), pET-32a and pTriEx-1.1 (all from Novagen), pFLAG-CTC (SIGMA) were used, and as for host cells, *E. coli* Rosetta (DE3) pLacI Competent Cells (Novagen, Code No. 70920-4) were used.

TABLE 2

| | Vector | | |
|---|---|---|---|
| | pTriEx-1.1 | pET-31b(+) | pFLAG-CTC |
| Without Tag | pTri (KAP04) | pET (KAP04) | pFLAG (KAP04) |
| | pTri (KAP05) | pET (KAP05) | pFLAG (KAP05) |
| | pTri (KAP08) | pET (KAP08) | pFLAG (KAP08) |
| | pTri (KAP11) | pET (KAP11) | pFLAG (KAP11) |
| | pTri (KAP12) | pET (KAP12) | pFLAG (KAP12) |
| | pTri (KAP15) | pET (KAP15) | pFLAG (KAP15) |
| With Tag | pTri (KAP04-His 6) | pET (KAP04-His 6) | pFLAG (KAP04-FLAG) |
| | pTri (KAP05-His 6) | pET (KAP05-His 6) | pFLAG (KAP05-FLAG) |
| | pTri (KAP08-His 6) | pET (KAP08-His 6) | pFLAG (KAP08-FLAG) |

TABLE 2-continued

| Vector | | |
|---|---|---|
| pTriEx-1.1 | pET-31b(+) | pFLAG-CTC |
| pTri (KAP11-His 6) | pET (KAP11-His 6) | pFLAG (KAP11-FLAG) |
| pTri (KAP12-His 6) | pET (KAP12-His 6) | pFLAG (KAP12-FLAG) |
| pTri (KAP15-His 6) | pET (KAP15-His 6) | pFLAG (KAP15-FLAG) |

Figure 12:
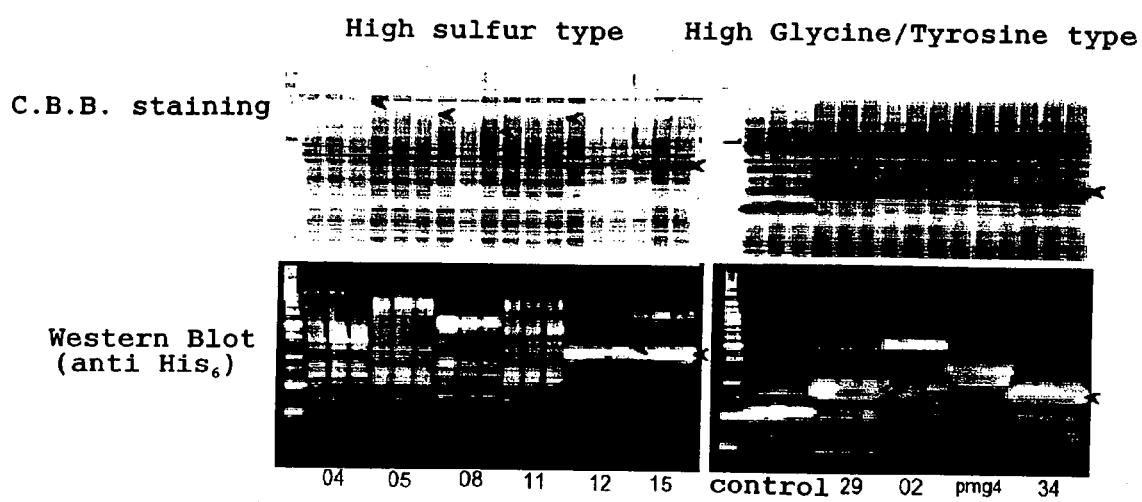

First, by using, pTriEx-1.1, pET-31b(+) and pFLAG-CTC vectors, 36 types of expression systems of recombinant human KAPs as shown in Table 2 were prepared. The expression of each recombinant human KAPs was observed by C.B.B. staining, and for 18 types having His-tag and FLAG-tag, the presence or the absence of the expression was observed by Western Blot Analysis. The results of Coomassie Brilliant Blue (C.B.B.) staining and Western Blot are shown in FIG. 11. The expression of all recombinant human high sulfur type KAPs were observed by Western Blot (FIG. 11, right), but it was not possible to obtain a high expression system that can be verified by C.B.B. staining (FIG. 11, left). Thus, by using pET-32a vector, the expression system was constructed again. Moreover, as it is shown in Table 3, a similar expression system was prepared for human high G/Y type KAPs at the same time. As pET-32a had a 20 kDA His-tag and S-tag at N-terminal side, the increase in translation efficiency and the elevation of solubilization level were expected. The results of C.B.B. staining and Western Blot are shown in FIG. 12. As a result of C.B.B. staining (FIG. 12, top) and Western Blot (FIG. 12, bottom), the expression level of high sulfur type of low molecule was improved. Moreover, as for high G/Y type, high expression level was observed for all.

TABLE 3

| vector | pET-32a |
|---|---|
| high sulfur type | KAP04, KAP05, KAP08, KAPII, KAP12, KAP15 |
| high G/Y type | GY02, GY29, GY34, pmg04 |

EXAMPLE 6

Purification of Recombinant Human KAPs

Figure 13:
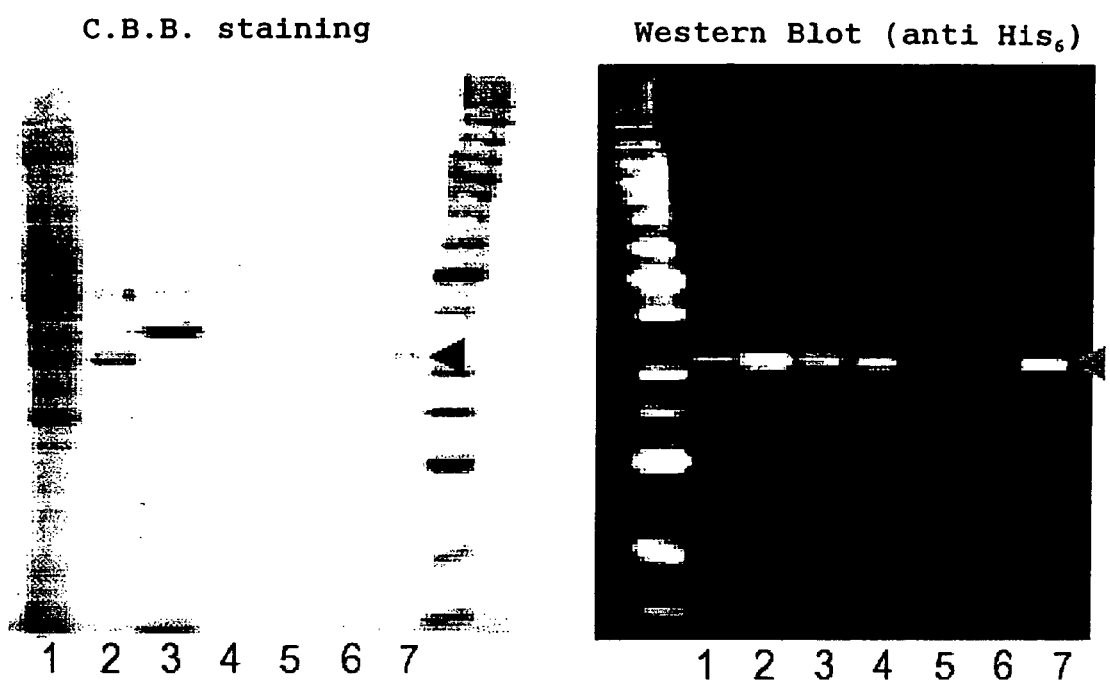
FIG. 13 is a picture that shows the results of C.B.B. staining and Western Blot Analysis of recombinant human high sulfur type KAP15-His$_6$ (pET-32a), purified with the use of Ni-NTA resin.

Recombinant human high sulfur type KAP 15-His$_6$ (pEt-32a) was purified by using Ni-NTA resin. The result is shown in FIG. 13. In FIG. 13, lane 1 shows a fungus-soluble fraction, lane 2 a fraction treated with 7.5M guadine hydrochloride and 40 mM DTT, lane 3 a fungus-insoluble fraction, lane 4 a fraction treated with 7.5M guadine hydrochloride, lane 5 a non-adsorptive fraction, lane 6 a washing fraction with 20 mM imidazole, lane 7 an elution fraction with 300 mM imidazole. As a result, as a part was dissolved with 7.5M guadine hydrochloride, it was demonstrated that purification was possible. However, most part was still recovered in insoluble fraction. Therefore, having as an object the cleavage of S—S binding and blocking of re-binding, the insoluble fraction was treated with 40 mM DTT and TAPS sulfonate, which is SH group protectant, and KAP15-His$_6$ was recovered as a soluble fraction (lane 2). After dialyzing this fraction, it was purified with Ni-NTA resin and KAP15-His$_6$ was obtained with a purity of 90% or more (lane7).

Figure 14:
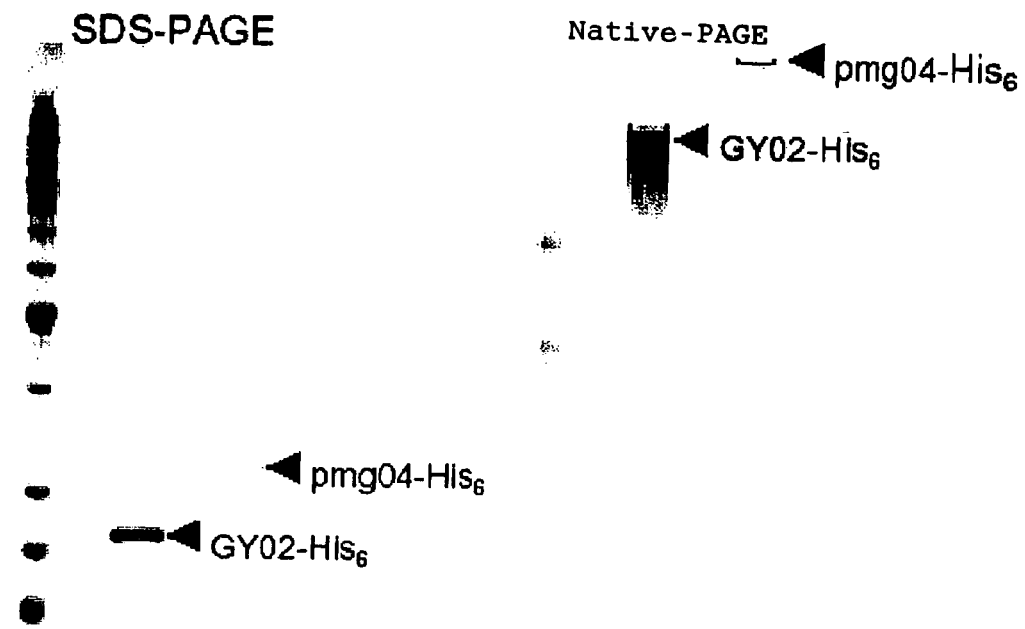
FIG. 14 is a picture that shows the results of C.B.B. staining and Western Blot Analysis of recombinant human High G/Y type GY02-His$_6$ (pET-32a) and pmg04-His$_6$, (pET-32a), purified with the use of Ni-NTA resin.

Recombinant human High G/Y type GY02-His$_6$ (pET-32a) and pmg04-His, (pET-32a) were purified with Ni-NTA resin. Moreover, fungus-insoluble fraction was solubilized with 7.5M guadine hydrochloride and purified with Ni-NTA resin. The results are shown in FIG. 14. In FIG. 14, lane 1 shows a fungus-soluble fraction, lane 2 a fraction treated with 7.5M guadine hydrochloride (pH8.0) treatment, lane 3 a fungus insoluble fraction, lane 4 a non-adsorptive fraction, lane 5 a washing fraction with 20 mM imidazole, lane 6 an elution fraction with 500 mM imidazole. As a result, it was confirmed that it was possible to purify both GY02-His$_6$, and pmg04-His$_6$ at a high yield.

Figure 15:
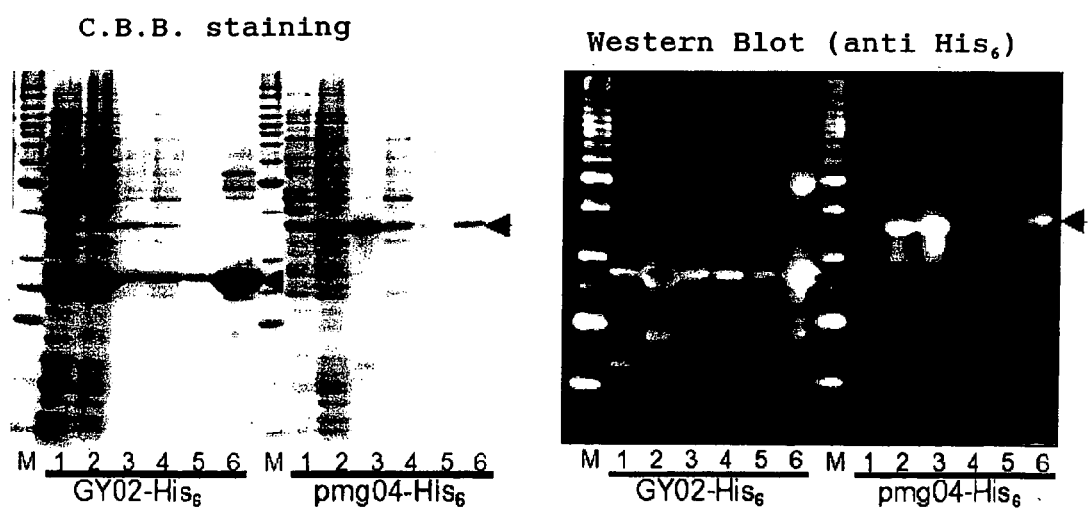
FIG. 15 is a picture that shows the results of SDS-polyacrylamide gel electrophoresis (SDS-PAGE) and Native PAGE of recombinant human High G/Y type GY02-His$_6$ and pmg04-His$_6$, being refolded.

Therefore, purification for large amount of GY02-His$_6$, and pmg04-His$_6$ was performed and refolding conditions for the purified GY02-His$_6$, and pmg04-His$_6$, were examined. As a result of examination, as for GY02-His$_6$ wherein refolding was performed with the following condition, as it was detected in a single-band form by a non-reducing acrylamide gel electrophoresis (Native-PAGE) as shown in FIG. 15, it has been cleared that GY02-His$_6$ can be obtained in a condition where it is normally folded. On the other hand, as for pmg04-His$_6$, it can not be detected by Native-PAGE and it is estimated that it forms an aggregate.

[refolding conditions]

50 mM Tris—HCl (pH 8.0), 20% glycerol, 500 mM NaCl, 6M Urea, 20 mM DTT

↓RT,4 hours 50 mM Tris—HCl (pH 8.0), 20% glycerol, 500 mM NaCl, 2M Urea, 10 mM DTT ↓RT,4 hours 50 mM Tris—HCl (pH 8.0), 20% glycerol, 500 mM NaCl, 1M Urea, 1 mM DTT ↓4° C., overnight 50 mM Tris—HCl (pH 8.0), 20% glycerol, 500 mM NaCl ↓4° C., 8 hours concentration by ultra filtration (MILLIPORE,M/W 3,000 cut)

EXAMPLE 7

Detection of Mouse KAPs

To investigate clinical actions of human KAPs as factors for hair growing, hair restorer and hair growth, mouse high sulfur type KAPs and mouse high G/Y type KAPs were searched. In other words, in order to perform the direct application experiment using mouse, mouse KAPs were first searched. A data base search using Mouse whole genome shot-gun and BLAST was performed for amino acid sequences having high homology to human KAPs of the present invention, amino acid primary sequences of 14 mouse high G/Y type KAPs and 29 mouse high sulfur type KAPs were obtained. All of 14 mouse high G/Y type KAPs were known mouse KAPs, and as it is shown in FIGS. 16 to 18, their amino acid sequences can be classified to Group 1–3 based on the homology of amino acid sequence. The base sequences of the 14 mouse high G/Y type KAP genes are shown in Seq. ID No. 2n−1 (n shows any integer from 59 to 72), in the order of MMUKrtap 14, UKrtap 15, . . . Likewise, the amino acid sequences of KAP proteins are shown in Seq. ID No. 2 (n shows any integer from 59 to 72), in the order of MMUKrtapl4, MMUKrtap 15, . . . Moreover, the amino sequences of the 29 mouse high sulfur type KAPs can be classified in Class 1 to 7 based on the homology of amino acid sequence, as shown in FIGS. 19–25. The base sequences of the 29 mouse high sulfur type KAP genes are shown in Seq. ID No. 2n−1 (n shows any integer from 73 to 101), in the order of mKAP 1-1, mKAP 1-2 . . . . Similarly, the amino acid sequences of KAP proteins are shown in Seq. ID No. 2n (n shows any integer from 73 to 101), in the order of mKAP 1-1, MKAP 1-2 . . . . Although the base sequences and amino acid sequences of the 29 mouse high sulfur type KAPs were already known, as shown in FIG. 26, except mKAP1-1, mKAP1-2, mKAP1-3, mKAP1-5, MKAP6-3, it was not known that they function as KAP.

EXAMPLE 8

Design of Functional Peptide

Figure 27:
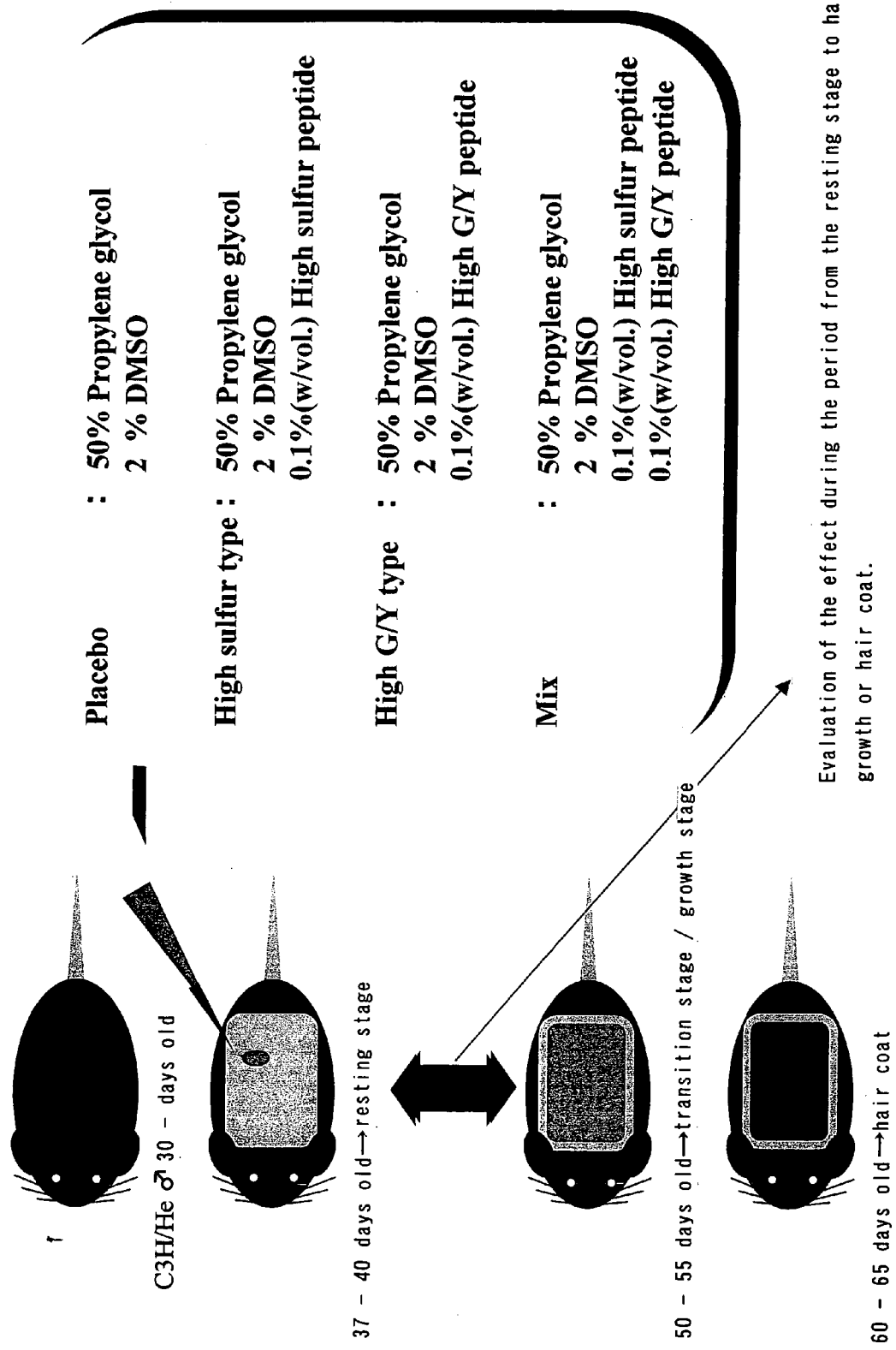
FIG. 27 is a figure that shows the outline of the experiment examining the effect of the functional peptide to the hair cycle.
Figure 28:
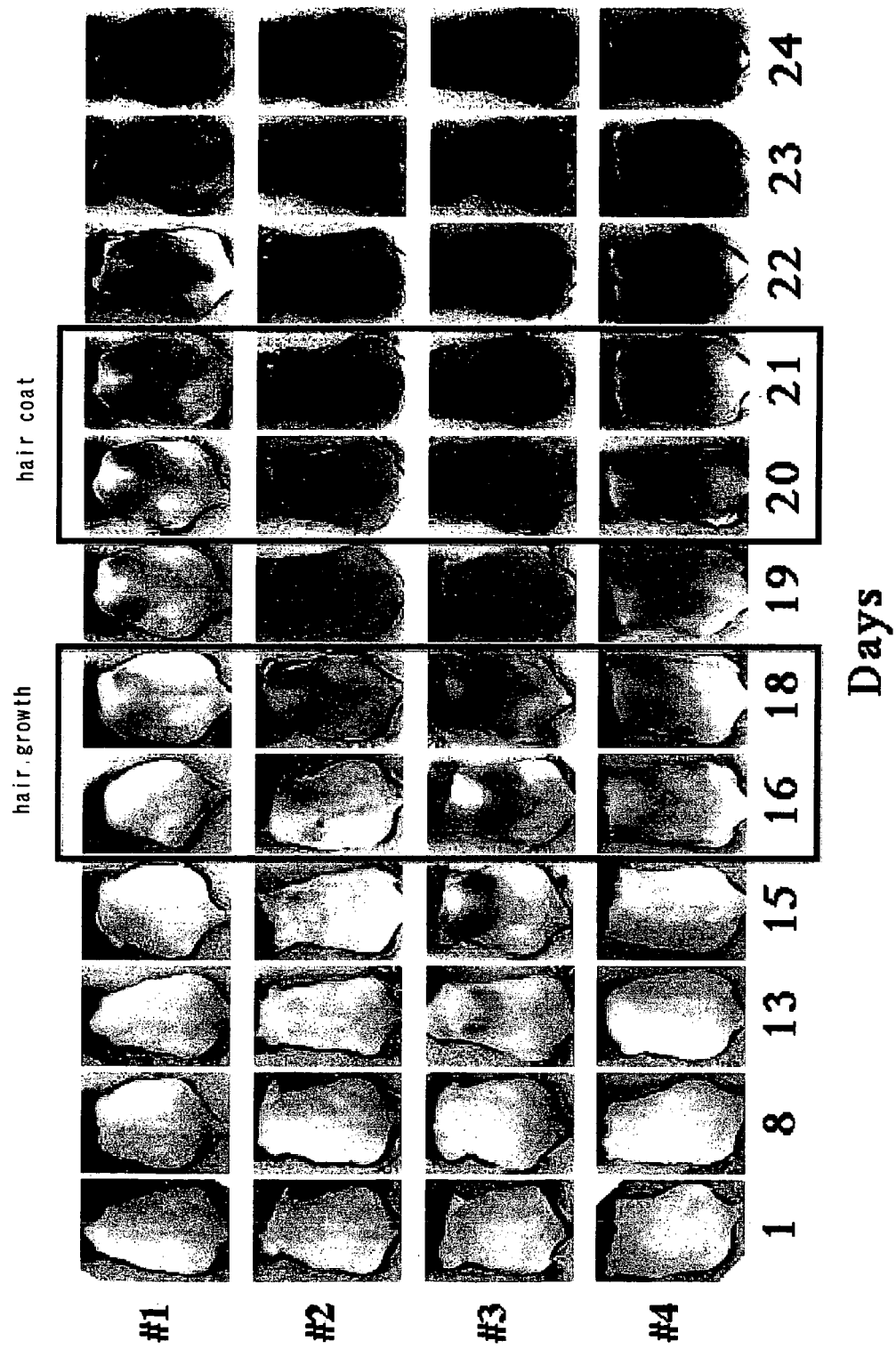
FIG. 28 is a figure that shows the result of the effect of high sulfur type peptide to the hair cycle.
Figure 29:
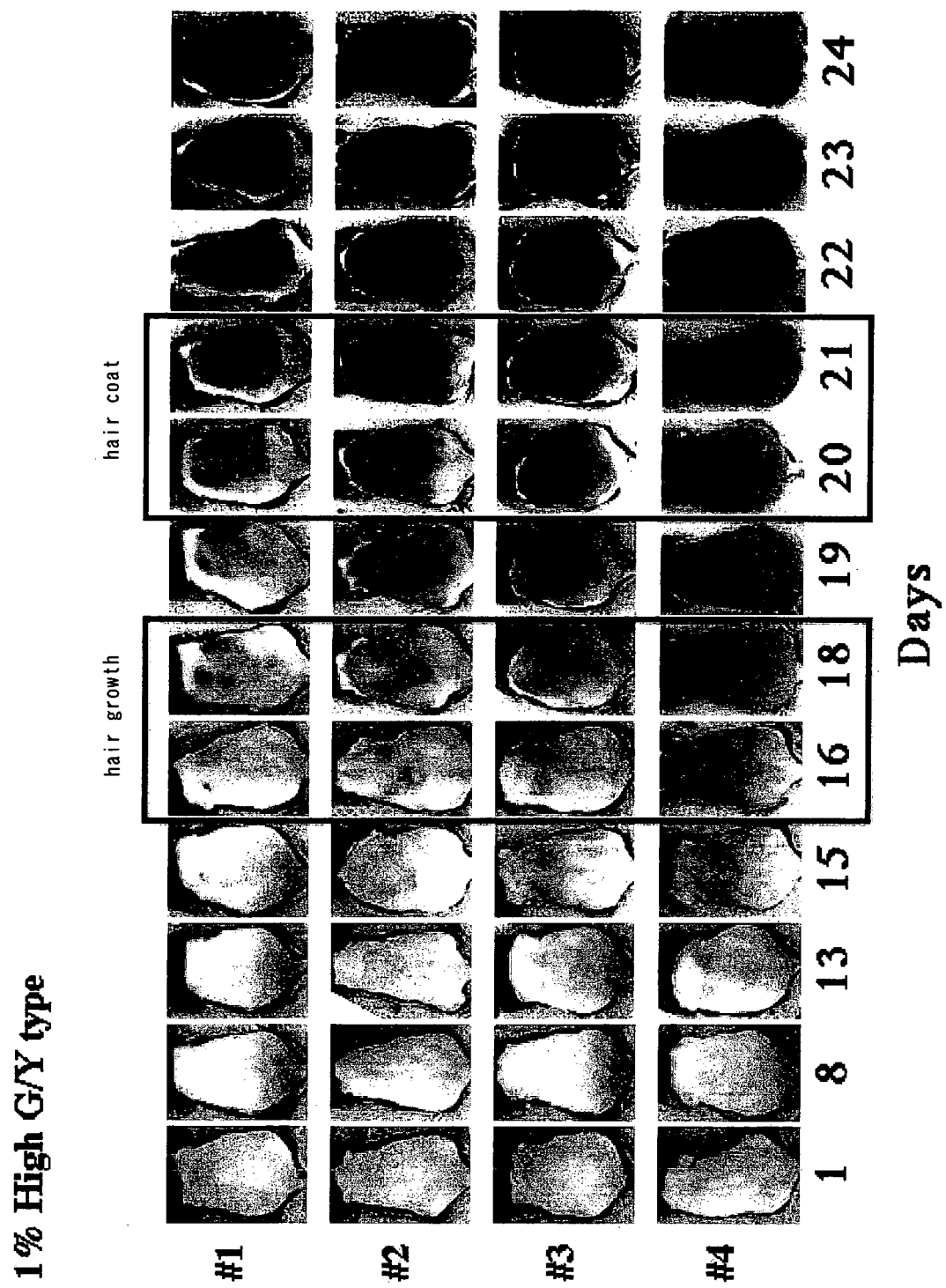
FIG. 29 is a figure that shows the result of the effect of high glycine-tyrosine (G/Y) type peptide to the hair cycle.
Figure 30:
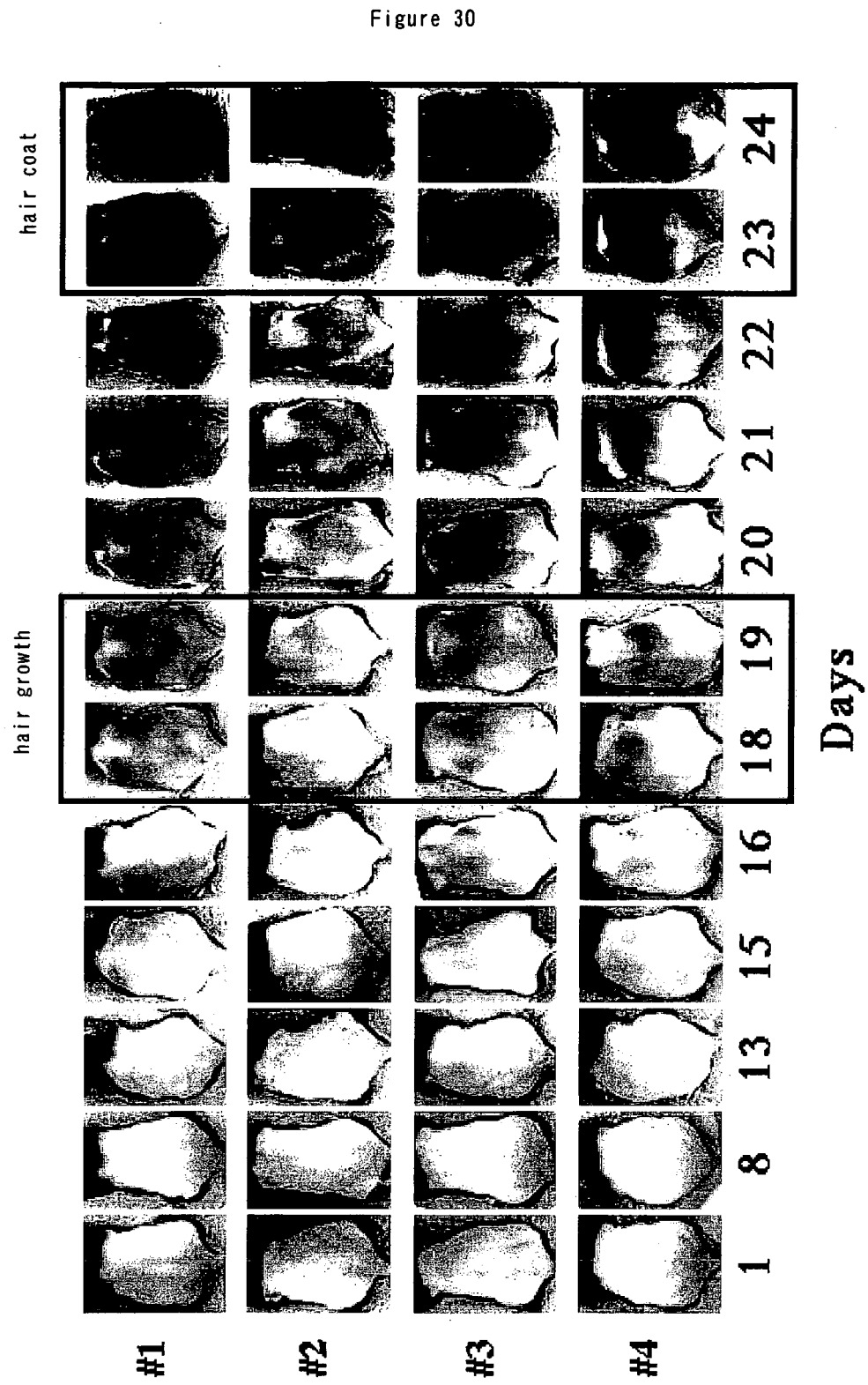
FIG. 30 is a figure that shows the result of the effect of peptide solvent, which is a negative control to the hair cycle.
Figure 31:
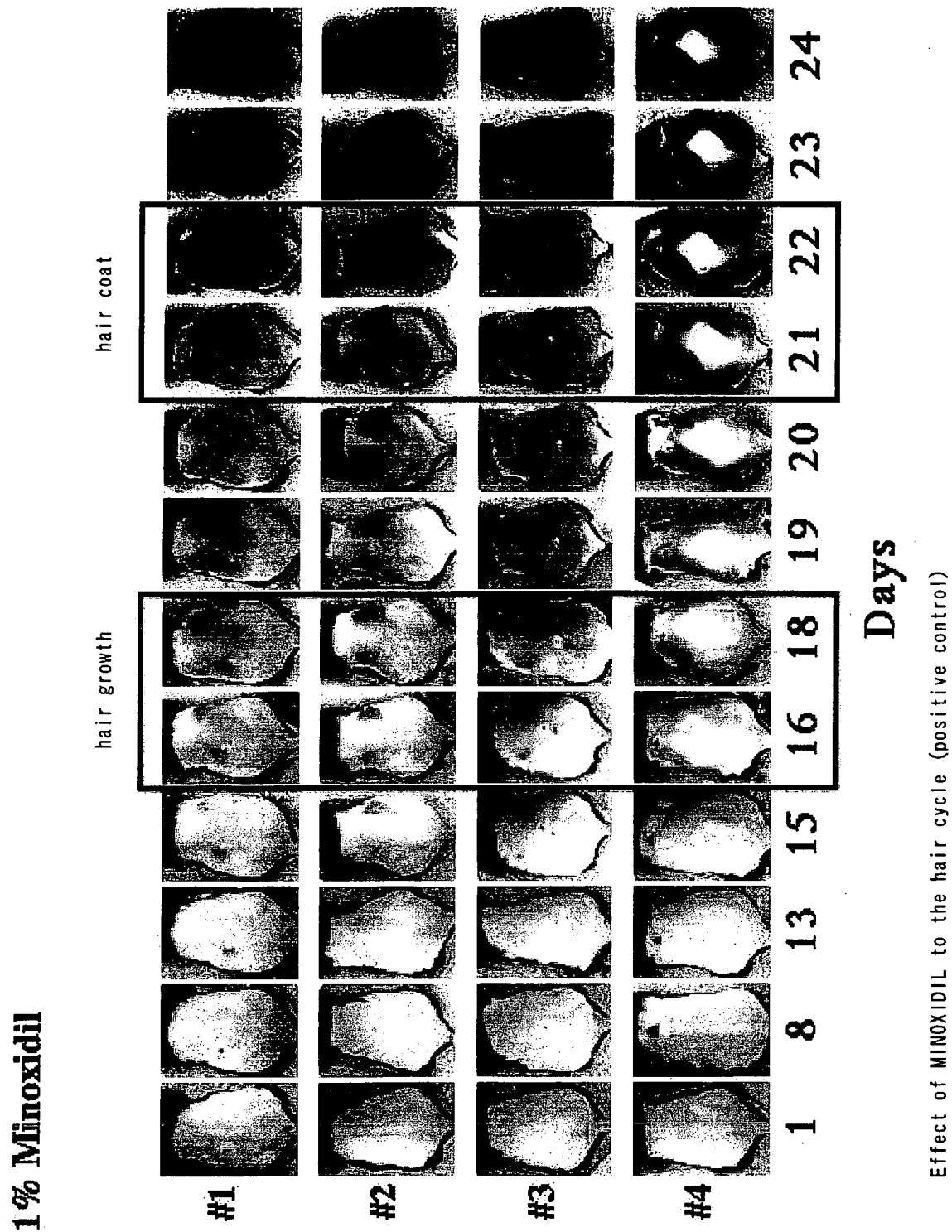
FIG. 31 is a figure that shows the result of the effect of MINOXIDIL, which is a positive control to the hair cycle.
Figure 32:
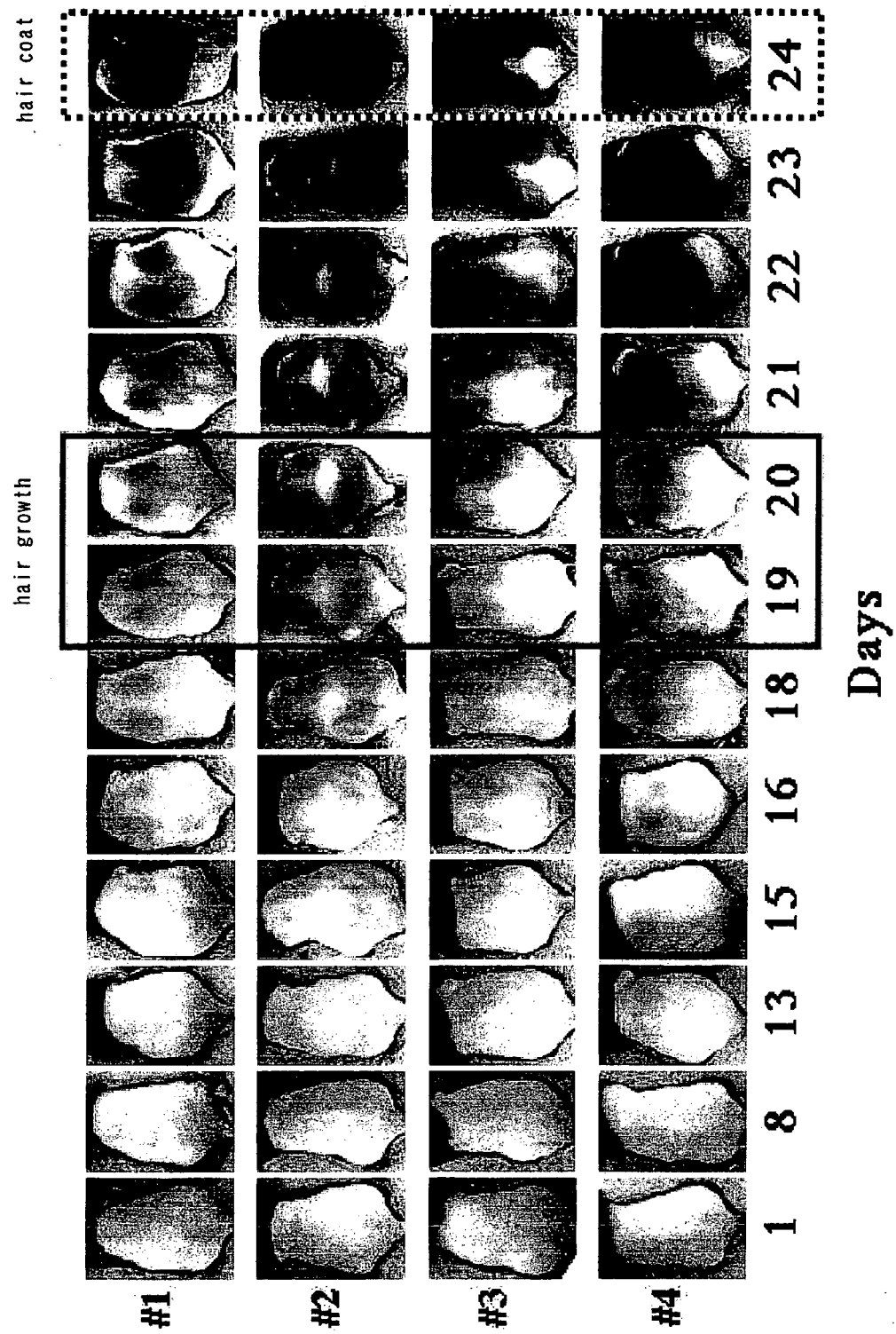
FIG. 32 is a figure that shows the result of the effect to the hair cycle of mixed peptide of both peptides, high sulfur type and high G/Y type.

For the application of KAPs as hair growth agent, there is a possible problem for permeability to tissues in an intact size. Therefore, from the point of view of being a hair constituent element, the minimum repeat unit on KAP sequences was searched and designing of peptides was attempted with the crosslinking within the tissues as a goal. After preparing alignment from the primary sequence of amino acid obtained in Example 7, repeat motifs are searched, and 2 functional peptides, namely mouse high sulfur type KAPs: N'-SCCXPSCCXP-C' (X: Q, V, R, I) [Seq. ID No. 203], and mouse high G/Y type KAPs: N'-YGGXGYGSGY-C' (X: Y, L, F)[Seq. ID No. 204] were designed. By using these functional peptides, the action to hair formation and hair-matrix cells was evaluated. First, as shown in FIG. 27, 1% of high sulfur type peptide and 1% of high glycine-tyrosine (G/Y) type peptide were applied subsequently to each of four C3H/He mouse groups, to observe the effect to the hair cycle of mouse body hair. Peptide solvent (Plasebo) was used as a negative control, and 1t MINOXIDIL was used as a positive control. As a result, the shortening effect of the duration until hair coat was observed with the application of high sulfur type alone (FIG. 28), and high G/Y type alone (FIG. 29). The effect was significant compared not only with peptide solvent as a negative control (FIG. 30), but also with MINOXIDIL of the same concentration, being a positive control (FIG. 31). On the other hand, with the application of a mixture of both high sulfur type and high G/Y type peptides, an action delaying the formation of body hair was observed (FIG. 32).

Moreover, in mouse hair-matrix cells isolated, when the action of hair-matrix cells activation was estimated with the energy metabolism activity in the mitochondria of cells as index, a significant hair-matrix cells activation with the high sulfur type peptide treatments was observed. Furthermore, during the high sulfur type peptide and high G/Y type peptide treatment, a change of form of hair-matrix cells associated with the differentiation was observed.

From the above-mentioned, as the peptides derived from KAPs had either action of activating cells or promoting differentiation individually, it is suggested that the shortening of the duration for mouse body hair formation is a result of the action to hair-matrix cells. Further, delayed formation of body hair was observed when the peptide mixture was used. In other words, it can be thought that the peptide of the invention is very useful as a functional factor that is able to control formation and suppression of hair. Moreover, as the conserved sequence of mouse KAPs correspond almost entirely to the conserved sequences of human KAPs used in the present test, it is expected that there is a similar action in human.

INDUSTRIAL APPLICABILITY

As the genes encoding keratin-associated protein of the present invention are genes specifically related to hair, by performing analysis of properties of the proteins and identifying protein that binds particularly with hair keratin, or by designing functional peptides, it is useful for the development of hair cosmetics/therapeutic agents such as hair restorer agent for head hair, beard and the like, hair coloring agent, transforming agent of hair characteristics (curl and the like) and the like. Furthermore, it could be used for screening substances promoting or suppressing hair keratin binding activity or screening substances promoting or suppressing the expression of the protein/peptide of the present invention. The mechanism of hair fiber formation can also be elucidated.

The invention is further described by the following numbered paragraphs:

1. A DNA that encodes keratin-associated protein which is (a) a protein comprising an amino acid sequence shown in Seq. ID No. 2n (n shows any integer from 1 to 39), or (b) a protein comprising an amino acid sequence shown in Seq. ID No. 2n (n shows any integer from 1 to 39), wherein one or several amino acids are deleted, substituted or added, and has hair-keratin binding activity.

2. A DNA comprising a base sequence shown in Seq. ID Nos. 2n−1 (n shows any integer from 1 to 39) or its complementary sequence, or a sequence containing a part or whole of these sequences.

3. A DNA comprising a base sequence shown in Seq. ID Nos. 151, 155, 157, 159, 161, 163, 165, 167, 169, 171, 173, 175, 177, 179, 181, 183, 185, 187, 189, 193, 195, 197, 199 or 201 or its complementary sequence, or a sequence containing a part or whole of theses sequences.

4. A DNA that encodes a protein hybridizing under a moderate condition with the DNA according to paragraph 2 or 3, and has hair keratin binding activity.

5. A protein comprising an amino acid sequence shown in Seq. ID No. 2n (n shows any integer from 1 to 39).

6. A protein comprising an amino acid sequence shown in Seq. ID No. 2n (n shows a integer from 1 to 39) wherein one or several amino acids are deleted, substituted or added, and has hair keratin binding activity.

7. A protein comprising an amino acid sequence having hair keratin binding activity, shown in Seq. ID Nos. 152, 156, 158, 160, 162, 164, 166, 168, 170, 172, 174, 176, 178, 180, 182, 184, 186, 188, 190, 194, 196, 198, 200 or 202.

8. A protein comprising an amino acid sequence shown in Seq. ID Nos. 152, 156, 158, 160, 162, 164, 166, 168, 170, 172, 174, 176, 178, 180, 182, 184, 186, 188, 190, 194, 196, 198, 200 and 202, wherein one or several amino acids are deleted, substituted or added, and has hair keratin binding activity.

9. A peptide comprising a part of the protein according to any of paragraphs 5 to 8, and binds specifically to keratin.

10. A peptide comprising SCCXPSCCXP (X: Q, V, R, I) as set forth in Seq. ID No. 203, or whole or a part of SCCXPSCCXP (X: Q, V, R, I).

11. A peptide comprising YGGXGYGSGY (X: Y, L, F) as set forth in Seq. ID No. 204, or whole or a part of YGGXGYGSGY (X: Y, L, F).

12. A fusion protein or a fusion peptide wherein the protein according to any of paragraphs 5 to 8 or the peptide according to any of paragraphs 9 to 11 is bound with a marker protein and/or a peptide tag.

13. An antibody that binds specifically to the protein according to any of paragraphs 5 to 8 or the peptide according to any of paragraphs 9 to 11.

14. The antibody according to paragraph 13, wherein the antibody is a monoclonal antibody.

15. A recombinant protein or peptide, wherein the antibody according to paragraph 13 or 14 binds specifically.

16. A recombinant vector comprising one or more DNA selected from the DNA that encodes the protein according to any of paragraphs 5 to 8 or the peptide according to any of paragraphs 9 to 11.

17. A host cell comprising an expressing system that can express one or more protein or peptide selected from the protein according to any of paragraphs 5 to 8 or the peptide according to any of paragraphs 9 to 11.

18. A preparation method of the protein according to any of paragraphs 5 to 8 or the peptide according to any of paragraphs 9 to 11, wherein the host cell according to paragraph 17 is cultured.

19. A non-human animal wherein gene function that encodes the protein according to any of paragraphs 5 to 8 or the peptide according to any of paragraphs 9 to 11 is deleted on its chromosome.

20. A non-human animal that overexpresses the protein according to any of paragraphs 5 to 8 or the peptide according to any of paragraphs 9 to 11.

21. The non-human animal according to any of paragraph 19 or 20, wherein the non-human animal is a mouse or a rat.

22. A screening method for substances promoting or suppressing hair keratin binding activity, wherein the protein according to any of paragraphs 5 to 8 or the peptide according to any of paragraphs 9 to 11, or the cell membrane expressing the protein according to any of paragraphs 5 to 8 or the peptide according to any of paragraphs 9 to 11, and a test substance are used.

23. A screening method for substances promoting or suppressing hair keratin binding activity, or substances promoting or suppressing the expression of said protein or peptide, wherein the cells expressing the protein according to any of paragraphs 5 to 8 or the peptide according to any of paragraphs 9 to 11 and a test substance are used.

24. The screening method for substances promoting or suppressing hair keratin binding activity or substances promoting or suppressing the expression of said protein or peptide according to paragraph 23, wherein the cells expressing the protein according to any of paragraphs 5 to 8 or the peptide according to any of paragraphs 9 to 11 are the host cell according to paragraph 17.

25. The screening method for substances promoting or suppressing hair keratin binding activity or for substances promoting or suppressing the expression of the protein according to any of paragraphs 5 to 8 or the peptide according to any of paragraphs 9 to 11, wherein the non-human animal according to any of paragraphs 19 to 21 and a test substance are used.

26. A substance promoting hair keratin binding activity obtained by the screening method according to any of paragraphs 22 to 25.

27. A substance suppressing hair keratin binding activity obtained by the screening method according to any of paragraphs 22 to 25.

28. A substance promoting the expression of the protein according to any of paragraphs 5 to 8 or the peptide according to any of paragraphs 9 to 11, obtained by the screening method according to any of paragraphs 22 to 25.

29. A substance suppressing the expression of the protein according to any of paragraphs 5 to 8 or the peptide according to any of paragraphs 9 to 11, obtained by the screening method according to any of paragraphs 22 to 25.

30. A cosmetic/therapeutic agent, wherein the active ingredients are one or more types selected from a group comprising the protein according to any of paragraphs 5 to 8 or the peptide according to any of paragraphs 9 to 11, the recombinant protein or peptide according to paragraph 15, the recombinant vector according to paragraph 16, the host cell according to paragraph 17, the substance promoting hair keratin binding activity according to paragraph 26, or the substance promoting the expression according to paragraph 28.

31. A cosmetic/therapeutic agent, wherein the active ingredients are one or more types selected from a group comprising the antibody according to paragraph 13 or 14, the substance suppressing hair keratin binding activity according to paragraph 27 or the substance suppressing, the expression according to paragraph 29.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A peptide consisting of SCCXPSCCXP (X is Q, V, R, or I) as set forth in SEQ ID NO: 203.

2. The peptide of claim 1 wherein the peptide is SCCQPSCCQP, as set forth in SEQ ID NO: 203.

3. A cosmetic agent comprising one or more peptides having hair keratin binding activity, wherein the one or more peptides having hair keratin binding activity is a peptide consisting of SCCXPSCCXP (X is Q, V, R, or I) as set forth in SEQ ID NO: 203.

4. The cosmetic agent of claim 3 wherein the peptide having hair keratin binding activity is a peptide consisting of SCCQPSCCQP, as set forth in SEQ ID NO: 203.

* * * * *